US009609861B2

(12) United States Patent
Liu et al.

(10) Patent No.: US 9,609,861 B2
(45) Date of Patent: Apr. 4, 2017

(54) PLATELET ADDITIVE SOLUTION HAVING A β-GALACTOSIDASE INHIBITOR

(71) Applicants: Velico Medical, Inc., Beverly, MA (US); The Brigham and Women's Hospital, Inc., Boston, MA (US)

(72) Inventors: Qiyong Peter Liu, Newton, MA (US); Karin Hoffmeister, Chestnut Hill, MA (US); Robert Sackstein, Sudbury, MA (US)

(73) Assignees: Velico Medical Inc., Beverly, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/047,689

(22) Filed: Oct. 7, 2013

(65) Prior Publication Data

US 2014/0099629 A1 Apr. 10, 2014
US 2016/0174543 A9 Jun. 23, 2016

Related U.S. Application Data

(63) Continuation-in-part of application No. 13/474,627, filed on May 17, 2012, now abandoned, which is a continuation of application No. 13/474,473, filed on May 17, 2012, now abandoned.

(60) Provisional application No. 61/710,273, filed on Oct. 5, 2012, provisional application No. 61/813,885, filed on Apr. 19, 2013, provisional application No. 61/613,876, filed on Mar. 21, 2012, provisional application No. 61/613,837, filed on Mar. 21, 2012, provisional application No. 61/503,984, filed on Jul. 1, 2011, provisional application No. 61/487,077, filed on May 17, 2011.

(51) Int. Cl.
 *A01N 1/02* (2006.01)
(52) U.S. Cl.
 CPC .................. *A01N 1/0226* (2013.01)
(58) Field of Classification Search
 CPC .... A61K 35/19; C07K 14/47; C12N 2830/85; C12P 21/005; A01N 1/00; G01N 2800/222
 USPC .......................................................... 435/2
 See application file for complete search history.

(56) References Cited

U.S. PATENT DOCUMENTS

| | | | |
|---|---|---|---|
| 4,695,460 A * | 9/1987 | Holme | A01N 1/02 424/532 |
| 5,198,357 A | 3/1993 | Holmovist et al. | |
| 5,234,808 A | 8/1993 | Murphy | |
| 5,236,716 A | 8/1993 | Carmen et al. | |
| 5,256,559 A | 10/1993 | Maraganore et al. | |
| 5,269,946 A | 12/1993 | Goldhaber et al. | |
| 5,344,752 A | 9/1994 | Murphy | |
| 5,376,524 A | 12/1994 | Murphy et al. | |
| 5,399,268 A | 3/1995 | Pall et al. | |
| 5,459,030 A | 10/1995 | Lin et al. | |
| 5,466,573 A | 11/1995 | Murphy et al. | |
| 5,474,891 A | 12/1995 | Murphy | |
| 5,510,261 A | 4/1996 | Goochee et al. | |
| 5,529,821 A | 6/1996 | Ishikawa et al. | |
| 5,550,108 A | 8/1996 | Sims et al. | |
| 5,569,579 A | 10/1996 | Murphy | |
| 5,571,686 A | 11/1996 | Rosenberg et al. | |
| 5,582,821 A | 12/1996 | Kaye | |
| 5,622,867 A | 4/1997 | Livesey et al. | |
| 5,627,290 A | 5/1997 | Iida et al. | |
| 5,631,283 A | 5/1997 | Cross et al. | |
| 5,660,825 A | 8/1997 | Sims et al. | |
| 5,714,509 A | 2/1998 | Luo et al. | |
| 5,753,428 A | 5/1998 | Yuasa et al. | |
| 5,763,156 A | 6/1998 | Sims et al. | |
| 5,919,614 A | 7/1999 | Livesey et al. | |
| 6,037,356 A | 3/2000 | Lu et al. | |
| 6,066,323 A | 5/2000 | Cross et al. | |
| 6,204,263 B1 | 3/2001 | Lu et al. | |
| 6,221,669 B1 | 4/2001 | Livesey et al. | |
| 6,235,778 B1 | 5/2001 | Tomczuk et al. | |
| 6,245,763 B1 | 6/2001 | Lu et al. | |
| 6,277,556 B1 | 8/2001 | Grode et al. | |
| 6,326,492 B1 | 12/2001 | Wang et al. | |
| 6,344,466 B2 | 2/2002 | Soll et al. | |
| 6,344,486 B1 | 2/2002 | Soll et al. | |
| 6,350,764 B2 | 2/2002 | Lu et al. | |
| 6,417,161 B1 | 7/2002 | Lu et al. | |
| 6,420,397 B1 | 7/2002 | Pan et al. | |
| 6,472,399 B2 | 10/2002 | Lu et al. | |
| 6,476,016 B2 | 11/2002 | Wang et al. | |
| 6,497,823 B1 | 12/2002 | Rothman et al. | |
| 6,514,978 B2 | 2/2003 | Lu et al. | |
| 6,518,310 B2 | 2/2003 | Tomczuk et al. | |
| 6,521,663 B2 | 2/2003 | Pan et al. | |
| 6,566,379 B1 | 5/2003 | Lu et al. | |
| 6,635,637 B2 | 10/2003 | Wang et al. | |

(Continued)

FOREIGN PATENT DOCUMENTS

CA  2 817 787 A 1  5/2012
CN  101181302 A  5/2008

(Continued)

OTHER PUBLICATIONS

Jansen et al. Surface sialic acid prevents loss of GPIbalpha during platelet storage and rescues in vivo survival of murine platelets. Blood. 2007;110:Abstract 138.*

(Continued)

*Primary Examiner* — Lynn Y Fan
(74) *Attorney, Agent, or Firm* — Antoinette G. Giugliano; AGG Intellectual Property Law

(57) ABSTRACT

The present invention relates to a platelet additive solution (PAS) having an amount of one or more β-galactosidase inhibitors with or without an amount of one or more sialidase inhibitors, and optionally one or more glycan-modifying agents; and one or more of PAS components that include a salt, a citrate source, a carbon source, or any combination thereof.

18 Claims, 54 Drawing Sheets

(56) References Cited

U.S. PATENT DOCUMENTS

| | | |
|---|---|---|
| 6,638,931 B1 | 10/2003 | Tomczuk et al. |
| 6,693,115 B2 | 2/2004 | Asai et al. |
| 6,706,021 B2 | 3/2004 | Lu et al. |
| 6,706,765 B2 | 3/2004 | Tomczuk et al. |
| 6,730,783 B2 | 5/2004 | Tomczuk et al. |
| 6,866,992 B2 | 3/2005 | Lin et al. |
| 6,900,231 B2 | 5/2005 | Pan et al. |
| 7,005,253 B2 | 2/2006 | Polyak et al. |
| 7,029,654 B2 | 4/2006 | Lu et al. |
| 7,030,110 B2 | 4/2006 | Wang et al. |
| 7,241,282 B2 | 7/2007 | Stossel et al. |
| 7,816,500 B2 | 10/2010 | Sackstein |
| 7,858,295 B2 | 12/2010 | Stossel et al. |
| 7,875,585 B2 | 1/2011 | Sackstein |
| 7,989,159 B2 | 8/2011 | Gyongyossy-Issa et al. |
| 7,998,740 B2 | 8/2011 | Sackstein |
| 8,052,667 B2 | 11/2011 | Rosiello et al. |
| 8,084,236 B2 | 12/2011 | Sackstein |
| 8,835,104 B2 | 9/2014 | Mayaudon et al. |
| 2003/0044457 A1 | 3/2003 | Faour et al. |
| 2004/0062801 A1 | 4/2004 | Faour et al. |
| 2006/0057658 A1 | 3/2006 | Ying et al. |
| 2006/0074047 A1 | 4/2006 | Cross et al. |
| 2007/0074300 A1 | 3/2007 | Igdoura et al. |
| 2008/0044383 A1 | 2/2008 | Sackstein |
| 2008/0199845 A1 | 8/2008 | Rosiello et al. |
| 2009/0053198 A1 | 2/2009 | Sackstein |
| 2009/0074737 A1 | 3/2009 | Rosiello et al. |
| 2009/0131524 A1 | 5/2009 | Gibson et al. |
| 2009/0155763 A1* | 6/2009 | Rosiello et al. ............... 435/2 |
| 2009/0175805 A1 | 7/2009 | Prince et al. |
| 2009/0191537 A1 | 7/2009 | Mayaudon et al. |
| 2009/0239296 A1 | 9/2009 | Sackstein |
| 2010/0047892 A1 | 2/2010 | Laine et al. |
| 2010/0285028 A1 | 11/2010 | Marth et al. |
| 2011/0064746 A1 | 3/2011 | Liu et al. |
| 2011/0136203 A1 | 6/2011 | Nystedt et al. |
| 2011/0280813 A1 | 11/2011 | Prince et al. |
| 2012/0046355 A1 | 2/2012 | Schoenhofen et al. |
| 2012/0107924 A1 | 5/2012 | Sackstein |

FOREIGN PATENT DOCUMENTS

| | | |
|---|---|---|
| EP | 1 640 383 A1 | 3/2006 |
| EP | 2 077 074 A2 | 7/2009 |
| WO | WO 92/16612 | 10/1992 |
| WO | WO 93/10260 | 5/1993 |
| WO | WO 03/027245 | 4/2003 |
| WO | WO 2004/043381 | 5/2004 |
| WO | WO 2004/043381 A2 | 5/2004 |
| WO | WO 2004/098675 | 11/2004 |
| WO | WO 2005/056047 | 6/2005 |
| WO | WO 2006/044790 A2 | 4/2006 |
| WO | WO 2007/047687 A2 | 4/2007 |
| WO | WO 2008/054475 A2 | 5/2008 |
| WO | WO 2008/011094 | 12/2008 |
| WO | WO 2009/038853 A2 | 3/2009 |
| WO | WO 2009/126564 | 10/2009 |
| WO | WO 2011/006208 | 1/2011 |
| WO | WO 2011/097717 A1 | 8/2011 |
| WO | WO 2011/162831 | 12/2011 |
| WO | WO 2012/158983 A2 | 11/2012 |

OTHER PUBLICATIONS

Jansen et al. Desialylation accelerates platelet clearance after refrigeration and initiates GPIbalpha metalloproteinase-mediated cleavage in mice. Blood. 2012;119(5):1263-1273.*

Huber et al. Strong inhibitory effect of furanoses and sugar lactones on beta-galactosidase of *Escherichia coli*. Biochemistry. 1987;26:1526-1531.*

Bosmann H. Identification, purification and characteristics of glycosidases of human blood platelets. Biochim. Biophys. Acta. 1972;258:265-273.*

Beta-galactosidase. Beta-galactosidase. Sigma. 2015;1-2.*

Shimizu et al. Roles of acetate and phosphate in the successful storage of platelet concentrates prepared with an acetate-containing additive solution. Transfusion. 1993;33(4):304-310.*

Jansen, G., "Surface Sialic Acid Prevents Loss of GPIbα During Platelets Storage and Rescues In Vivo Survival of Murine Platelets," Blood, 2007, 119, Abstract No. 138.

Jansen, G., et al., "1133 Inhibition of Sialic Acid Loss Greatly Improves Survival of Refrigerated Platelets." Presented at the 53rd ASH Annual Meeting and Exposition, San Diego, CA (Dec. 2011).

Grozovsky, R., et al., "3257 Desialylated Platelets Are Cleared From the Circulation by the Hepatic Asualoglycoprotein Receptor." Presented at the 53rd ASH Annual Meeting and Exposition, San Diego, CA (Dec. 2011).

Rumjantseva, V., et al., "Novel and Unexpected Clearance Mechanism for Cold Platelets," *Transfusion and Apheresis Science* 42:63-70 (2010).

Sorensen, et al., "Role of Sialic Acid for Platelet Life Span: Exposure of 2-Galactose Results in the Rapid Clearance of Platelets From the Circulation by Asialoglycoprotein Receptor Expressing Liver Macrophages and Hepatocytes," *Blood*, 114:1645-1654 (2009).

Rumjantseva, V., et al., "Dual Roles for Hepatic Lectin Receptors in the Clearance of Chilled Platelets," *Nat. Med.* 15:1273-1280 (2009).

Hoffmeister, K., "The Role of Lectins and Glycans in Platelet Clearance," *J. of Thromb. Haemost.*, 9(1):35-43 (2011).

Hoffmeister K., et al., "Glycosylation Restores Survival of Chilled Blood Platelets," *Science*, 301:1531-1534 (2003).

Hornsey, V., et al., "Extended Storage of Platelets in SSP Platelet Additive Solution," *Vox Sang.*, 91(1):41-6 (2006).

Hoffmeister, K., et al., "The Clearance Mechanism of Chilled Blood Platelets," *Cell*, 10:87-97(2003).

Hartwig, J., et al., "Thrombin Receptor Ligation and Activated Rac Uncap Actin Filament Barbed Ends Through Phosphoinositide Synthesis in Permeabilized Human Platelets," *Cell*, 82:643-653 (1995).

Hartwig, J., et al., "D3 Phosphoinositides and Outside-In Integrin Signaling by GPIIb/IIIa Mediate Platelet Actin Assembly and Filopodial Extension Induced by Phorbol 12-Myristate 13-Acetate," *J. Biol. Chem.* 271:32986-32993 (1996).

Hoffmeister, K., et al., "Mechanisms of Cold-Induced Platelet Actin Assembly," *J. Biol. Chem.* 276: 24751-24759 (2001).

Gadhoum, S., et al., "Lewis x/CD15 Expression in Human Myloid Cell Differentiation Is Regulated by Sialidase Activity," *Nature Chemical Biology*, 4:51-757 (2008).

Josefsson, E., et al., "The Macrophage $\alpha_M\beta_2$ Integrin $\alpha_M$ Lectin Domain Mediates the Phagocytosis of Chilled Platelets," *J. Biol. Chem.*, 280:18025-18032 (2005).

Ashford, P., et al., "Standard Terminology for Platelet Additive Solutions," *Vox Sanguinis*, 98:577-578 (2010).

Kovacsovics, T., et al., "Thrombin-Induced GP1b-IX Centralization on the Platelet Surface Requires Actin Assembly and Myosin H Activation," *Blood*, 87:618-629 (1996).

Miyagi T, Sagawa J, Konno K, Handa S, Tsuiki S., "Biochemical and immunological studies on two distinct ganglioside-hydrolyzing sialidases from the particulate fraction of rat brain" *J Biochem.* 107(5):787-93 (1990).

Miyagi, T., et al., "Molecular Cloning and Characterization of a Plasma Membrane-Associated Sialidase Specific for Gangliosides," *J. Biol. Chem.* 274:5004 5011 (1999).

Gut, H., et al., "Structural Basis for *Streptococcus pneumonia* NanA Inhibitor by Influenza Antivirals Zanamivir and Oseltamivir Carboxylate," *J. Molec. Biol.*, 409:496-503 (2011).

Endo, T., et al., "Large-Scale Production of CMP-NeuAc and Sialylated Oligosaccharides Through Bacterial Coupling," *Appl. Microbiol. Biotechnol.*, 53:257-261 (2000).

Trappetti, C., et al., "Sialic Acid: A Preventable Signal for Pneumococcal Biofilm Formation, Colonization, and Invasion of the Host," *J. Infectious Diseases*, 199:1497-505 (2009).

(56) References Cited

OTHER PUBLICATIONS

AuBuchon, J., et al., "Experience With Universal Bacterial Culturing to Detect Contamination of Apheresis Platelet Units in a Hospital Transfusion Service," *Transfusion*, 42:855-861 (2002).

Becker, G., et al., "Studies of Platelet Concentrates Stored At 22C and 4C," *Transfusion*, 13:61-68 (1973).

Denis, C., et al., "A Mouse Model of Severe Von Willebrand Disease: Defens in Hemostatis and Thrombosis," *Proc. Natl. Acad. Sci. USA*, 95:9524-9529 (1998).

Dumont, L., et al., "Bacterial Growth Kinetics in ACD-A Apheresis Platelets: Comparison of Plasma and PAS III Storage," *Transfusion*, 51:1079-1085 (2011).

Jacobs, M., et al., "Don't Bug Me: The Problem of Bacterial Contamination of Blood Components—Challenges and Solutions," *Transfusion*, 41:1331-1334 (2001).

Jayanth, P., et al., "Neu1 Sialidase and Matrix Metalloproteinase-9 Cross-Talk Is Essential for Neurotrophin Activation of Trk Receptors and Cellular Signaling," *Cell Signal*, 22:1193-1205 (2010).

Kaplan, C., "Toddy for Chilled Platelets?" *Blood*, 119(5):1100-1273 (2012).

Klumpp, K., et al., "Optimization of Small Molecule Drugs Binding to Highly Polar Target Sites: Lessons From the Discovery and Development of Neuraminidase Inhibitors," *Curr. Top. Med. Chem.*, 6(5):423-34 (2006).

Burnaugh, A., et al., "Growth of *Streptococcus pneumonia* on Human Glycoconjugates Is Dependent Upon the Sequential Activity of Bacterial Exoglycosidases," *J. Bacteriol.*, 190(1):221-230 (2008).

Schmidt, M., et al., "Comparison of Three Bacterial Detection Methods Under Routine Conditions," *Vox Sanguinis*, 92:15-21 (2007).

Pilatte, Y., et al., "Sialic Acids As Important Molecules in the Regulation of the Immune System: Pathophysiological Implications of Sialidases in Immunity," *Glycobiology* 3(3):201-217 (1993).

Schauer, R., "Sialic Acids and Their Role As Biological Masks," *Trends Biochem. Sci.*, 10:357-360 (1985).

Soslau, G., et al., "The Loss of Sialic Acid and It's Prevent in Stored Human Platelets," *Thrombosis Research*, 26:443-455 (1982).

Steiner, M., et al., "Asymmetrical Loss of Sialic Acid From Membrane Glycoproteins During Platelet Aging," *Thromb. Res.*, 40:465-471 (1985).

Wang, P., et al., "Induction of Lysosomal and Plasma Membrane-Bound Sialidases in Human T-Cells Via T-Cell Receptor." *Biochem. J.* 380:425-433 (2004).

Wessels, M.R., et al., "Studies of Group B *Streptococcal* Infection in Mice Deficient in Complement Component C3 or C4 Demonstrate an Essential Role for Complement in Both Innate and Acquired Immunity," *Proc. Natl. Acad. Sci. USA.*, 92:11490-11494 (1995).

Yomtovian, R., et al., "A Prospective Microbiologic Surveillance Program to Detect and Prevent the Transfusion of Bacterially Contaminated Platelets," *Transfusion*, 33:902-909 (1993).

Zucker, M., et al., "Reversible Alteration in Platelet Morphology Produced by Anticoagulants and by Cold," *Blood* 28:524-534 (1954).

Zanoteli, E., et al., "Muscle Degeneration in Neuraminidase 1-Deficient Mice Results From Infiltration of the Muscle Fibers by Expanded Connective Tissue," *Biochim. Biophys. Acta.*, 1802:659-672 (2010).

Yan, J., et al., "Critical Role of Kupffer CellCR3 (CD11b/CD18) In the Clearance of IgM-Opsonized Erythrocytes or Soluble P-Glucan," *Immunopharmacology*, 46:39-54 (2000).

White, J., et al., "An Ultrastructural Basis for the Shape Changes Induced in Platelets by Chilling," *Blood*, 30:625-635 (1967).

Warren, L., "The Thiobarbituric Acid Assay of Sialic Acids," *J. Biol. Chem.*, 234(8):1971 (1995).

Ware, J., et al., "Generation and Rescue of a Murine Model of Platelet Dysfunction: The Bernard-Soulier Syndrome," *Proc. Natl. Acad. Sci. USA.*, 97(6):2803-2808 (2000).

Ward, C., et al., "Mocarhagin, A Novel Cobra Venom Metalloproteinase, Cleaves the Platelet Von Willebrand Factor Receptor Glycoprotein Ibα. Identification of the Sulfated Tyrosine/Anionic Sequence Tyr-276-Glu-282 of Glycoprotein Ibα As a Binding Site for Von Willebrand Factor and α-Thrombin," *Biochemistry*, 35:4929-4938 (1996).

Wang, Y., et al., "A Close Association of the Ganglioside-Specific Sialidase Neu3 With Caveolin in Membrane Microdomains," *J. Biol. Chem.*, 277(29):26252-26259 (2002).

Wandt, H., et al., "Safety and Cost Effectiveness of a 10 × 10 (9)/L Trigger for Prophylactic Platelet Transfusions Compared With the Traditional 20 × 10 (9)/L Trigger: A Prospective Comparative Trial in 105 Patients With Acute Myeloid Leukemia," *Blood*, 91:3601-3606 (1998).

Von Andrian, U.H., "Intravital Microscopy of the Peripheral Lymph Node Microcirculation in Mice," *Microcirculation*, 3:287-300 (1996).

Von Andrian, U.H., "T Cell Activation in Six Dimensions," *Science*, 296:1815-1817(2000).

Winokur, R., et al., "Mechanism of Shape Change in Chilled Human Platelets," *Blood*, 85:1796-1804 (1995).

Verschoor, A., et al., "A Platelet Mediated System for Shuttling Blood-Borne Bacteria to CD8α+ Dentritic Cells Dependents on Glycoprotein GPIb and Complement C3," *Nature Immunol.*, 12(12):1194-201 (2011).

Tablin, F., et al., "Membrane Phase Transition of Intact Human Platelets: Correlation With Cold-Induced Activation," *J. Cell. Phys.*, 168:305-313 (1996).

Stossel, T., et al., "Filamins As Integrators of Cell Mechanics and Signaling," *Nat. Rev. Mol. Cell Biol.* 2:138-145 (2001).

Simon, D., et al., "Mac-1 (CD11b/CD18) and the Urokinase Receptor (CD87) Form a Functional Unit on Monocytic Cells," *Blood*, 88:3185-94 (1996).

Simon, D., et al., "Platelet Glycoprotein Ibα Is a Counterreceptor for the Leukocyte Integrin Mac-1 (CD11b/CD18)," *J. Exp. Med.*, 192:193-204 (2000).

Shen, Y., et al., "Requirement of Leucine-Rich Repears of Glycoprotein (GP) Iba for Shear-Dependent and Static Binding of Willebrandt Factor to the Platelet Membrane GPIb-IX-V Complex," *Blood*, 95:903-910 (2000).

Schreiber, G.B., et al., "The Risk of Transfusion-Transmitted Viral Infections. The Retrovirus Epidemiology Donor Study," *New England J. Med.* 334:1685-1690 (1996).

Slichter, S., et al., "Preparation and Storage of Platelet Concentrates," *Brit. J. Haemat.*, 34:403-419 (1976).

Rebulla, P., et al., "The Threshold for Prophylactic Platelet Transfusions in Adults With Acute Myeloid Leukemia," *New England J. Med.*, 337:1870-1875 (1997).

Rabie, T., et al., "Diverging Signaling Events Control the Pathway of BPVI Down-Regulation In Vivo," *Blood*, 110:529-535 (2012).

Qiao, J., et al., "Proteolysis of Platelet Receptors in Human and Other Species," *Biol. Chem.*, 391:893-900 (2010).

Ostrowska, H., et al., "Lysosomal High Molecular Weight Multienxyme Complex," *Cell. Mol. Biol. Lett.*, 8:19-24 (2003).

Morton, L., et al., "Integrin α2β1- Independent Activation of Platelets by Simple Collagen-Like Peptides: Collagen Tertiary (Triple-Helical) and Quaternary (Polymeric) Structures Are Sufficient Along for α2β1-Independent Platelet Reactivity," *Biochem. J.*, 306:337-344 (1995).

Michelson, A., et al., "In Vivo Tracking of Platelets: Circulating Degranulated Platelets Rapidly Lose Surface P-Selectin But Continue to Circulate and Function," *Proc. Natl. Acad. Sci. USA*, 93:11877-11882 (1996).

Michelson, A., et al., "Reversible Inhibition of Human Platelet Activation by Hyperthermia In Vivo and In Vitro," *Thromb. Haemost.* 71:633-640 (1994).

Mazurov, A.V., et al., "Characterization of an Antiglycoprotein Ib Monoclonal Antibody That Specifically Inhibits Platelet-Thrombin Interaction," *Thromb. Res.*, 62:673-684 (1991).

Maynard, J., et al, "Antibody Engineering," *Ann. Rev. Biomed. Eng.*, 2:339-77 (2000).

Marwaha, N., et al., "Consensus and Controversies in Platelet Transfusion," *Trans. Apher. Sci.*, 41:127-133 (2009).

(56) References Cited

OTHER PUBLICATIONS

Marion, C., et al., "Identification of an ATPase, MsmK, Which Energizes Multiple Carbohydrate ABC Transporters in *Streptococcus pneumonia*," *Infection and Immunity*, 79(10):4193-4200 (2011).

MacPhee, P.J., et al., "Evidence for Kupffer Cell Migration Along Liver Sinusoids, From High Resolution In Vivo Microscopy," *Am. J. Physiol.*, 263:17-23 (1992).

Liu, Z., et al., "Combined Biosynthetic Pathways for De Novo Production of UDP-Galactose: Catalysis With Multiple Enzymes Immobilized on Agarose Beads," *ChemBioChem*, 3:348-355 (2002).

Kaufman, R., "Platelets: Testing, Dosing and the Storage Lesion—Recent Advances," *Hematology*, 492-496 (2006).

Janmey, P., et al., "Gelsolin-Polyphosphoinositide Interaction. Full Expression of Gelsolin-Inhibiting Function by Polyphosphoinositides in Vesicular Form and Inactivation by Dilution, Aggregation, or Masking of the Inositol Head Group," *J. Biol. Chem.*, 264:4825-4831 (1989).

Italiano, J., et al., "Angiogenesis Is Regulated by a Novel Mechanism: Pro-And Anti-Angiogenic Proteins Are Organized Into Separate Platelet $\alpha$-Granules and Differentially Released," *Blood*, 111(3):1227-1233 (2007).

Hudson, P., "Recombinat Antibody Fragments," *Curr. Opin. Biotechnol.*, 9:395-402 (1998).

Heidlas, J., et al., "Practical Enzyme-Based Syntheses of Uridine 5'-Diphosphogalactose and Uridine 5'-Diphospho-N-Acetylgalactosamine on a Gram Scale," *J. Org. Chem.*, 57:152-157 (1992).

Hartwig, J., et al., "The Cytoskeleton of the Resting Human Blood Platelet: Structure of the Membrane Skeleton and Its Attachment to Actin Filaments," *J. Cell Biol.*, 112:407-425 (1991).

Grewal, P. K., et al., "The Aswell-Morell Receptor," *Methods Enzymol.*, 479:223-241 (2010).

Grewal, P. K., et al., "The Ashwell Receptor Mitigates the Lethal Coagulopathy of Sepsis," *Nat. Med.*, 14(6):648-655 (2008).

Gardiner, E., et al., "Regulation of Platelet Membrane Levels of Glycoprotein VI by a Platelet-Derived Metalloproteinase," *Blood*, 104:3611-3617 (2004).

Gardiner, E., et al., "Controlled Shedding of Platelet Glycoprotein (GP)VI and GPIb0IX-V by ADAM Famuly Metalloproteinases," *J. Thromb Haemost*, 5:1530-1537 (2007).

Faraday, N., et al., "In Vitro Hypothermia Enhances Platelet GPIIb-IIIa Activation and P-Selectin Expression," *Anesthesiology*, 88:1579-1585 (1998).

Engelfriet, C., et al., "Bacterial Contamination of Blood Components," *Vox Sang.* 78:59-67 (2000).

Endo, T., et al., "Large-Scale Production of N-Acetyllactosamine Through Bacterial Coupling," *Carbohydr. Res.*, 316:179-183 (1999).

Chernoff, A., et al., :The Cellular and Molecular Basis of the Platelet Storage Lesion: A Symposium Summery, Transfusion, 32:386-390 (1992).

Chen, X.-P., et al., "The Control of IL-4 Gene Expression in Activated Murine T Lymphocytes," *J. Immunol.*, 158:3070-3080 (1997).

Cauwenberghs, N., et al., "Epitope Mapping of Inhibitory Antibodies Against Platelet Glycoprotein Ibalpha Reveals Interaction Between the Leucine-Rich Repeat N-Terminal and C-Terminal Flanking Domains of Glycoprotein Ibalpha," *Blood*, 98:652-66— (2001).

Canault, M., et al. "p38 Miogen-Activated Protein Kinase Activation During Platelet Storage: Consequences for Platelet Recovery and Hemostatic Function In Vivo," *Blood*, 115:1835-1842 (2010).

Brown, S., et al., "Constitutive Death of Platelets Leading to Scavenger Receptor-Mediated Phagocytosis. A Caspase Independent Program," *J. Biol. Chem.*, 275:5987-5996 (2000).

Breacher, M., et al., "Evaluation of an Automated Culture System for Detecting Bacterial Contamination of Platelets: An Analysis With 15 Contaminating Organisms," *Transfusion*, 41:477-482 (2001).

Bratosin, D., et al., "Flow Cytofluorimetric Analysis of Young and Senescent Human Erythrocytes Probed With Lectins. Evidence That Sialic Acids Control Their Life Span," *Glycoconj. J.*, 12:258-267 (1995).

Berndt, M.C., et al., "Ristocetin-Dependent Reconstitution of Binding of Von Willebrandt Factor to Purified Human Platelet Membrane Glycoprotein Ib-IX Complex," *Biochemistry*, 27:633-640 (1088).

Berman, C., et al., "A Platelet Alpha Granule Membrane Protein That Is Associated With the Plasma Membrane After Activation. Characterization and Subcellular Localization of Platelet Activation-Dependent Granule-External Membrane Protein," *J. Clin. Invest.*, 78:130-137 (1986).

Bergmeier, W., et al., "Structural and Functional Characterization of the Mouse Von Willebrand Factor Receptor GP1b-IX With Novel Monoclonal Antibodies," Blood, 95:886-983 (2000).

Bergmeier, W., et al., "GPVI Down-Regulation in Murine Platelets Through Metalloproteinase-Dependent Shedding," *Thromb. Haemost.*, 91:951-958 (2004).

Bergmeiers, W., et al., "Tumor Necrosis Factor-$\alpha$-Converting Enzyme (ADAM 17) Mediates GPIb$\alpha$ Shedding From Platelets In Vitro and In Vivo," Circ. Res., 95:677-683 (2004).

Bergmeier, W., et al., "Rhodocytin (Aggretin) Activates Platelets Lacking $\alpha_2\beta_1$ Integrin, Glycoprotein VI, and the Ligand-Binding Domain of Glycoprotein Ib$\alpha$," *J. Biol. Chem.*, 276:25121-25126 (2001).

Bergmeier, W., et al., "Metalloproteinase Inhibitors Improve the Recovery and Hemostatic Function of In Vitro-Aged or -Injured Mouse Platelets," *Blood*, 102:4229-4235 (2003).

Berger, G., et al., "P-Selectin and Platelet Clearance," *Blood*, 92:4446-4452 (1998).

Baker, G., et al., "A Simple, Fluorescent Method to Internally Label Platelets Suitable for Physiological Measurments," *Am. J. Hem.*, 56:17-25 (1997).

Badlou, B., et al., "Role of Glycoprotein Ibalpha in Phagocytosis of Platelets by Macrophages," *Transfusion*, 46:2090-2099 (2006).

Aktas, B., et al., "Asprin Induces Platelet Receptor Shedding Via ADAM 17 (TACE)," *J. Biol. Chem.*, 280:39716-39722 (2005).

Aas, R. K., et al., "Survival of Blood Platelets With Chromium 51," *J. Clin. Invest.*, 37:1257-1268 (1958).

Jansen, G., et al., "Surface Sialic Acid Prevents Loss of GPIb during Platelet Storage and Rescues In Vivo Survival of Murine Platelets," ASH Annual Meeting Abstracts, 2007. (From *Blood*, 2007, 110, Abstract No. 138).

Jansen, G., et al., "Desialylation Accelerates Platelet Clearance Following Refrigeration and Initiates GPIb $\alpha$ Metalloproteinase-Mediated Cleavage in Mice," *Blood*, 119(5): 1263-1273, (2012).

Christopher M. Ward , Robert K. Andrews , A. Ian Smith , and Michael C. Berndt "Mocarhagin, a Novel Cobra Venom Metalloproteinase, Cleaves the Platelet von Willebrand Factor Receptor Glycoprotein Ib$\alpha$. Identification of the Sulfated Tyrosine/Anionic Sequence Tyr-276-Glu-282 of Glycoprotein Ib$\alpha$ as a Binding Site for von Willebrand Factor and $\alpha$-Thrombin," Biochemistry, 35 (15), pp. 4929-4938 (1996).

Greenberg, J., et al., "Effects on Platelet Function of Removal of Platelet Sialic Acid by Neuraminidase," *Lab Invest.*, 32: 476-484, (1975).

Slichter, S.J., "Evidence-Based Platelet Transfusion Guidelines," *Am. Soc. Hematol. Educ. Program*, 2007(1):172-178, (2007).

Li, Y ., et al., "Identifying Selective Inhibitors Against the Human Cytosolic Sialidase NEU2 by Substrate Specificity Studies," *Mol. Biosyst.*, 7: 1060-1072, (2011).

von Itzstein M., "The War Against Influenza: Discovery and Development of Sialidase Inhibitors," *Nat Rev Drug Discov.*, 6: 967-974, (2007).

Mason, K., et al., "Programmed Anuclear Cell Death Delimits Platelet Life Span," *Cell*, 128: 1173-1186, (2007).

Nohle, U., Beau, J., and S.R., "Uptake, Metabolism, and Excretion of Orally and Intravenously Administered, Double-Labeled

(56) References Cited

OTHER PUBLICATIONS

N-Glycoylneuraminic Acid and Single-Labeled 2-Deoxy-2, 3-Dehydro-N-Acetylneuraminic Acid in Mouse and Rat," *Eur. J. Biochem.*, 126:542-548, (1982).
Alhumaidan, H. and Sweeney, J., "Current Status of Additive Solution for Platelets," *J. Clin. Apher.*, 27: 93-98, (2012).
Miyagi, T., et al., "Immunological Discrimination of Intralysosomal, Cytosolic, and Two Membrane Sialidases Present in Rat Tissues," *J. Bicohem.*, 107: 1263-1273, (1990).
Wada, T., et al., "Cloning, Expression, and Chromosomal Mapping of a Human Ganglioside Sialiadase," *Biochem. Biophys. Res. Commun.*, 261: 21-27, (1999).
Finlay, T.M., et al., "Thymoquinone From Nutraceutical Black Cumin Oil Activates Neu4 Sialidase in Live Macrophage, Dendritic, and Normal and Type I Sialidosis Human Fibroblast Cells via GPCR Galphai Proteins and Matrix Metalloproteinase-9," *Glycoconj. J.*, 27:329-348, (2010).
Finlay, T.M., et al., "Thymoquinone-Induced Neu4 Sialidase Activates NFkappaB in Macrophage Cells and Pro-Inflammatory Cytokines In Vivo," *Glycoconj. J.*, 27: 583-600, (2010).
Tsuji, T. and Osawa, T., "The Carbohydrate Moiety of Human Platelet Glycocalicin: The Structures of the Major Asn-Linked Sugar Chains," *J. Biochem. (Tokyo)*, 101: 241-249, (1987).
Tsuji, T., et al., "The Carbohydrate Moiety of Human Platelet Glycocalicin," *J. Biol. Chem.*, 258: 6335-6339, (1983).
Bauvois, B., et al., "Glycoprotein-Sialyltransferase Activity of Normal Human, Thrombasthenic and Bernard-Soulier Platelets," *Vox. Sang.*, 40: 71-78, (1981).
Tribulatti, M.V., et al., "The Trans-Sialidase from Trypanosoma Cruzi Induces Thrombocytopenia During Acute Chagas' Disease by Reducing the Platelet Sialic Acid Contents," *Infect. Immun.*, 73: 201-207, (2005).
Venkata, C., Sampathkumar, P., and Afessa, B., "Hospitalized Patients With 2009 H1N1 Influenza Infection: The Mayo Clinic Experience," *Mayo Clin. Proc.*, 85(9): 798-805, (2010).
Bautista, E., et al., "Clinical Aspects of Pandemic 2009 Influenza A (H1N1) Virus Infection," *N. Engl. J. Med.*, 362: 1708-1719, (2010).
Iskratsch, T., et al., "Specificity Analysis of Lectin and Antibodies Using Remodeled Glycoproteins," *Anal. Biochem.*, 386: 133-146 (2009).
Hammond, K.S. and Papermaster, D.S., "Fluorometric Assay of Sialic Acid in the Picomole Range: A Modificaiton of the Thiobarbituric Acid Assay," *Anal. Biochem.*, 74: 292-297, (1976).
Hammond, M. S., et al., "Neural Cell Adhesion Molecule-Associated Polysialic Acid Inhibits NR2B-Containing N-Methyl-D-Aspartate Receptors and Prevents Glutamate-Induced Cell Death," *J. Biol. Chem.*, 281: 34859-34869, (2006).
Amith, S.R., et al., "Dependence of Pathogen Molecule-Induced Toll-Like Receptor Activation and Cell Function on Neu1 Sialidase," *Glycoconj. J.*, 26: 1197-1212, (2009).
Chang, M., et al., "Tissue Uptake of Circulating Thrombopoietin is Increased in Immune-Mediated Compared with Irradiated Thrombocytopenic Mice," *Blood*, 93: 2515-2524, (1999).
Ellies, L., et al., "Sialyltransferase ST3Gal-IV Operates as a Dominant Modifier of Hemostasis by Concealing Asialoglycoprotein Receptor Ligands," *Proc. Natl. Acad. Sci., USA*, 99: 10042-10047, (2002).
Dumont, L.J., et al., "A Randomized Controlled Trial Comparing Autologous Radiolabeled In Vivo Platelet (PLT) Recoveries and Survival of 7-day-stored PLT-Rich Plasma and Buffy Coat PLTs from the Same Subjects," *Transfusion*, 51: 1241-1248, (2011).
Stinchcombe, J., et al., "Linking Albinism and Immunity: The Secrets of Secretory Lysosomes," *Science*, 305: 55-59, (2004).
Richardson, J.L., et al., "Mechanisms of Organelle Transport and Capture Along Proplatelets During Platelet Production," *Blood*, 106: 4066-4076, (2005).
Wu, M., et al., "Differential Targeting of Secretory Lysosomes and Recycling Endosomes in Mast Cells Revealed by Patterned Antigen Arrays," *J. Cell. Sci.*, 120: 3147-3154, (2007).
Valeri, C., et al., "Effect of Thrombopoietin Alone and a Combination of Cytochalasin B and Ethylene Glycol bis (beta-aminoethyl ether) N, N'-Tetraacetic Acid-AM on the Survival and Function of Autologous Baboon Platelets Stored at 4 Degrees C for as Long as 5 Days," *Transfusion*, 44: 865-870, (2004).
Jackson, S. and Schoenwaelder, S., "Procoagulant Platelets: Are they Necrotic?," *Blood*, 116: 2011-2018, (2010).
Hermann, M., et al., "Real-Time Live Confocal Fluorescence Microscopy as a New Tool for Assessing Platelet Vitality," *Transfus Med. Hemother.*, 37: 299-305, (2010).
Battinelli, E., M., et al., "Delivering New Insight Into the Biology of Megakaryopoiesis and Thrombopoiesis," *Curr. Opin. Hematol.*, 14: 419-426 (2007).
Dodd, R.Y., "The Risk of Transfusion Transmitted Infection," *N. Engl. J. Med.*, 327: 419-421, (1992).
Coxon, A., et al., "A Novel Role for the β2 Integrin CD11b/CD18 in Neutrophil Apoptosis: a Homeostatic Mechanism in Inflammation," *Immunity*, 5: 653-666, (1996).
Wandall, H. H., K. M. Hoffmeister, et al. (2008). "Galactosylation does not prevent the rapid clearance of long-term, 4 degrees C-stored platelets." *Blood* 111(6): 3249-3256.
Wandall, H. H., V. Rumjantseva, et al. (2012). "The origin and function of platelet glycosyltransferases." *Blood* 120(3): 626-635.
Park, E. I., and Baenziger, J. U. (2004). "Closely related mammals have distinct asialoglycoprotein receptor carbohydrate specificities." J. Biol. Chem. 279,40954-40959.
Rowley, J. W., A. J. Oler, et al. (2011). "Genome-wide RNA-seq analysis of human and mouse platelet transcriptomes." *Blood* 118(14): e101-111.
Robert K. Andrews, Jeffrey J. Gorman, William J. Booth, Gary L. Corino, Peter A. Castaldi, and Michael C. Berndt, "Cross-Linking of a Monomeric 39 /34-kDa Dispase Fragment of von Willebrand Factor (Leu-480/Val-481-Gly-718) to the N-Terminal Region of the α-Chain of Membrane Glycoprotein Ib on Intact Platelets with Bis(sulfosuccinimidyl) Suberate," *Biochemistry* 28, 8326-8336 (1989).
Madoff et al., Sialic Acid of Human Blood Platelets, Journal of Clinical Investigation, vol. 43, No. 5 (1964).
Varki et al., The release and purification of sialic acids from glycoconjugates: Methods to minimize the loss and migration of O-acetyl groups, Analytical Biochemistry, vol. 137, Issue 1, pp. 236-247 (1984).
Varki et al., Essentials of Glycobiology. 2nd edition. Cold Spring Harbor (NY): Cold Spring Harbor Laboratory Press; Chapter 14 Sialic Acids (2009).
Miyagi et al., Mammalian sialidases: Physiological and pathological roles in cellular functions, Glycobiology vol. 22 No. 7 pp. 880-896 (2012).
Monti et al., Sialidases in Vertebrates : A Family of Enzymes Tailored for Several Cell Functions, Advances in Carbohydrate Chemistry and Biochemistry, vol. 64, pp. 403-479 (2010).
Colli, Trans-sialidase: a unique enzyme activity discovered in the protozoan Trvpanosoma cruzi, FASEB Journal, 7: 1257-1264 (1993).
WHO Guidelines for Pharmacological Management of Pandemic Influenza A(H1N1) 2009 and other Influenza Viruses, Source, Geneva: World Health Organization; Feb. 2010 WHO Guidelines Approved by the Guidelines Review Committee (2010).
Eguchi et al., Modification of oligosaccharides by reactive oxygen species decreases sialyl lewis x-mediated cell adhesion, Glycobiology vol. 15 No. 11 pp. 1094-1101 (2005).
Krotz et al., Reactive Oxygen Species: Players in the Platelet Game, Arterioscler Thromb Vasc Biol., Nov;24(11):1988-96 (2004).
Streicher H., Inhibition of Microbial Sialidases—What has Happened Beyond the Influenza Virus?, Curr. Med. Chem.—Anti-Infective Agents, 3: 149-161 (2004).
Skripchenko A., et al., Addition of Sialidase or P38 MAPK Inhibitors does not Ameliorate Decrements in all in vitro Platelet Storage Properties Caused by 4 C Storage, Transfusion 53 (S2): SP45.
Remington's pharmaceutical sciences. Mack Publishing Company. 1985; Jan. 2006.

(56) References Cited

OTHER PUBLICATIONS

Rumjantseva V., et al., "Dual roles for hepatic lectin receptors in the clearance of chilled platelets", Nature Medicine 15(11): 1273-80 (2009).

Sorensen A.L., et al., "Role of sialic acid for platelet life span: exposure of beta-galactose results in the rapid clearance of platelets from the circulation by asialoglycoprotein receptor-expressing liver macrophages and hepatocytes", Blood 114(8):1645-54 (2009).

Parker et al. The NanA neuraminidase of streptococcus pneumoniae is involved in biofilm formation. Infection and Immunity,77(9):3722-3730 (2009).

Ternovskaia et al. Neuraminidase activity of staphylococci. Zh Mikrobiol Epidemiol lmmunobiol, 4:30-32 (1984).

Liu, Q P, et al "Variations in Platelet Surface Glycans Among Health Volunteers" Transfusion 52 : No. 3S, Supplement 126A, Abstract No. SP191 (2012).

Mohan et al. Evaluation of antimicrobial peptides as novel bactericidal agents for room-temperature-stored platelets.Transfusion. 50:166-173 (2010).

Oskari K. Karjalainen et al: "Short and Straightforward Synthesisof (−)-1-Deoxygalactonojirimycin",Organic Letters, vol. 12, No. 6, Mar. 19, 2010 (Mar. 19, 2010), pp. 1145-1147, XP055091776,ISSN: 1523-7060, DOI: 10.1021/o1100037c (2010).

Maria Giulia Egidi et al: "Troubleshooting in platelet storage temperatureand new perspectives through proteomics",Blood transfusion = Trasfusione del sangue, Jun. 1, 2010 (Jun. 1, 2010),pp. s73-s81, XP055091647,ItalyDO1: 10.2450/201 0.012S; Retrieved from the Internet: URL:http://www.pubmedcentral.nih.gov/articlerender.fcgi?artid=2897204&tool=pmcentrez&rendertype=abstract (2010).

Wandall, Hans H. et al. Galactosylation does not prevent the rapid clearance of long-term, 4° C.-stored platelets *Blood*, Mar. 15, 2008 111 (6): 3249-3256 (2008).

\* cited by examiner

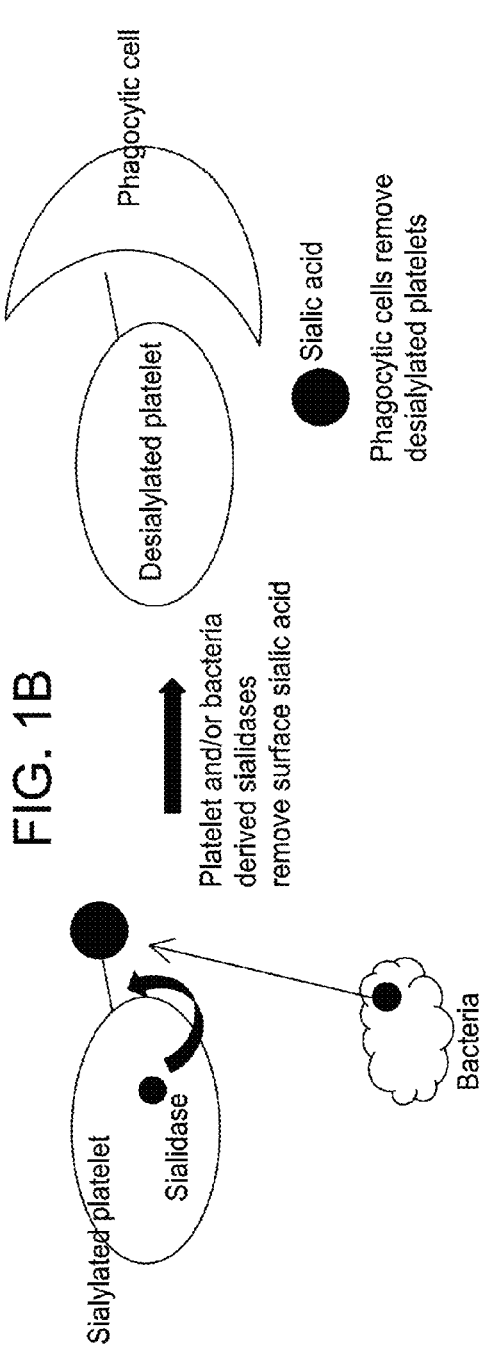
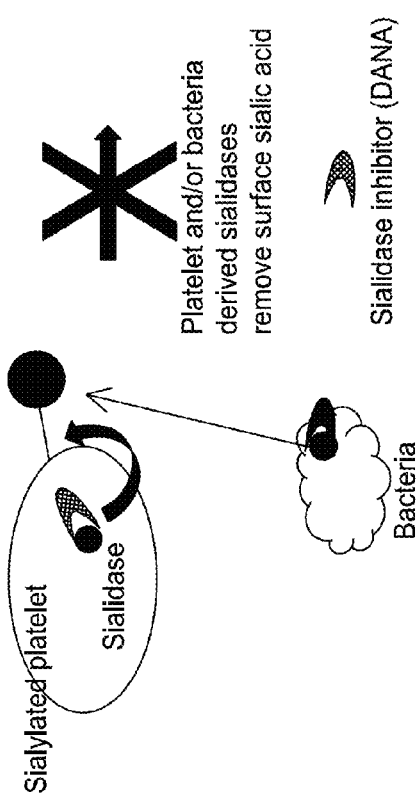
FIG. 1B
FIG. 1C (A)

(B)

(C)

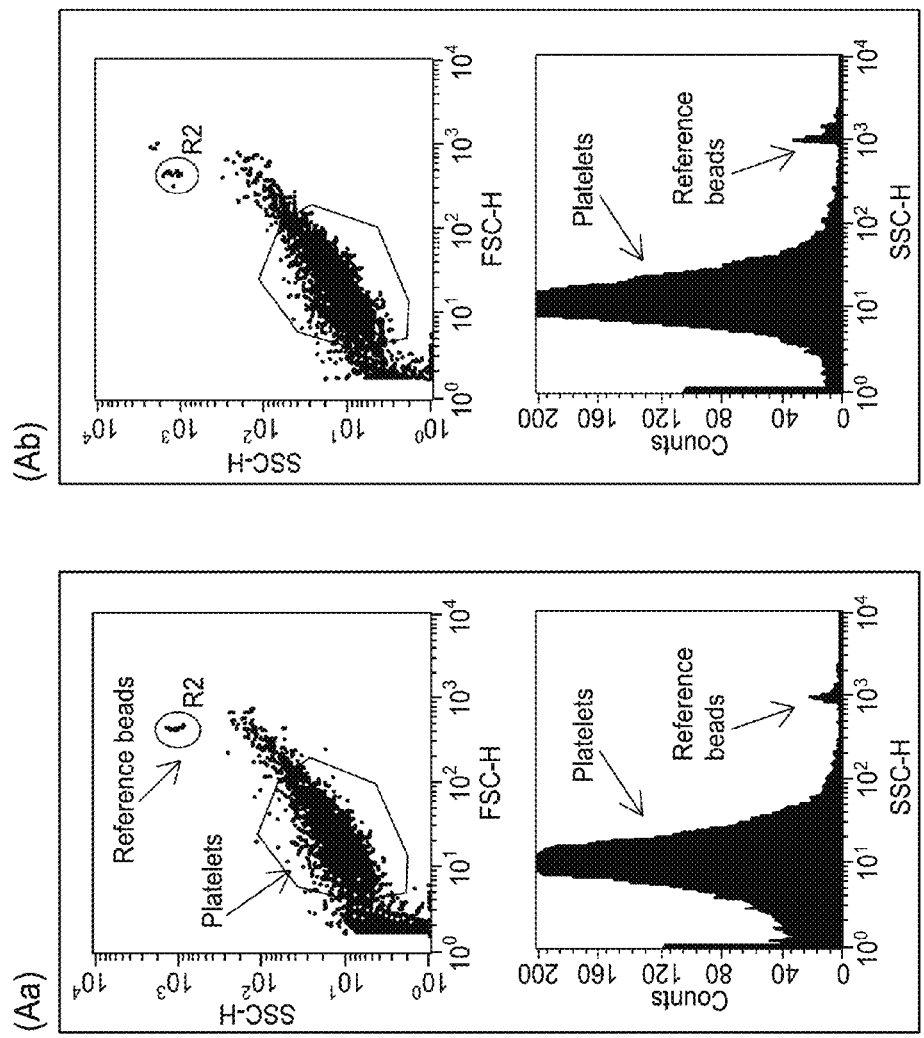
FIG. 33 (Aa)
FIG. 33 (Ab)

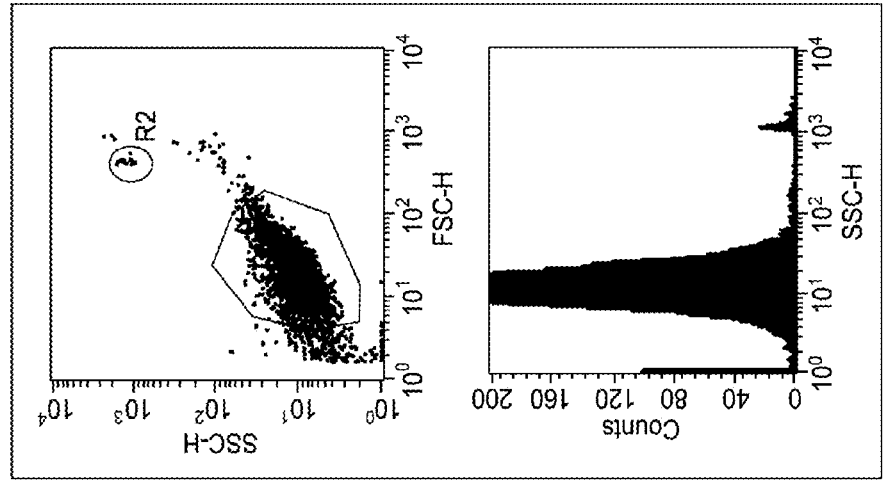
FIG. 33 (Ad)
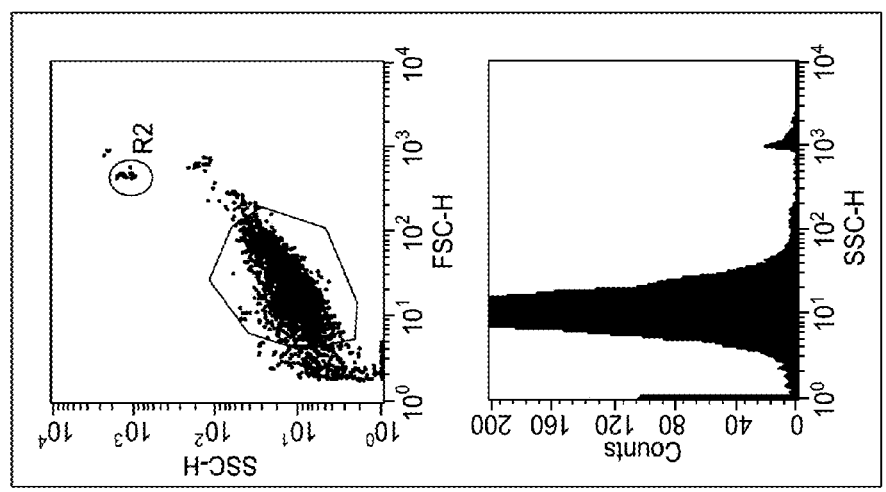
FIG. 33 (Ac)

(B)

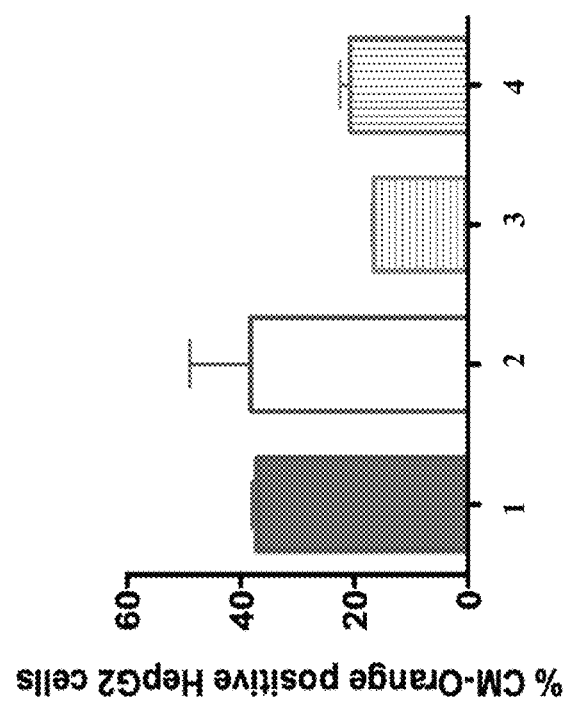
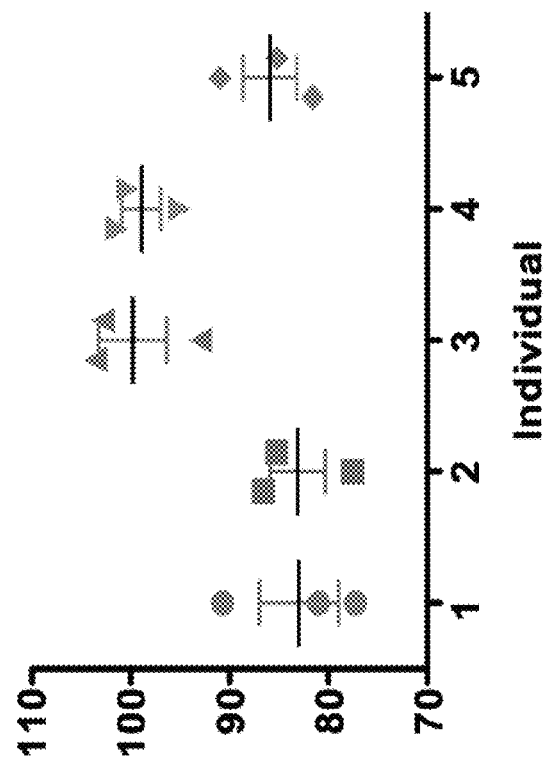
FIG. 39A
FIG. 39B

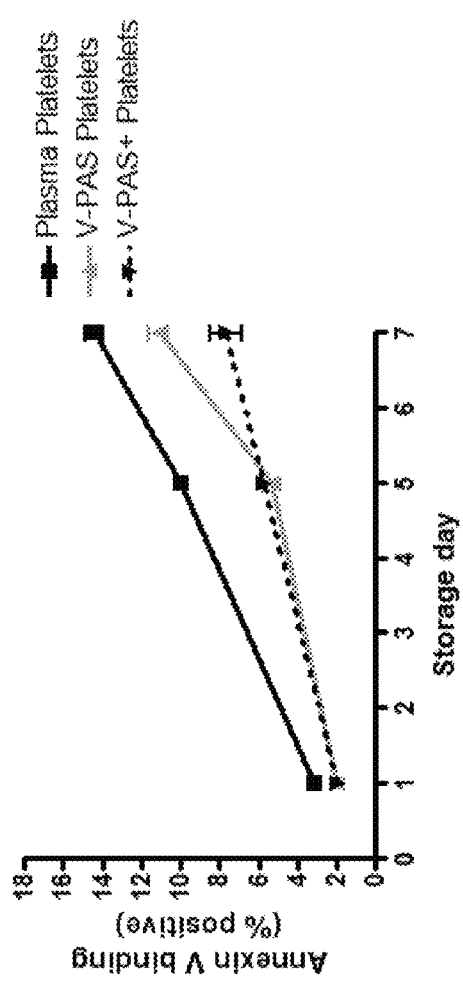
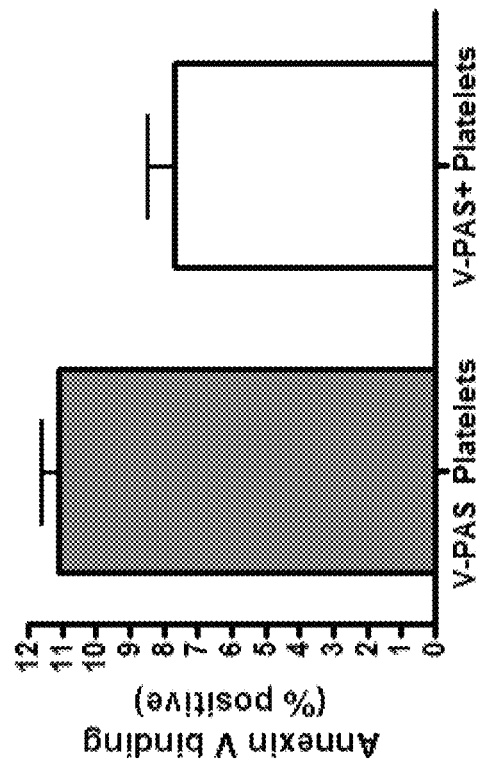
FIG. 45A
FIG. 45B

PLATELET ADDITIVE SOLUTION HAVING A β-GALACTOSIDASE INHIBITOR

RELATED APPLICATIONS

This application claims the benefit of U.S. Provisional Application No. 61/813,885, filed Apr. 19, 2013, entitled, "Platelet Additive Solution Having a Platelet Enhancing Agent;" and U.S. Provisional Application No. 61/710,273, filed Oct. 5, 2012, entitled, "Platelet Additive Solution Having a Sialidase Inhibitor and/or a Beta-Galactosidase Inhibitor"; and this application is a Continuation-In-Part of U.S. application Ser. No. 13/474,627, entitled "Platelet Storage and Reduced Bacterial Proliferation In Platelet Products Using A Sialidase Inhibitor" by Liu et al., filed May 17, 2012, which is a continuation of U.S. application Ser. No. 13/474,473, entitled "Increased In Vivo Circulation Time of Platelets After Storage With A Sialidase Inhibitor" by Liu et al., filed May 17, 2012, and U.S. application Ser. No. 13/474,627 claims the benefit of U.S. Provisional Application No. 61/613,876, filed Mar. 21, 2012; U.S. Provisional Application No. 61/613,837, filed Mar. 21, 2012; U.S. Provisional Application No. 61/503,984, filed Jul. 1, 2011; and U.S. Provisional Application No. 61/487,077, filed May 17, 2011.

The entire teachings of the above applications are incorporated herein by reference.

GOVERNMENT SUPPORT

The invention was made with Government support under grant No. HL089224 awarded by the National Institutes of Health. The Government has certain rights in the invention.

BACKGROUND OF THE INVENTION

Collected platelets intended for transfusion are highly perishable. Platelets are non-nucleated bone marrow-derived blood cells that protect injured mammals from blood loss by adhering to sites of vascular injury and by promoting the formation of plasma fibrin clots. Humans depleted of circulating platelets by bone marrow failure suffer from life threatening spontaneous bleeding, and less severe deficiencies of platelets contribute to bleeding complications following trauma or surgery.

As the count of circulating platelets falls (e.g., ~70,000 per μL), patients become increasingly susceptible to cutaneous bleeding. Patients with platelet counts of less than 20,000 per μL are highly susceptible to spontaneous hemorrhage from mucosal surfaces, especially when the thrombocytopenia is caused by a bone marrow disorder or failure. Platelet deficiencies associated with bone marrow disorders such as aplastic anemia, acute and chronic leukemia, metastatic cancer, and deficiencies resulting from cancer treatment such as ionizing radiation or chemotherapy all contribute to a major public health problem. Patients that suffer from thrombocytopenia associated with major surgery, injury and sepsis also require significant numbers of platelet transfusions.

A major advance in medical care half a century ago was the development of platelet transfusions to correct such platelet deficiencies, resulting in about 2.6 million platelet transfusions in the United States per year at current transfusion rates. However, platelets collected for transfusion are highly perishable because, upon storage at or below room temperature, they quickly lose in vivo hemostatic activity. Hemostatic activity broadly refers to the ability of a population of platelets to mediate bleeding cessation.

Platelets, unlike all other transplantable tissues, do not tolerate refrigeration and disappear rapidly from the circulation of recipients if subjected to even very short periods of chilling. Importantly, the cooling effect that shortens in vivo platelet survival is thought to be irreversible and, therefore, cooled platelets become unsuitable for transfusion. One of the first visible effects of platelet impairment is an irreversible conversion from a discoid morphology towards a spherical shape, and the appearance of spiny projections on the surface of platelets due to calcium dependent gelsolin activation and phosphoinositide-mediated actin polymerization. When platelets are exposed to temperatures lower than 20° C., they rapidly undergo such shape modifications.

The need to keep platelets at room temperature prior to transfusion has imposed a unique set of costly and complex logistical requirements on platelet storage. Because platelets are metabolically active at room temperature, they require constant agitation in gas permeable containers to allow for the exchange of gases to prevent the toxic consequences of metabolic acidosis. Room temperature storage conditions result in macromolecular degradation and reduced hemostatic functioning of platelets, a set of defects known as the "platelet storage lesion" (PSL). In addition, storage at room temperature encourages the growth of bacteria, thereby creating a higher risk of bacterial infection, which effectively limits the duration of such storage to about 5 days. These bacteria include endogenous ones as well as skin-derived ones associated with venipuncture. In this regard, bacterial contamination of platelets is by far the most frequent infectious complication of blood component use. At current rates, from one in 1,000 to one in 2,000 units of platelets are contaminated with bacteria at a level sufficient to pose a significant risk to the recipient.

Thus, there remains a pressing need to develop agents, solutions and methods to (i) improve or prolong in vivo hemostatic activity of human platelets upon storage at or below room temperature, (ii) stabilize platelets during storage to prevent their premature clearance from circulation following transfusion, and (iii) more significantly, inhibit bacterial proliferation during room temperature platelet storage.

SUMMARY OF THE INVENTION

The present invention relates to a platelet additive solution (PAS) that includes an amount of one or more β-galactosidase inhibitors with or without an amount of one or more sialidase inhibitors and, optionally, one or more glycan-modifying agents; and one or more PAS components that include a salt (e.g., sodium source, a chloride source, a potassium source, a magnesium source, a calcium source, or a combination thereof), a citrate source (e.g., monosodium citrate, disodium citrate, trisodium citrate, citric acid, or a combination thereof), and/or a carbon source (e.g., acetate, glucose, sucrose, or any combination thereof). For example, the PAS can include an amount of one or more of any of the following: β-galactosidase inhibitors; β-galactosidase inhibitors and sialidase inhibitors; β-galactosidase inhibitors and glycan-modifying agents; or β-galactosidase inhibitors, sialidase inhibitors and glycan-modifying agents. The PAS, in an embodiment of the present invention, is maintained at a pH ranging between about 6.4 and about 7.6. In one embodiment, the PAS of the present invention further includes a phosphate source (e.g., sodium monophosphate, diphosphate, triphosphate or a combination thereof). An acetate source can include, for example, sodium acetate, potassium acetate, magnesium acetate or a combination thereof. In an aspect, the sodium source can be sodium chloride, sodium citrate, sodium acetate, sodium phosphate or a combination thereof. Similarly, the chloride source can be sodium chloride, magnesium chloride, potassium chloride or a combination thereof. The potassium source, in an example, can be potassium chloride, potassium citrate, potassium acetate, potassium phosphate, potassium sulfate or a combination thereof. Examples of sources of magnesium include magnesium chloride, magnesium citrate, magnesium sulfate and a combination thereof. In an embodiment, the calcium source encompasses calcium chloride, calcium acetate, calcium citrate or a combination thereof.

In a particular embodiment, the PAS of the present invention includes an amount of one or more β-galactosidase inhibitors with or without an amount of one or more sialidase inhibitors and, optionally, one or more glycan-modifying agents; a sodium source in an amount between about 100 mM and about 300 mM; a chloride source in an amount between about 40 mM and about 110 mM; a citrate source in an amount between about 2 mM and about 20 mM; an acetate source in an amount between about 10 mM and about 50 mM; a phosphate source in an amount between about 5 mM and about 50 mM; a potassium source in an amount between about 0.5 mM and about 10 mM; a magnesium source in an amount between about 0.5 mM and about 2.5 mM; a calcium source in an amount between about 0.5 mM and about 2.5 mM and a glucose source in an amount between about 0.5 mM and about 25 mM. An alternative to the embodiment above has the same components and is maintained at a pH of between about 6.4 and about 7.6 (e.g., about 7.1 to about 7.4, or about 7.2).

In yet another embodiment, the present invention pertains to platelet compositions having isolated platelets; the PAS of the present invention; and plasma, wherein the platelet composition is maintained at a pH ranging between about 6.4 and about 7.6. In an aspect, the plasma is present in an amount between about 1% and about 50% by volume (e.g., between 20% and 40% plasma, or about 30% plasma). In yet another embodiment, the platelet additive solution is present in an amount between about 50% and about 99% by volume.

The present invention further relates to a bag or container suitable for platelet storage having the PAS of the present invention. The bag or container can further include isolated platelets that can be maintained at a pH ranging between about 6.4 and about 7.6.

The present invention relates to a method of storing platelets, wherein isolated platelets are obtained from one or more donors. The method includes the steps of contacting the isolated platelets with the PAS described herein. The sialidase inhibitor can be e.g., fetuin; 2,3-dehydro-2-deoxy-N-acetylneuraminic acid (DANA); Oseltamivir (ethyl(3R,4R,5S)-5-amino-4-acetamido-3-(pentan-3-yloxy)-cyclohex-1-ene-1-carboxylate); Zanamivir ((2R,3R,4S)-4-guanidino-3-(prop-1-en-2-ylamino)-2-((1R,2R)-1,2,3-trihydroxypropyl)-3,4-dihydro-2H-pyran-6-carboxylic acid); Laninamivir ((4S,5R,6R)-5-acetamido-4-carbamimidamido-6-[(1R,2R)-3-hydroxy-2-methoxypropyl]-5,6-dihydro-4H-pyran-2-carboxylic acid); Peramivir ((1S,2S,3S,4R)-3-[(1S)-1-acetamido-2-ethyl-butyl]-4-(diaminomethylideneamino)-2-hydroxy-cyclopentane-1-carboxylic acid); any combination thereof or a pharmaceutically acceptable salt thereof. In an embodiment, the sialidase inhibitor is the sodium salt of 2,3-dehydro-2-deoxy-N-acetylneuraminic acid. The β-galactosidase inhibitor can be, e.g., 1-deoxygalactonojirimycin (DGJ); N-(n-butyl)deoxygalactonojirimycin; N-(n-nonyl)deoxygalactonojirimycin; 5-deoxy-L-arabinose; galactostatin bisulfite; 3',4',7-trihydroxyisoflavone; D-ribonolactone; N-octyl-4-epi-β-valienamine; phenylethyl β-D-thiogalactopyranoside; difluorotetrahydropyridothiazinone; 4-aminobenzyl 1-thio-β-D-galactopryranoside; a combination thereof; or a pharmaceutically acceptable salt thereof.

The method allows isolated platelets to be stored for a period of about 1 to about 21 days. The isolated platelets are stored a temperature of between about 1° C. and about 25° C. (e.g., about 2° C. to about 24° C.). The method, in an embodiment, includes the steps of cooling the platelet composition to a temperature below room temperature; storing the platelet composition for a period of time; and then rewarming the platelet composition back to room temperature. In an aspect, the population of platelets is treated with the β-galactosidase inhibitor, or both with the β-galactosidase inhibitor and the sialidase inhibitor within a time period, wherein the time period is in a range between about 1 minute to about 48 hours.

BRIEF DESCRIPTION OF THE DRAWINGS

FIGS. 1A-C are schematics depicting a sialylated platelet containing intracellular sialidase and sialidase-containing bacteria. (FIG. 1A) Both bacterial and platelet derived sialidases remove sialic acid from platelet surfaces, leading to the formation of platelets with impaired function (1). The released sialic acids support the proliferation of contaminating bacteria (short-dashed line and 2), which leads to platelet activation (3), formation of platelet-bacteria aggregates (3), and biofilm formation (long-dashed line and 4). (FIG. 1B) Desialylated platelets are recognized and removed from the circulation by phagocytes upon transfusion. (FIG. 1C) Addition of the sialidase inhibitor DANA (sodium salt of 2,3-dehydro-2-deoxy-N-acetylneuraminic acid) inhibits the sialidase activities derived from platelets and bacteria, and prevents platelet desialylation so that platelets are not recognized by phagocytic cells after transfusion.

FIG. 31 in panel B depicts biofilm formation of S. marcescens, incubated for 48 h in different media with or without 1 mM DANA in the wells of 96-well PVC plate. Also shown in panel (B), the biofilm in each well was stained with crystal violet, and the dye was recovered and measured at 595 nm. The absorption at 595 nm (A595 nm) is proportional to the bacterial cells in the biofilm.

DANA+Glucose) (depicted in (Ad)). Note, that the platelet population appears resting, as judged by their forward and side scatter characteristics. FIG. 33 (B) is a bar graph showing the percent of acquired events in the gated platelet population for the INTERSOL® solution (depicted in (Ba)), INTERSOL® solution with DANA (depicted in (Bb)), INTERSOL® solution with glucose (depicted in (Bc)), or INTERSOL® solution with both glucose and DANA (depicted in (Bd)).

FIG. 35, panel (B), shows quantification of P-selectin positive platelets defined in M2 (as indicated in FIG. 35, panel (A)) and the corresponding MFI.

FIG. 39A is a graph showing the correlation of HepG2 cells' ingestion of human platelets with β-galactose exposure, by showing the quantification of platelets recovered from HepG2 cell incubation media. Isolated human platelets were labeled with CM-Orange, added to HepG2 cells and incubated for 30 min at 37° C. The number of platelets counted before addition to HepG2 cells was set to 100% for each individual.

FIG. 39B is a bar graph showing the ingestion of fluorescently (CM-orange) labeled fresh platelets, as detected using flow cytometry as an increase in hepatocyte associated orange fluorescence.

FIG. 45A is a line graph of platelet surface exposure of phosphatidylserine (PS) as measured by FITC labeled Annexin V binding over the time of platelet storage (n=4).

FIG. 45B is a bar graph of platelet surface exposure of PS as measured by FITC labeled Annexin V binding after storage for 7 days (n=4).

Figure 1A:
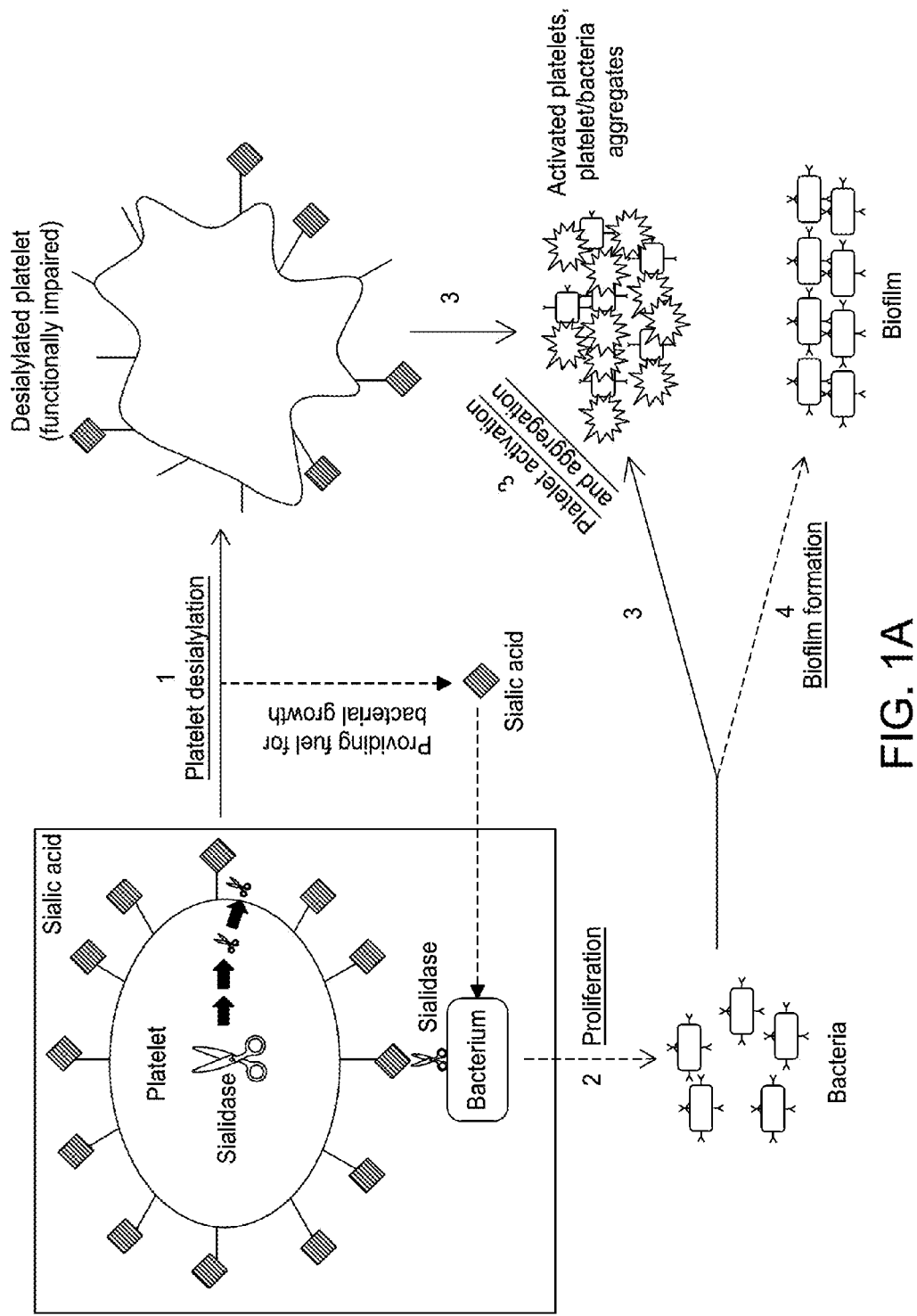

Plasma (70:30), or VPAS+/Plasma (70:30). Fresh non-stored platelets are used as control (n=3 for each group).

DETAILED DESCRIPTION OF THE INVENTION

A description of preferred embodiments of the invention follows.

Platelet Additive Solution (PAS)

After platelets are obtained from a donor, they can be suspended in fluid referred to as Platelet Additive Solution (PAS). Essentially, PAS replaces a portion of the plasma in which the isolated platelets are placed during apheresis. PAS is a medium that is generally a physiologically compatible, aqueous electrolyte solution. In addition to certain agents that can be normally present in such solutions in varying combinations and concentrations as described hereinafter, the PAS solution of the present invention includes one or more β-galactosidase inhibitors with or without one or more sialidase inhibitors, and optionally one or more glycan modifying agents.

Heretofore, PAS solutions are used because they are believed to reduce allergic and febrile transfusion reactions, facilitate ABO-incompatible platelet transfusions, optimize the use of pathogen inactivation techniques and make more plasma available for other purposes (e.g., for fractionation).

One embodiment of the present invention includes a PAS solution having the β-galactosidase inhibitor, and optionally a glycan-modifying agent. Another embodiment of the present invention includes a PAS solution having the β-galactosidase inhibitor, the sialidase inhibitor and optionally a glycan-modifying agent. More specifically, the present invention includes a PAS composition having a β-galactosidase inhibitor with or without a sialidase inhibitor, and/or a glycan-modifying composition, and one or more of PAS components (e.g., salts, buffers, nutrients, or any combination thereof). PAS of the present invention can include a variety of components such as one or more salts (e.g., NaCl, KCl, $CaCl_2$, $MgCl_2$, and $MgSO_4$), one or more buffers (e.g., acetate, bicarbonate, citrate, or phosphate) and nutrients (e.g., acetate, gluconate, glucose, maltose, or mannitol).

The term "Platelet Additive Solution" or "PAS" of the present invention refers to the solution or medium having at least one or more β-galactosidase inhibitors, or both one or more β-galactosidase inhibitors and one or more sialidase inhibitors; and one or more storage medium components and, optionally, one or more glycan modifying agents. The "inventive composition" includes one or more β-galactosidase inhibitors, or both one or more β-galactosidase inhibitors and one or more sialidase inhibitors and, optionally, one or more glycan modifying agents. The phrase "platelet composition" or "platelet storage composition" refers to the resulting storage composition (prior to transfusion into a recipient), which includes the PAS of the present invention, the platelets, and optionally, any plasma and/or anticoagulant associated with the platelets.

Additionally, the medium of the PAS of the present invention includes a physiologically compatible, aqueous electrolytic solution. Such solutions can contain ionic elements in solution such as sources of sodium, potassium, magnesium, calcium, chloride and phosphate. The PAS of the present invention can also contain, e.g., sources of citrate that can be added in the form of citric acid or sodium salt. The solution of the present invention further includes, for example, carbon or nutrient source, such as acetate, glucose or gluconate, and can be present in combination with a salt. A phosphate source, in an embodiment, can be included to help maintain ATP production. These elements can be present in the solution of the present invention in an amount ranging from about 5 mM to about 450 mM (e.g., 10, 20, 30, 40, 50, 60, 70, 80, 90, 100, 150, 200, 250, 300, 350, 400, 450 mM). The solution is maintained at a pH ranging from about 6.4 and about 7.6 (e.g., about 7.1 to about 7.4), and preferably at pH of about 7.2.

In an embodiment, a source of sodium (Na) can be present in the PAS of the present invention in an amount between about 100 and 300 mM (e.g., between about 150 mM and about 250 mM). In a particular embodiment, a source of sodium is present at about 190 mM. Sodium can be present as a salt or in combination as a buffer, or carbon source. For example, sodium can be present in the form of sodium chloride (NaCl), sodium citrate, sodium acetate, sodium phosphate or a combination thereof. Other suitable sources of sodium can be used in the PAS of the present invention including those known in the art or later discovered.

A source of chloride (Cl) can also be present in the PAS of the present invention in an amount between about 40 mM and about 110 mM (e.g., between about 60 mM and about 90 mM). In a particular aspect, the source of chloride is present at about 87.2 mM. Chloride can be present in the form of sodium chloride (NaCl), magnesium chloride ($MgCl_2$), potassium chloride (KCl), or a combination thereof. Any source of chloride known in the art or later discovered can be used with the present invention so long as it is suitable for use with PAS of the present invention. $Na^+$ and $Cl^-$, mainly in the form of NaCl, are tonicity modifiers that contribute to the isotonicity of platelet additive solution.

A source of potassium, in an embodiment, can be present in the PAS of the present invention. It can be present in an amount ranging between about 0.5 mM and about 10 mM, and for example, between about 3 mM and about 8 mM. In a particular embodiment, potassium is present in an amount of about 5 mM. Potassium sources include potassium chloride, potassium citrate, potassium acetate, potassium phosphate, potassium sulfate, or a combination thereof. Other sources of potassium known in the art or later discovered can be used with the present invention. The presence of potassium ion in the medium can assist, in certain aspects, in maintaining intracellular magnesium ion concentration. Potassium ion could also be involved in the transport of pyruvate across the mitochondria membrane for oxidative phosphorylation in the citric acid cycle (TCA cycle). In addition, $K^+$ plays important roles in membrane stability by contributing to the electrical continuity of lipids and proteins.

Magnesium is another salt that can be included in the PAS of the present invention. A source of magnesium can be present in an amount ranging between about 0.5 mM and about 2.5 mM, and in particular, in an amount ranging between about 1 mM and 2 mM. In an embodiment, magnesium is present in the PAS of the present invention at about 1.5 mM. Sources of magnesium include magnesium chloride, magnesium citrate, magnesium sulfate, and a combination thereof. Sources of magnesium known in the art or later discovered can be used. In one embodiment, magnesium ion can be present in the PAS of the present invention at concentrations close to plasma levels, which will be about 3 mEq/L (1.5 mM). $Mg^{2+}$ might be necessary to maintain membrane ATPase activity. In an aspect, magnesium ion in the medium should maintain the optimal intercellular magnesium levels in the platelets and may promote oxidative phosphorylation in the platelets and in so doing help maintain the pH of the medium. Furthermore, $Mg^{2+}$ plays important roles in membrane stability by contributing to the electrical continuity of lipids and proteins.

Calcium is another yet salt that can be included in the PAS of the present invention. A source of calcium can be present in an amount ranging between about 0.5 mM and about 2.5 mM (e.g., between about 1 mM and 2 mM). In a certain embodiment, calcium is present in the PAS of the present invention in about 1.5 mM. Sources of calcium include calcium chloride, calcium acetate, calcium citrate, or a combination thereof. Sources of calcium known in the art or later discovered can be used.

Citrate can be used to buffer the solution. A source of citrate is present in the PAS of the present invention in an amount ranging between about 2 mM and about 20 mM, and for example, in an amount between about 5 mM and about 15 mM. In an aspect, the PAS of the present invention includes about 10 mM of citrate. Examples of citrate sources that can be used in the present invention include sodium citrate (e.g., monosodium citrate, disodium citrate, trisodium citrate), citric acid, potassium citrate, magnesium citrate and a combination thereof. Other sources of citrate can be used including those known in the art or later discovered so long as it is suitable for use with PAS of the present invention. Citrate plays multiple roles in PAS of the present invention as an anticoagulant, a carbon source for the TCA cycle and buffer.

Acetate is yet another component of the PAS of the present invention. Acetate is a carbon source used as a nutrient for the isolated platelets. A source of acetate can be present in an amount ranging between about 10 mM and about 50 mM, and for example, in an amount ranging between about 25 mM and about 45 mM. The PAS of the present invention includes about 30 mM of acetate. Sources of acetate include sodium acetate, potassium acetate, magnesium acetate or a combination thereof. Other sources of acetate can be used including those known in the art or later discovered so long as it is suitable for use with PAS of the present invention. Acetate serves as carbon and buffer.

In the PAS of the present invention, a nutrient source can be provided. Acetate and other carbohydrates such as glucose or sucrose, as well as citrate, can be used individually or in various combinations to provide a source of energy for platelets in storage by being a source of intermediate metabolites for the production of energy in the citric acid cycle. A combination of a carbon source can be used. In the case that glucose and/or sucrose is used, the concentration can be present in an amount ranging from about 0.5 mM to about 25 mM (e.g., about 2 mM to about 22 mM).

Other nutrients can be substituted for or included with the acetate of the PAS of the present invention. For example, oxaloacetate can be present in the PAS of the present invention or can be added to platelet suspension after the PAS of the present invention has been added to a platelet rich fraction. Oxaloacetate is a four-carbon molecule found in the mitochondria that condenses with Acetyl Co-A to form the first reaction of the TCA cycle (citric acid cycle). Oxaloacetate can be supplied to the stored platelets either directly or in the form of precursor amino acids such as aspartate. In some embodiments, oxaloacetate can be present in the PAS of the present invention from about 10 mM to about 45 mM. More particularly, oxaloacetate can be present in the PAS of the present invention from about 20 mM to about 40 mM, or from about 24 mM to about 36 mM, or from about 28 mM to about 33 mM.

Phosphate ($PO_4$) is another component that can be used in the PAS of the present invention. A source of phosphate can be present in the PAS of the present invention in an amount ranging between about 5 mM and about 50 mM (e.g., between about 20 and 40 mM). In a particular embodiment, a source of phosphate is present in about 28 mM. Forms of phosphate include sodium monophosphate, diphosphate, triphosphate, or a combination thereof. Other sources of phosphate known in the art or discovered in the future can be used.

Components such as acetate, citrate and phosphate can be added in combination with one or more salts, such as the calcium, magnesium, potassium, or sodium salts or any sub-combination of these salts to balance the osmolarity of the buffered solution.

In an embodiment, the PAS of the present invention includes one or more β-galactosidase inhibitors with or without one or more sialidase inhibitors, and optionally, one or more glycan modifying agents, and the components described in Table 1:

TABLE 1

|  | Range (mM) | | Amount for a specific formulation (mM) | | | |
| --- | --- | --- | --- | --- | --- | --- |
|  | Low | High | PAS1 | PAS2 | PAS3 | PAS4 |
| Sodium [Na] | 100.0 | 300.0 | 156.7 | 148.3 | 155.2 | 146.8 |
| Chloride [Cl] | 40.0 | 110.0 | 87.2 | 78.8 | 87.7 | 79.3 |
| Citrate | 2.0 | 20.0 | 10.0 | 10.0 | 10.0 | 10.0 |
| Acetate | 10.0 | 50.0 | 30.0 | 30.0 | 30.0 | 30.0 |
| Phosphate [$PO_4$] | 5.0 | 50.0 | 9.4 | 9.4 | 9.4 | 9.4 |
| Potassium [K] | 0.5 | 10.0 | 5.0 | 5.0 | 5.0 | 5.0 |
| Magnesium [Mg] | 0.5 | 5.0 | 1.5 | 1.5 | 1.5 | 1.5 |
| Calcium [Ca] | 0.5 | 2.5 | 0.0 | 0.0 | 1.0 | 1.0 |
| [Glucose] | 5.0 | 30.0 | 0.0 | 16.8 | 0.0 | 16.8 |
| [DANA] | 0.1 | 10.0 | 1.0 | 1.0 | 1.0 | 1.0 |
| 1-Deoxygalactonojirimycin (DGJ) | 0.1 | 10.0 | 1.0 | 1.0 | 1.0 | 1.0 |
| Total (mM) | 163.7 | 622.5. | 301.8 | 301.8 | 301.8 | 301.8 |

The PAS of the present invention as described herein can also be buffered, in an embodiment, by amino acids. The amino acids can be used as the primary buffering agents, or can be used in conjunction with other buffering agents such as phosphate. In one embodiment the amino acid, histidine, can be used to buffer the storage solution. Thus, the storage solution can contain amino acids from about 1 mM to about 7 mM, or from about 2 mM to about 5 mM.

In addition to or as an alternative to the foregoing, the PAS disclosed herein can further include other components that promote oxidative phosphorylation. An antioxidant can be added to the PAS or platelet composition of the present invention. Examples of antioxidants include glutathione, selenium, and the like. In some embodiments the antioxidant can be present in the PAS of the present invention in an amount ranging between about 0.5 µM to about 3 mM (e.g., about 1.0 µM to about 2 mM). In some embodiments, glutathione, or its precursor N-acetylcysteine, and/or selenium alone or in combination can be present in the PAS in an amount between about 0.5 µM to about 3 mM (e.g., about 1.0 µM to about 2 mM).

To further promote oxidative phosphorylation, the PAS of the present invention can further include components that assist in stabilizing membranes. For example, a phospholipid or a mixture or phospholipids can be included in the storage solution. In some embodiments, phospholipids can be present in the PAS of the present invention in an amount ranging from about 0.1 mg/mL to about 7.5 mg/mL (e.g., between about 0.25 mg/mL to about 5 mg/mL). More particularly, L-alpha phosphatidylcholine can be present in the PAS of the present invention in an amount between about 0.1 mg/mL to about 7.5 mg/mL (e.g., about 0.25 mg/mL to about 5 mg/mL).

Additional components that can be included in the PAS of the present invention are non-essential amino acids. For example, non-essential amino acids in an amount ranging from about 0.5 mM to about 14 mM can be present in the PAS (e.g., about 1.0 mM to about 10 mM). In an embodiment, L-alanine can be included in an amount ranging from about 0.5 mM to about 14 mM (e.g., about 1.0 mM to about 10 mM).

Unsaturated free long chain fatty acids can further be included in the PAS of the present invention. The PAS described herein can contain an amount of unsaturated free long chain fatty acids in a range between about 0.05 mM and about 1.5 mM (e.g., about 0.1 mM to about 1 mM). In an embodiment, the PAS of the present invention can contain palmitic acid from about 0.05 mM to about 1.5 mM, or about 0.1 mM to about 1 mM.

United States Pharmacopeia (USP) water for injection (WFI) can be used as a solvent to make the buffer solution for the PAS of the present invention.

The phrase "platelet composition" (e.g., the PAS of the present invention and isolated platelets) refers to a composition whose total volume contains between about 1% to about 50% by volume of plasma. The platelet composition, in one aspect, contains less than about 50% (e.g., less than about 45%, 40%, 35%, 30%, 25%, 20%, 15%, 10%, 9%, 8%, 7%, 6%, 5%, 4%, 3%, 2%, 1%) by volume plasma. Conversely, the platelet storage composition of the present invention has between about 50% and about 99% (e.g., about 55%, 60%, 65%, 70%, 75%, 80%, 85%, 90%, 95%) by volume of PAS of the present invention, which contains one or more β-galactosidase inhibitors with or without one or more sialidase inhibitors, in an electrolytic solution, and also phosphate and/or buffering compounds, carbon source (s), and optionally, one or more glycan modifying agents. In certain embodiments, the platelet storage composition is essentially plasma free having mostly the PAS of the present invention and platelets. In an embodiment, the platelets generally make up about 1% by volume of the total platelet composition.

In an embodiment, once the PAS of the present invention is added to the isolated platelets, PAS of the present invention constitutes about 70% and the plasma constitutes about 30% of the isolated platelet solution. The percentage of PAS of the present invention by volume can vary depending on its use, e.g., for transfusion into chronically anemic patients or acutely anemic patients. Hypervolemia is a concern especially in trauma patients suffering from acute anemia. Accordingly, the percentage of PAS can be modified to minimize or avoid hypervolemia.

The platelet composition in the PAS of the present invention can be assessed at one or more time points during storage. Assessment of the platelet content, platelet morphology, metabolism, bacterial proliferation, the extent of platelet activation, extent of lysis, or a combination thereof can be performed. Additionally, the amount of cleaved sialic acid or the amount of β-galactose exposed on the glycan molecules on the platelet surface can be determined as a measure of the platelet's likelihood to be cleared from circulation. The assessment of platelets, their function and bacterial proliferation is further described herein to assess the platelets' ability to be transplanted, survive in vivo and maintain hemostasis after transfusion. The PAS of the present invention allows platelets to be stored longer, and have longer circulation and maintain hemostasis after transfusion, as compared to platelets not stored in the PAS of the present invention. Storage times, circulation times and hemostasis are also further described herein.

Metabolism of platelets can be assessed by measuring ATP and levels of glucose, lactate and lactate dehydrogenase (LDH). ATP measurements can be carried out using assays known in the art such as Bioluminescent assay kit (Sigma, Poole, Dorset, UK). Glucose, lactate, and LDH can also be measured using assays known in the art, such as Vitros DT60 11 chemistry system (Shield, Kimbolton, Cambridgeshire, UK). The platelets use a carbon source such as acetate during metabolism to maintain ATP, a major energy carrier. The PAS of the present invention can maintain a pH of between about 6.4 and about 7.6, and preferably between about 7.1 to about 7.4.

Applicants have characterized several underlying mechanisms that account for the high susceptibility of platelets to irreversible intolerance by the recipients of transfusions and the resulting loss of platelet's in vivo hemostatic activity. Applicants' discoveries are related to sialic acid and its role in the viability of platelets.

Surprisingly, Applicants have found that the catalytic hydrolysis of sialic acid residues from platelet surface glycans by the platelet's own sialidase enzymes generally contributes to the irreversible intolerance of platelets. Applicants have further discovered that β-galactosidase enzyme surface activity actually increases during platelet storage. Additionally, the Applicants discovered that endogenous sialidase activity increases during platelet storage. Yet another surprising discovery is that sialidase-producing bacteria desialylate plasma and platelet sialioglycoconjugates to obtain nutrients such as sialic acid which supports bacterial growth and proliferation. See FIG. 1A. Bacterial proliferation leads to biofilm formation, platelet activation and aggregation. Desialylated platelets enhance bacteria-platelet interaction and eventually are cleared from circulation via lectin-mediated mechanism (FIG. 1B). Accordingly, the addition of a sialidase inhibitor prevents sialic acid from being cleaved from the platelet surface, thereby preventing platelet clearance and prolonging its survival. Also, addition of a β-galactosidase inhibitor prevents β-galactose from being cleaved from the platelet surface, which also helps to prevent platelet clearance and increase its in vivo survival. Additionally, a sialidase inhibitor inhibits the proliferation of bacteria in a platelet preparation (FIG. 1C). The dual sialidase inhibitor-function provides a superior platelet preparation with longer survivals and reduces the chance of causing bacteria-related sepsis when transfused into a recipient at the point of care.

With these counterintuitive and surprising results in hand, Applicants have developed methods to effectively treat platelets with inhibitors of sialidase after they are harvested from donors and prior to storage at or below room temperature. Treated with β-galactosidase inhibitors, or with sialidase inhibitors and β-galactosidase inhibitors, the inventive platelet compositions retain in vivo hemostatic activity for longer durations as compared to untreated platelets. The inventive platelet compositions treated with β-galactosidase inhibitors with or without sialidase inhibitors can be stored for prolonged periods at or below room temperature as compared to untreated platelets. The storage of platelets according to the inventive methods extends the shelf life of platelets and helps increase the supply of platelets that remain viable for transfusion with inhibited bacterial proliferation.

As noted, Applicants' discoveries are related to sialic acid and β-galactose and their role in the viability of platelets.

The hydrolysis of sialic acid from the outer membrane of platelets is believed to contribute to the unique and irreversible in vivo intolerance of platelets. Studies have reported that platelets lose sialic acid from membrane glycoproteins during aging and circulation, and that in vitro desialylated platelets are cleared rapidly. Loss of sialic acid exposes underlying immature glycans such as β-galactose. Asialoglycoprotein (ASGP) receptors are known to mediate endocytosis of proteins, cells and particles carrying exposed β-galactose. Many cells, including hepatic macrophages and hepatocytes, express and present the ASGP receptor. Accordingly, it is believed that when endogenous sialidase enzymes cleave sialic acid residues from the platelet surface, penultimate sugars such as β-galactose are exposed on the platelet surface and platelets undergo ASGP-mediated ingestion after transfusion. Similarly, it is also believed that when β-galactose is cleaved and N-acetylglucosamine (GlcNAc) is exposed on the platelet surface, the platelets with GlcNAc exposed are also cleared. It is also believed that GlcNAc removal exposes mannose, which can be readily recognized by macrophage mannose receptors, triggering immediate platelet clearance.

While the loss of surface receptors (e.g., GPIb and GPV) on platelets has been associated with platelet survival, prior to the present invention the role of surface sialic acid and/or β-galactose with respect to surface receptors on platelets was unknown. Furthermore, the role of surface sialic acid and/or β-galactose regarding the survival of platelets was unclear. Applicants have used in vitro and in vivo studies to characterize relationships between surface sialic acid/β-galactose, and platelet receptor loss. Accordingly, Applicants' results have been applied to the inventive methods described herein for prolonging the survival of platelets. This relationship between surface sialic acid/β-galactose and platelet receptor loss turns out to be an important factor in determining platelet survival. Applicants have found that inhibiting the loss of surface sialic acid and/or β-galactose prevents platelet surface receptor GPIb and GPV loss during storage in vitro and rescues platelet survival in vivo.

For example, mouse platelets stored at room temperature for 6 h lost surface sialic acid, as evidenced by flow cytometry data provided herein. See Exemplification. This loss correlated with a 30-60% loss of surface receptors GPIb and GPV, but not GPIX and integrin αIIbβ3. Furthermore, treatment of mouse platelets with the neuraminidase (NA) substrate, fetuin, partially decreases the loss of GPIb and GPV to 10-20%. In vitro, sialic acid was cleaved from the platelet surface by adding α2-3,6,8-neuraminidase (NA; *Vibrio cholerae*) or α2-3,6,-NA (*Clostridium perfringens*) to mouse platelets. Removal of sialic acid correlated with the removal of 50-60% of surface GPIbα and GPV, but not GPIX and integrin αIIbβ3. Addition of fetuin, or the more specific sialidase inhibitor, the sodium salt of 2,3-dehydro-2-deoxy-N-acetylneuraminic acid (DANA), completely prevented this loss, as determined by both flow cytometry and Western blot analysis, also provided herein.

The data described herein also show that human platelets have variable surface sialidase and β-galactosidase activities among donors, and show that both are up-regulated during platelet storage at room temperature (RT). The data also show that human platelets have variable surface β-galactose exposure/sialic acid loss among individual donors. During storage at RT, platelet surface β-galactose exposure appears to peak at day 2, then decrease during further storage. Platelet surface β-galactose content correlates positively with ingestion by HepG2 cells, and crosstalk with platelet surface glycosidase activities. Since the association with β-galactosidase goes along with Neu1 sialidase activity, the concerted up-regulation of sialidase and β-galactosidase activities on platelet surface indicates that the multi-enzyme complex is relocated from lysosome to platelet surface during platelet storage/aging, possibly through the fusion between platelet membrane and lysosomal membrane. See FIG. 37. The relocation of both Neu1 and β-galactosidase onto platelet surface catalyzes the sequential degradation of platelet surface glycans, loss of sialic acid, followed by β-galactose, exposing terminal N-acetylglucosamine (GlcNAc). GlcNAc can be further removed, exposing the mannose residues. Mannose can be readily recognized by macrophage mannose receptors, triggering immediate platelet clearance. Accordingly, inhibiting β-galactosidase activity prolongs the platelet storage and increases in vivo survival of platelets. Also, by inhibiting both sialidase enzyme and β-galactosidase activity, it is possible to prolong the platelet storage and increase in vivo survival of platelets.

The clearance of platelets is exacerbated upon cooling. It has been discovered that cooling of human platelets causes clustering of the von Willebrand factor (vWf) receptor complex a subunit (GPIbα) complexes on the platelet surface. The clustering of (GPIbα) complexes on the platelet surface elicits recognition by macrophage complement type three receptors (αMβ2, CR3) in vitro and in vivo. CR3 receptors recognize N-linked sugars with terminal β-GlcNAc on the surface of platelets, which have formed GPIbα complexes, and phagocytose the platelets, clearing them from the circulation and resulting in a concomitant loss of hemostatic function. Although capping the β-GlcNAc moieties by galactosylation prevents clearance of short-term-cooled platelets, this strategy is ineffective after prolonged refrigeration (e.g., refrigeration of platelets longer than 5 days). Prolonged refrigeration further increased the density and concentration of exposed galactose residues on platelets GPIbα such that hepatocytes, through Ashwell-Morell receptor (ASGP receptor or hepatic lectin) binding, become increasingly involved in platelet removal. Macrophages rapidly removed a large fraction of transfused platelets independent of their storage conditions. With prolonged platelet chilling, hepatocyte-dependent clearance further diminishes platelet recovery and survival after transfusion. Inhibition of chilled platelet clearance by both β2 integrin and Ashwell-Morell receptors may afford a potentially simple method for storing platelets in the cold.

As noted above, Applicants have discovered that sialidase enzyme activity is platelet-derived, not plasma-derived, and sialidase enzyme activity and β-galactosidase enzyme activity substantially increase on the platelet surface during the storage of platelets. Specifically, Applicants have discovered that human platelets contain the sialidases Neu1 and Neu3, and release Neu1 into plasma at room temperature, and more so upon storage in the cold, but it is the surface Neu1 being involved in the removal of surface sialic acid from glycans on the surface of platelets. Similarly, Applicants have also discovered that β-galactosidase is released from the platelet to the platelet surface, along with Neu1, and is involved in the removal of β-galactose from the glycans on the surface of platelets.

The present invention provides platelet compositions and methods for prolonging in vivo hemostatic activity and reducing platelet clearance, wherein the platelets are obtained from a donor and treated with a β-galactosidase inhibitor or with both a β-galactosidase inhibitor and a sialidase inhibitor to counteract the effects of β-galactosidase activity or both β-galactosidase activity and endogenous sialidase activity, and inhibit bacterial proliferation.

Also provided are compositions and methods for prolonging the storage of viable platelets, such as mammalian platelets, particularly human platelets. The invention also provides methods for making improved platelet compositions.

The present invention, in certain aspects, provides platelet compositions that have enhanced circulation properties and that retain substantially normal in vivo hemostatic activity. In certain embodiments, the invention provides a novel platelet composition comprising one or more β-galactosidase inhibitors with or without one or more sialidase inhibitors. As noted, sialidase enzymes catalyze the hydrolysis of terminal sialic acid residues from host cell receptors, and β-galactosidase enzymes catalyze the hydrolysis of β-galactose residues from the receptors. Thus, sialidase inhibitors and/or β-galactosidase inhibitors are used in numerous aspects of the present invention to reduce sialidase enzyme activity/β-galactosidase enzyme activity, prevent the hydrolysis of terminal sialic acid/β-galactose residues from platelet surface glycans, inhibit bacterial proliferation and prolong the in vivo hemostatic activity of platelets for transfusion.

The present invention provides for platelet compositions and related methods to prepare, store, and preserve platelet compositions that enhance the platelet function and/or allow platelets to retain substantially normal in vivo hemostatic activity after platelets have been stored at or below room temperature. Certain underlying mechanisms have been discovered that contribute to the high susceptibility of platelets to undergo irreversible intolerance or loss of platelet in vivo hemostatic activity experienced by recipients of platelet transfusions. The hydrolysis of β-galactose residues from platelet surface glycans by β-galactosidase enzymes contributes to the irreversible intolerance of platelets. Similarly, the hydrolysis of sialic acid and β-galactose residues from platelet surface glycans by sialidase and β-galactosidase enzymes, respectively, contributes to the irreversible intolerance of platelets. "Irreversible intolerance" refers to a platelet's inability to retain or return to normal platelet function survival after being subjected to temperatures below that of room temperature. "Platelet viability" is defined as the platelet's ability to survive in vivo.

The present invention provides platelet compositions and methods of inhibiting β-galactosidase enzyme activity, or both β-galactosidase enzyme activity and sialidase enzyme activity; in platelets isolated from a donor and stored at or below room temperature. Thus, in certain aspects, the invention provides compositions having one or more β-galactosidase inhibitors with or without one or more sialidase inhibitors, and optionally one or more glycan-modifying agents. The present invention, in other aspects, provides methods for increasing the circulation time of platelet compositions having one or more β-galactosidase inhibitors, or both one or more β-galactosidase inhibitors and one or more sialidase inhibitors. The present invention further provides platelet compositions and methods for reduced temperature storage of platelets, which increases the storage time of the platelets, as well as methods for reducing clearance of or increasing the circulation time of a population of platelets in a mammal. Also provided are platelet compositions and methods for the preservation of platelets with preserved hemostatic activity as well as methods for making platelet compositions and pharmaceutical compositions thereof containing the platelet compositions and for administering the pharmaceutical compositions to a mammal to mediate hemostasis. Also provided are kits for treating a platelet preparation for storage and containers for storing the same. the Platelet and how it is Isolated The term "isolated" as used herein means separated away from its native environment. As used herein with respect to a population of platelets, isolated refers to removing platelets from the blood of a mammal.

Based on standard blood collection methods, there are generally two types of donated platelets: random donor platelets and single donor platelets. Random donor platelets are platelets isolated from whole blood donations by means of any one of several standard methods practiced by those skilled in the art, and two or more random donor platelets are subsequently pooled in a quantity sufficient to constitute a therapeutic dose prior to transfusion to a patient. A single random donor platelet can also be used without pooling for pediatric patients. Current standard methods include isolating random donor platelets from a buffy coat, a platelet button, platelet rich plasma, and the like. Single donor platelets are platelets obtained from one donor by means of centrifugal separation in an apheresis machine in a quantity sufficient to constitute one or more therapeutic dose(s) for subsequent transfusion to a patient(s). Apheresis machines used currently for the collection of single donor platelets are manufactured by companies such as Terumo BCT (Terumo Corporation), Fenwal Inc., and Haemonetics Corporation. Current AABB (formerly the American Association of Blood Banks) Standards define a therapeutic dose of platelets as approximately $>3\times10^{11}$ platelets.

To carry out the methods described herein, either random donor platelets or single donor platelets are isolated from a donor by means of standard techniques known to one skilled in the art. The isolated platelet preparation is treated with one or more β-galactosidase inhibitors with or without sialidase inhibitors and/or glycan-modifying agents as described herein.

Random donor platelets are obtained from whole blood donations. Whole blood can be obtained from a donor and prepared by a suitable method depending on the type of blood components desired. The present invention involves isolating platelets in the form of a buffy coat, a platelet button, platelet concentrate, platelet rich plasma, and the like.

In the United States, the collection and processing of all blood components for transfusion are controlled by FDA regulations and AABB Standards.

Whole blood is comprised of a number of components including plasma, red blood cells, platelets, white blood cells, proteins and other components. Accordingly, in addition to platelets, other components from whole blood can be isolated and prepared (e.g., red blood cells, plasma, etc.) when a unit of blood is obtained from a donor. Whole blood is generally collected from a donor by venipuncture. The container (e.g., bag or tube) into which one deposits the blood can contain an anticoagulant such as a citrate or citrate dextrose based component, e.g., citrate phosphate dextrose (CPD or CP2D), citrate phosphate dextrose adenine1 (CPDA-1).

During routine blood collection, a 600 mL bag that contains 70 mL of anticoagulant is used to collect approximately 500 mL±10% of whole blood, or 63 mL of anticoagulant is used to collect 450 mL±10% of whole blood. The whole blood collection bag often has satellite bags attached thereto to hold isolated components. At the time whole blood is collected, tubes of donor blood samples are also collected for use in performing certain required tests on each blood donation, including ABO and Rh determination, infection disease markers testing, and the like.

Platelets are normally separated from whole blood and other blood components by centrifugation. Centrifuge technology allows separation of blood components by their various densities. Therefore, the liquid and cellular constituents of whole blood are separated into distinct layers as the result of centrifugation, ranging from red blood cells (RBC), the most dense, to plasma, the least dense. The time of centrifugation varies depending on the centrifuge and the g-force provided by the centrifuge. The amount of time of centrifugation can be determined by one of skill in the art. Companies such as Sorvall and Beckman manufacture centrifuges that can be used for this process.

Appropriate centrifugation (e.g., a soft spin) results in a bag that contains a mass of RBC at its distal end and a mass of platelet rich plasma (PRP), a mixture of platelets and plasma at its proximal end, with a meniscus formed primarily by white cells in between the two layers. By means of the use of a plasma expressor or extractor (made by companies such as Fenwal, Inc. and Terumo Corporation), the PRP is expressed into a satellite bag, leaving the mass of RBC in the original whole blood collection bag.

The satellite bag containing the PRP is centrifuged again (e.g., hard spin) to separate the plasma from the platelets. Upon re-centrifugation, the platelets, because of their greater density, form a loosely aggregated cluster called a platelet button. By use of a plasma expresser or extractor, the platelet poor plasma (PPP) can then be expressed into a second satellite bag leaving the platelet button and a small volume of plasma (together, known as platelet concentrate) in the first satellite bag. The platelet concentrate consists of a volume of approximately 30 to 70 mL, and the PPP consists of a fluid volume of approximately 180 to 320 mL. Each separated blood component, i.e., RBC, PPP or platelet concentrate is known as a "unit", and each is transfused separately.

Generally, the bag of platelet concentrate contains a minimum of $5.5 \times 10^9$ platelets. Units of platelet concentrate are stored at 20-24° C. on mechanical rotators. Platelets not treated with the compositions of the present invention have a shelf life of about 5 days.

As generally practiced by those skilled in the art, 4-6 platelet concentrate units are pooled to obtain a single therapeutic dose for transfusion to a patient. The pooled platelet concentrate has about $3.0 \times 10^{11}$ platelets or more. The pooled and non-pooled platelet concentrate obtained from this process comprise one form of "isolated platelets" that can be utilized in the present invention or treated with the inventive compositions described herein. In a particular embodiment, the bag used for pooling the platelet concentrate can have the inventive compositions described therein (e.g., β-galactosidase inhibitor; β-galactosidase inhibitor and sialidase inhibitor; β-galactosidase inhibitor and glycan-modifying agent; β-galactosidase inhibitor and sialidase inhibitor and glycan modifying agent), as further described herein. Alternatively, the inventive composition can be added to the platelet concentrate before, after, or during pooling.

Random donor platelets may also be isolated by the "buffy coat" method generally used in Europe and Canada. Whole blood is obtained, as described herein, and undergoes a hard spin centrifugation. The hard spin results in a bag having plasma as the top fraction, red blood cells as the bottom fraction, and a middle layer containing platelets and leukocytes. This middle layer is known as the buffy coat.

For the purpose of producing buffy coat prepared platelets, buffy coats are generally isolated and pooled by one of two methods depending on the format of the bag in which the whole blood was collected. The first method is known as the "top and bottom drain method" in which the bag into which the whole blood was collected has a top and bottom drain with one or more satellite containers attached to each end. An extractor (e.g., Optipress® Extractor from Fenwal) presses the bag flat such that the plasma layer is drained through the top drain and the red blood cells are drained through the bottom drain. The extractor is designed such that the buffy coat containing primarily platelets and leukocytes with a small volume of plasma and RBC, together comprising approximately 30 to 60 mL of fluid volume, is retained within the bag. Approximately 4-6 buffy coat units are pooled to make a therapeutic dose of platelets for transfusion to a patient. In pooling, individual buffy coat units are sterilely connected in a chain format often referred to as the "chain method" (e.g., the bottom drain of a bag is connected to the top drain of the next bag, and so on.). A platelet additive solution or plasma can be sterilely connected to the chain and used to help rinse individual buffy coat containers as the buffy coats are transferred to the bottom pooling bag along with the platelet additive solution or plasma.

A second method for isolating and pooling buffy coat prepared platelets utilizes a similar whole blood collection bag as used with PRP prepared platelets. Following the isolation of the buffy coat in the whole blood as described previously, the buffy coat is separated from the whole blood by first removing the plasma into one of the attached satellite containers and transferring the buffy coat into a second attached satellite container, sometimes referred to as "milking the buffy coat" leaving the RBC in the original container. Approximately 4-6 buffy coat units are pooled to make a therapeutic dose of platelets for transfusion to a patient. In pooling, individual buffy coat units are sterilely connected and pooled into a pooling container along with a platelet additive solution or plasma. In this method, the pooling bag has multiple docks (e.g., like legs of a "spider") to which the individual units are connected. Each buffy coat unit is then transferred from the individual bag into the pooling bag using the platelet additive solution or plasma as a rinsing agent to help reduce platelet loss in pooling. This pooling method is sometimes referred to as the "spider method" and can also be used with buffy coats prepared by top and bottom separation.

Regardless of the method used to pool the individual units, the pooled bag undergoes centrifugation again. This centrifugation is a long, soft spin in which a fraction containing platelets and the plasma/platelet additive solution is formed at the top of the pooling bag and the remaining red blood cells and leukocytes become part of the bottom fraction. Using a plasma expresser or extractor, the top layer of platelets and plasma/platelet additive solution is transferred to another bag resulting in a therapeutic dose of platelets.

Single donor platelets are platelets obtained from one donor by means of centrifugal separation in an automated apheresis machine in a quantity sufficient to constitute one or more therapeutic dose(s) for subsequent transfusion to a patient(s). Platelets isolated by this method are generally known as single donor platelets because a therapeutic dose can be collected from a single donor. In such a procedure, the donor's blood flows from a point of venipuncture through a sterile centrifuge in which the platelets and a certain volume of plasma are centrifugally separated and isolated, with the balance of the donor's blood being returned to the donor through the initial venipuncture or a second point of venipuncture. Anticoagulant compositions, described herein, can be added to the platelets or be present in the bag into which the platelets are collected. Various automated apheresis devices are commercially available from companies such as Haemonetics Corporation (Braintree, Mass.), Terumo BCT (Lakewood, Colo.), Fenwal, Inc., Lake Zurich, Ill., and Fresenius Kabi, Friedberg, Germany.

The collection of platelets by apheresis generally produces 2 platelet units, wherein each unit contains approximately 200 to 300 mL of plasma and approximately $3.5 \times 10^{11}$ platelets. Single donor platelets can be stored at 20-24° C. for about 5 days.

Apheresis collection kits often include two platelet collection bags since most apheresis machines collect two units of platelets. The composition of the present invention, as described herein, can be included in the platelet collection bags for apheresis machines or can be added to the bag before, during or after collection of the platelets using a sterile connection technique. Platelet collection bags can be manufactured with the composition of the present invention and further include additional components such as anticoagulant compositions as described herein or known in the art.

After platelets are collected by apheresis, they can be suspended in the PAS of the present invention, as described herein.

The compositions and methods present invention can be used with platelets isolated by any technique known in the art or developed in the future so long as a therapeutic concentration of platelets is obtained.

The present invention includes bags or containers including the β-galactosidase inhibitor with or without the sialidase inhibitor and/or glycan-modifying composition, or the "inventive composition" as described herein. Based on the platelet isolation process, the inventive composition can be included or manufactured with various platelet collection bags. Platelet collection bags can be gas permeable or made from a plastic material such as PVC material. Platelet collections bags can be used in the random donor collection process or in the single donor collection process. With respect to the random donor collection process, the inventive composition can be placed into the collection bag in which the platelet units are pooled; therefore the present invention includes a pooled collection bag having the inventive composition.

Similarly, in the single donor collection process, the inventive composition can be included in apheresis platelet collection bags. Along with the inventive composition, such bags include other components used in the apheresis process such as anticoagulant compositions.

Conventional platelet bags or packs are formed of materials that are designed and constructed of a sufficiently permeable material to maximize gas transport into and out of the pack ($O_2$ in and $CO_2$ out). The present invention allows for storage of platelets at temperatures below room temperature or at room temperature, as further described herein. The methods described herein reduce or diminish the amount of $CO_2$ generated by the platelets during storage. Accordingly, in an embodiment, the present invention further provides platelet containers that are substantially non-permeable to $CO_2$ and/or $O_2$, which containers are useful particularly for cold storage of platelets. In another embodiment, the containers or bags include gas permeable containers.

With either collection process described above, the inventive compositions can alternatively be added to the isolated platelets using a sterile technique or connection. In such case, the inventive composition can be sold separately in a separate bag, container, syringe, tube or other similar blood collection medium.

In one embodiment, the composition of the present invention having the β-galactosidase inhibitor with or without sialidase inhibitor and/or glycan-modifying agent, as further described herein, is contacted with the platelets in a closed system, e.g., a sterile, sealed platelet pack so as to avoid microbial contamination. Typically, a venipuncture conduit is the only opening in the pack during platelet procurement or transfusion. Accordingly, to maintain a closed system during treatment of the platelets with the composition of the present invention, such composition is placed in a relatively small, sterile container which is attached to the platelet pack by a sterile connection tube (see e.g., U.S. Pat. No. 4,412,835, the contents of which are incorporated herein by reference). The connection tube may be reversibly sealed, or have a breakable seal, as will be known to those of skill in the art. After the platelets are isolated, the seal to the container including the composition of the present invention is opened and the composition is introduced into the platelet bag. In one embodiment, the composition of the present invention is contained in a separate container having a separate resealable connection tube to permit the sequential addition of the composition to the platelets.

The Sialidase Inhibitor and the β-Galactosidase Inhibitor

Once the isolated platelets are obtained, platelets are treated with the composition of the present invention, which includes one or more β-galactosidase inhibitors, or both one or more β-galactosidase inhibitors and one or more sialidase inhibitors; and optionally one or more storage enhancing compositions such as glycan-modifying agents (e.g., monosaccharides such as arabinose, fructose, fucose, galactose, mannose, ribose, gluconic acid, galactosamine, glucosamine, N-acetylgalactosamine, muramic acid, sialic acid (N-acetylneuraminic acid), and nucleotide sugars such as cytidine monophospho-N-acetylneuraminic acid (CMP-sialic acid), uridine diphosphate galactose (UDP-galactose) and UDP-galactose precursors such as UDP-glucose). In some preferred embodiments, the glycan-modifying agent is UDP-galactose and/or CMP-sialic acid. The composition of the present invention includes a "cocktail" in which more than one or a combination of these constituents is included. The phrase, "composition" or "inventive composition" refers to one or more β-galactosidase inhibitors, or both one or more β-galactosidase inhibitors and one or more sialidase inhibitors, and optionally one or more glycan-modifying agents.

Figure 8:
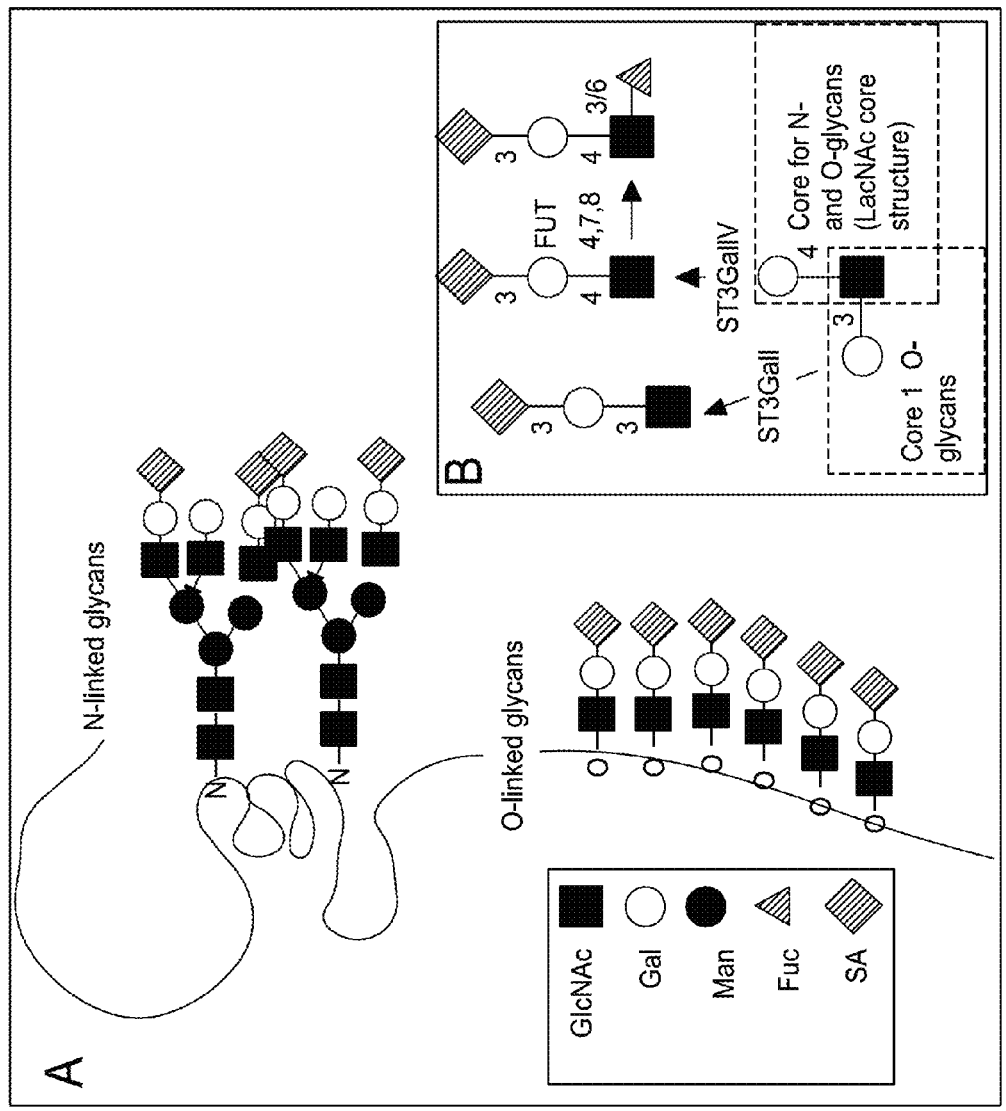
FIG. 8 is a schematic that shows (A) the structure of the primary GPIbα structure and O- and N-linked glycans. (B) shows the structure and biosynthetic modifications of terminal Galβ1,4GlcNAc (lactosaminoglycan/LacNAc) and the Core-1 O-glycan.

"Sialidase enzymes," "sialidases," also called "neuraminidases," as used herein, are glycoside hydrolase enzymes that cleave the glycosidic linkages of neuraminic acids. Sialidase enzymes catalyze the hydrolysis of terminal sialic acid residues from platelet surface glycans. See FIG. 8. Thus, sialidase inhibitors are used in several aspects of the present invention. Sialidase inhibitors reduce sialidase enzyme activity, prevent the hydrolysis of terminal sialic acid residues from platelet surface glycans, preserve the integrity of platelet surface glycans, and/or maintain the function of platelets that are stored prior to transfusion.

"β-Galactosidase enzymes" as used herein, are glycoside hydrolase enzymes that cleave the glycosidic linkages between sialic acid and β-galactose. β-galactosidase enzymes catalyze the hydrolysis of β-galactose residues from platelet surface glycans. Thus, β-galactosidase enzymes inhibitors are used in several aspects of the present invention. β-galactosidase inhibitors reduce β-galactosidase enzyme activity, prevent the hydrolysis of β-galactose residues from platelet surface glycans, assists in preserving the integrity of platelet surface glycans, and/or maintain the function of platelets that are stored prior to transfusion.

Sialidase/neuraminidase enzymes are a large family, found in a range of organisms. Neuraminidase enzymes are glycoside hydrolase enzymes (EC 3.2.1.18) that cleave the glycosidic linkages of neuraminic acids. A commonly known neuraminidase is a viral neuraminidase, a drug target for the prevention of influenza infection. Other homologs are found in mammalian cells, and at least four mammalian sialidase homologs have been described in the human genome [e.g., Neu1 (Uniprot accession numbers: Q5JQI0, Q99519), Neu2 (Q9Y3R4), Neu3 (Q9UQ49.1), and Neu4 (A8K056, B3KR54, Q8WWR8).

β-Galactosidase enzymes catalyze the hydrolysis of β-galactosides into monosaccharides. Substrates of different β-galactosidases include β-galactose, ganglioside GM1, lactosylceramides, lactose, and various glycoproteins. β-Galactosidase is generally an exoglycosidase which hydrolyzes the β-glycosidic bond formed between a galactose and its organic moiety.

As used herein, "sialidase inhibitor," "neuraminidase inhibitor," or "β-galactosidase inhibitor" can be any compound, small molecule, peptide, protein, aptamer, ribozyme, RNAi, or antisense oligonucleotide and the like. As used herein, "inhibit" means to interfere with the binding or activity of an enzyme. Inhibition can be partial or total, resulting in a reduction or modulation in the activity of the enzyme as detected.

For example, a sialidase or neuraminidase inhibitor/β-galactosidase inhibitor according to the invention can be a protein, such as an antibody (monoclonal, polyclonal, humanized, and the like), or a binding fragment thereof, directed against a neuraminidase protein. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) Ann. Rev. Biomed. Eng. 2:339-76; Hudson (1998) Curr. Opin. Biotechnol. 9:395-402). Antibodies can be obtained commercially, custom generated, or synthesized against an antigen of interest according to methods established in the art (Janeway et al., (2001) Immunobiology, 5th ed., Garland Publishing).

Additionally, a sialidase or neuraminidase inhibitor/β-galactosidase inhibitor can be a non-antibody peptide or polypeptide that binds a neuraminidase/galactosidase (e.g., a bacterial neuraminidase or bacterial galactosidase). A peptide or polypeptide can be a portion of a protein molecule of interest other than the full-length form, and includes peptides that are smaller constituents that exist within the full-length amino acid sequence of a protein molecule of interest. These peptides can be obtained commercially or synthesized via liquid phase or solid phase synthesis methods (Atherton et al., (1989) Solid Phase Peptide Synthesis: a Practical Approach. IRL Press, Oxford, England). The peptide or protein-related sialidase or neuraminidase inhibitors/β-galactosidase inhibitors can be isolated from a natural source, genetically engineered or chemically prepared. The type and source of the β-galactosidase inhibitor, in embodiments that also have a sialidase inhibitor, can be same, similar, or different from those of the sialidase inhibitor. These methods are well known in the art.

A sialidase or neuraminidase inhibitor/β-galactosidase inhibitor can also be a small molecule that binds to a neuraminidase and disrupts its function. Small molecules are a diverse group of synthetic and natural substances generally having low molecular weights. They are isolated from natural sources (for example, plants, fungi, microbes and the like), are obtained commercially and/or available as libraries or collections, or synthesized. Candidate sialidase or neuraminidase inhibitor/β-galactosidase inhibitor small molecules can be identified via in silico screening, fragment based drug discovery (FBDD), or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries as described below (Werner et al., (2006) Brief Funct. Genomic Proteomic 5(1):32-6). In a preferred embodiment of the invention, a small-molecule sialidase/neuramindase inhibitor is the sodium salt of 2,3-dehydro-2-deoxy-N-acetylneuraminic acid (DANA).

According to the present invention, the sialidase/neuraminidase inhibitor can also be an FDA approved viral sialidase/neuraminidase inhibitor, such as the viral sialidase/neuraminidase inhibitor oseltamivir also known as ethyl(3R, 4R,5S)-5-amino-4-acetamido-3-(pentan-3-yloxy)-cyclohex-1-ene-1-carboxylate (Tamiflu; Genentech, Cambridge, Mass.), zanamivir also known as ((2R,3R,4S)-4-guanidino-3-(prop-1-en-2-ylamino)-2-((1R,2R)-1,2,3-trihydroxypropyl)-3,4-dihydro-2H-pyran-6-carboxylic acid) (Relenza; Glaxo Smith Kline, Research Triangle Park, N.C.); and Peramivir ((1S,2S,3S,4R)-3-[(1S)-1-acetamido-2-ethyl-butyl]-4-(diaminomethylideneamino)-2-hydroxy-cyclopentane-1-carboxylic acid) (BioCryst, Birmingham, Ala.), or a variant thereof. For example, the viral sialidase/neuraminidase inhibitor, oseltamivir is an ethyl ester prodrug that can be purchased from Roche Laboratories (Nutley, N.J.). Amino acid sequences of FDA approved viral sialidase/neuraminidase inhibitors may also be derivatized, for example, bearing modifications other than insertion, deletion, or substitution of amino acid residues, thus resulting in a variation of the original product (a variant). These modifications can be covalent in nature, and include for example, chemical bonding with lipids, other organic moieties, inorganic moieties, and polymers. For reviews on viral sialidase/neuraminidase inhibitors, see "The war against influenza: discovery and development of sialidase inhibitors." Nature Reviews: Drug Discovery (2007) 6 (12): 967-74. Klumpp et al., (2006) Curr. Top. Med. Chem. 6(5):423-34; Zhang et al., (2006) Mini Rev. Med. Chem. 6(4):429-48; Jefferson et al., (2006) Lancet 367(9507):303-13; Alymova et al., (2005) Curr Drug Targets Infect. Disord. 5(4):401-9; Moscona (2005) N. Engl. J. Med. 353(13):1363-73; De Clercq (2004) J. Clin. Virol. 30(2):115-33; Stiver (2003) CMAJ 168(1): 49-56; Oxford et al., (2003) Expert Rev. Anti. Infect. Ther. 1(2):337-42; Cheer et al., (2002) Am. J. Respir. Med. 1(2):147-52; Sidewell et al., (2002) Expert Opin. Investig. Drugs. 11(6):859-69; Doucette et al., (2001) Expert Opin. Pharmacother. 2(10):1671-83; Young et al., (2001) Philos. Trans. R. Soc. Lond. B. Biol. Sci. 356(1416):1905-13; Lew et al., (2000) Curr. Med. Chem. 7(6):663-72); Taylor et al., (1996) Curr. Opin. Struct. Biol. 1996 6(6): 830-7 and published U.S. Patent Application. Nos. 2009/0175805, 2006/0057658, 2008/0199845 and 2004/0062801, the entirety of each of which is incorporated herein by reference.

Accordingly, a "sialidase inhibitor" includes, but is not limited to one or more of the following: fetuin; 2,3-dehydro-2-deoxy-N-acetylneuraminic acid (DANA); Oseltamivir (ethyl(3R,4R,5S)-5-amino-4-acetamido-3-(pentan-3-yloxy)-cyclohex-1-ene-1-carboxylate); Zanamivir ((2R,3R, 4S)-4-guanidino-3-(prop-1-en-2-ylamino)-2-((1R,2R)-1,2,3-trihydroxypropyl)-3,4-dihydro-2H-pyran-6-carboxylic acid); Laninamivir ((4S,5R,6R)-5-acetamido-4-carbamimidamido-6-[(1R,2R)-3-hydroxy-2-methoxypropyl]-5,6-dihydro-4H-pyran-2-carboxylic acid); Peramivir ((1S,2S,3S,4R)-3-[(1S)-1-acetamido-2-ethyl-butyl]-4-(diaminomethylideneamino)-2-hydroxy-cyclopentane-1-carboxylic acid); or a pharmaceutically acceptable salt thereof. Pharmaceutically acceptable salts of any of the foregoing can be used. In a still further preferred embodiment, the sialidase inhibitor is the sodium salt of 2,3-dehydro-2-deoxy-N-acetylneuraminic acid or a combination thereof. Sialidase inhibitors used with the present invention include those known in the art or those later developed.

Accordingly, a "β-galactosidase inhibitor" includes, but is not limited to one or more of the following: 1-deoxygalactonojirimycin (DGJ); N-(n-butyl) deoxygalactonojirimycin; N-(n-nonyl)deoxygalactonojirimycin; 5-deoxy-L-arabinose; galactostatin bisulfite; 3',4',7-trihydroxyisoflavone; D-ribonolactone; N-octyl-4-epi-β-valienamine; phenylethyl β-D-thiogalactopyranoside; difluorotetrahydropyridothiazinone; and 4-aminobenzyl 1-thio-β-D-galactopryanoside; or a pharmaceutically acceptable salt thereof. In a still further preferred embodiment, the β-galactosidase inhibitor is the 1-deoxygalactonojirimycin (DGJ). β-galactosidase inhibitors used with the present invention include those known in the art or those later developed.

As used herein, a "glycan" or "glycan residue" is a polysaccharide moiety on the surface of the platelet, exemplified by the GPIbα polysaccharide. A "terminal" glycan residue is the monosaccharide/sugar residue at the terminus of the polysaccharide chain, which typically is attached to polypeptides on the platelet surface. A glycan-modifying agent includes an agent that modifies glycan residues on the platelet. The glycan-modifying agent repairs cleavage that occurs on the glycan residue. In an embodiment, the glycan-modifying agent alters the sugar residues of the polysaccharide chain of GPIbα on the surface of the platelet.

Whereas β-galactosidase inhibitors, and sialidase inhibitors included in some of the embodiments, serve to preserve the integrity of the glycan structures, and specifically the glycan termini, the glycan-modifying agents serve to modify or repair glycans by the addition of monosaccharide(s) to the glycan. Thus, sialidase inhibitors/β-galactosidase inhibitors and glycan-modifying agents serve distinct and complementary functions.

"Glycan-modifying agents," as described herein, include monosaccharides such as arabinose, fructose, fucose, galactose, mannose, ribose, gluconic acid, galactosamine, glucosamine, N-acetylgalactosamine, muramic acid, sialic acid (N-acetylneuraminic acid), and nucleotide sugars such as cytidine monophospho-N-acetylneuraminic acid (CMP-sialic acid), uridine diphosphate galactose (UDP-galactose), and UDP-galactose precursors such as UDP-glucose. Glycan-modifying agents include precursors of CMP-sialic acid or UDP-galactose. In some preferred embodiments, the glycan-modifying agent is UDP-galactose or CMP-sialic acid, or both.

UDP-galactose is an intermediate in galactose metabolism, formed by the enzyme UDP-glucose-α-D-galactose-1-phosphate uridylyltransferase which catalyzes the release of glucose-1-phosphate from UDP-glucose in exchange for galactose-1-phosphate to make UDP-galactose. UDP-galactose and sialic acid are available from several commercial suppliers such as Sigma. In addition, methods for synthesis and production of UDP-galactose are known in the art and described in the literature (see for example, Liu et al., Chem Bio Chem 3, 348-355, 2002; Heidlas et al., J. Org. Chem. 57, 152-157; Butler et al., Nat. Biotechnol. 8, 281-284, 2000; Koizumi et al., Carbohydr. Res. 316, 179-183, 1999; Endo et al., Appl. Microbiol., Biotechnol. 53, 257-261, 2000). UDP-galactose precursors are molecules, compounds, or intermediate compounds that may be converted (e.g., enzymatically or biochemically) to UDP-galactose. One non-limiting example of a UDP-galactose precursor is UDP-glucose. In certain embodiments, an enzyme that converts a UDP-galactose precursor to UDP-galactose is added to a reaction mixture (e.g., in a platelet container).

In certain embodiments, the glycan-modifying agent is CMP-sialic acid or a CMP-sialic acid precursor. In further embodiments, the platelet compositions comprising a CMP-sialic acid precursor further comprise an enzyme that converts the CMP-sialic acid precursor to CMP-sialic acid. In certain embodiments, the glycan-modifying agent is CMP-sialic acid. In certain embodiments, the glycan-modifying agent is UDP-galactose. In certain embodiments, the glycan-modifying agents are CMP-sialic acid and UDP-galactose.

In certain embodiments, the sialidase inhibitor or the β-galactosidase inhibitor is a protein. In further embodiments, the sialidase inhibitor/β-galactosidase inhibitor is an antibody directed against a neuraminidase or β-galactosidase protein wherein the antibody is monoclonal, polyclonal, humanized, or a binding fragment thereof. In certain embodiments, the methods comprising a sialidase inhibitor/β-galactosidase inhibitor that is a protein or an antibody further comprise an effective amount of at least one glycan-modifying agent. As mentioned, the nature, source, and other properties of the β-galactosidase can be the same, similar, or different from those of the sialidase inhibitor, for embodiments in which a sialidase inhibitor is included. In certain embodiments, the glycan-modifying agent is CMP-sialic acid or a CMP-sialic acid precursor. In certain embodiments, the CMP-sialic acid precursor further comprises an enzyme that converts the CMP-sialic acid precursor to CMP-sialic acid. In certain embodiments, the glycan-modifying agent is UDP-galactose. In certain embodiments, the glycan-modifying agents are CMP-sialic acid and UDP-galactose.

Treating Platelets

The isolated platelets are treated by the composition of the present invention. Briefly, the overall process is described as follows. Within a time period of being isolated, the composition of the present invention is contacted with the isolated platelets to thereby obtain a treated platelet composition (e.g., referred to herein as a "platelet composition"). The platelet composition can be stored either at room temperature or in cold temperature and then warmed. The platelet composition is transfused into an individual in need of platelets and, as a result of the treatment with the inventive compositions, the transfused platelets exhibit reduced bacterial proliferation and in vivo remain in circulation longer, and maintain hemostasis longer, as compared to untreated platelets.

In an embodiment, the platelet composition includes one or more β-galactosidase inhibitors, or both one or more β-galactosidase inhibitors and one or more of the sialidase inhibitors, as described herein. In a certain embodiment, DANA is used as the sialidase inhibitor. In an embodiment in which a cocktail of the composition of the present invention is used, in addition to one or more β-galactosidase inhibitors with or without one or more sialidase inhibitors, one or more of the glycan-modifying agents, such as UDP-galactose and/or CMP-sialic acid, can be added.

After isolation of the platelets, as described herein or using other methods known in the art, the platelets are treated with the composition of the present invention. The composition of the present invention is contacted with the isolated platelets in an amount that reduces β-galactosidase activity, or both β-galactosidase activity and sialidase activity, inhibits bacterial proliferation, allows platelets to maintain hemostasis, and/or allows platelets to retain the ability to activate and form a clot. In an embodiment, an effective amount of either one or more β-galactosidase inhibitors or one or more β-galactosidase inhibitors in combination with one or more sialidase inhibitors and/or or one or more glycan-modifying agents is that amount that preserves or alters a sufficient number of glycan residues on the surface of platelets, such that when introduced to a population of platelets, reduces β-galactosidase activity or reduces both β-galactosidase activity and sialidase activity, inhibits bacterial proliferation, and/or increases circulation time of platelets or reduces the clearance of the population of platelets in a mammal following transfusion of the platelets into the mammal.

For example, an "effective amount" of either a sialidase inhibitor, a (3-galactosidase inhibitor, and/or a glycan-modifying agent to contact with isolated platelets ranges from about 1 micromolar to about 2,000 micromolar, and most preferably about 200 micromolar to about 1.2 millimolar (e.g., between about 1 and 10 micromolar, about 1 and about 100 micromolar, about 100 and about 500 micromolar, about 500 micromolar and about 1.0 millimolar, about 1.0 and about 1.5 millimolar, and about 1.0 and about 2.0 millimolar). In another aspect, the concentrations are in a range between about 10 micromolar to about 1000 micromolar, between about 100 micromolar to about 150 micromolar, or between about 200 micromolar to about 1200 micromolar.

When using the cocktail of the present invention, modification of platelets with a β-galactosidase inhibitor, a sialidase inhibitor/β-galactosidase inhibitor, or a sialidase inhibitor/β-galactosidase inhibitor in combination with one or more glycan-modifying agents can be performed as follows. The population of platelets is contacted with the selected β-galactosidase inhibitor(s) or sialidase inhibitor(s) in combination with one or more β-galactosidase inhibitor(s), and/or in combination with one or more glycan-modifying agents. Multiple sialidase inhibitors, β-galactosidase inhibitors, and/or glycan-modifying agents (e.g., two, three, four or more) can be used simultaneously or sequentially. If used sequentially in time, the sialidase inhibitors, β-galactosidase inhibitors, and/or glycan-modifying agents are provided close enough in time to confer the desired effect. In some embodiments, 0.1-500 mU/mL galactose transferase or sialyl transferase is added to the population of platelets. Galactose transfer can be monitored functionally using lectins such as FITC-ECL or sWGA binding. The goal of the glycan modification reaction is to reduce sWGA binding to resting room temperature sWGA binding-levels. Galactose transfer can be quantified using $^{14}$C-UDP-galactose. UDP-galactose is mixed with $^{14}$C-UDP-galactose to obtain appropriate galactose transfer. Platelets are extensively washed, and the incorporated radioactivity measured using a γ-counter. The measured cpm (counts per minute) permits calculation of the incorporated galactose. Similar lectin-binding techniques are applicable to monitoring sialic acid transfer.

The isolated platelets can be treated with the platelet composition in a time period before significant reduction in quality and/or hydrolysis of sialic acid and/or β-galactose occurs. The addition of the composition to the platelets can occur during the isolation process, shortly after the isolation process or within another time period.

As single donor platelets are removed from the donor's circulation by apheresis, as described herein, the composition of the present invention can be added in a sterile manner. For example, after the blood is centrifuged by the apheresis machine and the platelets are separated from the rest of the blood components, the composition of the present invention can be added into the bag containing platelets. In another embodiment, the collection bag into which the platelets are deposited after centrifugation can already contain the composition of the present invention. In another embodiment, the composition of the present invention can be added to the bag into which the platelets are being collected simultaneously with the collection of the platelets. Once the platelets come into contact with the composition of the present invention, the components can be mixed or agitated (e.g., bag turned upside down and right side up) to ensure that the platelets come into contact with inventive composition. In this example, little or no time passes between the collection of the platelets and their treatment with the inventive composition. Accordingly, contact of the inventive composition and the isolated platelets can occur during platelet donation or soon after platelet isolation (e.g., between 1 minute and about 120 minutes within platelet isolation).

In an embodiment, the composition of the present invention can be added to the isolated platelets "immediately" after donation, within a certain time period after donation, or "simultaneously" during donation. In an embodiment, the composition of the present invention is contacted with the platelets in a range between about 1 minute and about 48 hours (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 min, 1½ h, 2 h, 2½h, 3 h, 3½h, 4 h, 4½h, 5 h, 5½h, 6 h, 12 h, 18 h, 24 h, 30 h, 36 h, 42 h, or 48 h).

When random donor platelets are isolated from multiple donors, the inventive composition can be added after the platelets are isolated from the whole blood. In an embodiment, the addition of the inventive composition to the platelets can occur when the platelets from the donors are pooled. The pooling bag that generally holds about 6 units of random donor platelets can include the inventive composition so that when the platelets are added to the pooling bag, the isolated platelets come into contact with the composition. Alternatively, the composition can be sterilely connected to and introduced into the pooling bag during or after the platelets are pooled. In an embodiment, the methods of the present invention include contacting the isolated platelets within 1 hour to about 8 hours (e.g., between 1 and about 3 hours). In an embodiment, contacting the inventive composition with the isolated platelets should occur before platelets are refrigerated.

According to still yet another aspect of the invention, a device for collecting and processing platelets is provided. The device has a container or bag for collecting platelets, wherein the container or bag includes the composition of the present invention. In another embodiment, the device includes a container or bag that contains the isolated platelets and at least one satellite container or bag, wherein the satellite container includes the composition of the present invention. The bag containing the platelets and the bag containing the composition of the present invention can be in sterile communication with one another.

The platelets, after being contacted with the inventive composition, can be stored at room temperature or be refrigerated. In certain aspects, platelets are refrigerated to enable storage for longer periods of time. However, as further described herein, β-galactosidase inhibitors, as well as the combination of β-galactosidase inhibitors with sialidase inhibitors inhibit bacterial proliferation and allow platelets to be stored at room temperature.

In certain embodiments, the platelet compositions of the present invention include an effective amount of a β-galactosidase inhibitor, or β-galactosidase inhibitor together with sialidase inhibitor, that is added to a population of platelets after the platelets have been obtained from a donor. In another embodiment, the novel platelet composition comprises an effective amount of a β-galactosidase inhibitor or β-galactosidase inhibitor together with sialidase inhibitor, that is added to a population of platelets after the platelets have been obtained from a donor and the resulting platelet composition is stored for a period of time at room temperature without a substantial loss of in vivo hemostatic activity and inhibition of bacterial proliferation. In another preferred embodiment, the novel platelet composition comprises an effective amount of β-galactosidase inhibitor or a β-galactosidase inhibitor together with a sialidase inhibitor, that is added to a population of platelets after the platelets have been obtained from a donor; the resulting platelet composition is cooled to a temperature below room temperature; stored for a period of time at a temperature below room temperature and rewarmed back to room temperature without a substantial loss in vivo hemostatic activity.

The terms "cooling," "cold temperature," "temperature below room temperature," and "temperature below ambient temperature," interchangeably refer to any temperature between 28° C. and −100° C. In any of the embodiments of the invention described herein, the temperature is alternatively selected from the group of temperatures consisting of 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., 0° C., −1° C., −2° C., −3° C., −4° C., −5° C., −6° C., −7° C., −8° C., −9° C., and −10° C. In some embodiments, the platelet preparation is stored at a temperature of less than about 15° C., preferably less than 10° C., and more preferably less than 5° C. In some other embodiments, the platelet preparation is stored at room temperature. In other embodiments, the platelets are frozen, e.g., 0° C., −20° C., or −80° C., or cooler.

As used in all of the aspects and embodiments of the invention herein, the term "period of time" refers to a duration of time during which platelets or platelet compositions are stored at any given temperature. The term "period of time" can range from seconds to minutes to hours to days to weeks. In preferred embodiments, the term "period of time" refers a number of hours including about 3 to about 120 hours, e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120 hours. In certain embodiments the period of time for which treated platelets can be stored include about 1 and about 30 days (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30).

In an embodiment, treated platelets can be stored at room temperature for about 1 to about 14 days (e.g., about 7 days). In an aspect, the platelets can be refrigerated on any day or days during storage.

In various other embodiments, the treated platelets are stored at room temperature. Treatment with one or more β-galactosidase inhibitors, or a combination of both one or more β-galactosidase inhibitors and one or more sialidase inhibitors, and optionally for any of the above embodiments, one or more glycan-modifying agents preserves/modifies the platelet population, i.e., preserves or improves the hemostatic function of the platelet population following transfusion into a mammal, and reduces the incidence of storage lesions in room temperature stored platelets, when compared to untreated platelet samples over a period of time following treatment. Treated platelet samples stored at or below room temperature are thus suitable for autologous or heterologous transfusion after extended periods of storage time, in an embodiment, for at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 21 days, or at least about 28 days.

As used in all of the aspects and embodiments of the invention herein, the term "warmed slowly" refers a gradual rate of warming (e.g., 0.1, 0.2, 0.3, 0.4, 0.5, 0.6, 0.7, 0.8, 0.9, 1, 2, 3, 4, 5, 6, 7, 8, 9, or 10° C. per hour or per day). As described herein, any of the aspects or embodiments of the invention further comprises a step of warming the treated platelet preparation above room temperature, for example, by warming the platelets to 37° C. Warming can occur gradually or by stepwise temperature increases. It is preferable to warm either room-temperature-stored or cold-stored and treated platelet population by slow addition of heat, and with continuous gentle agitation such as is common with the rewarming of blood products. A blood warming device is disclosed at WO/2004/098675 and is suitable for rewarming a treated platelet population from cold storage conditions.

Inhibition of Bacterial Proliferation and Pathogen-Induced Platelet Degradation

This invention provides a novel method to reduce pathogen-induced platelet degradation and inhibit pathogen growth/propagation by inhibiting β-galactosidases, or both β-galactosidases and sialidases, any of which may be from a pathogenic source. Sialidase and/or β-galactosidase inhibitors exhibit anti-microbial properties that prevent pathogenic proliferation.

The term "pathogen" as used herein, refers to one or more microorganisms or the like that cause infection as described in (Dodd, R. Y. *New Engl. J. Med.* 327:419-421 (1992); Soland, E. M., et al. *J. Am. Med. Assoc.* 274:1368-1373 (1995) and Schreiber, G. B., et al. *New Engl. J. Med.* 334:1685-1690 (1996)). Exemplary pathogens include, but are not limited to a virus, bacteria, parasite, protozoa, or fungus. Examples of viruses include, but are not limited to Herpes simplex virus, HIV, hepatitis, hepatitis A, hepatitis B, hepatitis C, Respiratory syncycial virus, blue tongue virus, and bovine diarrhea virus. Virus also includes Cytomegalovirus, Epstein-Barr virus, Herpes Simplex type I and II viruses, and other viruses that circulate freely in the blood, as well as cell-associated viruses. Fungus includes, but is not limited to e.g., *Aspergillus*. And typical parasites include, but are not limited to, for example: *Ameoba, Plasmodiunm, Leishmania, Mycosus profundus, Trypanosoma, Spirochete,* and *Arbovius*.

Bacteria commonly associated with platelets and whose proliferation is inhibited by a sialidase inhibitor and/or a β-galactosidase inhibitor include, but are not limited to *Aspergillus, Bacillus* sp, *Bacteroides eggerthii, Candida albicans, Citrobacter* sp, *Clostridium perfringens, Corynebacterium* sp, *Diphtheroid, Enterobacter aerogenes, Enterobacter amnigenus, Enterobacter cloacae, Enterococcus avium, Enterococcus faecalis, Escherichia coli, Fusobacterium* spp., *Granulicatella adiacens, Heliobacter pylori, Klebsiella* sp, (*K. pneumonia, K. oxytoca*), *Lactobacillus* sp, *Listeria* sp, *Micrococcus* sp, *Peptostreptococcus, Proteus vulgaris, Pseudomonas* sp, *Pseudomys oxalis, Propionibacterium* sp, *Salmonella* sp, *Serratia* sp, *Staplhylococcus* sp (Coagulase-negative *Staphylococcus, Staphylococcus epidermidis, Staphylococcus aureus*), *Streptococcus* sp, (*S. gallolyticus, S. bovis, S. pyogenes, S. viridans*), *Serratia marcescens*, and *Yersinia enterocolitica*.

The term "pathogen-induced platelet degradation" as used herein, refers to any degree of platelet degradation, decrease in hemostatic activity, or increase in the clearance rate of platelets that is caused by one or more pathogens.

The term "detrimental effect" as used herein, can refer to a detrimental effect upon the viability of platelets (e.g., an increase in platelet degradation, decrease in hemostatic activity, or increase in the clearance rate of platelets) that is caused by one or more pathogens. The term "detrimental effect" as used herein, can also refer to the detrimental effect upon the patient (e.g., the consequences of the infection itself) that is caused by one or more pathogens such as sepsis.

The term "bacterial contamination" as used herein, refers to contamination by any of the above-described bacterial pathogens or by non-pathogenic bacteria that are capable of producing bacteria-derived sialidase. "Inhibiting bacterial proliferation" refers to reducing and/or inhibiting the growth of bacteria in a platelet preparation.

The term "bacteria-derived sialidase" as used herein, refers to sialidase that is produced by bacteria. The inhibition of "bacteria-derived sialidase" as used herein, can optionally inhibit platelet-derived sialidase and/or patient-derived sialidase in addition to the inhibition of bacteria-derived sialidase.

The invention, in other aspects, provides a novel method to inhibition of bacterial proliferation in a platelet preparation by obtaining a population of platelets from a donor and contacting the platelets with an effective amount of the inventive compositions e.g., a β-galactosidase inhibitor or β-galactosidase inhibitor together with sialidase inhibitor. In a preferred embodiment, the methods of the present invention further include storing the treated platelet composition for a period of time at room temperature without a substantial loss of in vivo hemostatic activity. Alternatively, as described herein, the treated platelets or the resulting platelet compositions can be cooled to a temperature below room temperature; stored for a period of time at a temperature below room temperature, and rewarmed back to room temperature without a substantial loss of in vivo hemostatic activity.

Preferred embodiments of the inventive method to reduce pathogen growth in a platelet preparation, as described herein, include contacting platelets with an effective amount of a β-galactosidase inhibitor, or a β-galactosidase inhibitor together with a sialidase inhibitor as described herein, and optionally with an effective amount of at least one glycan-modifying agent, as described herein.

The anti-proliferative inhibition of bacteria by the β-galactosidase inhibitor with or without the sialidase inhibitor allows platelets to be stored for longer with a reduced risk of bacterial contamination, and for the time period described herein.

Bacterial contamination of platelets is a concern because it causes sepsis in patients receiving them. Bacterial contamination can be the result of non-sterile techniques in obtaining blood and/or platelets from the donor, or in poor handling of the platelets after donation. Despite good sterile techniques in obtaining donated blood or platelets, bacteria can still persist in the platelet preparation. For example, even though a technician uses an antibacterial agent to clean the skin at the site of donation, bacteria can be embedded within the layers of the skin, i.e., intradermally. So, upon penetration of the skin with a needle, bacterial contamination of the platelet donation can occur. As a result, bacterial testing at the point of care (e.g., at the time the recipient receives the platelets) is performed to reduce the risk of sepsis.

Additionally, bacterial contamination can result in the formation of biofilm on the interior surfaces of blood containers/bags. The biofilm formation is the result of bacteria attaching to the interior surface of the bag and proliferating using the surface as a support. As the bacterial proliferation increases, the biofilm formation also increases.

Accordingly, contacting the platelet preparation with β-galactosidase inhibitors or both β-galactosidase inhibitors and sialidase inhibitors provides unexpected anti-proliferative inhibition of bacteria and a reduction in biofilm formation on the interior surface of the platelet bag. Using the methods described herein the platelet preparation is contacted with an effective amount of one or more β-galactosidase inhibitors with or without one or more sialidase inhibitors, which inhibits endogenous platelet enzymes but also bacterial enzymes. This treatment of platelets results in prolonged storage of platelets with reduced bacterial growth/proliferation, which provides platelets with an increased survival and hemostasis in vivo after transfusion into a recipient.

Encompassed in the method of the present invention is testing for bacterial proliferation at one or more time points to determine that bacterial proliferation is in fact inhibited before being transfused into the recipient. Bacterial testing can occur at a single time point (e.g., at the point of care) and the results can be compared to a standard to determine if bacterial proliferation has occurred in the treated platelets to be transferred. Additionally, bacterial testing of the treated platelets can occur at more than one time point to assess if the particular sample has exhibited inhibition of bacterial proliferation. An increase in bacterial proliferation or the presence of bacterial proliferation indicates that the treated platelets are contaminated and cannot be used for transfusion. The absence of bacterial proliferation indicates that the treated platelets can be used for transfusion. Using the β-galactosidase inhibitor, or the β-galactosidase inhibitor together with the sialidase inhibitor of the present invention results in treated platelets that are suitable for transfusion.

A number of tests exist to determine the presence of bacterial contamination in a treated platelet preparation. Bacteria can be tested by the presence of a polypeptide or protein that is common to bacteria and not found in platelets, by culture techniques, Gram staining, scanning techniques, the presence of nucleic acid that is conserved in bacteria, scans, and the like.

A commonly used test in determining bacterial contamination of a platelet preparation is the Pan Genera Detection (PDGC® test) (Verax Biomedical, Incorporated, Worcester Mass.). The PGD® test can detect an array of bacteria in blood components. This broad detection is based on the existence of shared, or conserved, antigens that are common to the cell walls of the two broad classes of bacteria: lipoteichoic Acids on Gram-positive bacteria and lipopolysaccharides on Gram-negative bacteria. The test targets these conserved Gram-positive and Gram-negative antigens to test biological samples for a broad range of bacterial contaminants by using binding agents to directly bind to these targets. Although the level or presence of the specific bacteria is not determined by this test, the test does determine the presence of a number of bacteria in the platelet preparation.

Culture methods can be employed to determine the presence or absence of bacterial contamination and/or bacterial proliferation. One commercially available test is referred to as the BacT/ALERT® test (bioMérieux, Inc., Durham, N.C.). Bacterial detection is based on the evolution of carbon dioxide by proliferating bacteria. A carbon-dioxide-sensitive liquid emulsion sensor at the bottom of the culture bottle changes color and is detected through alteration of light reflected on the sensor. BacT/ALERT® test detects the presence of a number of bacteria, fungi, and yeasts.

Another method for bacterial detection involves measuring the oxygen content in a platelet preparation sample. An example is the Pall eBDS test (Pall Corporation, Port Washington, N.Y.). The approach to detection measures the oxygen content of air within the sample pouch as a surrogate marker for bacteria. An oxygen analyzer is used to measure the percent of oxygen in the headspace gas of the pouch or bag having the platelets. If bacteria are present in the platelet sample collected, an increasing amount of oxygen is consumed through the metabolic activity and proliferation of the bacteria in the sample during incubation, resulting in a measurable decrease in oxygen content of the plasma as well as the air within the sample pouch.

A more conventional method for determining the presence of bacterial proliferation is a platelet preparation is Gram staining Gram staining allows one to differentiate bacterial species into classes (Gram-negative or Gram-positive) in an effort to begin to identify the microorganism. The test detects peptidoglycan, a glycan in the cell wall of the bacteria.

A sample from the treated platelet preparation can be obtained and cultured to determine if any bacteria are present. The growth media is inoculated or plated with the sample and under controlled conditions suitable for bacterial growth. Bacteria can be grown and identified.

Other methods known in the art or developed in the future can be used to determine bacterial proliferation in the treated platelet preparation of the present invention.

The methods of the present invention involve reducing bacterial proliferation and/or biofilm formation by contacting the platelet preparation with an effective amount of one or more β-galactosidase inhibitors, or both one or more β-galactosidase inhibitors and one or more sialidase inhibitors. The bacterial proliferation is reduced, as compared to a standard or to another assessment taken at a different time point. The methods described herein reduce bacterial proliferation and/or biofilm formation by at least about 5% (e.g., by about 10%, 20%, 30%, 40%, 50%, 60%, 70%, 80%, 90%, or 100%). In an embodiment, the methods of the present invention completely inhibit bacterial proliferation and/or biofilm formation, as compared to that at the time of treatment of the platelet preparation with the β-galactosidase inhibitor, or both the β-galactosidase inhibitor and the sialidase inhibitor.

Storage of Platelets

The invention embraces a method for increasing the storage time of platelets. During storage with the β-galactosidase inhibitor, or with the β-galactosidase inhibitor and the sialidase inhibitor described herein, platelets can be stored with reduced β-galactosidase, or reduced sialidase/β-galactosidase activity, inhibited bacterial proliferation, and without substantial loss of platelet function or hemostatic activity such as the loss of the ability to circulate or without an increase in the rate of platelet clearance.

The platelets are collected from blood by standard techniques known to those of ordinary skill in the art, as described herein. The storage composition includes at least one β-galactosidase inhibitor, or at least one of both a sialidase inhibitor and a (3-galactosidase inhibitor; and optionally, at least one glycan-modifying agent in an amount sufficient to reduce platelet clearance. In some embodiments, the storage composition further comprises an enzyme that catalyzes the modification of a glycan moiety on the platelet.

The invention, in certain aspects, provides a novel method of storing a platelet composition in which the steps includes obtaining a population of platelets from a donor and treating the platelets with an effective amount of one or more β-galactosidase inhibitors or both one or more β-galactosidase inhibitors and one or more sialidase inhibitors; and optionally one or more glycan modifying agents. In an embodiment, the novel method of storing a platelet composition involves obtaining a population of platelets from a donor; adding an effective amount of a β-galactosidase inhibitor or both an effective amount of a β-galactosidase inhibitor and a sialidase inhibitor to the population of platelets and storing the resulting platelet composition for a period of time at room temperature without a substantial loss in vivo hemostatic activity. In another embodiment, the novel method of storing a platelet composition encompasses obtaining a population of platelets from a donor; adding an effective amount of a β-galactosidase inhibitor, or both a β-galactosidase inhibitor and a sialidase inhibitor, to the population of platelets; cooling the resulting platelet composition to a temperature below room temperature; storing the platelet composition for a period of time at a temperature below room temperature and rewarming the platelet composition back to room temperature without a substantial loss in vivo hemostatic activity. In further embodiments, the platelet composition is rewarmed slowly. In certain embodiments, the platelet composition retains substantially normal hemostatic activity when transfused into a mammal after storage. In further embodiments, the platelet composition when transfused into a mammal after storage, has a circulation half-life of about 5% or greater than the circulation half-life of untreated platelets. In certain preferred embodiments, the platelet composition is suitable for transfusion into a human after storage.

In accordance with the invention, following treatment with a β-galactosidase inhibitor or both a β-galactosidase inhibitor and a sialidase inhibitor, the population of treated platelets can be stored at room temperature or chilled without the deleterious effects (cold-induced platelet activation) experienced upon chilling of untreated platelets. The preservation and/or selective modification of glycan moieties reduce clearance, thus permitting longer-term storage than is presently possible. In one aspect, one or more β-galactosidase inhibitors or both one or more β-galactosidase inhibitors and one or more sialidase inhibitors are added to the population of platelets that are kept between about room temperature (between about 20° C. and 25° C.)

and 37° C. As used herein, chilling refers to lowering the temperature of the population of platelets to a temperature that is less than about 25° C. In some embodiments, the platelets are chilled to a temperature that is less than about 15° C. In some preferred embodiments, the platelets are chilled to a temperature ranging from between about 0° C. to about 4° C. Chilling also encompasses freezing the platelet preparation, i.e., to temperatures less than 0° C., −20° C., −50° C., and −80° C. or cooler. Processes for the cryopreservation of cells are well known in the art.

In some embodiments, the population of platelets is stored at room temperature for at least 3 days. For example, the population of treated platelets is stored at room temperature for at least 4, 5, 6, 7, 8, 9, 10, 11, 12, 13, 14, 15, 16, 17, 18, 19, 20, 21, 22, 23, 24, 25, 26, 27, and 28 days or longer.

Additionally, in certain aspects, a population of treated platelets can be stored chilled for at least 3 days. A population of treated platelets is stored chilled e.g., for at least 4, 5, 6, 7, 8, 9, 10, 11, 12, 13, 14, 15, 16, 17, 18, 19, 20, 21, 22, 23, 24, 25, 26, 27, or 28 days or longer.

Transfusion of Platelets into Mammals (e.g., Humans)

After storage, the present invention, in some aspects, provides a method of transfusing a patient with a treated platelet composition having one or more β-galactosidase inhibitors, or both one or more β-galactosidase inhibitors and one or more sialidase inhibitors, wherein the platelet composition was prepared according to the methods described herein. Similarly, using these steps, the present invention provides a novel method for mediating hemostasis in a mammal.

Additionally, the present invention relates to methods for increasing the circulation time of platelets, or reducing the clearance of platelets. The circulation time of a population of platelets is defined as the time when one-half of the platelets in that population are no longer circulating in a mammal after transfusion into that mammal.

As used herein, "clearance" means removal of the treated platelets from the blood circulation of a mammal (such as but not limited to by macrophage phagocytosis). More specifically, clearance of a population of platelets refers to the removal of a population of platelets from a unit volume of blood or serum per unit of time. Reducing the clearance of a population of platelets refers to preventing, delaying, or reducing the clearance of the population of platelets or the rate at which platelets clear.

Patients in need of platelet transfusion include those with e.g., anemia, thrombocytopenia, dysfunctional platelet disorders, active platelet-related bleeding disorders, or serious risk of bleeding (e.g., prophylactic use). Patients with certain medical conditions at times require platelet transfusion. Such conditions include, among others: leukemia, myelodysplasia, aplastic anemia, solid tumors, congenital or acquired platelet dysfunction, central nervous system trauma. Patients undergoing extracorporeal membrane oxygenation or cardiopulmonary bypass also receive platelet transfusions.

In one aspect of the invention, the method for increasing circulation time of an isolated population of platelets involves contacting an isolated population of platelets with at least one β-galactosidase inhibitor, or both at least one β-galactosidase inhibitor and at least one sialidase inhibitor, in an amount effective to reduce the clearance of the population of platelets. As used herein, a population of platelets refers to a sample having one or more platelets.

Reducing the clearance of a platelet encompasses reducing the clearance of platelets that results after storage of the platelets at or below room temperature. Reducing the clearance of a platelet can result from reducing storage lesions obtained at or below room temperature, or reducing "cold-induced platelet activation" that occurs upon the cold storage of platelets. Cold-induced platelet activation is a term having a particular meaning to one of ordinary skill in the art. Cold-induced platelet activation can be manifested by changes in platelet morphology, some of which are similar to the changes that result following platelet activation. The structural changes indicative of room-temperature-induced or cold-induced platelet activation are most easily identified using techniques such as light or electron microscopy. On a molecular level, platelet activation results in actin bundle formation and a subsequent increase in the concentration of intracellular calcium. Actin-bundle formation is detected using, for example, electron microscopy. An increase in intracellular calcium concentration is determined, for example, by employing fluorescent intracellular calcium chelators. Many of the above-described chelators for inhibiting actin filament severing are also useful for determining the concentration of intracellular calcium (Tsien, R., 1980, supra.). Accordingly, various techniques are available to determine whether or not platelets have experienced room-temperature-induced or cold-induced activation.

The addition of a β-galactosidase inhibitor or sialidase inhibitor and β-galactosidase inhibitor to platelets prevents the hydrolysis of β-galactose or sialic acid/β-galactose residues, respectively, from the termini of glycans and preserves the structures of glycan moieties on platelets, resulting in diminished clearance of treated platelets. This effect can be measured, for example, using either an in vitro system employing differentiated THP-1 cells or mouse macrophages, isolated from the peritoneal cavity after thioglycolate injection stimulation. The rate of clearance of treated platelets compared to untreated platelets can be determined. To test clearance rates, the treated platelets are fed to the macrophages and ingestion of the platelets by the macrophages is monitored. Reduced ingestion of treated platelets as compared to untreated platelets (1.2-fold or greater) indicates successful modification of the glycan moiety for the purposes described herein.

Also, the addition of a β-galactosidase inhibitor or both a β-galactosidase inhibitor and a sialidase inhibitor to platelets inhibits bacterial proliferation, which in turn, reduces platelet clearance and prevents sepsis. Assessment of bacterial proliferation is described herein.

In certain embodiments of the invention, the circulation time of the population of platelets is increased by at least about 10%, 20%, 25%, 30%, or 40%. In some embodiments, the circulation time of the population of platelets is increased by at least about 50% to about 100%. In still yet other embodiments, the circulation time of the population of platelets is increased by about 150% or greater.

Platelet Compositions

After being subjected to the β-galactosidase inhibitor, or to the β-galactosidase inhibitor and the sialidase inhibitor as described herein, the platelets are treated and are referred to herein as "platelet compositions" or "treated platelets." The present invention includes a novel platelet composition comprising one or more β-galactosidase inhibitors or both one or more β-galactosidase inhibitors and one or more sialidase inhibitors, as described herein. In another embodiment, the novel platelet composition further comprises an effective amount of at least one glycan-modifying agent. The treated platelets have a plurality of intact glycan molecules on the surface of the platelet that would otherwise have been cleaved without β-galactosidase inhibitor treatment or without β-galactosidase inhibitor and sialidase inhibitor treatment. The glycan molecules of the platelet composition of the present invention include those in which sialic acid/β-galactose cleavage is prevented and the glycan molecules remain intact. In the event that sialic acid/β-galactose is cleaved, then the glycan-modifying agents (e.g., CMP-sialic acid, or UDP-galactose, or both) allow for sialic acid/β-galactose additions to the terminal sugar residues, or galactosylation of the terminal sugar residues, or both sialylation and galactosylation of the terminal sugar residues. In some embodiments, the modified glycan moieties are GPIbα molecules. The invention also encompasses a platelet composition in a storage medium. In some embodiments, the storage medium can be a pharmaceutically acceptable carrier.

In some embodiments, the terminal glycan molecules so modified are GPIbα molecules. The treated platelets include glycan structures with terminal GPIbα molecules that following treatment have terminal galactose or sialic acid attached to the GPbα molecules. In another aspect, the invention provides a platelet composition comprising a plurality of treated platelets. In some embodiments, the platelet composition further comprises a storage medium. In some embodiments, the platelet composition further comprises a pharmaceutically acceptable carrier.

In some embodiments, the population of platelets treated according to the inventive methods described herein demonstrates inhibited bacterial proliferation and substantially normal hemostatic activity, preferably after transfusion into a mammal. In some embodiments, the population of platelets treated according to the inventive methods described herein demonstrates reduced bacterial proliferation and improved hemostatic activity, relative to a similarly stored but untreated population of platelets.

In a further preferred embodiment, the novel platelet composition, as described above, provides a stable platelet preparation. In certain embodiments, the stable platelet preparation of the invention is capable of being stored for at least 24-360 hours, and the platelet preparation is suitable for administration/transfusion to a human after storage without significant loss of hemostatic function or without a significant increase in platelet clearance in the human as compared to the same for untreated platelets. In certain preferred embodiments, the stable platelet preparation is capable of being cold-stored. In certain other preferred embodiments, the platelets are capable of being stored at room temperature without substantial reduction in biological activity compared to the same for non-treated platelets.

The invention, in other aspects, provides compositions comprising a novel platelet composition, as described herein, and further comprising at least one pharmaceutically acceptable excipient. A "pharmaceutically acceptable excipient," as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention.

In certain embodiments, the platelet composition is suitable for transfusion into a human patient afflicted with a bleeding disorder or anemia. In preferred embodiments, the platelet composition can be stored for at least 5 days with inhibited bacterial proliferation prior to administration to a human, and wherein the composition can be transfused into a human after storage without significant loss of hemostatic function or without a significant increase in platelet clearance in the human as compared to untreated platelets.

The term "pharmaceutically acceptable" means a non-toxic material that does not interfere with the effectiveness of the biological activity of the platelets and that is a non-toxic material that is compatible with a biological system such as a cell, cell culture, tissue, or organism. Pharmaceutically acceptable carriers include diluents, fillers, salts, buffers, stabilizers, solubilizers, and other materials which are well known in the art, for example, a buffer that stabilizes the platelet preparation to a pH of 7.3-7.4, the physiological pH of blood, is a pharmaceutically acceptable composition suitable for use with the present invention.

The invention further embraces a method for making a pharmaceutical composition for administration to a mammal. In a preferred embodiment, the novel pharmaceutical composition comprising platelets further comprises an effective amount of a β-galactosidase inhibitor or both a β-galactosidase inhibitor and a sialidase inhibitor that are added to a population of platelets after the platelets have been obtained from a donor and the resulting platelet composition is stored for a period of time at room temperature without a substantial loss in vivo hemostatic activity. In another preferred embodiment, the novel pharmaceutical composition comprising platelets further comprises an effective amount of a β-galactosidase inhibitor or both a β-galactosidase inhibitor and a sialidase inhibitor that are added to a population of platelets after the platelets have been obtained from a donor; the resulting platelet composition is cooled to a temperature below room temperature; stored for a period of time at a temperature below room temperature and rewarmed back to room temperature without a substantial loss in vivo hemostatic activity. In some embodiments, the method of preparing the novel pharmaceutical compositions comprising platelets comprises neutralizing, removing or diluting the β-galactosidase inhibitor and/or sialidase inhibitors/β-galactosidase inhibitor and/or glycan-modifying agent(s) and/or the enzyme(s) that preserve and/or catalyze the modification of the glycan moiety, and placing the treated platelet preparation in a pharmaceutically acceptable carrier. In one preferred embodiment, the platelets are stored at room temperature (about 22° C.) prior to and during neutralization or dilution. In another preferred embodiment, the platelets are chilled, stored and then warmed to room temperature (about 22° C.) prior to neutralization or dilution. In some embodiments, the platelets are contained in a pharmaceutically acceptable carrier prior to contact with the β-galactosidase inhibitor and/or sialidase inhibitors/β-galactosidase inhibitor and/or glycan-modifying agent(s) and/or the enzyme(s) that preserve and/or catalyze the modification of the glycan moiety and it is not necessary to place the platelet preparation in a pharmaceutically acceptable carrier following neutralization or dilution.

As used herein, the terms "neutralize" or "neutralization" refer to a process by which β-galactosidase inhibitors, the β-galactosidase inhibitors and the sialidase inhibitors, and/or glycan-modifying agent(s) and/or the enzyme(s) that preserve and/or catalyze the modification of the glycan moiety are rendered substantially incapable of glycan modification of the glycan residues on the platelets, or their concentration in the platelet solution is lowered to levels that are not harmful to a mammal, for example, to less than 50 micromolar for the glycan-modifying agents. In some embodiments, the chilled platelets are neutralized by dilution, e.g., with a suspension of red blood cells. Alternatively, the treated platelets can be infused into the recipient, which is equivalent to dilution into a red blood cell suspension. This method of neutralization advantageously maintains a closed system and minimizes damage to the platelets. In a preferred embodiment, no neutralization is required.

An alternative method to reduce toxicity is by inserting a filter in the infusion line, the filter containing, e.g., activated charcoal or an immobilized antibody, to remove the β-galactosidase inhibitors, the sialidase inhibitors if present, and/or glycan-modifying agent(s) and/or the enzyme(s) that preserve and/or catalyze the modification of the glycan moiety.

Either or all of the β-galactosidase inhibitors, sialidase inhibitors if present, and/or glycan-modifying agent(s) and/or the enzyme(s) that preserve and/or catalyze the modification of the glycan moiety also may be removed or substantially diluted by washing the treated platelets in accordance with standard clinical cell washing techniques.

The invention further provides a method for mediating hemostasis in a mammal. The method includes administering the above-described treated platelets. The transfusion of the treated platelets or pharmaceutical composition can be done in accordance with standard methods known in the art. According to one embodiment, a human patient is transfused with red blood cells before, after, or during administration of the treated platelets. The red blood cell transfusion serves to dilute the administered, treated platelets, thereby neutralizing the β-galactosidase inhibitors, the sialidase inhibitors if present, and/or glycan-modifying agent(s) and/or the enzyme(s) that preserve and/or catalyze the modification of the glycan moiety.

The dosage regimen for mediating hemostasis using the treated platelets is selected in accordance with a variety of factors, including the type, age, weight, sex and medical condition of the subject, the severity of the disease, the route and frequency of administration. An ordinarily skilled physician or clinician can readily determine and prescribe the effective amount of treated platelets required to mediate hemostasis.

The dosage regimen can be determined, for example, by following the response to the treatment in terms clinical signs and laboratory tests. Examples of such clinical signs and laboratory tests are well known in the art and are described, for example in, HARRISON'S PRINCIPLES OF INTERNAL MEDICINE, 15th Ed., Fauci A S et al., eds., McGraw-Hill, New York, 2001.

For example, to determine the optimal concentrations and conditions for preventing room-temperature-induced activation or cold-induced activation of platelets by treating them with one or more β-galactosidase inhibitors or both one or more β-galactosidase inhibitors and one or more sialidase inhibitors; and optionally a glycan-modifying agent, increasing amounts of these agents are contacted with the platelets prior to storing platelets at room temperature and/or exposing the platelets to a chilling temperature. The optimal concentrations of the β-galactosidase inhibitors, the sialidase inhibitors if used together with the β-galactosidase inhibitors, and/or glycan-modifying agent(s) that prevent cleavage of the sialic acid, prevent cleavage of β-galactose, and/or catalyze the modification of the glycan moiety are the minimal effective concentrations that preserve intact platelet function as determined by in vitro tests (e.g., observing morphological changes in response to glass, thrombin, cryopreservation temperatures; ADP-induced aggregation) followed by in vivo tests indicative of hemostatic function (e.g., recovery, survival, and shortening of bleeding time in a thrombocytopenic animal or recovery and survival of $^{51}$Cr-labeled platelets in human subjects).

Methods of Preparing Platelet Compositions

The invention, in other aspects, provides a novel method of preparing a platelet composition involving obtaining a population of isolated platelets from a donor and treating the platelets with an effective amount of a β-galactosidase inhibitor, or both an effective amount of a β-galactosidase inhibitor and a sialidase inhibitor within a time period described herein. In a preferred embodiment, the novel method of preparing a platelet composition comprises obtaining a population of platelets from a donor; adding an effective amount of a β-galactosidase inhibitor or both an effective amount of a β-galactosidase inhibitor and a sialidase inhibitor to the population of platelets and storing the resulting platelet composition for a period of time at room temperature without a substantial loss of in vivo hemostatic activity. In another preferred embodiment, the novel method of preparing a platelet composition includes obtaining a population of platelets from a donor; adding an effective amount of a β-galactosidase inhibitor or both an effective amount of a β-galactosidase inhibitor and a sialidase inhibitor to the population of platelets; cooling the resulting platelet composition to a temperature below room temperature; storing the platelet composition for a period of time at a temperature below room temperature and rewarming the platelet composition back to room temperature without a substantial loss in vivo hemostatic activity. In further embodiments, the platelet composition is rewarmed slowly. In certain embodiments, the population of platelets retains substantially normal hemostatic activity when transfused into a mammal. In further embodiments, the population of platelets when transfused into a mammal, has a circulation half-life of about 5% or greater (e.g., 10%, 20%, 30%, 40%, 50%, 60%, 70%, 80%, 90%, 100%, or 150%) than the circulation half-life of untreated platelets. In certain preferred embodiments, the treated platelet population is suitable for transfusion into a human.

Preferred embodiments of the inventive methods of preparing a platelet composition as described herein encompass treating the population of platelets with an effective amount of a β-galactosidase inhibitor or both an effective amount of a (3-galactosidase inhibitor and a sialidase inhibitor as described herein.

Further preferred embodiments of the inventive methods of preparing a platelet composition, as described herein, involve treating a population of platelets an effective amount of a β-galactosidase inhibitor or both an effective amount of a β-galactosidase inhibitor and a sialidase inhibitor, and further treating the population of platelets with an effective amount of at least one glycan-modifying agent, as described herein.

In some embodiments the invention provides for the combination of the methods of treating platelet described herein with one or more other methods of platelet preservation known in the art. For example the methods of platelet modification provided in the present invention are useful in combination with the methods described in, e.g., but not limited to, the following US Patent Publication No.: 20090053198 A1, and U.S. Pat. Nos. 7,030,110; 7,029,654; 7,005,253; 6,900,231; 6,866,992; 6,730,783; 6,706,765; 6,706,021; 6,693,115; 6,638,931; 6,635,637; 6,566,379; 6,521,663; 6,518,310; 6,514,978; 6,497,823; 6,476,016;

6,472,399; 6,420,397; 6,417,161; 6,350,764; 6,344,486; 6,344,466; 6,326,492; 6,277,556; 6,245,763; 6,235,778; 6,221,669; 6,204,263; 6,037,356; 5,919,614; 5,763,156; 5,753,428; 5,660,825; 5,622,867; 5,582,821; 5,571,686; & 5,569,579; 5,550,108; 5,529,821; 5,474,891; 5,466,573; 5,399,268; 5,376,524; 5,344,752; 5,269,946; 5,256,559; 5,236,716; 5,234,808; and 5,198,357.

Kits

The present invention also provides kits that are used for platelet collection, processing and storage, further including suitable packaging materials and instructions for using the kit contents. It is preferred that all reagents and supplies in the kit be sterile, in accordance with standard medical practices involving the handling and storage of blood and blood products. Methods for sterilizing the kit contents are known in the art, for example, ethylene oxide gas, gamma irradiation, and the like. In certain embodiments, the kit may include venipuncture supplies and/or blood collection supplies, for example a needle set, solution for sterilizing the skin of a platelet donor, and a blood collection bag or container. Preferably the container is "closed", i.e., substantially sealed from the environment. Such closed blood collection containers are well known in the art, and provide a means of preventing microbial contamination of the platelet preparation contained therein. Other embodiments include kits containing supplies for blood collection and platelet apheresis. The kits may further include a quantity of one or more β-galactosidase inhibitors or both a quantity of one or more β-galactosidase inhibitors and one or more sialidase inhibitors with or without the glycan-modifying agent, sufficient to modify the volume of platelets collected and stored in the container. In other embodiments, the kit includes a blood collection system having a blood storage container wherein the β-galactosidase inhibitor agent or both β-galactosidase inhibitor agent and the sialidase inhibitor agent are provided within the container in an amount sufficient to treat the volume of blood or platelets held by the container. The quantity of the β-galactosidase inhibitor alone, the sialidase inhibitor and the β-galactosidase inhibitor together, or either embodiment with the optional glycan-modifying agent will depend, in part, on the volume of the container. It is preferred that the β-galactosidase inhibitor, or both the β-galactosidase inhibitor and the sialidase inhibitor, and optionally the glycan-modifying agent be provided as a sterile non-pyogenic solution, but any can also be supplied as a lyophilized powder. For example, a blood bag is provided having a capacity of 250 mL. Contained in the blood bag is a quantity of the β-galactosidase inhibitor, β-galactosidase inhibitor together with sialidase inhibitor, or a combination such that when 250 mL of blood is added, the final concentration of the inhibitor(s) is approximately 1200 micromolar. Other embodiments contain different concentrations of the β-galactosidase inhibitor, or combination of the β-galactosidase inhibitor and the sialidase inhibitor, for example but not limited to quantities resulting in final concentrations of 10 micromolar to 10 millimolar, and preferably 100 micromolar to 1.2 millimolar of the β-galactosidase inhibitor alone, the sialidase inhibitor and β-galactosidase inhibitor together, or with the combination of the sialidase inhibitor, the β-galactosidase inhibitor, and the glycan-modifying agent. Other embodiments use combinations of sialidase inhibitor/β-galactosidase inhibitor with the glycan-modifying agent, e.g., to effect sialyation or galactosylation of glycans on blood products introduced into the container.

Platelet Function and Assessment of Treated Platelets

After treatment of platelets, the platelet functions can be assessed with various in vitro methods. The recovery and survival of the treated platelets can be further evaluated, which are mostly performed with radioactive-labeled platelets in healthy volunteers.

"Hemostatic activity," as described herein, refers to the ability of a population of platelets to mediate bleeding cessation (e.g., to form a clot). Normal hemostatic activity refers to an amount of hemostatic activity seen in the treated platelets, that is functionally equivalent to or substantially similar to the hemostatic activity of untreated platelets in vivo, in a healthy (non-thrombocytopenic or non-thrombopathic mammal) or functionally equivalent to or substantially similar to the hemostatic activity of a freshly isolated population of platelets in vitro.

After treatment, platelets can be assessed to determine if they maintained their function, e.g., their ability to activate and form a clot. Various assays are available for determining platelet hemostatic activity (Bennett, J. S. and Shattil, S. J., 1990, "Platelet function," Hematology, Williams, W. J., et al., Eds. McGraw Hill, pp 1233-12250). In an embodiment, demonstration of "hemostasis" or "hemostatic activity" can also include a demonstration that platelets infused into a thrombocytopenic or thrombopathic (i.e., non-functional platelets) animal or human circulate and stop natural or experimentally-induced bleeding. To determine hemostatic activity of platelets, laboratories use in vitro tests. These tests, which include assays of aggregation, secretion, platelet morphology and metabolic changes, measure platelet functional responses to activation. These in vitro tests reliably evaluate and predict in vivo hemostatic platelet function.

In an embodiment, platelets treated with compositions of the present invention (e.g., β-galactosidase inhibitors; combinations of sialidase inhibitors and β-galactosidase inhibitors) exhibit a level of platelet function similar to that of untreated but freshly obtained/isolated platelets.

A test that measures the platelets' ability to clot is an aggregation assay. The platelet aggregation test uses an aggregometer to measure the cloudiness or turbidity of blood plasma. Agonists to promote clotting are used in an aggregation assay. Examples of agonists include adenosine diphosphate (ADP), epinephrine (adrenaline), thrombin, collagen, TXA2, and ristocetin. Since agonists are added to the sample in order to perform the test, the results are impacted if the donor of the sample is taking an anticoagulant. The addition of an agonist to a plasma sample causes the platelets to clump together, making the fluid more transparent. The aggregometer then measures the light transmission through the specimen to determine the extent of the clotting by the platelets in response to the agonist. When an agonist is added the platelets aggregate and absorb less light and so the transmission increases and this is detected by the photocell in the aggregometer. The normal time for platelet aggregation varies somewhat depending on the laboratory, the temperature, the shape of the vial in which the test is performed, and the patient's response to different agonists. Establishing normal clot times and amounts of agonists for an aggregation assay can be determined by one of skill in the art. Exemplary amounts of agonist are as follows: ADP between 1 μM to 10 μM, collagen between 1 and 4 μg/mL, Ristocetin between 0.5 mg/mL and 1.5, 5 mg/mL, adrenaline between 5 and 10 μM, arachadonic acid (precursor of TXA2) about 500 μg/mL, and thrombin between 50 nmol/L and 100 nmol/L. For example, the difference between the response to ristocetin and other products should be noted because ristocetin triggers aggregation through a different mechanism than other agonists. Platelets that have about 65% or greater platelet aggregation in response to adenosine diphosphate (ADP), arachidonic acid, collagen, thrombin, TXA2, epinephrine, and/or ristocetin are considered platelets with normal clotting function. Accordingly, platelets treated with the β-galactosidase inhibitors (or β-galactosidase inhibitors together with sialidase inhibitors) of the present invention and exhibiting about 65% or greater (e.g., about 65% to about 100%) platelet aggregation in an aggregation assay are considered to exhibit homeostatic activity.

Another test that measures coagulation is thrombelastography. Thrombelastography is available, for example, from Haemonetics Corporation (Braintree, Mass.) under the trade name TEG. In thrombelastography, a small sample of platelets (typically 0.36 mL) is placed into a cuvette (cup) which is rotated gently through 4° 45' (cycle time 6/min) to imitate sluggish venous flow and activate coagulation. When a sensor shaft is inserted into the sample a clot forms between the cup and the sensor. The speed and strength of clot formation is measured in various ways, and depends on the activity of the plasmatic coagulation system, platelet function, fibrinolysis and other factors that can be affected by illness, environment and medications. Generally, four values that represent clot formation are determined by this test: the R value (or reaction time), the K value, the angle, and the MA (maximum amplitude). The R value represents the time until the first evidence of a clot is detected. The K value is the time from the end of R until the clot reaches 20 mm and this represents the speed of clot formation. The angle is the tangent of the curve made as the K is reached and offers similar information to K. The MA is a reflection of clot strength. A mathematical formula determined by the manufacturer can be used to determine a Coagulation Index (CI), which takes into account the relative contribution of each of these 4 values into 1 equation. The treated platelets of the present invention are able to form clots, and maintain hemostasis.

Immunological Assessment of Platelet Markers/Function

Platelet function, including its ability to activate before and/or after treatment with the composition and also after transfusion into an individual, can be assessed. Examples of platelet activation markers include P-selectin, PAC-1, GPIIb, GPIIIa, GPIb, and GPIIIa. Soluble and membrane bound markers can be assessed to determine the state of platelet activation and assess homeostasis of the treated platelet preparation. Methods that measure soluble and membrane bound platelet markers include several suitable assays. Suitable assays encompass immunological methods, such as flow cytometry, radioimmunoassay, enzyme-linked immunosorbent assays (ELISA), chemiluminescence assays, and assessment with a volumetric capillary cytometry system. Any method known now or developed later can be used for measuring such markers.

The inventive methods use antibodies reactive with platelet markers or portions thereof. In a preferred embodiment, the antibodies specifically bind with membrane bound and/or soluble platelet makers or a portion thereof. When the antibodies bind, they inhibit the function of the protein or marker to which they bind. The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation. They are not intended to be limited to particular methods of production.

In several of the preferred embodiments, immunological techniques detect platelet marker levels by means of an anti-platelet marker antibody (e.g., one or more antibodies). An anti-platelet marker antibody includes monoclonal and/or polyclonal antibodies, and mixtures thereof. Labeling platelets with antibodies directed against surface membrane glycoproteins and then analyzing the binding by flow cytometry is a rapid and sensitive technique for assessing homeostasis. For example, GPIIb, GPIIIa, and GPIb can be assessed using antibodies CD41, CD61, and CD42b, respectively. Elevated levels of membrane bound or soluble P-selection can indicate the extent of platelet activation and can be detected using monoclonal antibodies S12 or W40. Antibodies for detecting such markers can be purchased commercially or raised against an appropriate immunogen using methods known in the art.

Any method known now or developed later can be used for measuring membrane bound platelet markers. One method for assessing membrane bound platelet marker levels which the invention utilizes is flow cytometry. Methods of flow cytometry for measuring platelet or membrane bound markers are well known in the art. (Shattil, Sanford J, et al. "Detection of Activated Platelets in Whole Blood using Activation-Dependant Monoclonal Antibodies and Flow Cytometry," Blood, Vol. 70, No 1 (July), 1987: pp 307-315; Scharf, Rudiger E., et al., "Activation of Platelets in Blood Perfusing Angioplasty-damaged Coronary Arteries, Flow Cytometric Detection," Arteriosclerosis and Thrombosis, Vol 12, No 12 (December), 1992: pp 1475-1487, the teachings of which are incorporated herein by reference in their entirety). For example, a sample comprising platelets can be contacted with an antibody having specificity for the marker under conditions suitable for formation of a complex between an antibody and marker expressed on platelets, and detecting or measuring (directly or indirectly) the formation of a complex. In an example, the level of membrane bound markers can be assessed by flow cytometry by obtaining a first and second sample comprising platelets, contacting said first sample, serving as a control, with a platelet activation agonist, such as phorbol myristate acetate (PMA), ADP (adenosine diphosphate), thrombin, collagen, and/or TRAP (thrombin receptor activating peptide), under conditions suitable for activation of platelets in said first sample, preferably for a period of time effective to maximally activate said platelets, and preferably while maintaining the second sample under conditions suitable for maintaining the endogenous platelet activation level. The method then involves contacting or staining the samples with a composition comprising an anti-platelet marker antibody, having a fluorescent label, preferably in an amount in excess of that required to bind the marker expressed on the platelets, under conditions suitable for the formation of labeled complexes between said antibody and activated platelets. Then one determines (detecting or measuring) the formation of complex in said samples, wherein the amount of complex detected indicates the extent of platelet activation in said second sample. In an embodiment, the amount of platelet activation in isolated platelets treated with the composition of the present invention and stored is similar to the amount of platelet activation from freshly obtained platelets from a donor.

In addition to using flow cytometry to measure membrane bound platelet markers, a radioimmunoassay can also be employed. Using a radioimmunoassay, endogenous platelet activation can be assessed by an immunobinding assay by obtaining a first and second sample comprising platelets, wherein each sample contains a preselected number of platelets; contacting said first sample with a platelet activation agonist, such as phorbol myristate acetate (PMA), ADP (adenosine diphosphate), thrombin, collagen, and/or TRAP (thrombin receptor activating peptide), under conditions suitable for activation of platelets in said first sample, preferably for a period of time effective to maximally activate said platelets, and preferably while maintaining the second sample under conditions suitable for maintaining the endogenous platelet activation level. Then the samples are contacted with an antibody composition that is specific to the marker being assessed. The antibody can have a radioactive label; or a binding site for a second antibody that has the radioactive label. The formation of the complex in the samples are detected, wherein the amount of complex detected in said second sample as compared to that detected in said first sample is indicative of the extent of platelet activation in said second sample.

Assaying for Detection of Soluble Platelet Markers

Any method known now or developed later can be used for measuring soluble platelet markers. In a preferred embodiment, soluble platelet marker is determined using an ELISA assay or a sandwich ELISA assay. For detection of a soluble platelet marker in a suitable sample, a sample (e.g., blood) is collected, and preferably platelets are removed (partially or completely) from the sample, for example by preparation of serum or plasma (e.g., isolation of platelet poor plasma). Samples are preferably processed to remove platelets within a time suitable to reduce artificial increases in soluble platelet marker, such as those due to secretion or proteolysis from platelets. Samples can be further processed as appropriate (e.g., by dilution with assay buffer (e.g., ELISA diluents)). Additionally, the technician can add a reagent that stabilizes and prevents in vitro platelet activations. Examples of these stabilizing reagents are apyrase and prostaglandin E1 ($PGE_1$).

To determine a measurement for soluble platelet markers using an ELISA assay in a suitable sample such as serum or platelet poor plasma (PPP), the method involves combining a suitable sample and a composition that includes an anti-platelet antibody as detector, such as biotinylated anti-platelet MAb and HRP-streptavidin, or HRP-conjugated anti-platelet Mab, and a solid support, such as a microtiter plate, having an anti-platelet marker capture antibody bound (directly or indirectly) thereto. The detector antibody binds to a different epitope from that recognized by the capture antibody, under conditions suitable for the formation of a complex between said anti-platelet maker antibodies and soluble platelet marker. The method involves determining the formation of complex in the samples.

The solid support, such as a microtiter plate, dipstick, bead, or other suitable support, can be coated directly or indirectly with an anti-platelet maker antibody. For example, an anti-platelet marker antibody can coat a microtiter well, or a biotinylated anti-platelet marker Mab can be added to a streptavidin coated support. A variety of immobilizing or coating methods as well as a number of solid supports can be used, and can be selected according to the desired format.

In a particularly preferred embodiment, the sample (or standard) is combined with the solid support simultaneously with the detector antibody, and optionally with one or more reagents by which detection is monitored.

A known amount of soluble platelet maker standard can be prepared and processed as described above for a suitable sample. This standard assists in quantifying the amount of the maker detected by comparing the level of platelet marker in the sample relative to that in the standard. A physician, technician, apparatus or a qualified person can compare the amount of detected complex with a suitable control to determine if the levels are elevated.

Typical assays for platelet markers are sequential assays in which a plate is coated with first antibody, plasma is added, the plate is washed, second tagged antibody is added, the plate is washed, and bound second antibody is quantified. However, binding kinetics revealed that in a simultaneous format, the off-rate of the second antibody was decreased and the assay was more sensitive. Thus, a simultaneous format in which the solid support is coated with a capture antibody, and plasma and detector antibody are added simultaneously, can achieve enhanced sensitivity and is preferred.

A technician, physician, qualified person or apparatus can compare the results to a suitable control such as a standard, levels of one or more platelet markers in normal individuals, and baseline levels of the platelet markers in a sample from the same donor. For example, the assay can be performed using a known amount of a platelet marker standard in lieu of a sample, and a standard curved established. One can relatively compare known amounts of the platelet marker standard to the amount of complex formed or detected.

Storage lesions can be assessed to determine the health of a platelet and its ability to activate and form a clot. Storage lesions include morphological and molecular changes to platelets upon storage at or below room temperature. One of the first visible effects of platelet impairment is the irreversible loss of the discoid morphology towards a spherical shape, and the appearance of spiny projections on the surface due to calcium-dependent gelsolin activation and phosphoinositide-mediated actin polymerization. Certain morphological changes induced in platelets can be readily observed under a microscope. A loss in shape is accelerated at low temperatures and particularly when platelets are exposed to temperatures lower than 20° C. In addition to increased modifications in shape, notable increases occur in intracellular calcium levels and in the degree of actin polymerization. Moreover, stored platelets secrete alpha granule and lysosomal contents, which can be assessed immunologically, as described herein, and reorganize the microtubule coil lying under the plasma membrane through depolymerization processes. Accordingly, storage lesions that occur at or below room temperature can readily be measured by methods known in the art and described herein to quantify the effectiveness of the inventive platelet compositions and related methods. The standard is to compare the quality of the platelet storage solution of the present invention to the quality of platelet storage solutions without a β-galactosidase inhibitor or to the quality of platelet storage solutions without a β-galactosidase inhibitor and a sialidase inhibitor. Accordingly, platelets treated with the composition of the present invention maintain shape and function that is at least similar to or better than platelets not stored in the PAS of the present invention (e.g., stored in a known platelet storage solution such as INTERSOL® solution (Fenwal) and SSP+™ solution (MacoPharma)).

EXEMPLIFICATION

Example 1

Human Platelets

Figure 2:
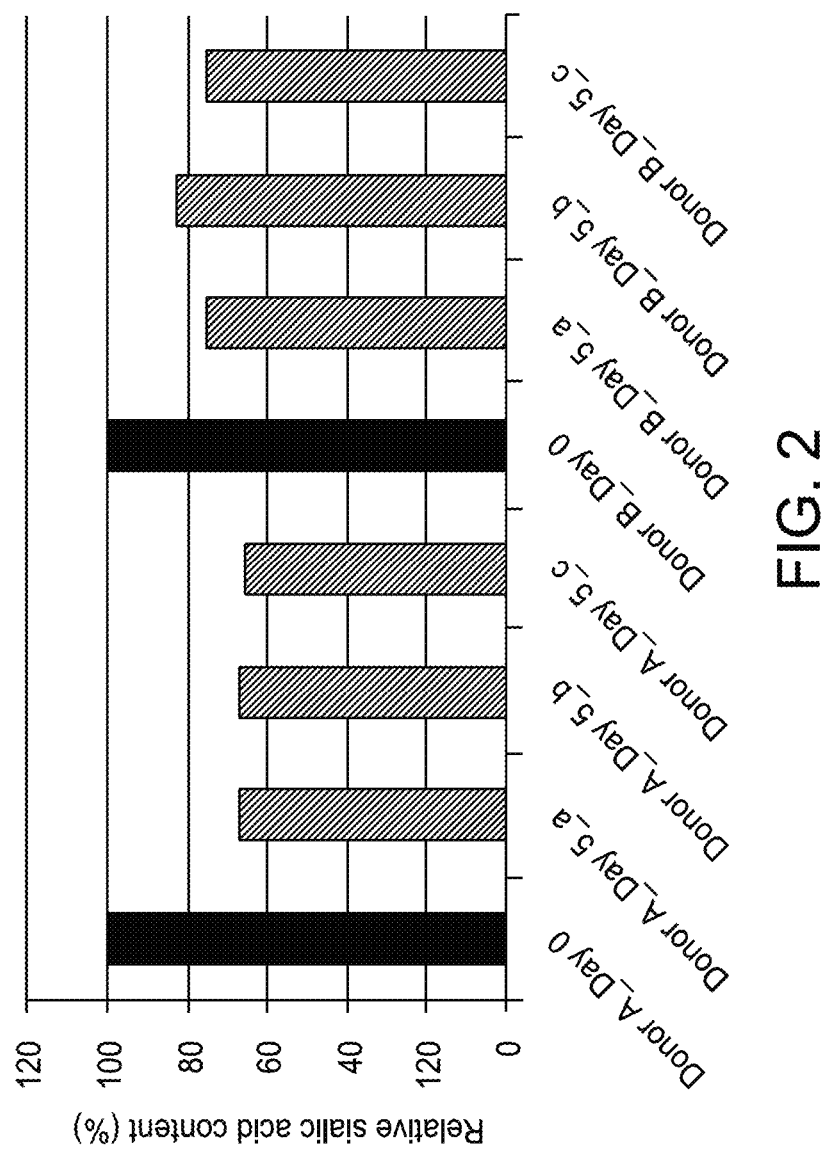
FIG. 2 is a bar graph showing that human platelets lose sialic acid during storage at 4° C. Platelet concentrates (A: Donor A and B: Donor B) were stored at 4° C. for 5 days in the absence of exogenous nucleotide sugar (a), in the presence of CMP-sialic acid (CMP-SA) and UDP-galactose (UDP-gal) (b) or UDP-gal alone (c). Sialic acid content of platelets at day 0 was set to 100%.

Prolonged storage at and below room temperature resulted in sialic acid loss and increased sialidase (neuraminidase) activity for human platelets Loss of Platelet Sialic Acid During Prolonged Storage Under Refrigeration:

Platelets were stored at 4° C. in the absence or presence of 1.2 mM nucleotide sugars and the total sialic acid was quantified. The platelets were centrifuged, thoroughly washed, and resuspended in 140 mM NaCl, 3 mM KCl, 0.5 mM $MgCl_2$, 5 mM $NaHCO_3$, 10 mM glucose and 10 mM HEPES, pH 7.4. Aliquots of the resuspended platelets were lysed with RIPA buffer (Cell Signaling Technology) for protein quantification using Pierce BCA Protein Assay Kit, or processed to quantify platelet sialic acid using QUANTICHROM® Sialic Acid Assay Kit per the manufacturer's instructions (BioAssays Systems). The assay kit uses an improved Warren method in which sialic acid is oxidized to formylpyruvic acid, which reacts with thiobarbituric acid to form a pink colored product. The absorbance at 549 nm is directly proportional to sialic acid concentration, which in the test sample can be calculated from a linear standard curve obtained from sialic acid standards per the manufacturer's instructions. Fresh platelets contain ~10 μg (i.e., approximately 10 micro-grams) of sialic acid per mg of platelet protein. Prolonged storage under refrigeration resulted in great loss of platelet sialic acid (Day 5_a, Donor A, ~35%; Donor B, ~25%), compared with fresh platelets (Day 0), normalized to 100%. However, the loss of sialic acid was slowed in donor B platelets by the presence of CMP-sialic acid and UDP-gal (B_Day 5_b) in the stored platelets, the donor sugar required for resialylation (FIG. 2). UDP-gal alone had no effect (Day 5_c). It is noted that the platelets from Donor B with less sialic acid loss had less initial sialidase surface activity than those from Donor A (See below, FIG. 3B).

Figure 3:
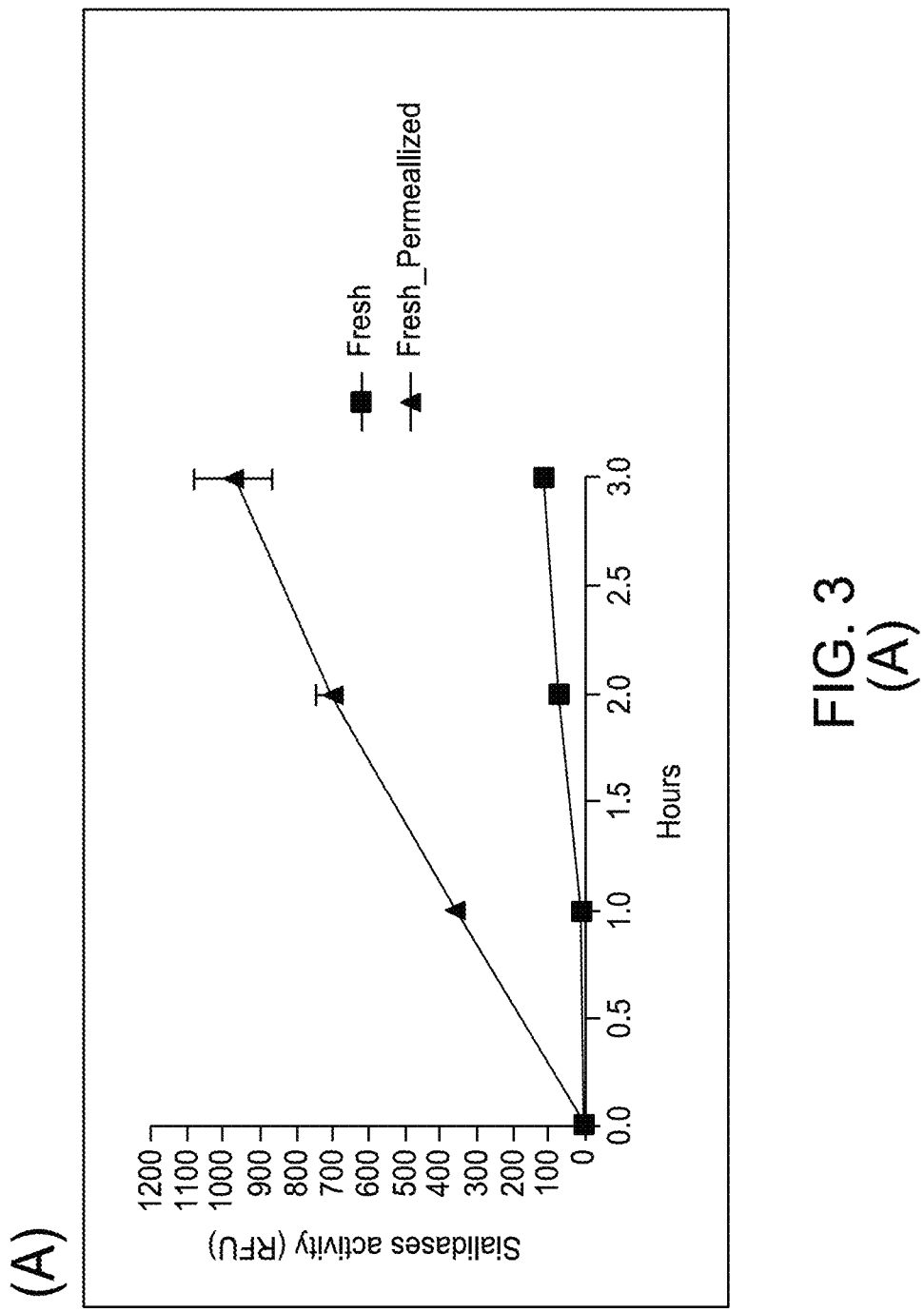
FIGS. 3 (A) (B) & (C) are line graphs showing that the human platelet sialidase surface activity increases following cold storage. (A) depicts the analysis of fresh platelets, with or without permeabilization. (B) depicts the analysis of fresh intact platelets (Donors A and B) at pH 5 and 6. (C) depicts the corresponding analysis of intact platelets (Donors A and B) after storage at 4° C. for 5 days.
Figure 3:
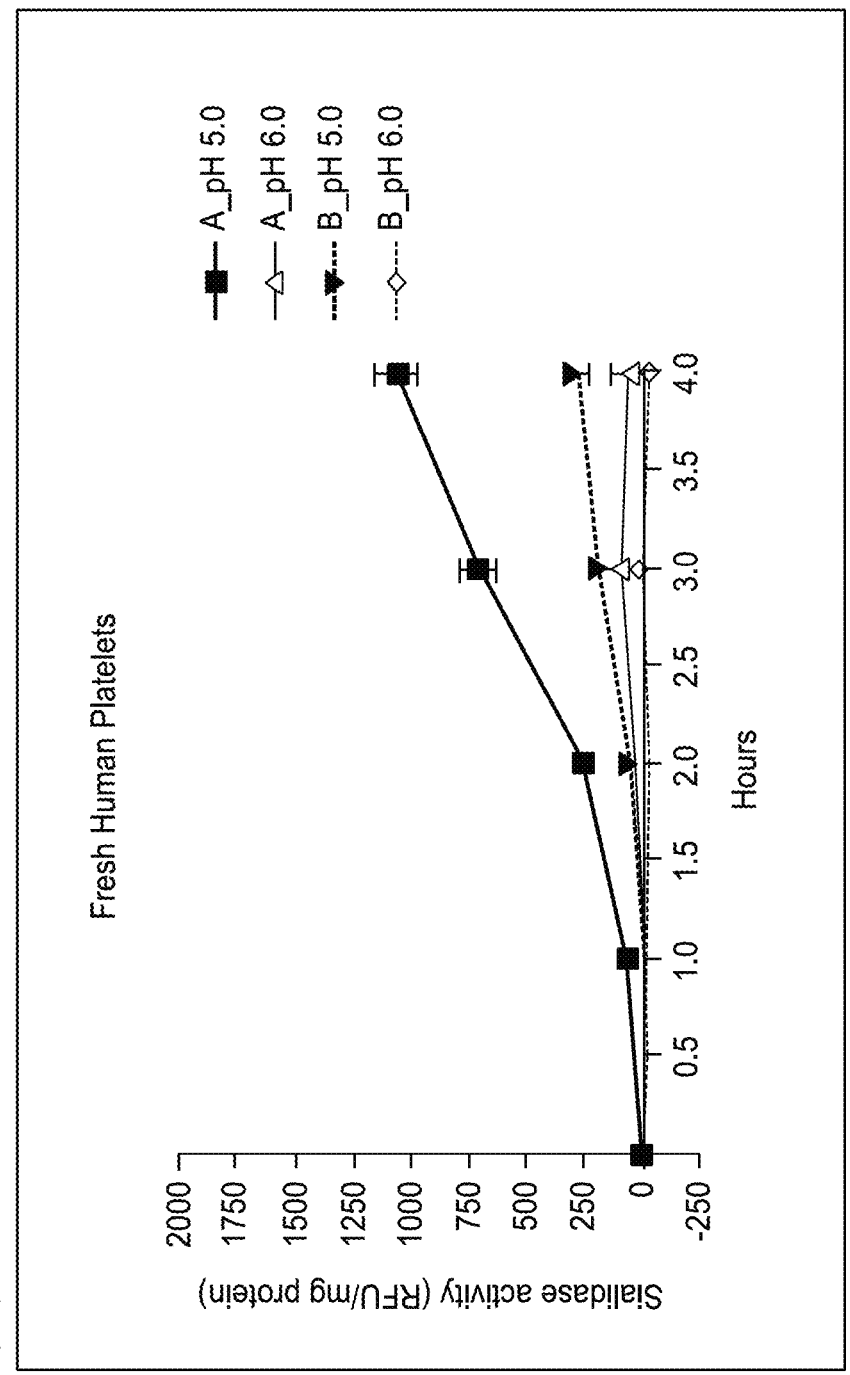
Figure 3:
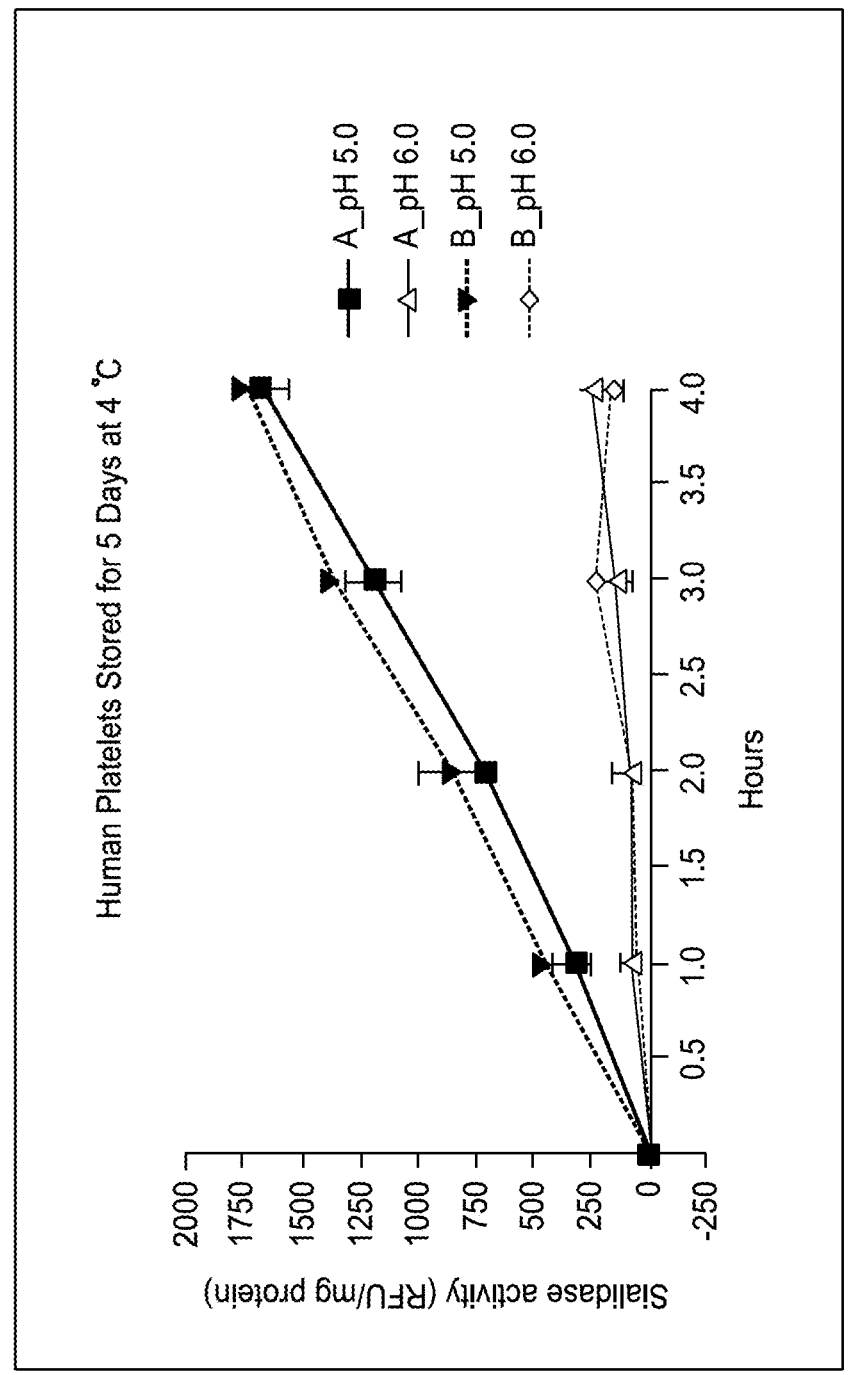

Sialidase Activity During Platelet Storage:

Human platelets express surface-exposed sialidases. Sialidase activity is a particular concern since it is presumably responsible for the loss of platelet sialic acid during storage. Therefore, in addition to the direct analysis of sialic acid content, quantification of the total platelet sialidase activity and surface sialidase activity during storage are critical to understand the mechanism of sialic acid loss. Furthermore, sialidase activity may hinder an attempted resialylation approach. A determination of the nature of the sialidases in fresh and stored platelets is important. Shown herein is a reliable and sensitive fluorometric assay method for platelet sialidase activity using 4-methylumbelliferyl-α-D-N-acetylneuraminic acid (4-MU-NeuAc) as a substrate. Cleavage of the substrate by sialidase released sialic acid and methylumbelliferone (MU), upon termination with $Na_2CO_3$, wherein the later was read at λex/em=355/460 nm. Sialidase activity was measured in non-permeabilized or permeabilized platelets. FIG. 3A shows that intact fresh platelets do not contain significant surface sialidase activity. In contrast, abundant sialidase activity, including both surface and intracellular sialidase activities, was measured in permeabilized fresh platelets. Further analysis indicates that surface sialidase activity of fresh platelets varies among donors (FIG. 3B, donor A and B), but increased platelet sialidase activity upon cold storage was observed in all cases including Donor A and B (FIG. 3C).

Figure 4:
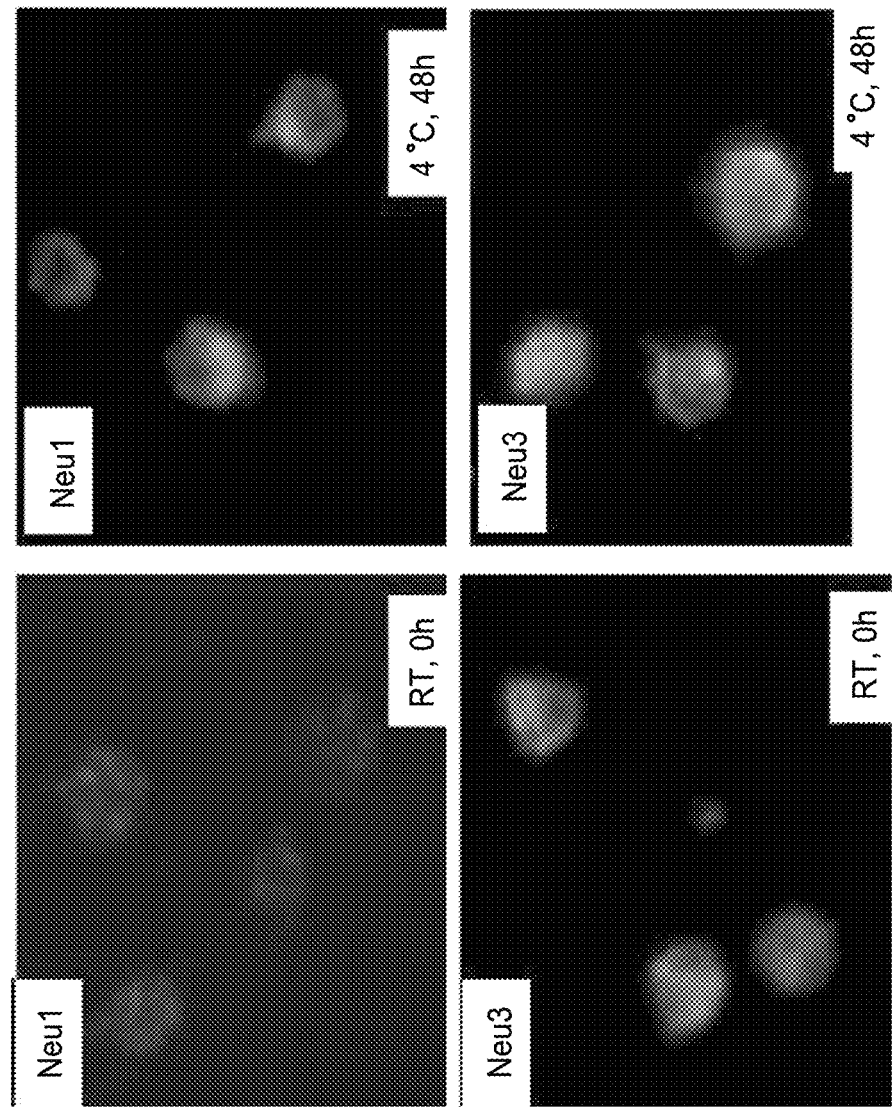
FIG. 4 shows immunofluorescence micrographs of fixed, non-permeabilized, resting room temperature (RT) (left panels) and refrigerated (right panels) human platelets demonstrating the presence of sialidase Neu3, but not Neu1, on their surfaces. Refrigeration (48 h) of platelets increases sialidase (Neu1) surface fluorescence, i.e, exposure. Anti-Neu1 antibody was used in the upper panels. Anti-Neu3 antibody was used in the lower panels.

The detection of increased platelet sialidase activity upon refrigeration and its absence in the storage media (not shown) suggested that cool temperatures may increase the surface exposure of sialidase(s). To test this assumption, the sialidase exposure on platelets was examined by immunofluorescence. Four human sialidases have been identified, Neu1, Neu2, Neu3 and Neu4. Neu1 is a lysosomal enzyme; Neu2 is a cytosolic sialidase; Neu3 is a plasma membrane sialidase, wherein its activity is specific for gangliosides; and Neu4 is a novel human luminal lysosomal enzyme. Neu1, Neu2, Neu3, and Neu4 share high degrees of similarity and amino acid blocks of highly conserved residues. However, these sialidases are different from one another in terms of subcellular localization, substrate preference in vitro, and tissue distribution. Neu1 is a lysosomal sialidase that is presumed to have a narrow substrate specificity. The natural substrate for this enzyme is unknown and activity has thus only been reported on artificial substrates such as 4-MU-NeuAc and nitro-phenyl-NeuAc, but not on gangliosidases, fetuin, or sialyllactose. Neu2 is a cytosolic enzyme with wide substrate specificity. Neu3 is a plasma membrane-bound sialidase, originally described as ganglioside sialidase. Neu3 preferentially hydrolyses gangliosides, although glycoproteins, 4-MU-NeuAc, sialyllactose, etc. are also hydrolysed. Lysosomal Neu1 and surface-bound Neu3 (antibodies are commercially available) were the focus of the current studies. As shown in FIG. 4, Neu3 can readily be visualized on the surface of fresh platelets and its expression is not affected by refrigeration. In contrast, Neu1 only demonstrated weak surface exposure on fresh platelets, consistent with its subcellular localization in an intracellular lysosomal granule. However, upon refrigeration for 48 h, its surface exposure is greatly increased. The data demonstrates that Neu1 is at least partially responsible for the platelet surface sialidase activity increase during refrigeration.

In summary, platelet storage under refrigeration promotes platelet surface sialic acid loss and increases platelet surface sialidase expression. Similar findings were also made for RT-stored platelets (not shown).

Example 2

Mouse Platelets

Sialidase activity increases during cold storage of mouse platelets and the sialidase inhibitor DANA increases mouse platelet survival in vivo.

Figure 5:
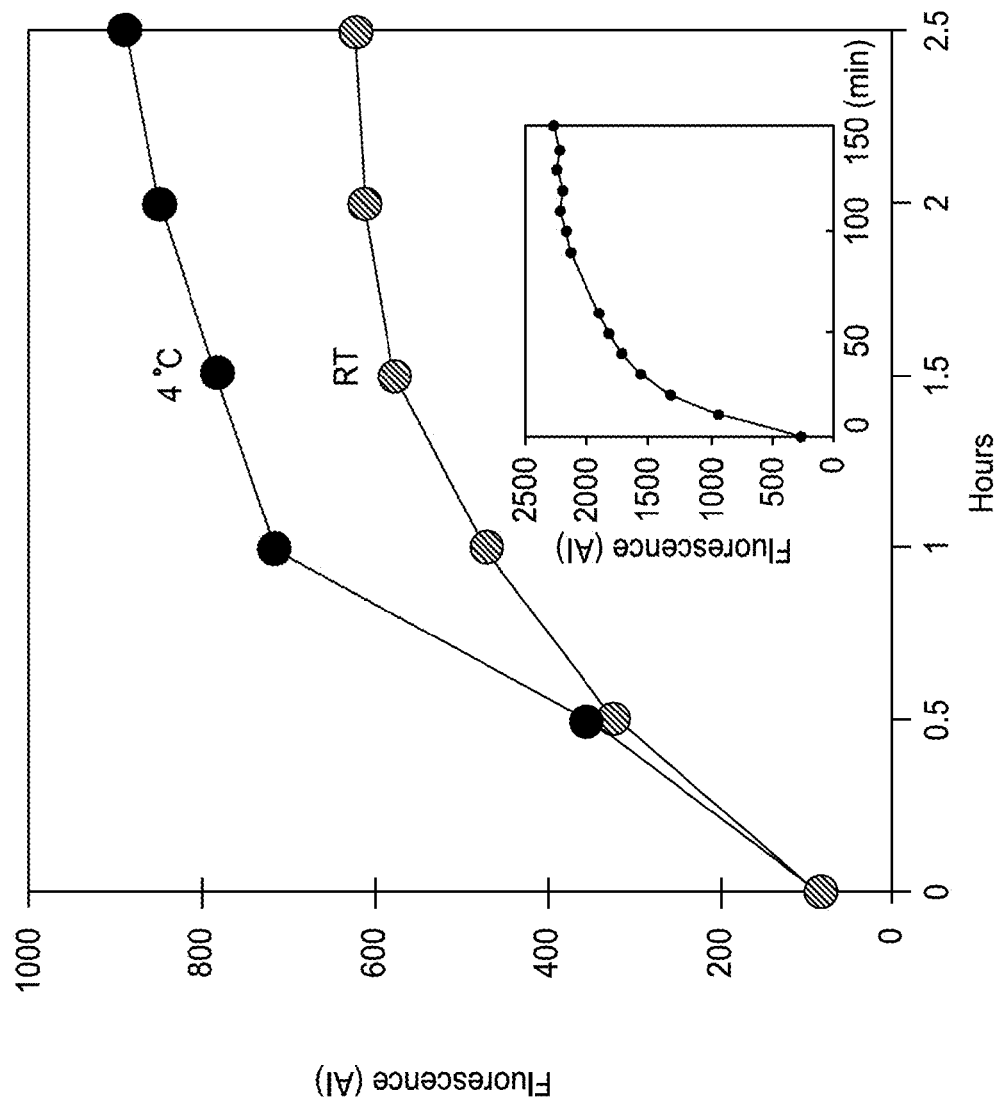
FIG. 5 shows that mouse platelet sialidase surface activity increases following 48 h cold storage and rewarming. Platelet-derived sialidase activity was measured in fluorescence (Absorption Intensity (AI)) over 0-2.5 h at room temperature. Platelet storage at cold temperatures (4° C., darker circles) was compared with fresh platelets (RT, lighter circles). As a control, sialidase activity (*Clostridium perfringens* (Component H)) was measured over the same time period (inset).

Mouse Platelet Sialidase Activity Increases Following 48 h Cold Storage:

We have determined sialidase surface activity in isolated, intact, fresh mouse platelets and following cooling and rewarming using Amplex Red Neuraminidase (Sialidase) Assay Kit (Molecular probes, Eugene, Oreg., USA). Mouse platelets ($2 \times 10^9$) maintained at room temperature or refrigerated for 48 h were isolated and suspended in the provided reaction buffer (0.5 M Tris-HCl, pH 7.2 and 1 mM $CaCl_2$). Platelet derived sialidase activity was measured over 2.5 h at room temperature. FIG. 5 shows that sialidase activity substantially increases following platelet storage in the cold (4° C.) compared to fresh room temperature platelets (RT). Critically, sialidase activity is not plasma derived, as platelets were extensively washed prior to sialidase activity assays. As a control, sialidase activity (*Clostridium perfringens* (Component H)) was measured over the same time period (inset). Neu1 surface expression is increased by 3.5 fold on stored platelets as determined by flow cytometry using anti-Neu1 specific antibodies (not shown).

Figure 6:
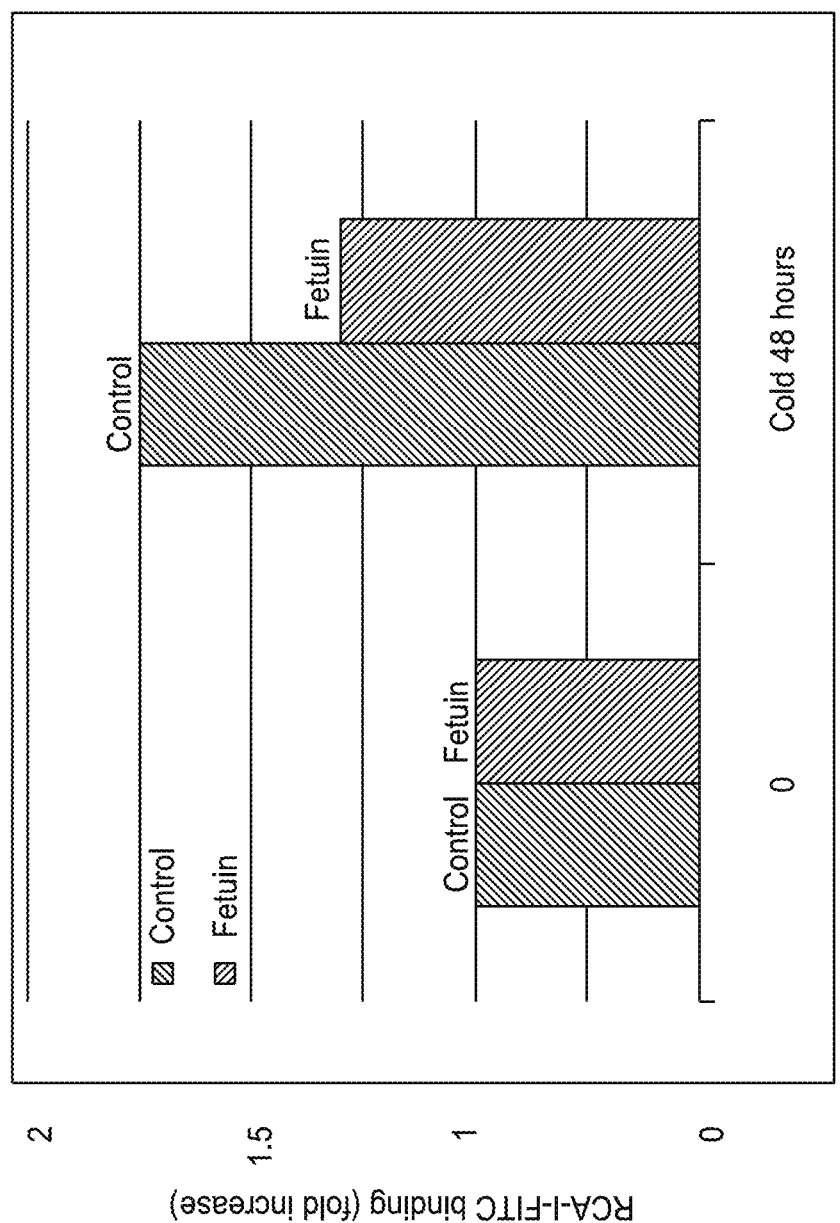
FIG. 6 shows that fetuin competes for sialidase surface activity during platelet storage and thus inhibits the hydrolysis of sialic acid from platelet glycans. The left pair of bars represents the β-galactose exposure on fresh platelets (0) in the absence (Control) or presence of fetuin (Fetuin). The right pair of bars represents the β-galactose in the absence (Control) or presence of fetuin following platelet refrigeration for 48 h. Sialic acid loss, i.e., β-galactose exposure, is measured by RCA I binding.

Fetuin as a Competitive Sialidase Substrate During Platelet Storage:

Fetuin (1 mg/mL) was added to mouse platelet rich plasma prior to cold storage or to fresh platelets at room temperature and β-galactose exposure measured by flow cytometry using FITC conjugated RCA-1-lectin, a lectin specific for exposed β-galactose. Addition of fetuin greatly inhibits sialic acid hydrolysis during platelet storage, preventing RCA-1 binding. Fetuin addition has no effect on RCA-1 binding to fresh platelets (FIG. 6). These results show that sialidase activity increases during platelet cold storage, presumably mediating sialic acid hydrolysis.

the Sialidase Inhibitor DANA Increases Platelet Life Span In Vivo:

The quantification of sialic acid was determined in freshly isolated platelets and long-term stored platelets using a Sialic Acid Quantification Kit (Sigma, St. Louis Mich., USA). The Sialic Acid Quantification Kit determines total N-acetylneuraminic acid (sialic acid) following the release from glycoconjugates using α2-3,6,8,9-neuraminidase to cleave all sialic acid linkages, including branched sialic acid. Results show that $2 \times 10^9$ freshly isolated mouse platelets (~2.5 mg protein) contain ~3 μmol sialic acid. Following long-term storage, platelets lose >50% of their sialic acid content (not shown).

Figure 7:
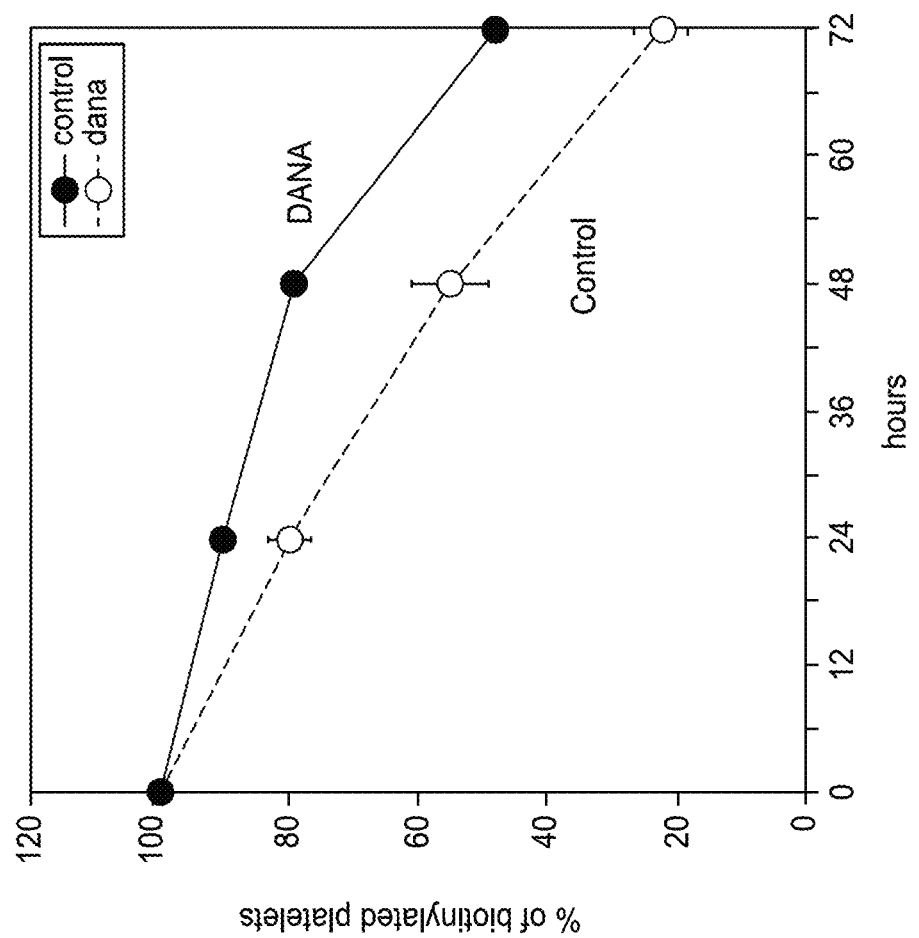
FIG. 7 shows that the sialidase inhibitor DANA increases mouse platelet life span in vivo. The bottom line represents the control platelet life span (Control). The top line represents the platelet life span upon addition of DANA (DANA).

It had been previously postulated that sialic acid normally covers β-galactose residues and permits platelet survival. These results show that normal platelet survival is regulated by hepatocyte ASGP receptor, independent of macrophages. Surface sialic acid is normally hydrolyzed by sialidases. These studies then addressed whether inhibition of sialidase activity in vivo has an effect on platelet survival. Mouse platelets have prolonged survival after injecting mice with the specific sialidase inhibitor, sodium salt of 2,3-dehydro-2-deoxy-N-acetylneuraminic acid (DANA). Mice were injected with 100 mM DANA or PBS (phosphate buffered saline) as a control, after in vivo platelet biotinylation Inhibition of sialidase activity with DANA increases the survival of biotinylated platelets (DANA) compared to biotinylated platelet survival in control mice (Control) (FIG. 7). These results indicate that inhibition of neuraminidase activity in vivo prolongs platelet survival. However, the effect may not be platelet specific. As shown, the recovery and survival of fresh platelets are significantly enhanced in Asgr-1 or Asgr-2 deficient mice (Sorensen et al., Blood, 2009, Vol. 114, pgs 1645-1654) revealing that the hepatocyte Ashwell-Morell receptors routinely survey the platelet surface for β-galactose exposure. Taken together, these data indicate that platelets lose sialic acid while circulating, possibly due to sialidase activity, representing a new clearance mechanism for senile platelets.

Example 3

The Role of Sialylation/Desialylation in Defining the Circulatory Lifetimes of Platelets Human Platelets Produce Neu1 and Neu3 and Release Neu1 into Plasma:

The studies herein address two novel mechanisms that contribute to increases in the clearance of platelets that occur upon storage. The first platelet clearance mechanism, which is induced rapidly by refrigeration in the absence of plasma, is mediated when GlcNAc residues on the N-linked glycan of GPIbα become exposed and are recognized by the lectin domain of the αMβ2 receptor on liver phagocytes. The second clearance mechanism, induced by long-term platelet storage in plasma in the cold, is of slow onset and occurs when GPIbα is desialylated and recognized by the ASGP receptors on both liver hepatocytes and macrophages. Recent data unveils an unexpected role for endogenous sialidases and glycosyltransferases (GTs) in modulating the circulatory life times of normal platelets. In addition, as demonstrated herein, platelets express GTs and sialidases on their surfaces and secrete both. The convergence of these two mechanistic pathways strongly suggests that platelets have an inherent capacity to self-regulate survival in blood by renewing the glycans of their surface glycoproteins and that platelet lifetimes can be modulated in either positive or negative directions by carbohydrate addition or removal machinery, respectively. The glycan structures promoting platelet circulation or clearance are thus ideally suited for therapeutic manipulation by sialidases or GT activity (See FIG. 8).

Figure 9:
FIG. 9 shows that human platelets contain the sialidases Neu1 and Neu3 by Western blot analysis of total platelet lysates.
Figure 10:
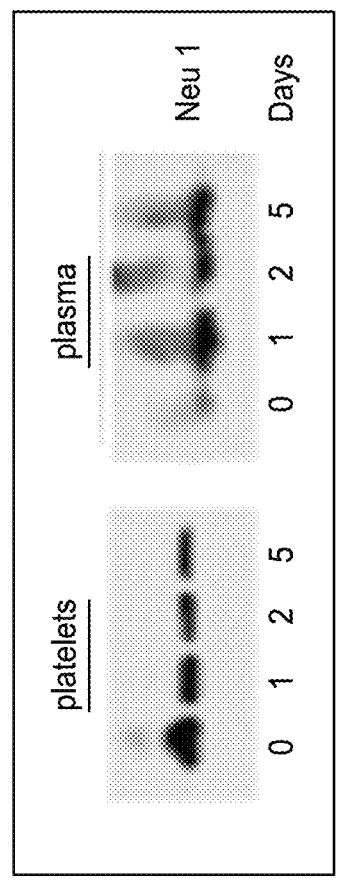
FIG. 10 shows that human platelets release Neu1 into plasma upon long-term refrigeration as analyzed by Western blot. Platelets and their corresponding plasma were analyzed at day 0 and following platelet refrigeration for 1, 2, and 5 days.

Lysates of human platelets were subjected to SDS-PAGE and immunoblotting using antibodies specific for Neu1 and Neu3 (provided by Dr. N. Stamatos, Univ. of Maryland). FIG. 9 shows that human platelets contain both Neu1 and Neu3. FIG. 10 shows that human platelets release Neu1 into plasma after 24 hours of storage in the cold, indicating that released Neu1 could mediate the removal of surface sialic acid from platelet GPIbα. As predicted from FIG. 10 and FIG. 4, sialidase activity associated with platelet surface increases with the time of cooling.

Figure 11:
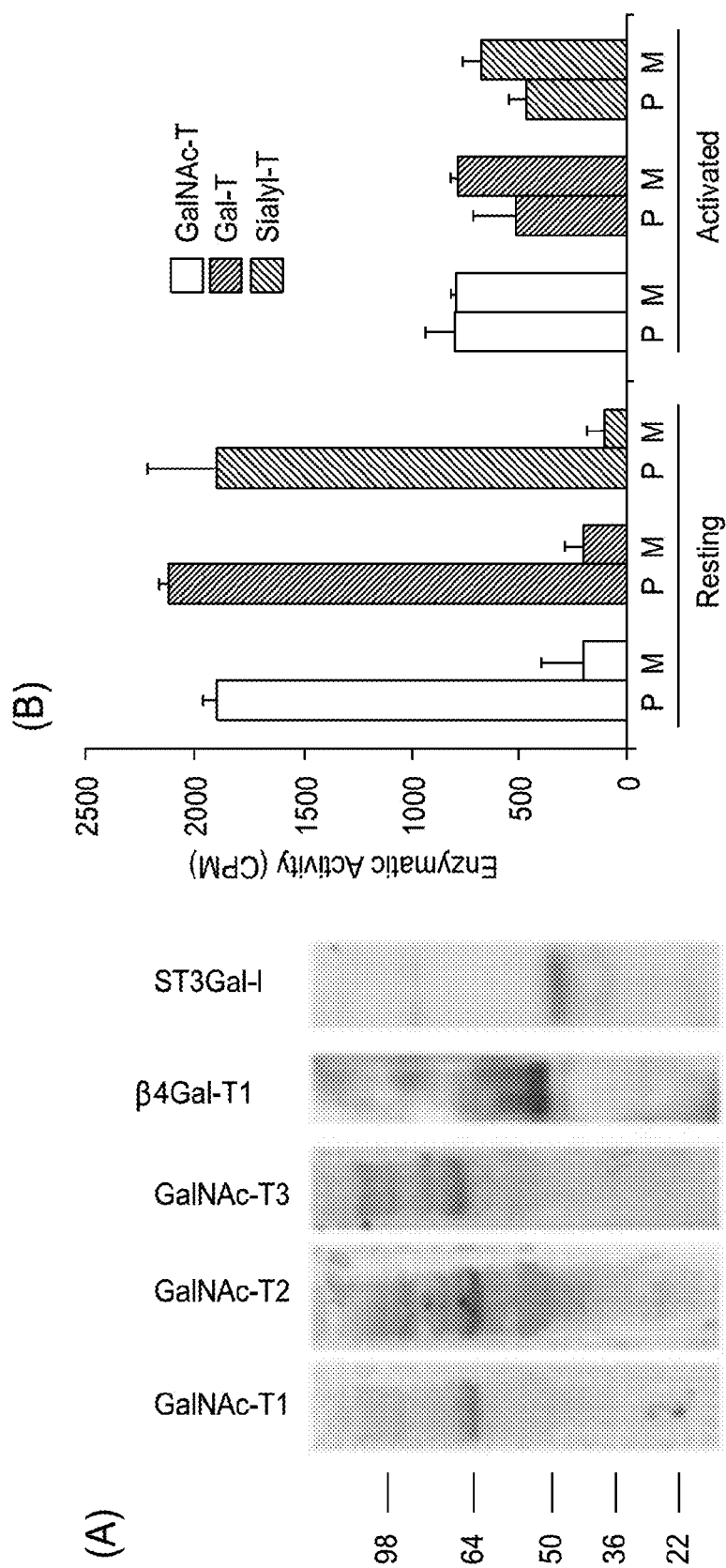
FIG. 11 (A) depicts the characterization of platelet glycosyltransferases (GTs). Human total platelet lysates were subjected to SDS-PAGE and were immunoblotted with monoclonal antibodies: anti-GalNAc transferases (GalNAc-T1, -T2, -T3), β4Gal-Transferase1 (β4Gal-T1), and sialyltransferase ST3Gal-1 (B) Platelets secrete GTs. Resting platelets were maintained at 37° C. or activated via the thrombin receptor PAR-1 with 25 μM TRAP, for 5 min. Maximal release was observed after 1 min. The Enzymatic Activity in counts per minute (CPM) was measured in the pelleted platelet fraction (P), or in their corresponding bathing media (M). The media was clarified at 100,000×g for 90 min to eliminate microparticles prior to activity measurements.

Human Platelets Express Glycosyltransferases and Release them into Plasma Upon Activation:

Glycosyltransferases (GTs) are expressed on platelets and packaged internally into a secretory compartment. Platelets have a surface associated β4gal-T (β4Gal-T1) that catalyzes the coupling of Gal in a β1-4 linkage to exposed N-acetylglucosamine (GlcNAc) residues on the N-linked glycans of GPIbα, improving short-term cooled mouse platelet circulation (Hoffmeister K M, Josefsson E C, Isaac N A, Clausen H, Hartwig J H, Stossel T P. Glycosylation restores survival of chilled blood platelets. Science. 2003 Sep. 12; 301(5639): 1531-4). The nature of this glycosylation machinery is becoming increasingly evident from the data provided herein. For example, platelets were paneled with antibodies to determine which enzymes are expressed. Human platelet lysates were displayed by SDS-PAGE and immunoblotted against antibodies that recognize GTs. Cross-reactive proteins are present against 3 GalNAc-Ts, a Gal-T, and a Sial-T (FIG. 11A).

The presence of internal GT stores suggests that platelets might move GTs to their surface upon activation. The amount of each GT isoform associated with either resting platelets or activated platelets was assessed, as was the amount released into the corresponding medium. Resting platelets were maintained at 37° C. or treated with 25 μM TRAP for 5 min. Maximal release was observed after 1 minute. Enzymatic activity remaining in the 800×g pelleted platelets (P) or was released into the media (M). The media was clarified at 100,000×g for 90 min prior to activity measurements. FIG. 11B shows that ~93% of the total GT activity associates with resting platelets, as collected by centrifugation (P), although a small portion of the activity is released into the bathing medium (M). However, following activation of platelets with 25 μM thrombin receptor activating peptide (TRAP) for 5 min, the amount of cell associated activity drops and ~50% of the total GalNAc-, Gal-, and Sial-T activities are released into the medium. Ultracentrifugation did not remove enzymatic activity from the supernatant, excluding the possibility that the secreted activity resides in platelet microparticles. Hence, GTs are packaged within platelets in a secretory compartment. The nature of this internal GT compartment was also addressed. Immunofluorescent labeling of fixed and permeabilized platelets with antibodies directed towards certain selected GTs, or the well-characterized Golgi matrix protein GM130, revealed internal staining of 2-5 granular structures per platelet (not shown). Hence, platelets contain abundant amounts of GTs and sialidases and the ability of platelets to circulate depends on having GPIbα in a maximally sialylated state.

Figure 12:
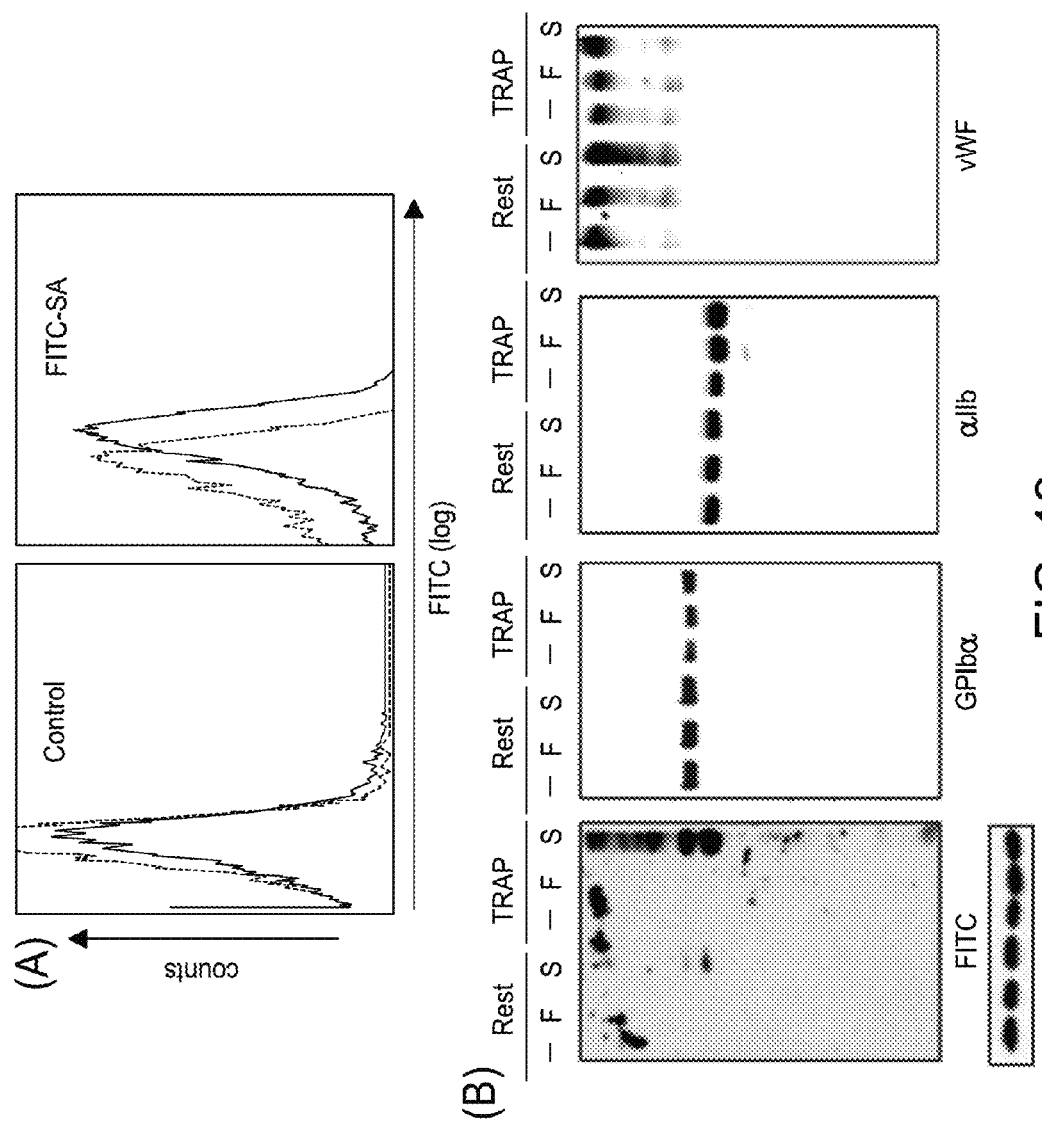
FIG. 12 depicts that endogenous platelet sialyltransferases incorporate sialic acid into platelet surface receptors. (A) Active human platelets' surface sialyltransferase incorporated FITC-conjugated CMP-SA (FITC-SA) into resting (dotted line) or TRAP-activated platelets. FITC alone (Control) was added to resting (dotted line) or TRAP activated platelets (solid line). (B) shows immunoblots of lysates from resting (Rest) or TRAP-activated platelets (TRAP) treated with FITC (F), FITC-CMP-sialic acid (S), or left untreated (−) and detected with antibodies to FITC, GPIbα, αIIb, and vWf. The blots shown are representative of two experiments. Actin is shown as a loading control.

Endogenous Active Platelet Sialyltransferases Incorporate Sialic Acid into GPIbα:

Endogenous resialylation was studied by following the fate of i. v. injected fluorescent-CMP-sialic acid (FITC-SA) in mouse platelets. After the injection, platelets were isolated and analyzed for the incorporation of fluorescence by flow cytometry (FIG. 12) and by determining the extent to which the fluorescent-tag was incorporated into mouse (not shown) and human GPIbα (FIG. 12) by SDS-PAGE and immunoblotting analysis. Similar results were obtained using $^{14}$C CMP-sialic acid, as shown in FIG. 12. FITC labeled CMP-SA (FITC-SA) or FITC alone (FITC) were injected into wild type mice. After 1 hour, the mice were bled and FITC incorporation into platelets was determined by flow cytometry. Isolated human platelets were incubated with FITC (F), FITC-SA, or left untreated (−). Resting (Rest) and TRAP (TRAP) activated platelets were subjected to immunoblotting using anti-FITC (FITC), -GPIbα, -αIIb or -von Willebrand factor (vWf) antibodies. Actin is shown as a loading control.

Figure 13:
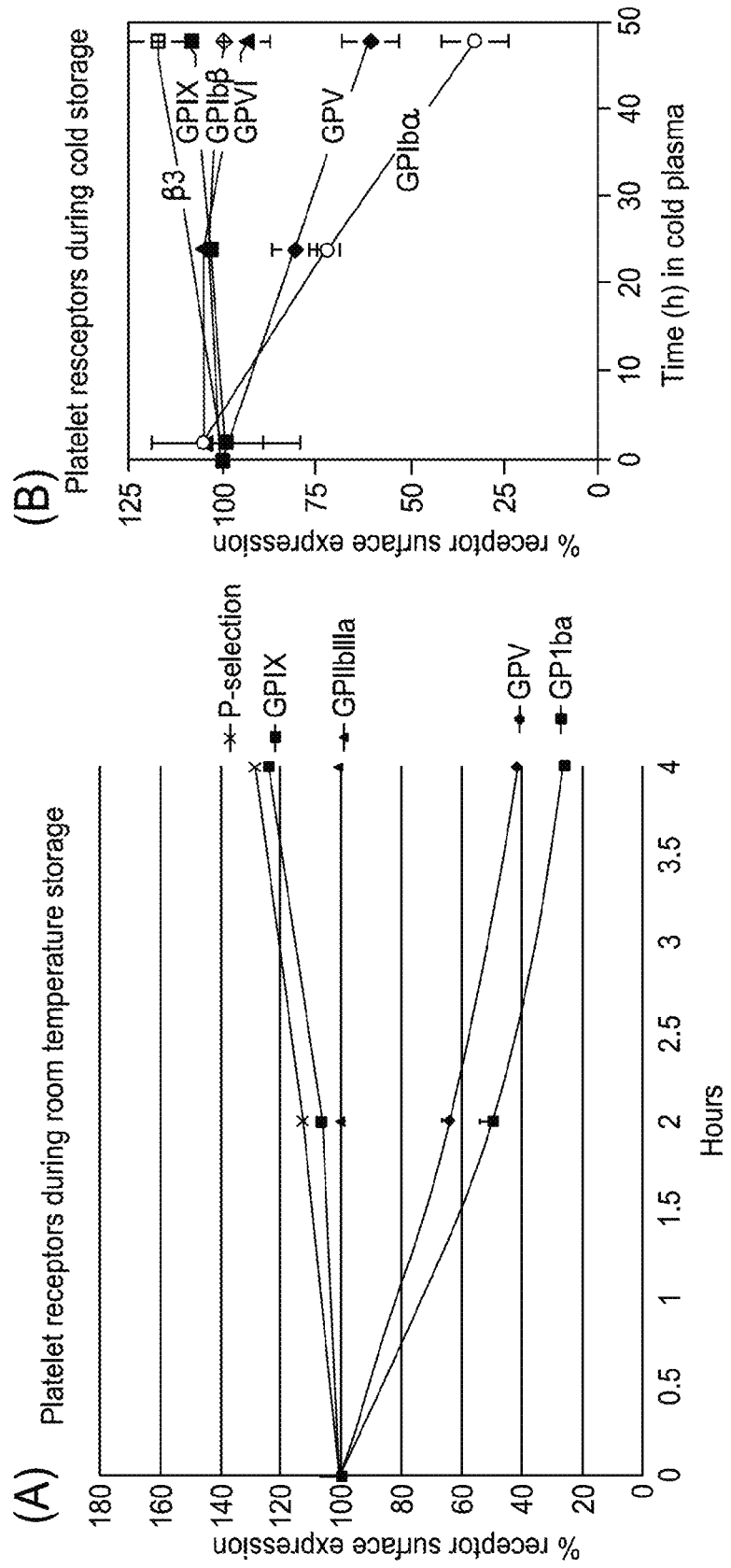
FIG. 13 shows that platelets lose GPIbα and GPV receptors during storage at room temperature (A) or under refrigeration (B). Expression of mouse vWf receptor complex components (GPIbα, GPIβ, GPIX, GPV), GPVI and $\alpha_{IIb}\beta_3$ was measured by flow cytometry before and after platelet storage in the cold at the indicated time points. Results are expressed as means±SD, n=5. Glycoprotein expression on freshly isolated platelets was set as 100%.
Figure 14:
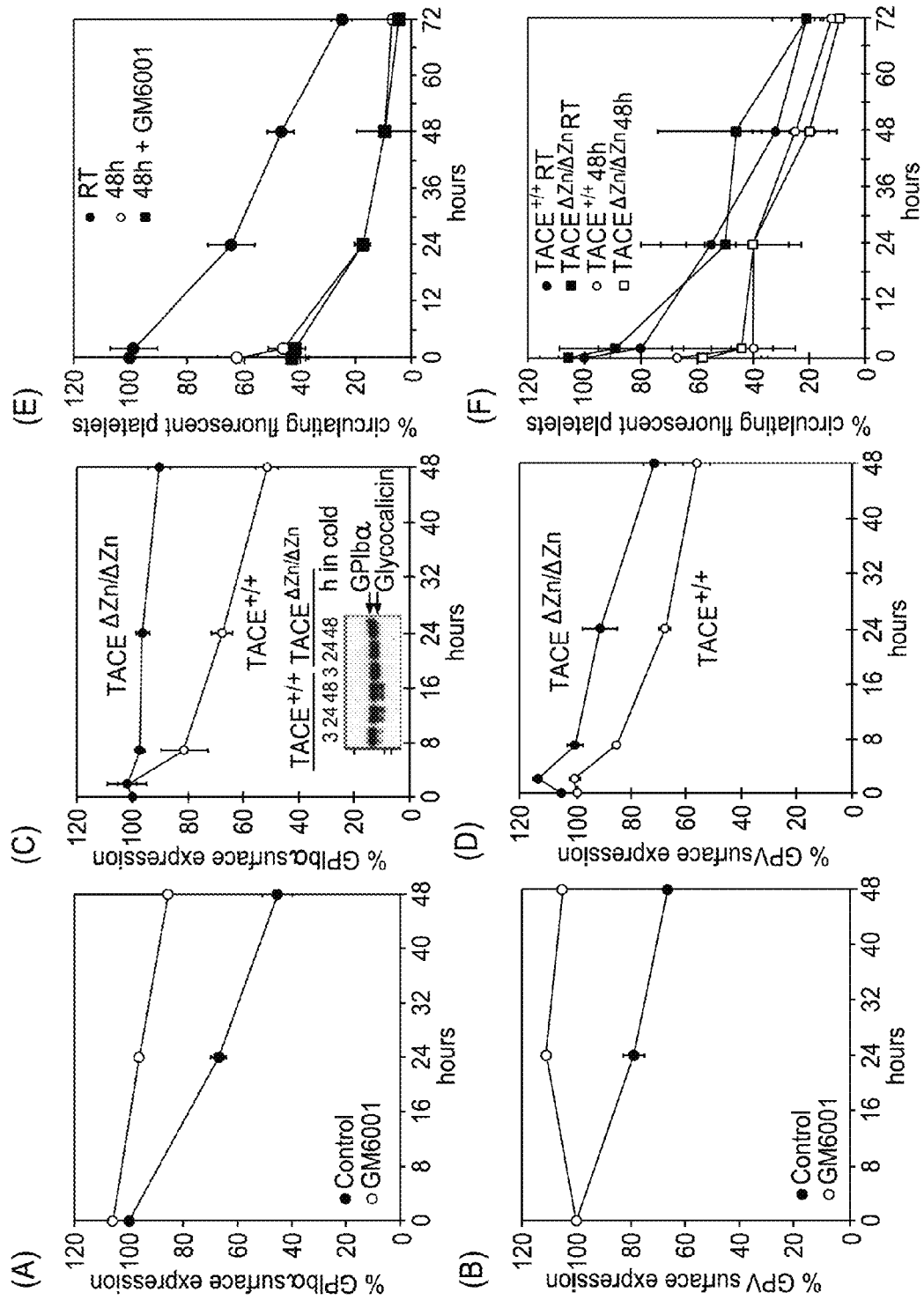
FIG. 14 shows that inhibition of metalloprotease-mediated GPIbα shedding alone does not improve mouse platelet recovery and survival. (A) GPIbα and (B) GPV surface expression were assessed by flow cytometry. Wild-type mouse platelet rich plasma was stored for 0, 24, and 48 h at 4° C. in the presence of DMSO (Control) or 100 μM of the metalloproteinase inhibitor GM6001 (n=6). Surface expression of (C) GPIbα and (D) GPV was determined by flow cytometry on freshly isolated or 24 and 48 h refrigerated platelet rich plasma from TACE$^{+/+}$ and TACE$^{-/-}$ mice. Results are the mean±s.e.m. n=5. (C, Inset) Immunoblot for GPIbα in lysates from TACE$^{+/+}$ and TACE$^{\Delta Zn/\Delta Zn}$ platelets stored for 3, 24, and 48 h in the cold. (E) Fluorescently-labeled (5-chloromethyl fluorescein diacetate, CMFDA) fresh PRP (RT) or platelets from stored platelet rich plasma in the absence (48 h) or presence of 100 μM GM6001(48 h+GM6001), were infused into wild-type mice (10$^8$ platelets/10 gm of body weight). Blood was drawn at the indicated time points, and platelets were immediately analyzed by flow cytometry. Results are mean percentage CMFDA-labeled platelets ±s.e.m. The percentage of CMFDA positive fresh platelets at time 5 min post-transfusion was set as 100%. n=5. *P<0.05. Cold-stored platelets are compared. (F) Fluorescently-labeled (CMFDA) fresh platelets (TACE$^{+/+}$ RT and TACE$^{-/-}$ RT) or platelets from stored platelet rich plasma (TACE$^{+/+}$ 48 h and TACE$^{-/-}$ 48 h) were infused intravenously into wild type mice (10$^8$ platelets/10 gm of body weight). Blood was drawn at the indicated time points, and platelets were immediately analyzed by flow cytometry. Results are mean percentage CMFDA-labeled platelets ±s.e.m. The percentage of CMFDA positive fresh TACE$^{+/+}$ platelets at 5 min post-transfusion was set as 100%. n=5.
Figure 15:
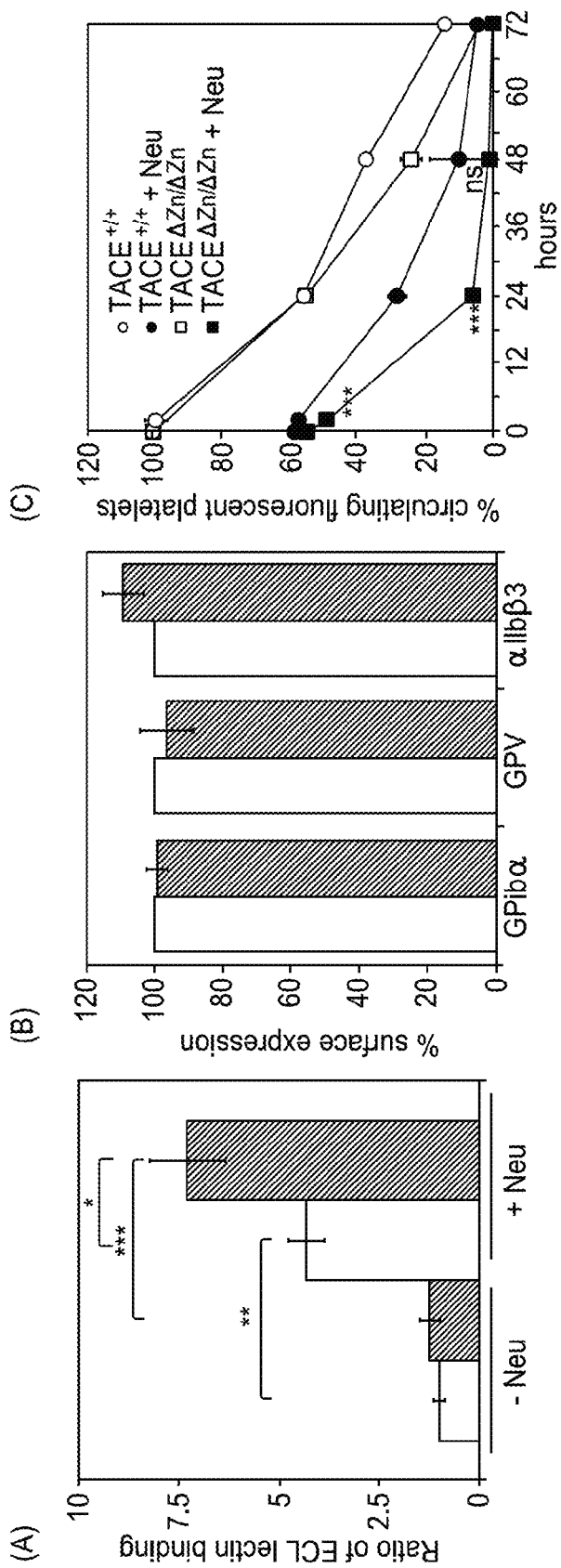
FIG. 15 shows that sialidase-treated TACE$^{\Delta Zn/\Delta Zn}$ platelets are rapidly cleared from the circulation. (A) Flow cytometric analysis of β-galactose exposure on glycoproteins, as detected with ECL FITC-labeled lectin is shown. Lectin binding to TACE$^{+/+}$ (white bars) or TACE$^{\Delta Zn/\Delta Zn}$ (hatched bars) platelets treated or not treated with α2-3,6,8,9-sialidase (Neu). The ratio of mean fluorescence intensity binding to untreated TACE$^{+/+}$ platelets is shown. Histograms report the mean±s.e.m. for three separate experiments. *P<0.05, P<0.01, *P<0.001. (B) GPIbα, GPV, and $\alpha_{IIb}\beta_3$ surface expression was assessed by flow cytometry. TACE$^{+/+}$ (not shown) and TACE$^{\Delta Zn/\Delta Zn}$ platelets were treated with sialidase (5 mU/mL) (hatched bars) or not (white bars). Results are expressed relative to the amount of GPIbα on TACE$^{\Delta Zn/\Delta Zn}$ platelets (mean % relative to control ±s.e.m.). n=3. (C) Fresh, room temperature and fluorescently-labeled (CMFDA) TACE$^{+/+}$ and TACE$^{\Delta Zn/\Delta Zn}$ platelets treated with α2-3,6,8,9-Sialidase (5 mU/mL) (filled symbols) or left untreated (open symbols) were infused intravenously into TACE$^{+/+}$ mice (10$^8$ platelets/10 g of body weight). Blood was drawn at the indicated time points, and the platelets were immediately analyzed by flow cytometry. Results are expressed as the mean percentage CMFDA-labeled platelets ±s.e.m. The percentage of CMFDA positive untreated TACE$^{+/+}$ platelets at 5 min post-transfusion was set as 100%. Each point represents 4 mice. n.s. not significant, ***P<0.0001. Sialidase treated TACE$^{+/+}$ and TACE$^{\Delta Zn/\Delta Zn}$ were compared.

Proteolysis of GPIbα and GPV by the Metalloprotease TACE (ADAM17) is not Required to Initiate Platelet Clearance after Desialylation:

During room temperature platelet storage or platelet storage under refrigeration, the loss of GPIbα and GPV is observed. In contrast, other platelet receptors, such as GPIX, GPIbβ, GPVI, or β3 remain unchanged following platelet storage independent of the storage temperature (FIG. 13). TACE mediates proteolysis of GPIbα and GPV during platelet refrigeration as shown by inhibition of TACE using the metalloprotease inhibitors GM6001 or platelets deficient for TACE (FIG. 14). Surprisingly preservation of receptor loss during platelet refrigerated storage does not prevent refrigerated platelet clearance (FIG. 14). Removal of sialic acid from TACE deficient platelets diminishes platelet circulatory lifetime (FIG. 15C). This demonstrates that proteolysis of GPIbα or GPV is not required to initiate platelet clearance after desialylation. Platelets were isolated from TACE activity deficient mice and treated with sialidase for 15 min at 37° C. (+Neu) or left untreated (−Neu). Fluorescently (CMFDA) labeled platelets (2×10$^8$) were injected into wild type mice and their circulation times were determined. Importantly, no differences in surface vWf receptor expression were observed in sialidase (Neu) treated and untreated TACE$^{-/-}$ platelets when measured by flow cytometry (FIG. 15B). In contrast, after sialidase treatment, β-galactose exposure increased by ~5 fold as determined using RCA I and ECL lectins (FIG. 15A)).

Example 4

Surface Sialic Acid Prevents Loss of GPIbα and GPV During Platelet Storage and Rescues In Vivo Survival of Mouse Platelets Platelet processing and storage are associated with platelet lesion (e.g., shape change, activation, release reaction, and apoptosis), which is partially due to loss of surface receptors. Surface sialic acid is considered to be a key determinant for the survival of circulating blood cells and glycoproteins. However, its role in platelet receptor loss and platelet survival is unclear. In this study, the relationship between surface sialic acid and platelet receptor loss was investigated in vitro and in vivo.

Figure 16:
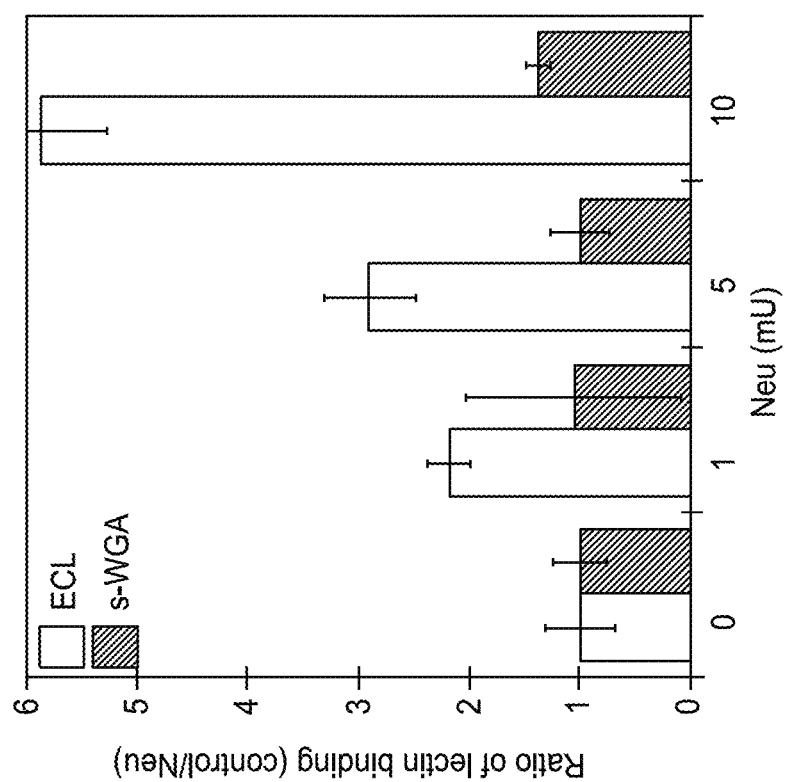
FIG. 16 shows that neuraminidase treatment of platelets increases β-galactose exposure (loss of sialic acid) as measured by ECL fluorescence lectin binding. Data is from flow cytometric analysis of β-galactose or β-GlcNAc exposure on platelet glycoproteins, as detected with ECL I (open bars) or s-WGA (closed bars) FITC-labeled lectins. Results have been obtained from lectin binding to fresh mouse platelets in the presence and absence of α2-3,6,8,9-Sialidase from *A. ureafaciens* (Neu) at the indicated concentrations, n=5.
Figure 17:
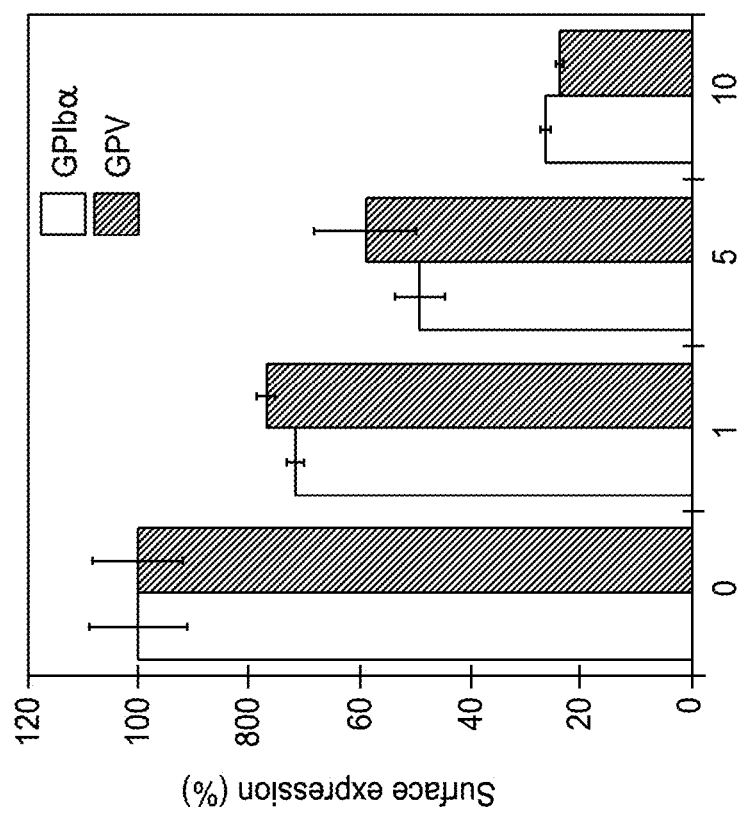
FIG. 17 shows the dose dependent loss of platelet GPIbα and GPV receptors with increasing neuraminidase concentrations. GPIbα and GPV surface expression on freshly isolated mouse platelets was assessed by flow cytometry. Surface receptor expression in the presence and absence of α2-3,6,8,9-sialidase (Neu) at the indicated concentrations is shown. The mean fluorescence of receptor expression at time 0 was set as 100%. n=4.
Figure 18:
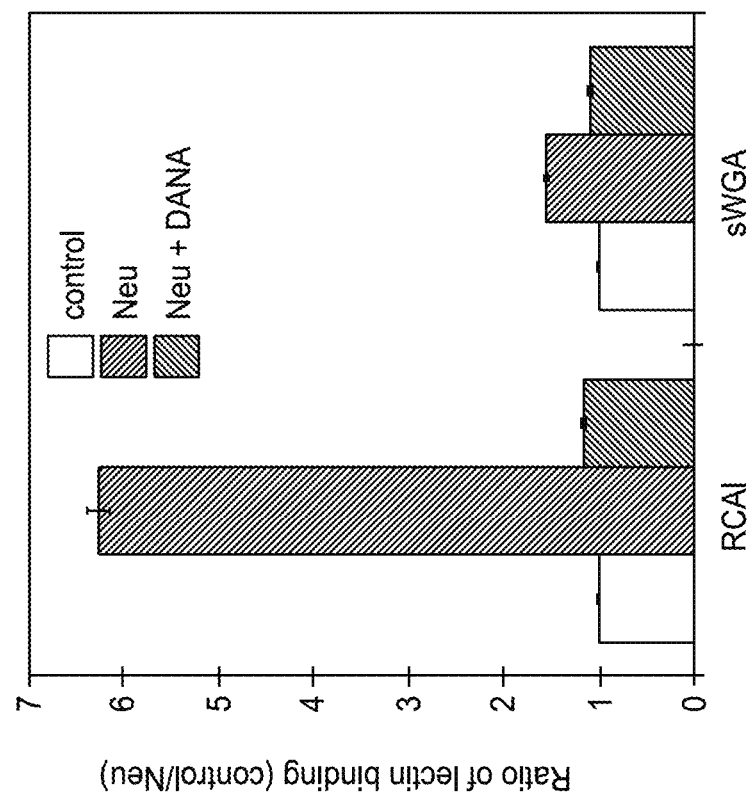
FIG. 18 shows that DANA inhibits the exposure of β-galactose by neuraminidase treatment. Data is from flow cytometric analysis of β-galactose or β-GlcNAc exposure on mouse platelet glycoproteins, as detected above in the presence (Neu) and absence (Control) of 5 mU α2-3,6,8,9-sialidase (Neu) and the competitive sialidase inhibitor DANA (Neu+DANA). n=4.
Figure 19:
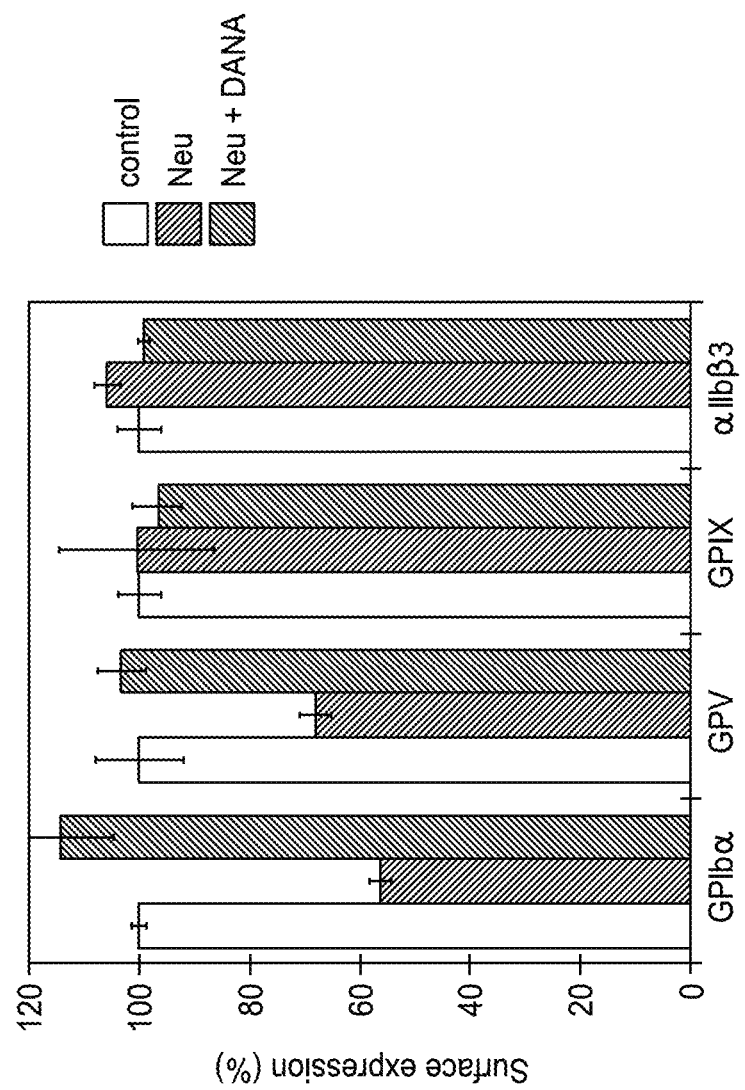
FIG. 19 shows that DANA inhibits the loss of platelet GPIbα, GPV, GPIX, and $α_{IIb}β_3$ receptors induced by neuraminidase treatment. Surface receptor expression (GPIbα, GPV, GPIX, and $α_{IIb}β_3$) was measured by flow cytometry on mouse platelets in the presence (bars hatched with negatively sloping lines) and absence (open bars) of 5 mU α2-3,6,8,9-sialidase. Receptor expression on platelets treated with sialidase and DANA is also shown (bars hatched with positively sloping lines). The mean fluorescence of receptor expression on untreated platelets was set as 100%. n=4.
Figure 20:
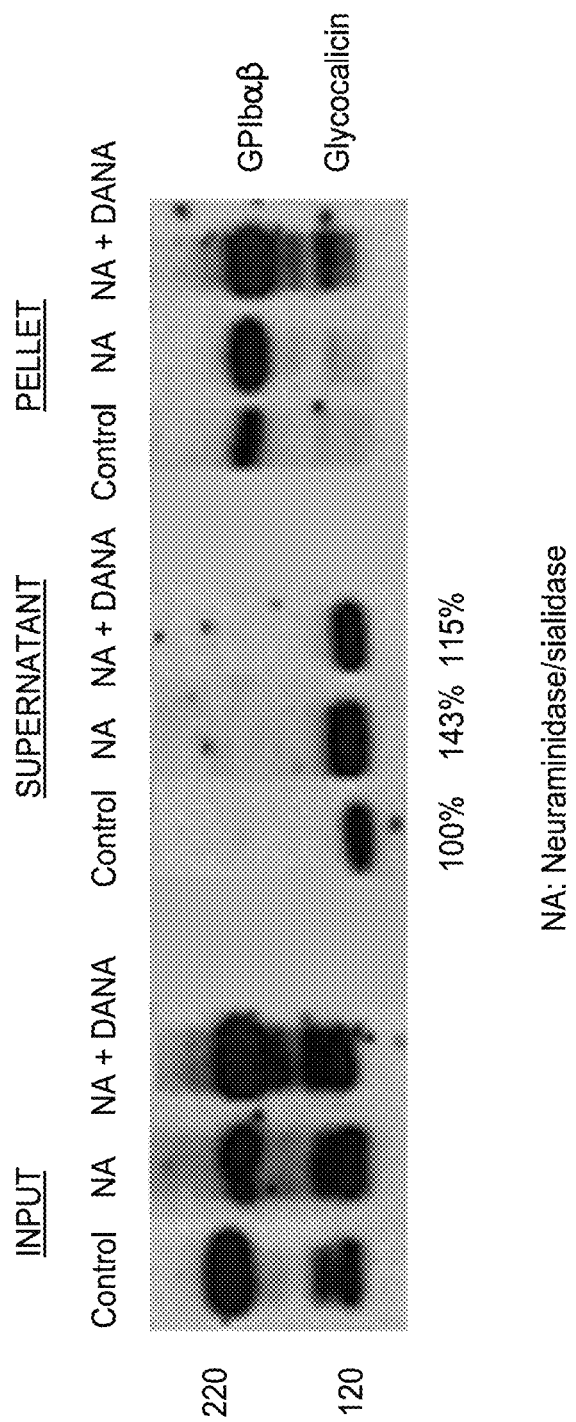
FIG. 20 depicts a non-reduced immunoblot of total platelet lysates (INPUT), supernatants (SUPERNATANT) and the corresponding platelets' pellet (PELLET) showing that DANA inhibits the loss of platelet GPIbα induced by neuraminidase (NA) treatment. Control represents untreated samples.
Figure 21:
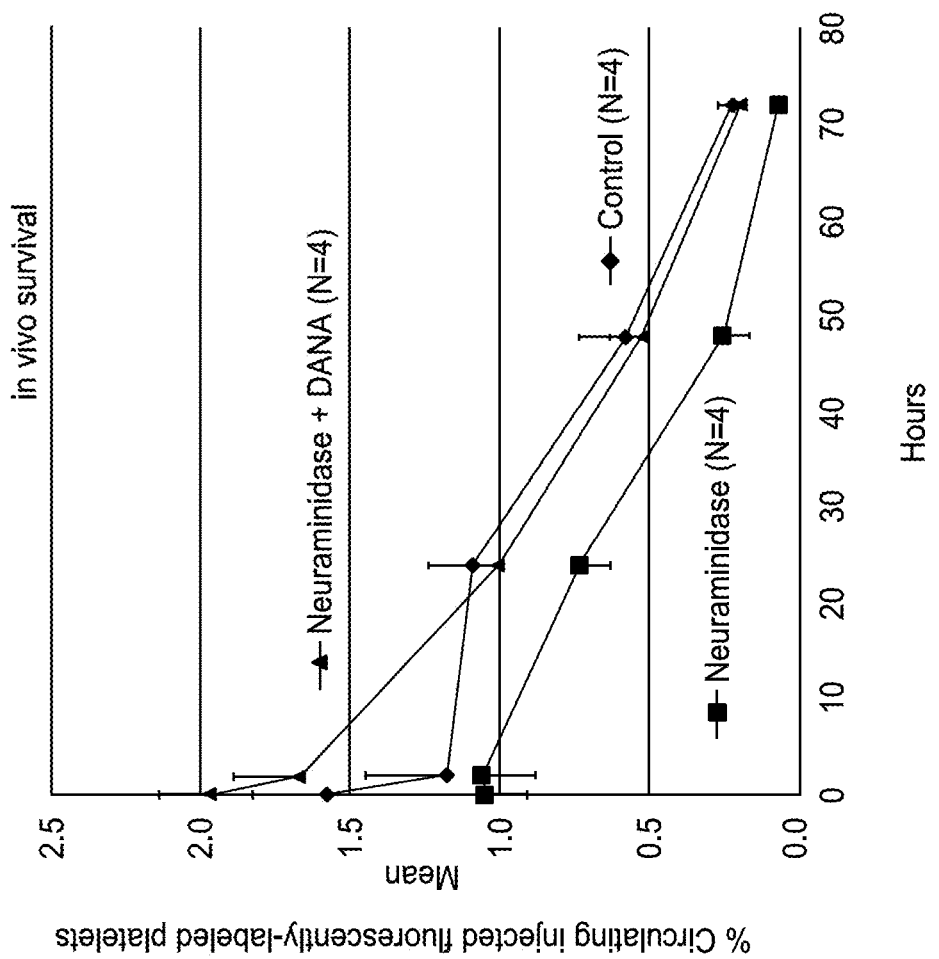
FIG. 21 is a graph showing that addition of DANA completely rescues the in vivo recovery and survival of mouse platelets treated with neuraminidase. Control depicts the survival of non-treated fresh room temperature platelets.
Figure 22:
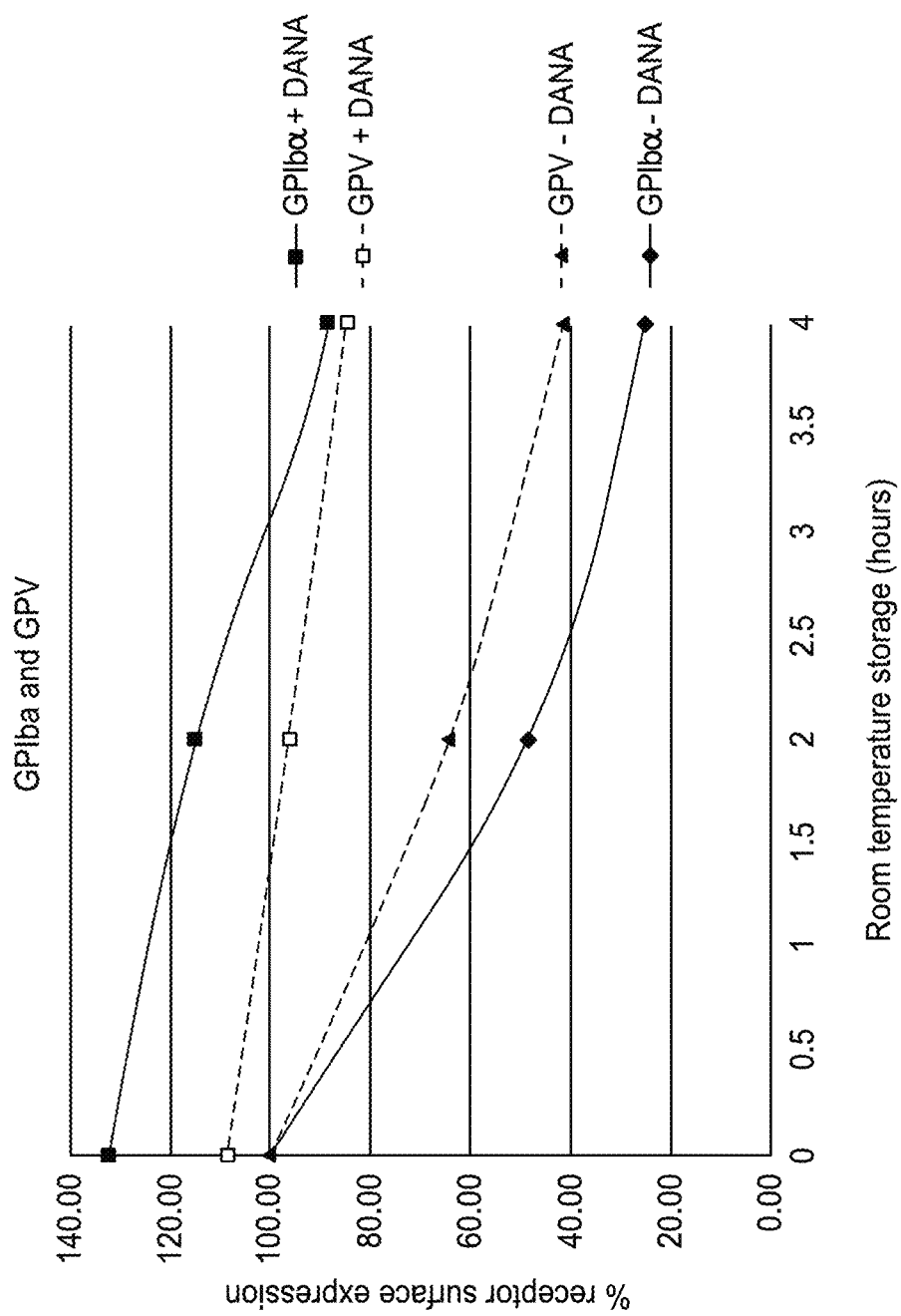
FIG. 22 is a graph showing that platelet GPIbα and GPV receptor loss during storage at room temperature is inhibited by the addition of DANA.

Removal of Sialic Acid from Platelet vWf Receptor Stimulates GPIbα and GPV Shedding:

Incubation of mouse platelets with increasing concentrations of the broad spectrum *A. ureafaciens* α2-3,6,8-sialidase increased surface β-galactose exposure, but not β-GlcNAc, as detected by lectin binding assays in the flow cytometer (FIG. 16). FIG. 17 presents progressive loss of surface of surface GPIbα and GPV in conjunction with decrease in sialic acid content (p<0.05). GPIbα receptor expression was followed with multiple anti-GPIbα antibodies to exclude the possibility that desialylation altered antibody binding to GPIbα. We detected a ~6 fold increase of terminal β-galactose, but not β-GlcNAc, following treatment with 5 mU sialidase. β-Galactose exposure was completely inhibited by of the competitive sialidase inhibitor DANA (FIG. 18). Sialidase treatment did not affect the expression of surface GPIX-receptor or integrin αIIbβ3 (p>0.05) (FIG. 19). Critically, addition of the competitive sialidase inhibitor DANA prevented all GPIbα and GPV shedding (FIG. 19), consistent with the hypothesis that sialic acid loss primes GPIbα and GPV for metalloprotease-mediated shedding. FIG. 20 confirms the flow cytometry data shown in FIG. 19 by using immunoblot analysis of total platelet lysates, platelet supernatants, and corresponding platelet pellets with or with addition of neuraminidase and DANA. In support of this notion, FIG. 21 shows that fresh platelets treated with sialidase are cleared rapidly from the circulation in a process prevented by DANA addition to the storage buffer. Importantly, addition of DANA preserved receptors expression of room temperature stored mouse platelets (FIG. 22) and platelet survival (not shown).

Figure 23:
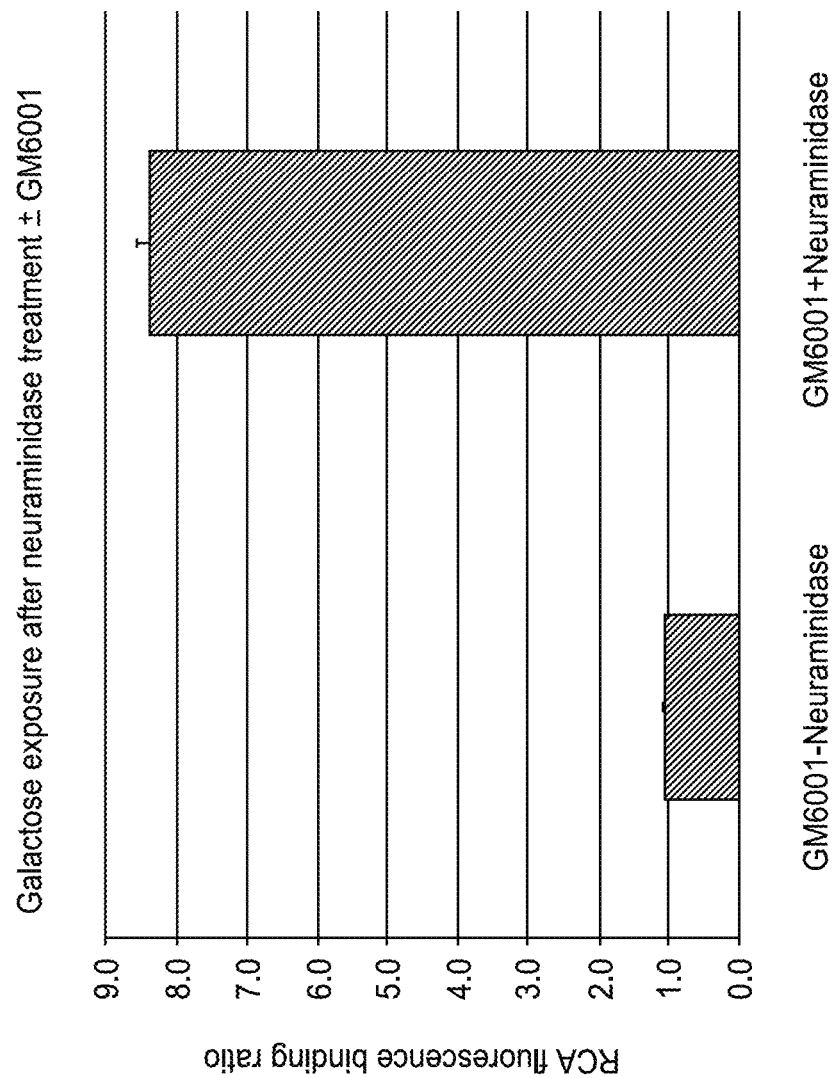
FIG. 23 is a bar graph depicting the effect of neuraminidase treatment on β-galactose exposure in the presence of 100 μM metalloproteinase (MP) inhibitor GM6001. β-Galactose exposure was measured by fluorescently-labeled RCA-1 lectin binding.
Figure 24:
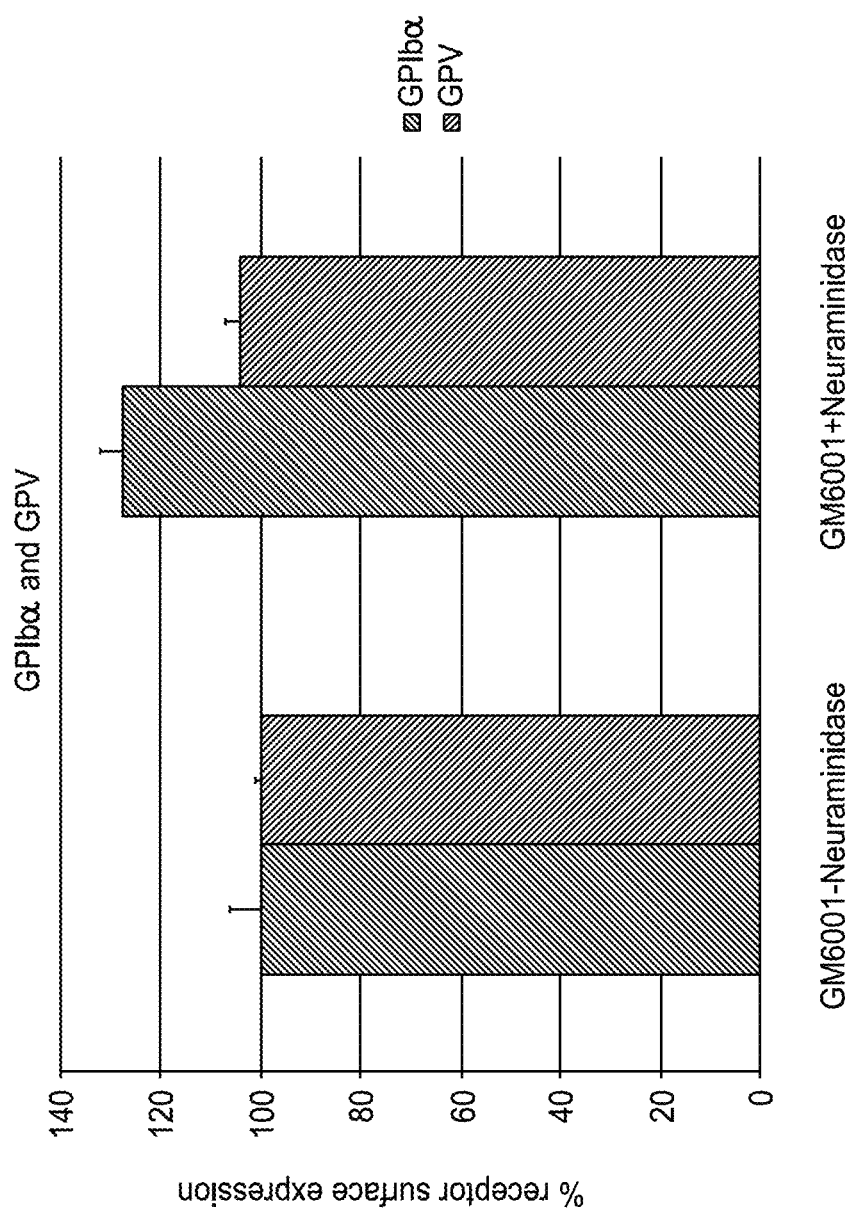
FIG. 24 is a bar graph depicting the effect of neuraminidase treatment on platelet GPIbα and GPV receptor surface expression in the presence of 100 μM metalloproteinase (MP) inhibitor GM6001. The receptor expression on MP inhibitor-neuraminidase was set to 100%.
Figure 25:
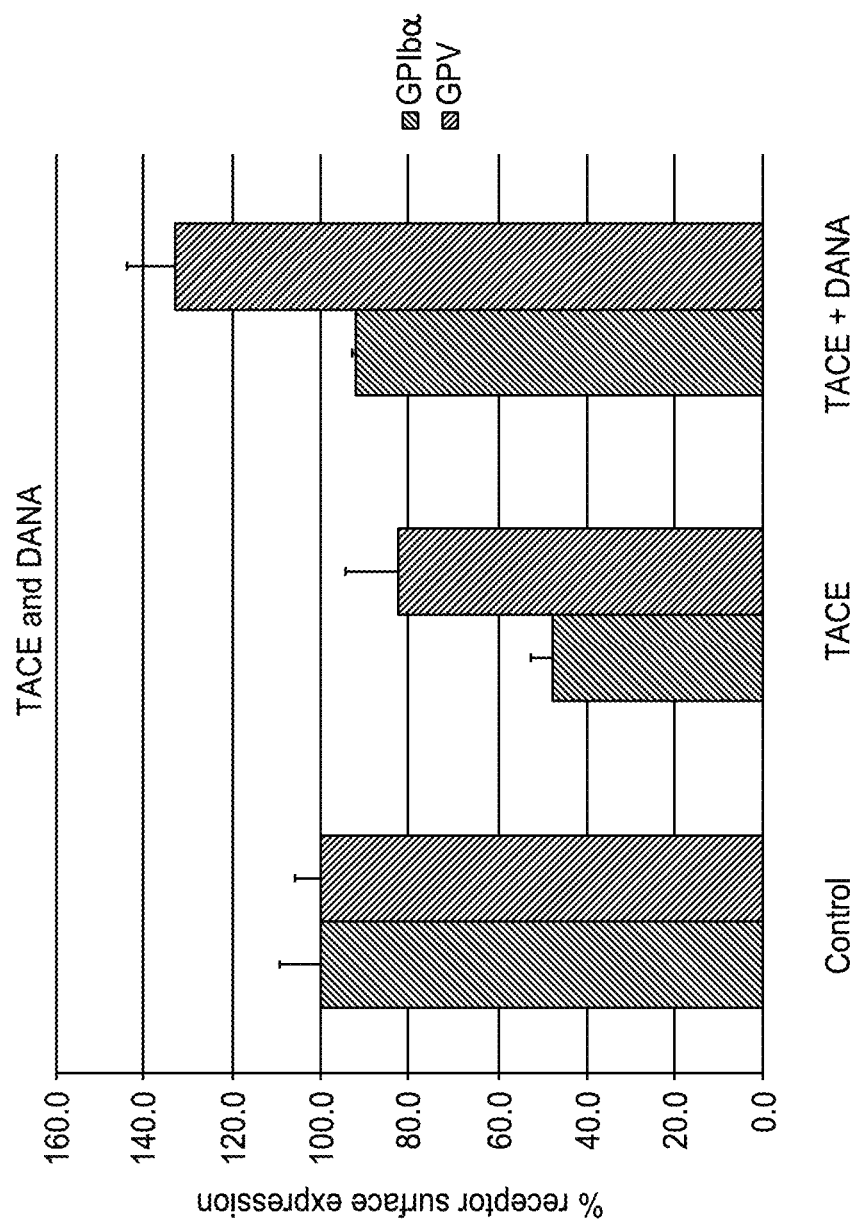
FIG. 25 is a bar graph depicting the effects of recombinant TACE (ADAM17) (TACE) and recombinant TACE and DANA (TACE+DANA) on platelet GPIbα and GPV receptor surface expression. The fact that inhibition of sialic acid loss prevents receptor cleavage by the metalloproteinase TACE shows that sialic acid has to be hydrolyzed from glycoproteins before the proteolysis of GPIbα and GPV. The receptors GPIX and αIIbβ3 were not affected by treatment with recombinant TACE (not shown).

Desialylation is Required for TACE-Mediated GPIbα and GPV Shedding:

To confirm that desialylated GPIbα and GPV are better TACE substrates than the sialylated forms, platelets were treated with recombinant TACE (rTACE) in the presence or absence of DANA. Platelets treated with rTACE released 47%±6 and 18%±12 of their GPIbα and GPV (p<0.05), respectively (FIG. 25), but negligible amounts of their GPIX and $α_{IIb}β_3$ (p>0.05) (not shown). Receptor shedding by rTACE, but not rTACE activity (not shown) was completely prevented by DANA (FIG. 25). Addition of the MMP inhibitor GM6001 to sialidase-treated platelets did not prevent β-galactose exposure, e.g. loss of sialic acid (FIG. 23), but inhibited receptor shedding by rTACE (FIG. 24) (p<0.05). β-galactose exposure induced by sialidase increased 7-fold in the presence of GM6001 and rTACE (FIG. 23), showing that GM6001 has no effect on sialidase activity but completely inhibits rTACE and endogenous metalloprotease function. Hence, the data show that desialylation of GPIbα and GPV is a likely prerequisite for TACE-mediated receptor shedding in the cold and support the concept that TACE cleavage of GPIbα depends on prior sialidase activation.

Example 5

Bacterial Contamination/Proliferation in Platelet Concentrates Leads to Formation of Excessive Free Sialic Acid in the Storage Media In hospitals and blood centers, platelets are stored at room temperature. To reduce the risk of bacterial growth and iatrogenic infections after transfusion, platelet shelf life is limited to 5 days in the United States. Platelets cannot be stored in a similar manner to red blood cells (RBC) under refrigeration with less risk for bacterial growth and transfusion related infections. Refrigerated platelets are rapidly cleared from the recipient's circulation, despite improved in vitro function. Refrigeration of platelets irreversibly clusters the platelet glycoprotein Ibα (GPIbα) complex, leading to rapid platelet clearance when infused through lectin-mediated pathways.

Storage of platelets for transfusion at room temperature promotes bacterial growth in bacterially contaminated (unsterile) platelets. Many bacteria are able to interact with platelets and induce platelet aggregation by direct interaction between a bacterial surface protein and a platelet receptor or an indirect interaction where plasma proteins bind to the bacterial surface and subsequently bind to a platelet receptor. See FIGS. 1A-C. Bacteria secrete a variety of biological active substances into their local milieu. Secreted proteins are particularly important in bacterial pathogenesis. These proteins have a range of biological functions ranging from host cell toxicity to more subtle alterations of the host cell for the benefit of the invader. In bacterial contaminated platelet products, the bacterial-derived products can be capable of triggering platelet activation or causing damage to the platelets. Many bacteria-secreted hydrolases such proteases and glycosidases (i.e secreted enzymes) contribute to the bacterial virulence or are thought to play a role in promoting bacterial growth as nutrients. In platelet products, enzymes secreted by contaminating bacteria can truncate platelet glycans and/or accelerate platelet receptor shedding. Platelets are especially susceptible to sialidase activity (sialic acid hydrolysis) since they are heavily decorated with glycans terminated by sialic acid. Sialidase-mediated loss of sialic acid residues will result in clearance of the desialylated platelets by the asialo-glycoprotein receptor (ASGR) of liver hepatocytes upon transfusion. The presence of sialidase-producing bacteria in platelet product will be particularly detrimental to platelets. In addition, after the loss of sialic acid, asialoglycoconjugates may become substrates for the additional bacterial glycosidases. Subsequent release of underlying glycans will generate nutrients that will enhance bacterial proliferation and generate ligands for bacteria-platelet interactions.

Although it is well-known that bacterial contamination in platelet products can lead to transfusion-related sepsis and platelet activation through bacteria-platelet interactions, the presence of sialidase-producing bacteria in platelet products and their potential impact on platelet quality have neither been recognized nor studied. It is expected that the presence of sialidase-producing bacteria in platelet products desialylates sialylglycoproteins on platelets and in plasma and increases the free sialic acid concentration in the storage media.

Materials and Methods:

One bag of platelet concentrate (Research Blood Components, Boston, Mass.) was aseptically split into two 50-mL Falcon tubes. Prostaglandin E1 (PGE1, Sigma-Aldrich) was added to 1 μg/mL and the samples were centrifuged for 20 min at 200×g to sediment contaminated red cells. The supernatant (purified platelet concentrate, PC) was removed from the contaminating RBC and pooled in a new 50 mL falcon tube. The purified PC was then split, providing identical products for storage at 4° C. and room temperature (RT), respectively. All steps were executed under aseptic conditions. On Days 0, 8, and 13 of storage, aliquots from each storage condition were removed and visually inspected for color change caused by bacterial growth at the time of sampling. The samples were centrifuged for 10 min at 1000 Δg. The resultant supernatants (platelet poor plasma, PPP) were further centrifuged for 10 min at 10,000×g, 4° C. The supernatants from the second spin (platelet-free plasma, PFP) were analyzed for free sialic acid using QUANTICHROM® Sialic Acid Assay Kit (BioAssay Systems, Hayward, Calif.) according to the manufacturer's instructions.

Results:

Color change was readily visible on Day 8 and 13 in the PC sample stored at room temperature, suggesting the proliferation of "naturally" (as opposed to spiked occurring bacteria under these conditions. No visible color change was noticed in the 4° C. stored samples.

Figure 26:
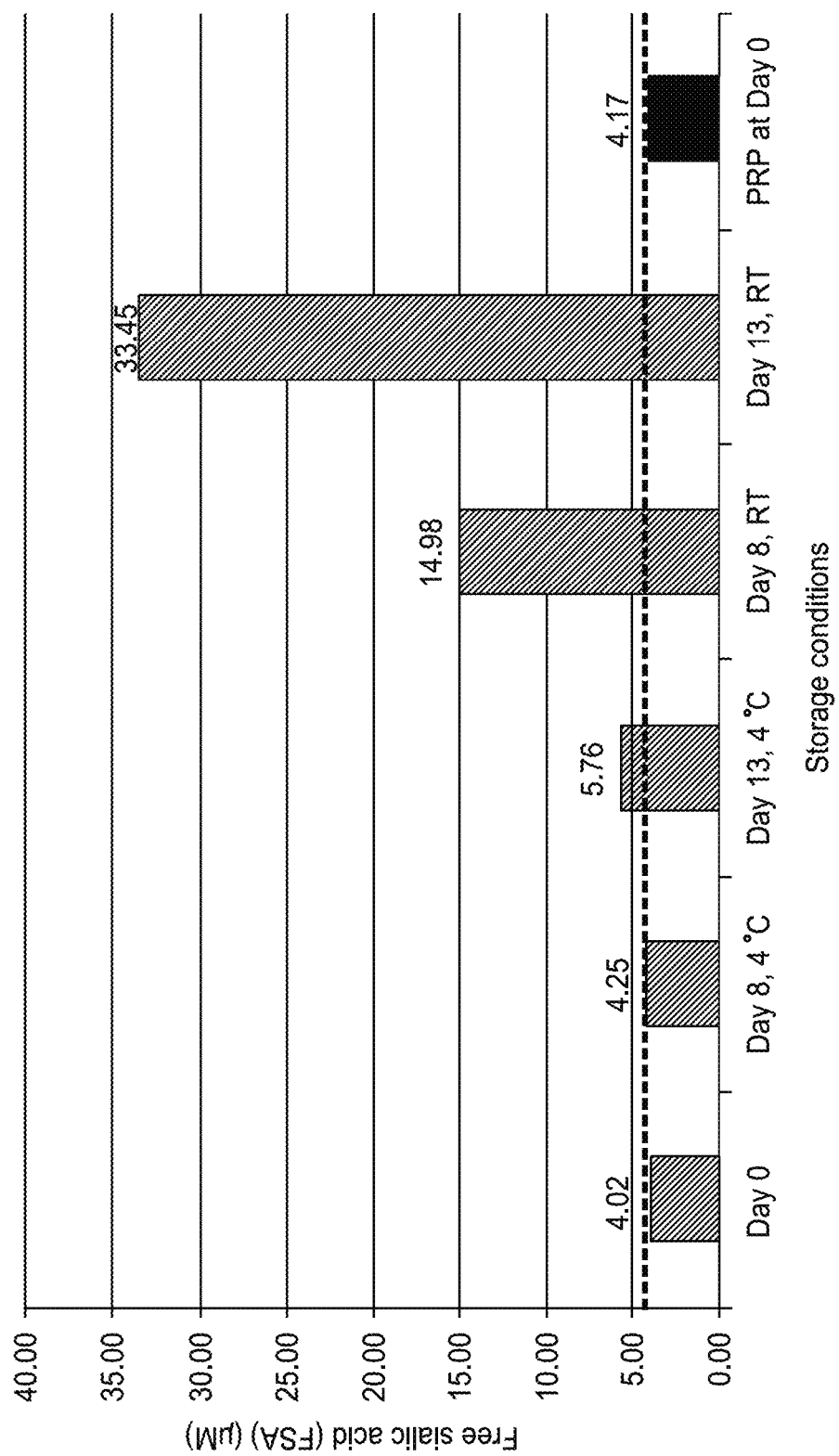
FIG. 26 is a bar graph depicting the quantification of free sialic acid (FSA) in fresh platelet samples and stored samples at 4° C. and RT for the indicated time points. FSA concentrations are also shown on the top of each bar graph. Note that FSA detected in RT-stored platelet samples was much higher when compared to samples stored at 4° C. for equivalent time periods.

The free sialic acid (FSA) in fresh PRP and PFP, and PFP recovered from storage samples were measured and the results are shown in FIG. 26. Although human plasma contains high concentrations of total sialic acid (1-2 mM), the amount of FSA in fresh PC or PFP is only ~4 μM, accounting for less than 0.5% of total sialic acid. The FSA level remained unchanged during 8-day storage at 4° C. and increased by 1.4 fold during the second week (day 13) of 4° C. storage (dashed line). This data shows that under the condition that bacterial growth is retarded, the platelet sialic acid loss due to the endogenous platelet sialidase is minimal. In contrast, during storage at RT, FSA increased by ~3-fold on Day 8 and ~9-fold on Day 13. The rapid increase of FSA in the RT-stored sample cannot be solely attributed to action of the endogenous platelet sialidase. It is likely the result of exogenous sialidase released by contaminating bacteria. The data also shows that the contaminating bacteria are sialidase-producing bacteria.

Conclusion:

Sialidase-producing bacteria are potentially present in all platelet products. The bacterial sialidase can desialylate platelets, compromising their biological functions.

Example 6

Bacterial Proliferation in Platelet Product can be Inhibited by Sialidase Inhibitor Sialidases play important role in pathogenicity and nutrition of sialidase-producing bacteria. Sialic acid occupies the terminal position within glycan molecules on the surfaces of many vertebrate cells, where it functions in diverse cellular processes such as intercellular adhesion and cell signaling. Pathogenic bacteria have evolved to use this molecule beneficially in at least two different ways: 1) they can coat themselves in sialic acid, providing resistance to components of the host's innate immune response, 2) or they can use it as a nutrient. Sialic acid itself is either synthesized de novo by these bacteria or scavenged directly from the host. Our discovery of the presence of sialidase-producing bacteria as contaminants in platelet product suggests a novel approach of inhibiting bacterial growth in platelet products by inhibiting sialidase activity with sialidase inhibitors.

Sialidase inhibitors are not new to the pharmaceutical industry. The influenza virus medicines Tamiflu and Relenza inhibit the influenza virus sialidase, which is required for spreading of the virus from infected cells. However, they have not been used in platelet products.

Conventionally, platelets are suspended in 100% plasma. Although plasma (rather whole blood) is the natural medium of platelets in vivo, it might have deleterious effects on platelets during storage, because plasma enzymes such as proteases can damage platelet membranes. A storage solution that can maintain platelet function as well or better than plasma is desirable, in part to make plasma available for other purposes, but especially to mitigate transfusion-related adverse reactions, such as TRALI. Therefore, much attention has been devoted to platelet additive solutions with satisfactory platelet preservation capacity with low residual plasma.

Platelet additive solutions (PASs) were first developed in the 1980s, and continue to be improved until today. The use of PASs as replacement for plasma has a number of benefits, both for the quality of the platelet concentrates and for the patients. The growth kinetics of model bacteria in platelets stored in a 35%:65% ratio of plasma to INTERSOL® solution (30 mM sodium phosphate, 10 mM sodium citrate, 30 mM sodium acetate and 70 mM sodium chloride, pH 7.4) where initial bacterial concentrations are 0.5 to 1.6 CFUs/mL have been studied. The more rapid initiation of log-phase growth for bacteria within a PAS storage environment resulted in a bacterial concentration up to 4 logs higher in the PAS units compared to the plasma units at 24 hours. This may present an early bacterial detection advantage for PAS-stored platelets.

To increase the formation of planktonic bacteria, thereby improving the sensitivity of the bacterial detection, platelet storage studies were performed in a mixture of PAS (INTERSOL® solution) and plasma (80:20). Many bacterial detection methods are available. We used SLP Reagent Set (297-51501, Wako Chemicals USA), containing silkworm larvae plasma (SLP) and 3,4-dihydrophenylalanine (DOPA), reconstituted according to manufacturer's instruction and stored as 100 µL aliquots at −80° C. When a sample is mixed with SLP reagent, peptidoglycan derived from the cell wall of Gram-positive and Gram-negative bacteria in the sample initiates a series of reactions including activation of multiple serine proteases called prophenoloxidase (proPO) cascade. The phenoloxidase (PO) produced in the cascade reactions oxidizes the substrate in the SLP reagent, 3,4-dihydrophenylalanine (DOPA), to form melain (dark blue). The bacteria concentration in the test sample is inversely proportional to the onset time of color development: shorter time=higher concentration of bacteria; longer time=lower concentration of bacteria.

Materials and Methods:

One bag of a platelet concentrate was split to two 50-mL Falcon tubes, PGE1 was added. After centrifugation at 900×g for 10 min, 80% of the supernatant (PPP) (relative to the total volume) was removed, and replaced with equal volume of platelet additive solution. The platelet was thoroughly re-suspended. The platelet suspensions were pooled and split to 4 aliquots in 15-mL Falcon tubes. DANA (1 mM) in PBS was added to two tubes while only PBS was added to the other tubes. One pair of samples with and without DANA was stored at 4° C. The second pair was kept at RT (22° C.-24° C.). Aliquots of 1.0 mL were removed on Day 0 and Day 9, and immediately pelleted (5 min, 15,800×g). The supernatants were discarded, and the pellets, containing platelets and bacteria, were stored at −80° C. until use. All experimental steps were carried out under aseptic conditions.

The pellet containing both platelets and bacteria, recovered from 1-mL aliquots sampled at different time points, was re-suspended in 100 µL of 0.1 M NaOH, and heated for 10 min at 70° C. After brief cooling, the solution was neutralized with 135 µL of 80 mM MES. The reaction mixtures were clarified by centrifugation (5 min at 15,800×g). Aliquots of 10 µL of the supernatant were mixed with equal volumes of SLP reagent, reconstituted from the components in the SLP kit following the manufacturer's instructions. The samples were left on the bench, and color development was monitored. The time of color detection (TOCD) was recorded.

Figure 27:
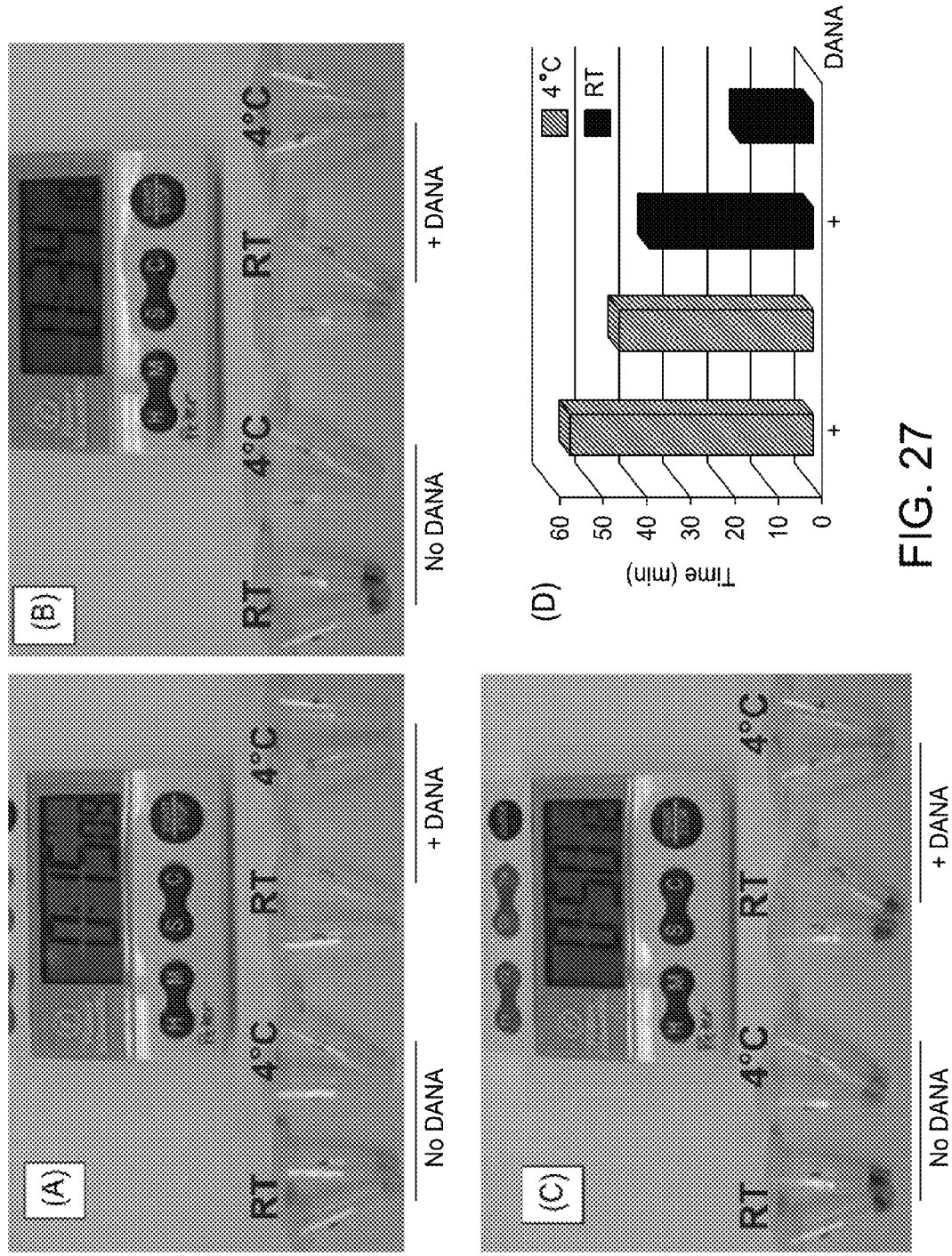
FIG. 27 are photographs showing the time required to detect bacteria in platelet samples (TOCD: Time of color detection) stored at 4° C. or at RT in the presence or absence of the sialidase inhibitor, DANA. The bacterial concentration in the test sample is inversely proportional to the onset time of color development, i.e., shorter time of color detection—higher concentration of bacteria; longer time color detection lower concentration of bacteria. Selected pictures for the analysis of Day 9 samples are shown (panels A, B, and C). Bacteria were detected using an assay technology as described in Example 6. Panel D is a bar graph showing the quantification of the bacterial analysis in platelet samples stored at 4° C. or RT in the presence or absence of sialidase inhibitor DANA. TOCD (min) was plotted against the platelet samples. Note that the time required for in RT stored samples with DANA is equivalent to 4° C. stored samples, indicating that DANA inhibits bacterial growth as effectively as 4° C.-storage.

Results:

The results are shown in FIG. 27. Selected photographs taken during the analysis of Day 9 samples are shown in FIG. 27, panels A-C. Light, but visible, color development was observed after 15 min for RT-stored sample without DANA, suggesting the highest bacterial concentration in this sample. TOCD was extended to ~34 min in the presence of DANA (#3, FIG. 27, panel B). Not surprisingly, bacterial growth is greatly inhibited at low storage temperatures, TOCD in 4° C.-stored samples (FIG. 27, panel C) (<45 min) was increased compared to TOCD in RT-stored sample in the absence or presence of DANA. Its TOCD at 4° C. is further extended in the presence of DANA (~50 min, FIG. 27 panel C). Quantitative data is shown in FIG. 27, panel D.

Conclusion:

Sialidase inhibitor DANA can effectively inhibit the bacterial growth during platelet storage. Although the nature of the bacteria is unknown, they are likely sialidase-producing bacteria. In addition, it was observed that the contaminating bacteria are not completely dormant at 4° C.

Example 7

DANA Inhibits Bacterial Proliferation in Stored Mouse Platelets and Improves the Survival and Recovery of Mouse Platelets In Vivo Mouse platelets have a life-span of approximately 4-5 days, considerably shorter than human platelets (8-10 days). They are also much less stable than human platelets when stored at room temperature or 4° C. The mechanism of the rapid deterioration in vitro of mouse platelet is not well understood, however it is possible that mouse platelet storage is affected by bacterial contamination due to a lack of aseptic platelet procurement protocol, in contrast to the collection of human platelets. To date, it remains unclear if potential bacterial contamination contributes to the rapid deterioration of mouse platelets.

Materials and Methods:

Mouse blood was obtained from anesthetized mice using 3.75 mg/g of Avertin (Fluka Chemie, Steinheim, Germany) by retro-orbital eye bleeding into 0.1 volume of Aster-Jandl anticoagulant and centrifuged at 300×g for 8 min at RT to obtain platelet rich plasma (PRP). Platelets were separated from plasma by centrifugation at 1200×g for 5 min and washed twice in 140 mM NaCl, 5 mM KCl, 12 mM trisodium citrate, 10 mM glucose, and 12.5 mM sucrose, 1 µg/mL PGE1, pH 6.0 (platelet wash buffer) by centrifugation. Washed platelets were re-suspended at a concentration of $1\times10^9$/mL in 140 mM NaCl, 3 mM KCl, 0.5 mM $MgCl_2$, 5 mM $NaHCO_3$, 10 mM glucose and 10 mM HEPES, pH 7.4 (platelet resuspension buffer), labeled with 5 µM 5-chloromethylfluorescein diacetate (CMFDA) for 15 min at 37° C. Unincorporated dye was removed by centrifugation and platelets suspended in plasma. DANA, sialyllactose, and glucose (as a nutrient) were added to final concentrations of 0.5, 0.5 and 8 mM, respectively, from their corresponding PBS stock solutions. Only PBS was added to the controls. The platelet suspensions were stored at 4° C. or RT for 48 h. After 48 h, the stored platelets were transfused by retro-orbital injection of $3\times10^8$ platelets in 200 µL. Following transfusion, blood was collected by retro-orbital eye bleeding at time points of 5 min, 2, and 24 h. The percentage of CMFDA positive platelets in PRP was determined by flow cytometry.

Figure 28:
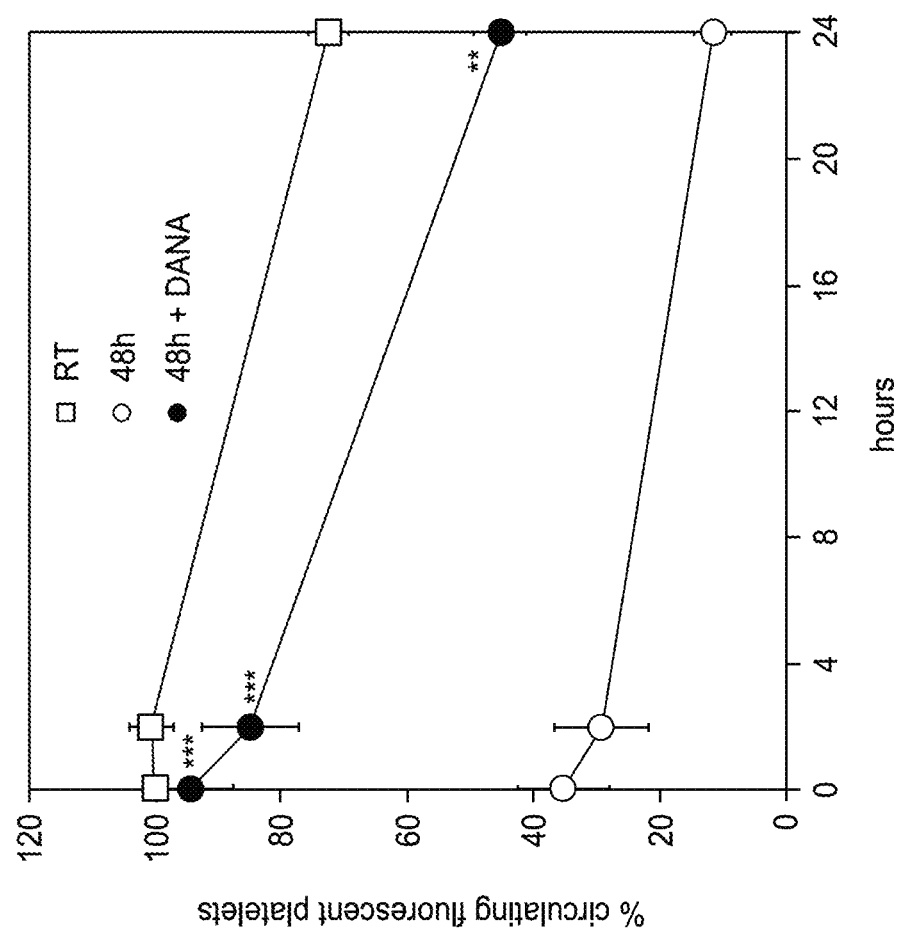
FIG. 28 is a line graph depicting the survival of mouse platelets stored for 48 h by refrigeration in the absence (48 h) or presence of 1 mM DANA (48 h+DANA) in the storage solution. The survival of fresh, isolated platelets (RT) is shown for comparison, n=7 for each survival graph.
Figure 29:
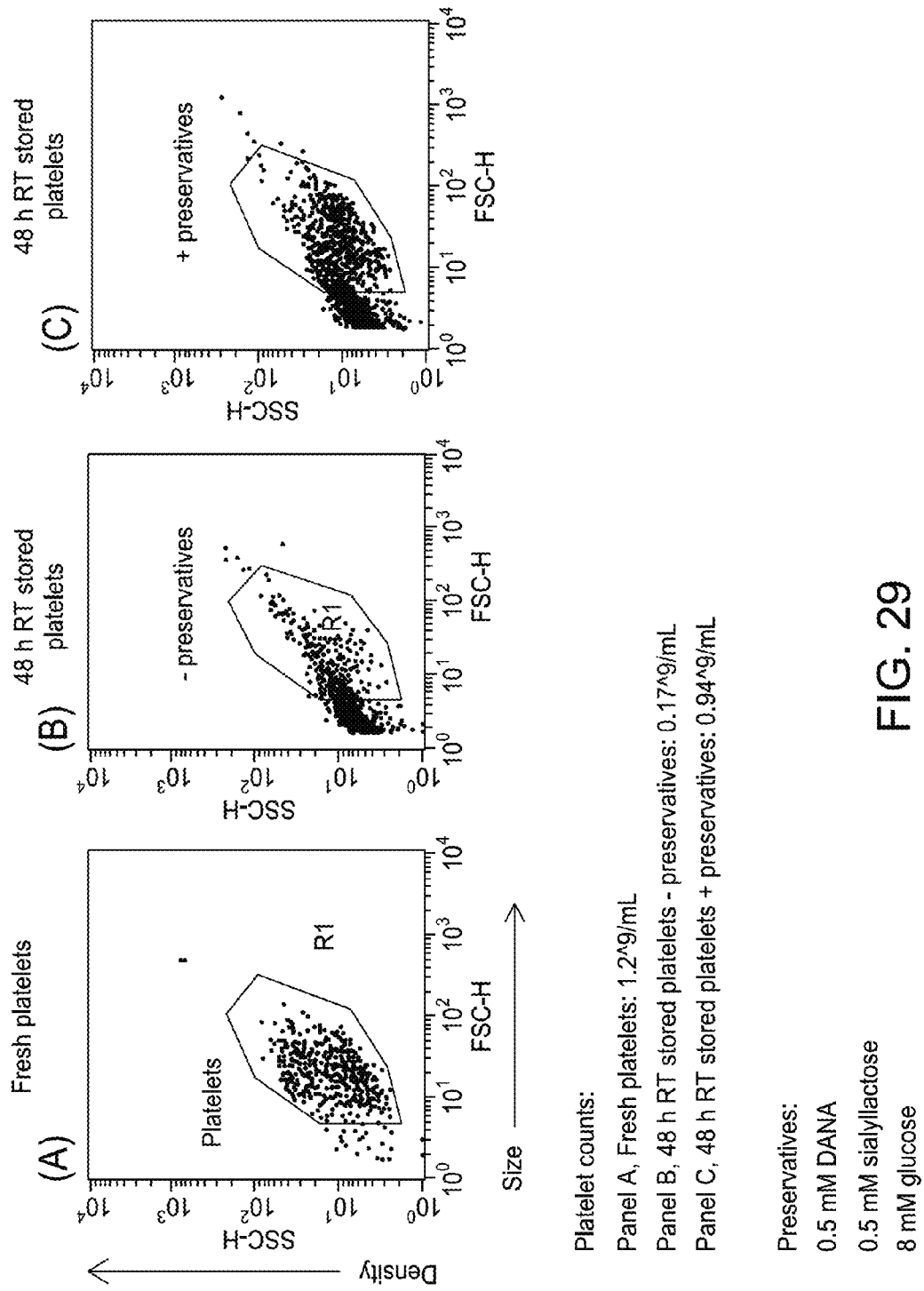
FIG. 29 is a flow cytometry analysis of fresh platelet (Fresh platelets) size and density (A) and the combined effect of DANA, sialylactose, and glucose on stabilizing RT-stored mouse platelet integrity, as judged by their size (FSC) and density (SSC). Analysis of mouse platelets stored for 48 h at RT in the absence (− preservatives) (B) and presence (+ preservatives) (C) of sialylactose, glucose, and DANA is shown. The corresponding platelet numbers are shown below the dot plots. The concentration of the preservatives is also shown.

Results:

All samples were visually inspected for evidence of bacterial contamination. Severe plasma color bleaching was observed for the room temperature-stored platelet in the absence of DANA, suggesting bacterial growth. No visible change was noted under all other conditions. The recovery and survival of mouse platelet, stored for 48 h at RT in the presence of platelet preservatives is greatly improved compared with stored platelets lacking preservatives (FIG. 28). Mouse platelets deteriorate rapidly when stored at RT, which is clearly shown in FIG. 29. Importantly, in the presence of DANA, sialyllactose, and glucose in the storage media approximately 5-fold more platelets were recovered (FIG. 29) compared to control samples.

Conclusion:

Sialidase inhibitor DANA is capable of effectively preserving mouse platelets from deterioration during storage and greatly improving the recovery and survival of transfused platelets.

Example 8

Preservation of Mouse Platelets in the Presence of Different Concentrations of DANA DANA is a potent, broad-spectrum sialidase inhibitor against viral, bacterial and mammalian sialidases with Ki in the low µM range. It is used routinely at 1 mM in all our studies. It is expected that its concentration can be dramatically lowered while maintaining its efficacy against the bacteria-caused deterioration of stored mouse platelets.

Materials and Methods:

Mouse platelets were isolated as described in Example 3, re-suspended in platelet resuspension buffer and split to four aliquots. Glucose was added 8 mM to all samples, and DANA was added to final concentrations of 0, 0.1, 1.0, and 10 mM, respectively, both from 100 mM stock solutions in PBS. The samples were incubated for 30 min at 37° C., centrifuged and supernatants removed. The platelets resuspended in plasma. DANA and glucose were restored to their initial concentrations. The platelet suspensions were stored at RT. After 48 h, platelets under each storage condition were counted by flow cytometry.

Figure 30:
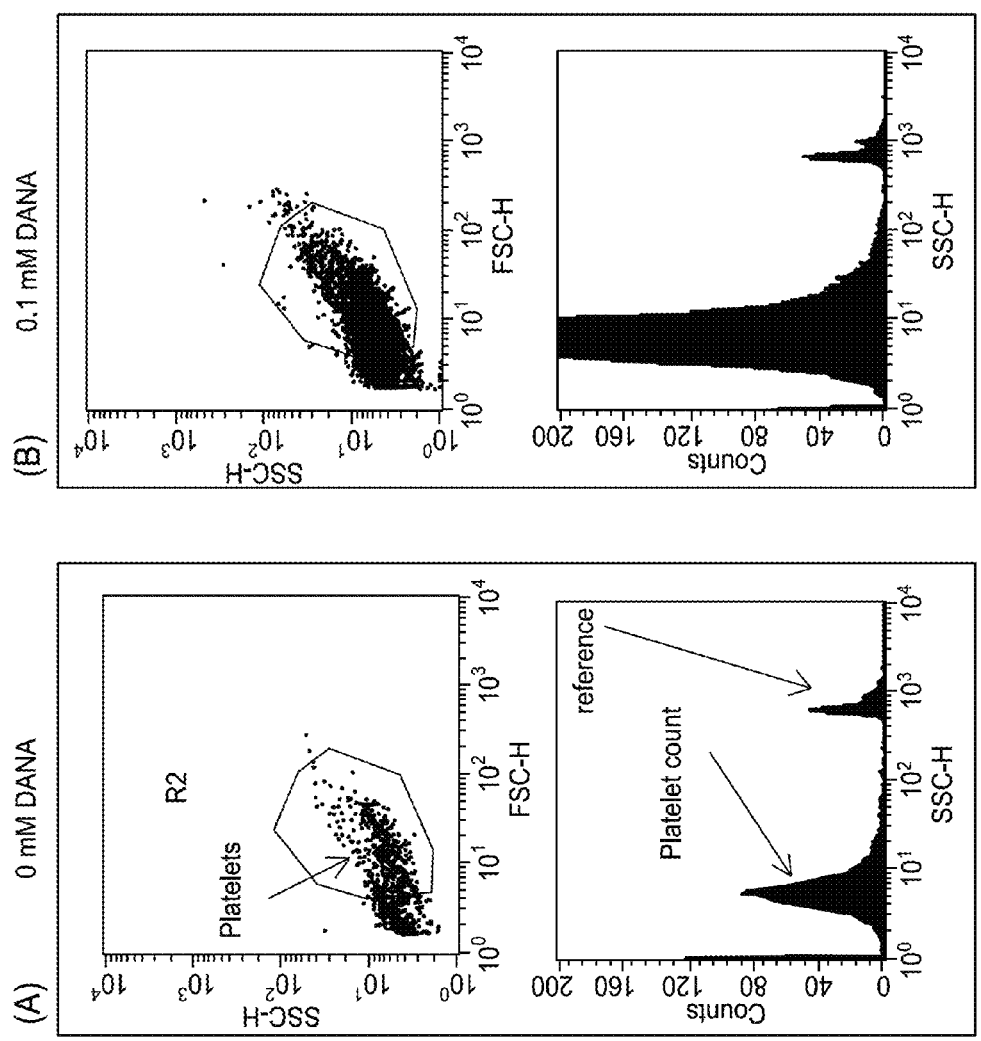
FIGS. 30 (A) (B) (C) & (D) is a flow cytometry dot plot analysis of mouse platelets stored at RT for 48 h in the absence (0 mM DANA; shown in panel (A) or presence of DANA at the indicated concentrations (0.1, 1.0, 10.0 mM DANA as shown in panels (B), (C), and (D), respectively). Note that 0.1 mM DANA efficiently preserved the size and density of platelets as judged by dot plot analysis. The dot plots are shown in the top panels. Corresponding flow cytometry histograms of platelet counts and beads (reference) are also shown (lower panels).
Figure 30:
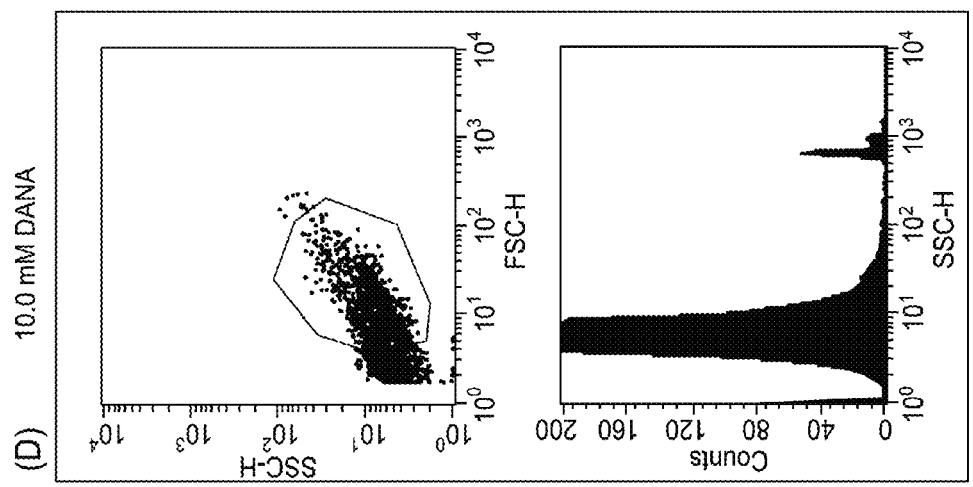
Figure 30:
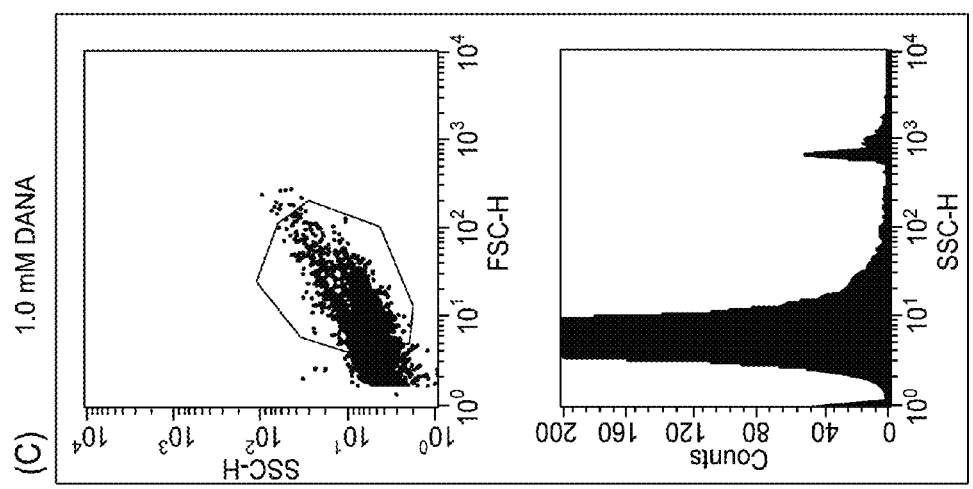

Results:

Mouse platelets perish rapidly when stored at RT, which is clearly shown in FIG. 30A. However, in the presence of mere 0.1 mM DANA in the storage media, approximately 5-fold more platelets were recovered (FIG. 30B). Further results for other concentrations of DANA are shown in FIG. 30C and FIG. 30D.

Conclusion:

Sialidase inhibitor DANA is capable of effectively preserving mouse platelets from deterioration, greatly improving the recovery and survival of the transfused platelets.

Example 9

Inhibition of the Proliferation and Biofilm Formation of *Serratia marcescens* by Sialidase Inhibitor DANA Bacterial contamination of blood products is currently the most significant transfusion-associated infectious risk. Platelet concentrates (PCs) are the most likely product to be contaminated due to their storage conditions (22° C. with agitation, neutral pH, and high glucose content), which are particularly amenable to bacterial growth. Although Gram-positive bacteria are most commonly recovered from contaminated PCs, Gram-negative bacteria are more frequently associated with severe illness and fatality. Gram-negative *Serratia marcescens* is a significant human opportunistic pathogen, which has been implicated in numerous adverse transfusion reactions (ATRs) involving contaminated PCs. The ability of this species to survive under unfavourable environmental conditions, resist disinfection and form surface-associated communities of micro-organisms (biofilms) presents a challenge for its elimination in the clinical environment. Recently, it has been shown that the closely related species *Serratia liquefaciens* forms biofilms under platelet storage conditions, which is associated with reduced detection by colony counting.

In order to proliferate in platelet products, the contaminated bacteria are likely to have a machinery to obtain and/or utilize sialic acid. *Serratia marcescens* is a Gram-negative bacterium that has been implicated in adverse transfusion reactions associated with contaminated platelet concentrates. It produces a range of extremely virulent products including proteases, nucleases, lipases, chitinases and haemolysin; however, the presence of a secreatable sialidase has not yet been described. Based on the virulent characteristics of the secreted products by *Serratia marcescens*, the presence of sialidases is highly plausible. Therefore, this strain was chosen to test our sialidase-inhibition strategy to inhibit bacterial growth. The *Serratia marcescens* strain (ATCC #43862) has previously been used in studies involving bacterial detection and growth in blood products.

Materials and Methods:

Bacterial Strain and Growth Conditions:

*Serratia marcescens* strain (ATCC #43862) was purchased from American Type Culture Collection (Manassas, Va.). Cells were grown in brain-heart infusion broth (ATCC media 3) at 37° C. and 250 rpm. Frozen stocks were prepared from overnight culture and stored at −80° C. in brain-heart infusion broth containing 15% glycerol by volume.

Biofilm Formation:

To prepare the seed culture, the cryostock of *Serratia marcescens* was inoculated into 3 mL of brain-heart infusion broth with a cotton swab and incubated at 37° C. with agitation at 250 rpm for 6 h. The cell density was determined at 600 nm on a dual wavelength spectrometer and diluted to 0.5 McFarland Standard ($1.5 \times 10^8$ cells/mL) with sterile PBS. Ten µL of the diluted culture was inoculated into 140 µL of 30% plasma in PAS, 30% PC by volume in PAS or 100% plasma, supplemented with or without 1 mM DANA, in the wells of 96-well PVC plates (Corning Biosciences). For each media, six replicates were performed. Ten µL of PBS was inoculated into the control wells. The microtiter plates were then sealed with sterile porous film (VWR) and placed on a platform shaker. The cultures were incubated for 48 h with gentle shaking (~100 rpm). The cultures were gently mixed and transferred to a polystyrene plate for the determination of planktonic cell density at OD 595 nm. The wells on the original microtiter plates were washed with 3×200 µL of PBS, air dried, stained for 15 min with an aqueous solution of 0.1% (wt/vol) crystal violet, rinsed with water, and air dried for 1 hr. The crystal violet retained by the biofilm was eluted with 200 µL of dimethyl sulfoxide (DMSO) or 30% acetic acid, and read at 595 nm.

Figure 31:
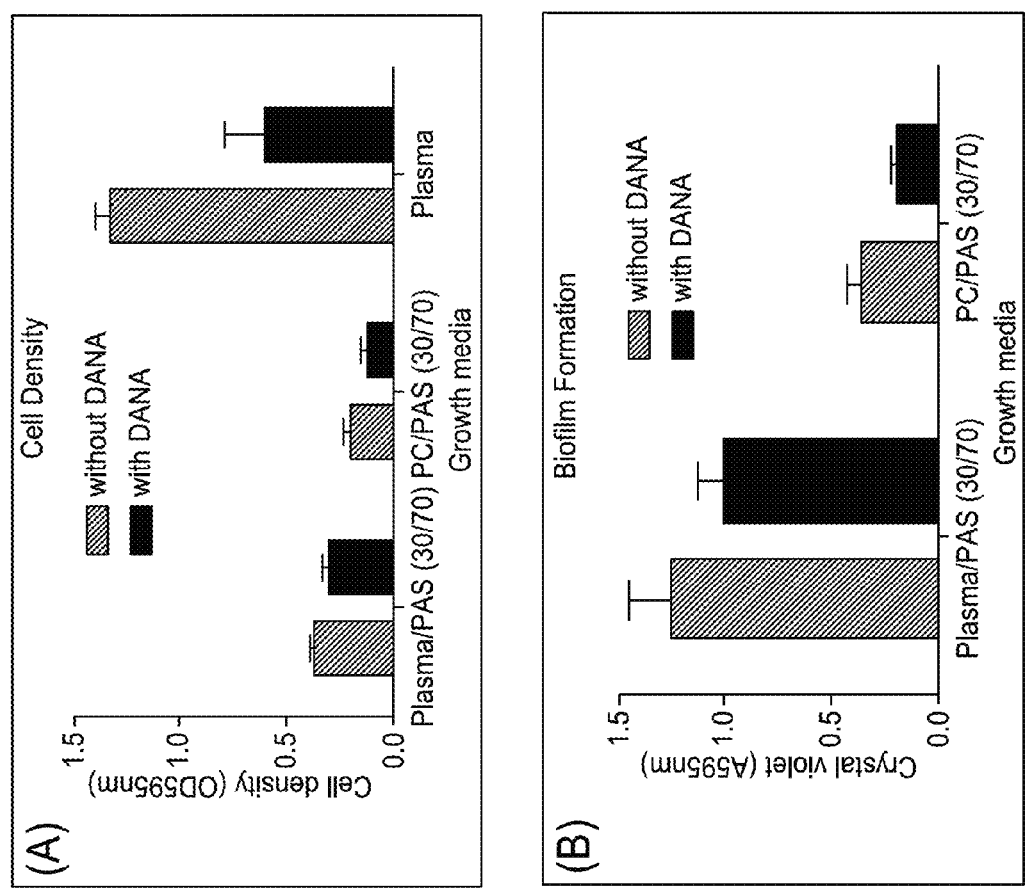
FIG. 31 shows bar graphs depicting the cell density of S. marcescens grown for 48 h in different media with or without 1 mM DANA in the wells of 96-well PVC plate (panel (A)).

Results:

Under suboptimal growth conditions on the microtiter plate, lacking of adequate agitation and aeration, and low temperature, S. marcescens grew well in pure plasma (FIG. 31A). The cell growths were dramatically retarded in 30% plasma or 30% PC in PAS. Remarkably, inclusion of 1 mM DANA in the growth media inhibited the bacterial growth under all conditions. In parallel with trends observed for bacterial growth, the formation of biofilm correlated well with planktonic cell density and negatively impacted by the presence of DANA in the growth media (FIG. 31B). The measurement of the A595 nm of the biofilm formation for the bacteria grown in plasma could not be accurately interpreted due to the signal overflow, suggesting stronger biofilm formation in pure plasma than in PAS-based media.

Conclusion:

Sialidase inhibitor DANA is capable of inhibiting the proliferation and biofilm formation of S. marcescens when analyzed with 96-well PVC plate. The data also show that S. marcescens contains a previously unreported machinery to obtain and/or utilize sialic acid to proliferate and/or form biofilms.

Example 10

Variations in Platelet Surface Glycans Among Healthy Volunteers

Platelets have the shortest shelf-life of all major blood components and are the most difficult to store; these limitations complicate platelet transfusion practices. Dr. Slichter and colleagues (Puget Sound Blood Center, Seattle, Wash.) have identified significant differences in recovery and survival of transfused fresh radiolabeled autologous platelets among healthy subjects. The cause of the inter-individual differences in platelet recovery and survival remains unclear. We demonstrated that the loss of sialic acid from the surfaces of cold-stored and transfused platelets promotes their clearance by hepatic Asialoglycoprotein receptors (Ashwell Morell receptors). The loss of platelet surface sialic acid correlates with increases in surface sialidase activity during platelet storage. Here we investigated whether fresh platelets from individual donors exhibit differences in surface glycan exposure, which may affect post-transfusion platelet recovery and survival.

Material and Methods:

Venous blood was obtained from volunteers by venipuncture into 0.1 volume of Aster Jandl citrate-based anticoagulant. Approval for blood drawing was obtained from the Institutional Review Board of Brigham and Women's Hospital, and informed consent was approved according to the Declaration of Helsinki Platelet-rich plasma (PRP) was prepared by centrifugation at 125×g for 20 min and platelets were separated from the plasma proteins by gel-filtration through a small Sepharose 2B column. Isolated platelets were incubated for 20 min at room temperature with 10 µg/mL of the β-galactose specific FITC-conjugated E. cristagalli lectin (ECL). The samples were diluted with 200 µL of PBS and immediately analyzed by flow cytometry on a FACSCalibur flow cytometer (Beckton Dickenson). The mean fluorescence intensity was determined in gated platelet population.

Figure 32:
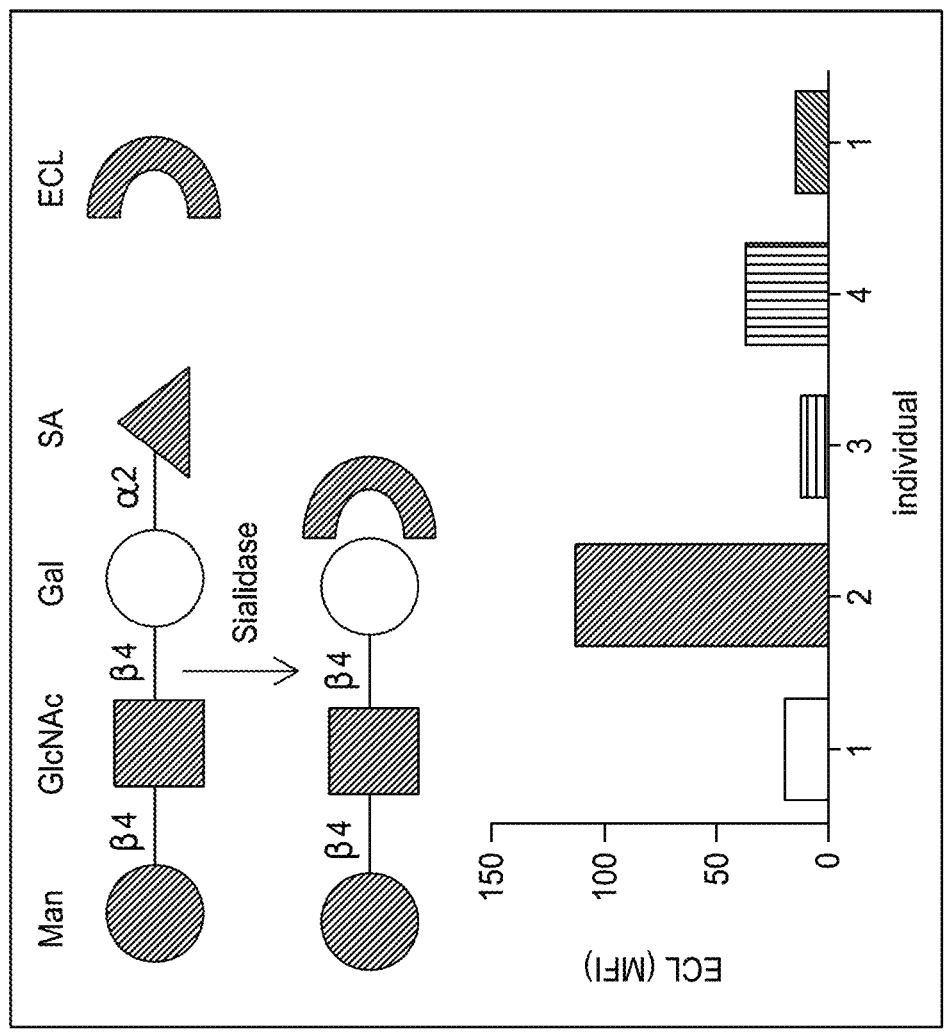
FIG. 32 is a bar graph showing the differences in terminal β-galactose content on fresh platelets isolated from healthy subjects. Platelet surface terminal galactose exposure was measured by flow cytometry using the β-galactose specific lectin ECL, as depicted in the schematic drawing of lectin binding to a glycan-structure.

Results:

The presence of a terminal galactose on surface glycoproteins (i.e. glycans lacking of SA) on freshly-isolated platelets varies considerably among healthy subjects (three of five individuals had low levels of exposed galactose (15.3±4.1, MFI), as expected. However, two subjects exhibited considerably higher (2-7.5-fold) levels of galactose exposure. These results were confirmed using a second galactose-specific lectin RCA I, and by repeated measurements of the same individuals at two different time points. Similarly, preliminary studies with platelet concentrates demonstrated a remarkable variation in platelet surface sialidase activity (FIG. 32), which correlated with rates of sialic loss during platelet storage and possibly during platelet circulation in vivo. Our results show that fresh platelets from healthy individuals vary in surface sialidase activity and sialic acid content.

These results indicate that the surface sialic acid could represent a factor that affects the recovery and survival of the transfused fresh platelets.

Example 11

General Procedure of Preparing Platelet Additive Solution Containing a Sialidase Inhibitor The PAS of the present invention can be made as follows. The total volume of the bag is 500 mL.

To prepare a platelet additive solution, the following components of USP grade are obtained:

1) Electrolytes such as Na, Cl, K, Ca, and Mg.
2) An energy source such as glucose or citrate to sustain aerobic metabolism.
3) A buffer such as phosphate.
4) Water for injection (WFI).
5) A sialidase inhibitor.

Table 2 provides the concentrations and amount (grams) of components including energy sources, buffers and electrolytes required to prepare 1000 mL of platelet additive solution. Water is added in an amount of 1000 mL and the solution is buffered to maintain a pH of pH 7.2.

Sialidase inhibitor such as DANA can be added from sterile 0.1-1000 mM stock solution in water to the desired concentrations.

TABLE 2

| Component | PAS 1 | | PAS 2 | | PAS 3 | | PAS 4 | |
|---|---|---|---|---|---|---|---|---|
| | mM | g/L | mM | g/L | mM | g/L | mM | g/L |
| Dibasic sodium phosphate, anhydrous ($Na_2HPO_4$), USP | 7.15 | 1.015 | 7.15 | 1.015 | 7.15 | 1.015 | 7.15 | 1.015 |
| Mono basic phosphate, monohydrate ($NaH_2PO_4 \cdot H_2O$), USP | 2.24 | 0.310 | 2.24 | 0.310 | 2.24 | 0.310 | 2.24 | 0.310 |
| Sodium citrate, dihydrate (C6H5Na3O7•2H2O), USP | 10.00 | 2.940 | 10.00 | 2.940 | 10.00 | 2.940 | 10.00 | 2.940 |
| Sodium acetate, trihydrate ($CH_3COONa$), USP | 29.98 | 4.080 | 29.98 | 4.080 | 29.98 | 4.080 | 29.98 | 4.080 |

TABLE 2-continued

| Component | PAS 1 mM | PAS 1 g/L | PAS 2 mM | PAS 2 g/L | PAS 3 mM | PAS 3 g/L | PAS 4 mM | PAS 4 g/L |
|---|---|---|---|---|---|---|---|---|
| Sodium chloride (NaCl), USP | 79.20 | 4.629 | 70.80 | 4.138 | 77.70 | 4.541 | 69.30 | 4.050 |
| Potassium chloride (KCl), USP | 5.00 | 0.373 | 5.00 | 0.373 | 5.00 | 0.373 | 5.00 | 0.373 |
| Magnesium chloride, hexahydrate ($MgCl_2 \cdot 6H_2O$), USP | 1.50 | 0.305 | 1.50 | 0.305 | 1.50 | 0.305 | 1.50 | 0.305 |
| Calcium chloride, dihydrate ($CaCl_2 \cdot 2H_2O$), USP | 0.00 | 0.000 | 0.00 | 0.000 | 1.00 | 0.147 | 1.00 | 0.147 |
| Glucose ($C_6H_{12}O_6$), USP | 0.00 | 0.000 | 16.80 | 3.028 | 0.00 | 0.000 | 16.80 | 3.028 |
| DANA, sodium salt (solid or stock aqueous solution) | 1.00 | 0.313 | 1.00 | 0.313 | 1.00 | 0.313 | 1.00 | 0.313 |
| Water for injection, USP, to 1000 mL | | | | | | | | |

Example 12

Preservation of Mouse Platelets in PAS Containing a Sialidase Inhibitor

Mouse platelets have a life span of approximately 4-5 days, considerably shorter than human platelets (8-10 days). They are also much less stable than human platelets when stored at room temperature or 4° C. However, these shortcomings of mouse platelets can be exploited to assess the efficiency of platelet additive solutions for the preservation of platelets.

Materials and Methods:

Mouse blood was obtained from anesthetized mice using 3.75 mg/g of Avertin (Fluka Chemie, Steinheim, Germany) by retro-orbital eye bleeding into 0.1 volume of Aster-Jandl anticoagulant and centrifuged at 200×g for 8 min at RT. The supernatant, containing platelet rich plasma, buffy coat, and some RBC, was removed and centrifuged at 300×g for 6 min to obtain platelet rich plasma (PRP). Four 150 μL aliquots of PRP were transferred to 4×1.5 mL Eppendorf tubes, and centrifuged at 1000×g for 5 min. About 70% of the supernatant (105 μL) was removed from each tube, and replaced with equal volume of INTERSOL® solution. DANA and/or glucose (as a nutrient) were added to final concentrations of 1.0 and 10 mM, respectively, from 100 mM stock solutions in PBS. The volumes in tubes lacking one or both additives were evened out with PBS. The platelet suspensions were stored at RT for 48 h on a shaker and analyzed by flow cytometry.

Figure 33:
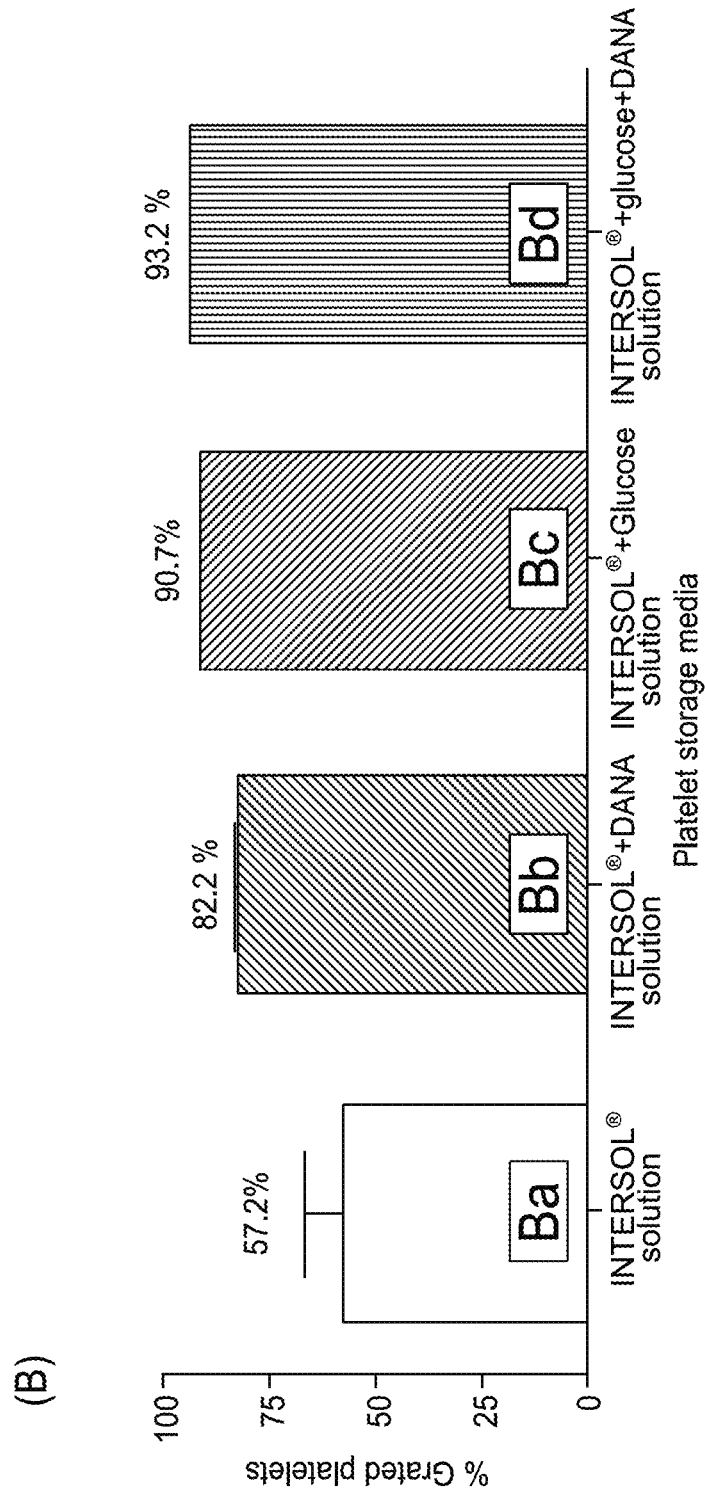
FIGS. 33(Aa), (Ab), (Ac), & (Ad) and FIG. 33(B) are a flow cytometry dot plot analysis and corresponding flow cytometry histograms (depicted in FIG. 33 (Aa), (Ab), (Ac), and (Ad)) of mouse platelets stored in 30% plasma and 70% PAS (referred to as INTERSOL® solution) by volume at RT for 48 h in the absence of additive (INTERSOL® solution) (depicted in (Aa)), the presence of 1 mM DANA (INTERSOL® solution+DANA) (depicted in (Ab)), 10 mM glucose (INTERSOL® solution+Glucose) (depicted in (Ac)), and 1 mM DANA plus 10 mM glucose (INTERSOL® solution+

Results:

Not surprisingly, mouse platelets deteriorated rapidly in INTERSOL® solution, when stored at RT (FIG. 33, panel Aa). Only 57% platelets were gated (FIG. 33, panel Ba). Remarkably, over 80% of the original platelet events were counted within the platelet gate when stored with 1 mM sialidase inhibitor DANA (FIG. 33, panels Ab and Bb). Addition of 10 mM glucose resulted in even higher platelet counts recovery after storage (FIG. 33, panels Ac and Bc). A combination of both DANA and glucose preserved all platelets (93% gated, FIG. 33, panels Ad and Bd). DANA alone or a combination with glucose results in a more resting platelet population as judged by their forward and side scatter characteristics (the population is "less elongated", i.e., formed less platelet aggregates) than glucose alone (FIG. 33, panels Ab and Ad, compare with FIG. 33, panel Ac). This data suggests that DANA is more effective than glucose in preserving platelets in a resting state and in preserving platelet numbers following platelet storage.

Conclusion:

Together, the data indicate that the presence of DANA during platelet storage improves the quality of the stored platelets in at least 30% plasma in platelet additive INTERSOL® solution.

Example 13

Improved In Vitro Quality of Human Platelets Stored in Plasma in the Presence of Sialidase Inhibitor DANA The state of a "healthy" platelet is partially defined by its shape and size. Platelet shape change and aggregation are hallmarks of platelet activation. Once activated, platelets change shape and secrete their granular contents. Storage of platelets is accompanied by platelet activation, i.e. platelet shape change and granule release. Human platelets also increase surface sialidase expression and lose surface sialic acid during storage. Presumably, sialidases are stored in granules and are released to the platelet surface during storage. The results from Example 12 suggest that mouse platelets may also lose sialic acid during storage and this process can be effectively inhibited by the presence of sialidase inhibitor DANA in the storage, greatly improving the post-transfusion recovery and survival of platelets. The data further indicate that the quality of stored human platelets can be improved by including a sialidase inhibitor in the storage media.

Resting platelets have a discoid shape and produce different side-scatter (SSC) signals in the flow cytometer, depending on their relative orientation to the laser beam. A resting platelet population has a wide ("round") distribution in the SSC/FSC signal. Upon stimulation, platelets form pseudopods and become spherical (shape change) thereby producing a characteristic SSC signal irrespective of their relative orientation to the laser beam. Therefore, an activated platelet population appears more "condensed" on a FCS/SSC plot.

Based on these considerations, we investigated if DANA affects human platelet activation (i.e. shape change and granule release) during storage in plasma.

Materials and Methods:

Venous blood was obtained from volunteers by venipuncture into 0.1 volume of Aster Jandl citrate-based anticoagulant. Approval for blood drawing was obtained from the Institutional Review Board of Brigham and Women's Hospital, and informed consent was approved according to the Declaration of Helsinki Platelet-rich plasma (PRP) was prepared by centrifugation at 125×g for 20 min and platelets were separated from PRP after adding PGE1 (1 μg/mL) by centrifugation for 5 min at 850×g. The supernatant (platelet-poor plasma, PPP) was saved. The platelet pellet was resuspended in PPP, ½ volumes of original PRP, and divided into aliquots. DANA was added to 1.0 mM from 100 mM stock in PBS to half of the aliquots, only PBS was added to the controls. The samples were stored in the wells of a 96-well microtiter plate covered with a gas-permeable film with agitation on a shaker at room temperature. Platelet size and density were measured by forward (FSC) and side scatter (SSC) on a FACSCalibur flow cytometer (BD). Platelets were gated by their forward and side scatter characteristics. For the analysis platelet degranulation, i.e., α-granule release, stored platelets were analyzed for P-selectin surface expression by incubating with 0.1 µg/mL of FTIC mouse anti-human CD62P (BD Pharmingen) antibody in 50 µL of PBS for 30 min at RT. The mixture was then diluted with 200 µL of PBS and immediately analyzed by flow cytometry. The percentage of P-selectin (FITC)-positive cells was determined in gated platelet population.

Figure 34:
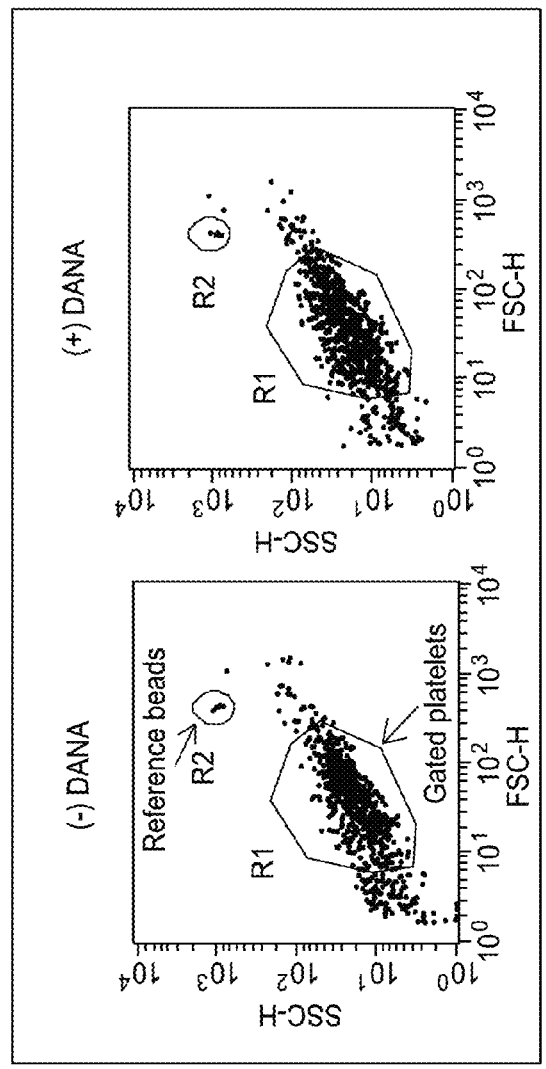
FIG. 34 is a representative flow cytometry dot plot analysis of platelets stored in the absence ((−) DANA) or presence of 0.5 mM DANA ((+) DANA) (upper panel (A)). A corresponding histogram of platelet counts vs side scatter (SSC) is also shown (lower panel (B)). The table represents the mean fluorescence intensity (MFI) measured in the side scatter (SSC-H (MFI)) in the absence or presence of DANA.
Figure 34:
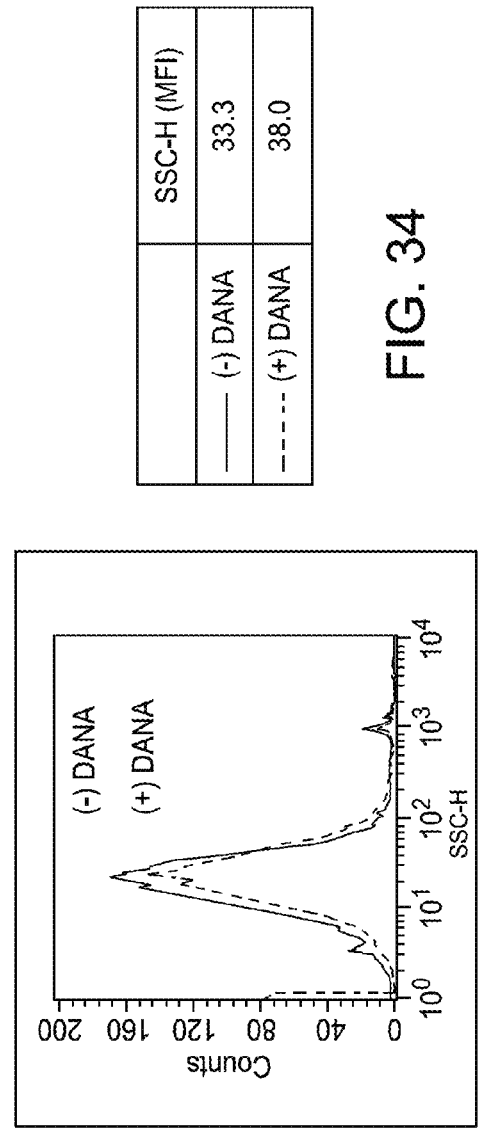

Results:

After 72 h storage at RT in plasma, human platelets displayed a decrease in side and forward scatter characteristics (FIG. 34, panel A, left side) compared with fresh RT platelets (not shown). The decrease in side and forward scatter characteristics is characteristic for platelet activation. In contrast, addition of 0.5 mM DANA during platelet storage led a visible improvement of the platelet shape (FIG. 34, panel B, right side). Comparisons of histograms of platelet count/SSC showed that platelets stored with DANA have increased mean fluorescence intensity (MFI), (FIG. 34, panel B, left side, note that the profile migrates slightly to the right side), suggesting that platelets stored in the presence of DANA have higher granularity or internal complexity and are less activated. Similarly, histograms of platelet count/FSC histograms showed that platelets stored with DANA have higher side scatter mean fluorescence intensity (FIG. 34, panel B, right side, note that the profile migrates slightly to the right side). These results show that platelets stored in the presence of DANA are bigger and retain a discoid, resting shape.

Figure 35:
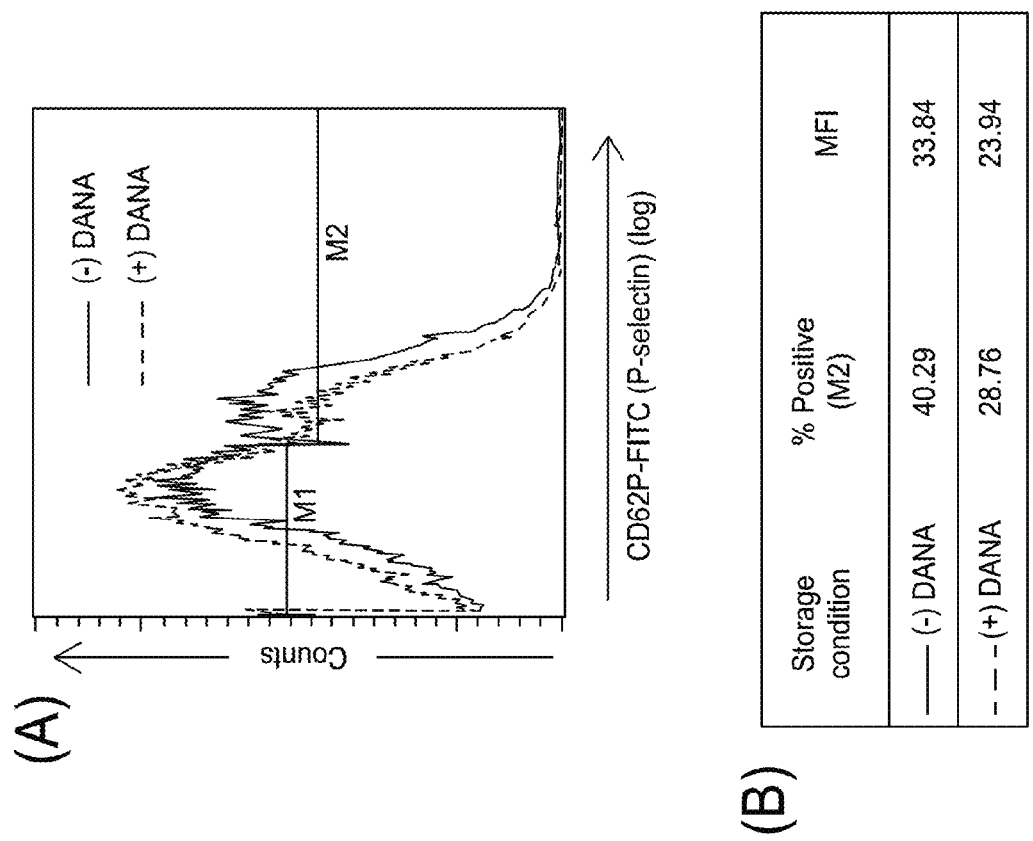
FIG. 35, panel (A), is a representative flow cytometry histogram analysis of surface P-selectin exposure after human platelet storage in plasma in the absence or presence of DANA as described in FIG. 34. P-selectin exposure was measured using a monocolonal FITC conjugated antibody to P-selectin (CD62P-FITC).

These results were confirmed by analyzing the P-selectin exposure of the stored platelets with FTIC mouse anti-human CD62P (P-selectin) antibody (FIG. 35). Inclusion of DANA during storage significantly prevented the exposure of P-selectin, and inhibited α-granule release.

Together, the data indicate that the presence of DANA during platelet storage improves the quality of the stored platelets in 100% plasma.

Example 14

Improved In Vitro Quality of Human Platelets Stored in PASs Containing Sialidase Inhibitor DANA Data described in Example 12 demonstrated that sialidase inhibitor DANA can effectively preserve the quality of mouse platelets stored 30% plasma in platelet additive solution referred to as INTERSOL® solution. Data described in Example 13 clearly showed that DANA is also effective for preserving the quality of human platelets in 100% plasma. In this Example, the studies were extended to human platelets stored in plasma/PAS in a ratio of 30:70, in the absence or presence of DANA.

Materials and Methods:

Human platelets were obtained as described in Example 13. The platelet pellet was resuspended in PPP, ⅕ volumes of original PRP, and aliquoted into wells of a 96-well microtiter plate (60 µL per well). PAS (designated as PASa), containing 7.15 mM $Na_2HPO_4$, 2.24 mM $NaH_2PO4$, 10 mM sodium citrate, 30 mM sodium acetate, 79.2 mM NaCl, 5.0 mM KCl, and 1.5 mM $MgCl_2$, was added to corresponding wells at 140 µL per well, DANA was added to 0, 0.1, and 0.5 mM from 10 or 100 mM stock in PBS to proper wells. The sample volumes in the wells were evened out with PBS. The plate was then covered with a gas-permeable film and placed on a shaker. Platelet size and density were measured by forward (FSC) and side scatter (SSC) on a FACSCalibur flow cytometer (BD) at Day 7, and pH was checked at Day 9.

Figure 36:
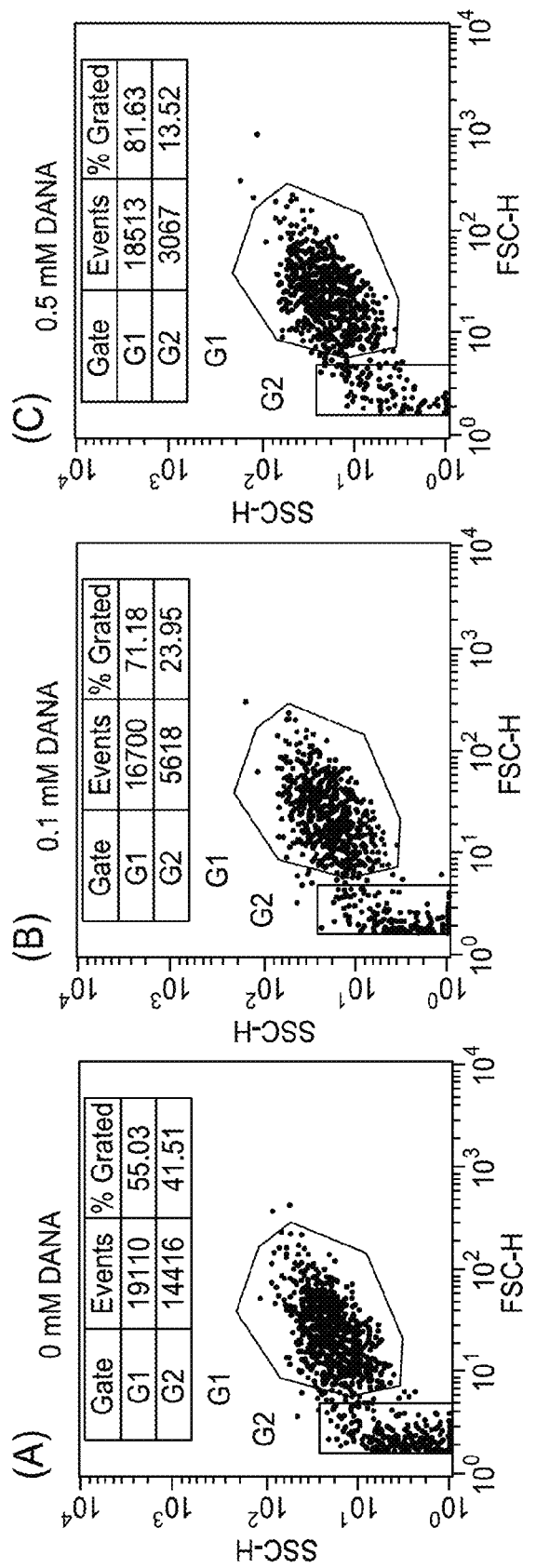
FIG. 36 is a flow cytometry dot plot analysis of human platelets stored at RT for 7 days in 30% plasma and 70% PAS solution (by volume) (PASa, 7.15 mM $Na_2HPO_4$, 2.24 mM $NaH_2PO_4$, 10 mM sodium citrate, 30 mM sodium acetate, 79.2 mM NaCl, 5.0 mM KCl, and 1.5 mM $MgCl_2$, pH 7.2) in the presence of 0 (A), 0.1 (B) and 0.5 (C) mM DANA. The platelets are defined in 'G1' while the platelet microparticles are defined in 'G2'. The gate statistics are shown for each dot plot.

Results:

All storage samples maintained at pH 6.8 after 9 days, demonstrating this PAS formulation has enough buffer capacity for storing platelets for at least 9 days. In contrast, under similar storage conditions in 100% plasma, the pH of the stored platelet samples dropped below pH 6.5. Significant deterioration of human platelets was noted after 7 days of storage at RT when stored in 30% plasma and 70% PAS solution. As shown in FIG. 36, panel A, only 55% of the total acquired events were gated in the gate defined for fresh platelets (G1) while more than 40% of the acquired total events were platelet microparticles (platelet microparticles are considered as a readout of platelet deterioration) defined in G2. In contrast, when platelets were stored in the presence of 0.1 mM DANA over 70% of the total acquired events were gated as platelets (FIG. 36, panel B, G1). Accordingly, a dramatic reduction of microparticle formation from 41.5% (FIG. 36, panel A, G2) to 23.95% (FIG. 36, panel B, G2) was observed. Increase of DANA concentration in the storage media to 0.5 mM further increased platelet counts (81.6% gated, FIG. 36, panel C, G1) and reduced the formation of microparticles (13.52%, G2). Of particular note is that the platelet population appears "resting" upon addition of DANA to the storage solution, as judged by their side and forward scatter characteristics.

Conclusion:

Consistent with results described in Examples 12 and 13, DANA can effectively preserve the quality of human platelets in 30% plasma in a platelet additive solution, i.e., reduce platelet activation and microparticle formation, showing that a sialidase inhibitor such as DANA can be used as an important component in PAS formulations for platelet storage.

Example 15

Figure 42:
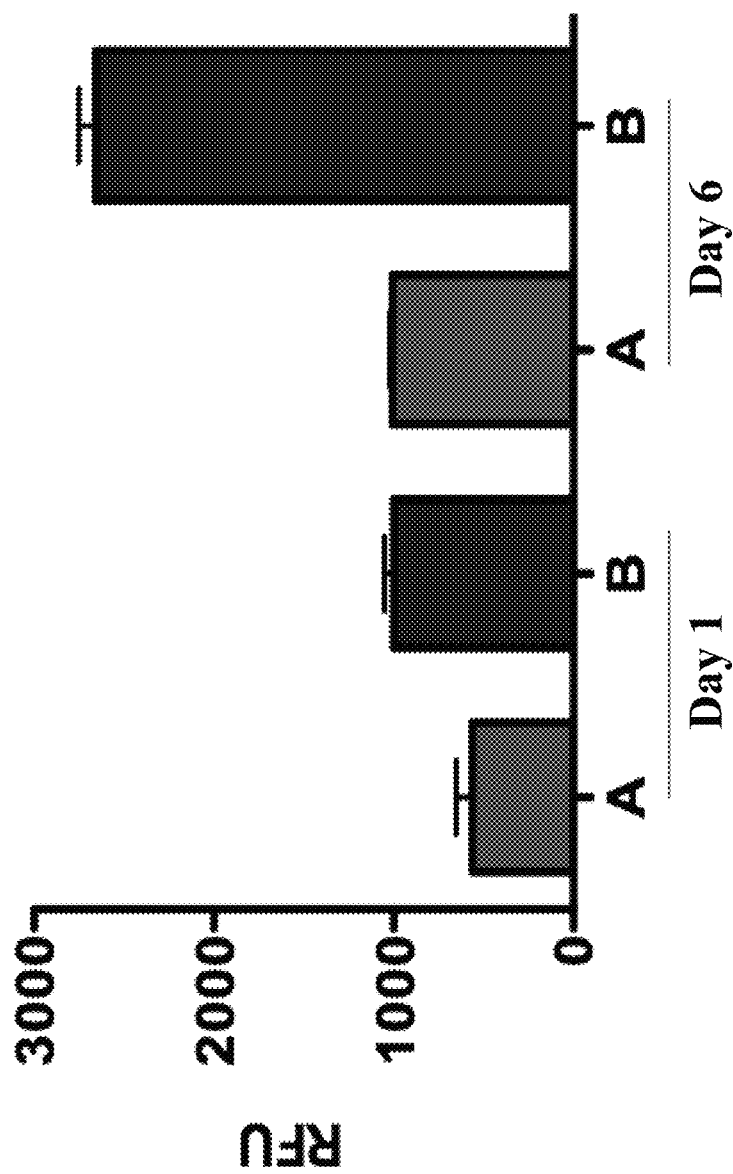
FIG. 42 is a bar graph showing the analysis of platelet surface sialidase activity. The enzyme activity was determined using a fluorometric assay by incubating the platelets isolated from platelet concentrates (Bag A or B), with 4-MU-NeuAc. The product 4-MU can be quantified by 355Ex/460Em at pH>10. The donors exhibited variable platelet surface sialidase activity at the early stage of the storage (Day 1), which became up-regulated after further storage (Day 6). Donor B has higher activity than Donor A on both Day 1 and Day 6. Sialidase activity on platelet surface increases during room temperature storage.

Variability of Platelet Surface Sialidase Activities Among Healthy Individuals and Up-Regulation of these Activities During Platelet Storage at RT Platelets have the shortest shelf life of all major blood components and are the most difficult to store; these limitations complicate platelet transfusion practices. The loss of sialic acid from the surfaces of cold-stored and transfused platelets promotes clearance of platelets by hepatic Asialo-glycoprotein receptors (Ashwell-Morell receptors). The loss of platelet surface sialic acid correlates with increases in surface sialidase activity during platelet storage under refrigeration. Significant differences have been identified in recovery and survival of transfused fresh radiolabeled autologous platelets among healthy subjects. The cause of the inter-individual differences in platelet recovery and survival remains unclear. Here, we investigated whether fresh platelets from individual donors exhibit differences in surface sialidase expression that may lead to differential β-galactose exposure and affect post-transfusion platelet recovery and survival.
Methods:

Platelets were isolated from platelet concentrates (PC) stored under blood banking conditions by centrifugation, washed, re-suspended at a concentration of $1$-$10\times10^9$/mL in 140 mM NaCl, 3 mM KCl, 0.5 mM $MgCl_2$, 5 mM $NaHCO_3$, 10 mM glucose, and 10 mM Hepes, pH 7.4 (buffer A). Platelet sialidase activity was determined by incubation of platelets (~$10^8$ platelets) at 37° C. with 125 μM 2'-(4-methylumbelliferyl)-α-D-N-acetylneuraminic acid (4-MU-NANA) in 100 mM NaOAc (pH 5.0), 80 mM NaCl. Reaction mixtures were sampled at various time points and the reactions were quenched with 1.5 volumes of 200 mM glycine/NaOH (pH 10.4). After clarification by centrifugation, the samples were read on a fluorescence plate reader with 355 nm excitation at 460 nm emission.
Results:

Each donor has readily detectable sialidase activity after 1 day storage at RT, which was up-regulated after prolonged storage (Day 6). Platelets from Donor B exhibited higher sialidase activity on both Day 1 and Day 6. See FIG. 42.
Conclusion:

The difference of platelet surface sialidase expression among individual donors suggests a possible difference of platelet surface β-galactose exposure among individual donors.

Example 16

Variability of Platelet Surface β-Galactosidase Activities Among Healthy Individuals and Up-Regulation of these Activities During Platelet Storage at RT Mammalian neuraminidases have been classified as lysosomal (Neu1), cytosolic (Neu2), plasma membrane (Neu3), and mitochondria/lysosomal (Neu4) based on their subcellular distributions, pH optima, kinetic properties, responses to ions and detergents, and substrate specificities. Of the four sialidases, only Neu1 is ubiquitously expressed at different levels in various tissues and cell types. The importance of these proteins in normal cellular physiology is illustrated by the numerous metabolic processes that they control, including cell proliferation and differentiation, cell adhesion, membrane fusion and fluidity, immunocyte function and receptor modification.

Neu1 initiates the intralysosomal hydrolysis of sialooligosaccharides, -glycolipids, and -glycoproteins by removing their terminal sialic acid residues. In human and murine tissues, Neu1 forms a complex with at least two other proteins, β-galactosidase and the protective protein/cathepsin A (PPCA). By virtue of their association with PPCA, Neu1 and β-galactosidase acquire their active and stable conformation in lysosomes. However, PPCA appears to function as a crucial chaperone/transport protein for Neu1. Because Neu1 is poorly mannose 6-phosphorylated, it depends on PPCA for correct compartmentalization and catalytic activation in lysosomes. Only a small amount of PPCA and β-galactosidase activities is found in the Neu1-PPCA-β-galactosidase complex, which instead contains all of the Neu1 catalytic activity. By understanding how and when Neu1 and PPCA interact, how they regulate each other in different cell types, and what determinants control their association, important insight is gained regarding their significance in physiologic and pathologic conditions.

Figure 43:
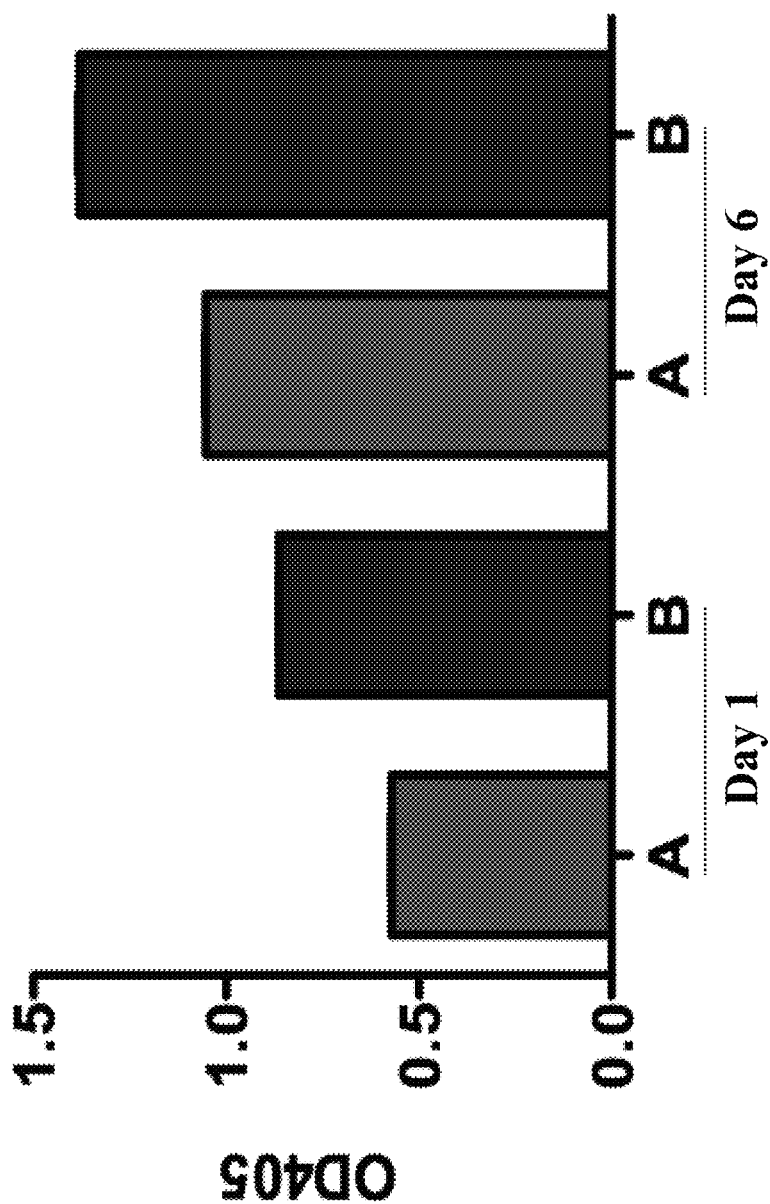
FIG. 43 is a bar graph showing the analysis of platelet surface β-galactosidase activity. The enzyme activity was determined using a colorimetric assay by incubation of platelets (Bag A or B) with Galβ-pNP. The product pNP can be read at 405 nm at pH>10. Donors A and B exhibited variable platelet surface β-galactosidase activity at the early stage of the storage (Day 1), which became up-regulated after further storage (Day 6). Donor B has higher activity than Donor A on both Day 1 and Day 6. β-Galactosidase activity on platelet surface increases during room temperature storage.

As described herein, we have previously demonstrated that Neu1 is rearranged to platelet surface after platelet refrigeration. Since the association with β-galactosidase goes along with Neu1 activity, the surface expression and up-regulation (during storage at RT) of Neu1 activity suggests similar observations for β-galactosidase activity. To test this hypothesis, we analyzed the platelet β-galactosidase activity before and after platelet storage.
Methods:

Platelets were isolated from platelet concentrates stored under blood banking conditions by centrifugation, washed, re-suspended in platelet wash Buffer A and counted by flow cytometry. Platelet β-galactosidase activity was determined by incubation of washed platelets (~5-$10^8$ platelets) or PC at 37° C. with 2.5 mM Galβ-pNP in 100 mM NaOAc (pH 5.0), 80 mM NaCl. Reaction mixtures were sampled at various time points and the reactions were quenched with 1.5 volumes of 200 mM glycine/NaOH (pH 10.4), clarified by centrifugation and read on a spectrophotometer plate reader at 405 nm.
Results:

β-Galactosidase activity was readily detected with washed platelets or directly with platelet concentrates. Enzyme activity varies among donors, but is up-regulated during platelet storage. It is noted that Donor B, exhibiting higher sialidase activity, also exhibited higher β-galactosidase activity. See FIG. 43.

Example 17

Isolated Platelets from Healthy Volunteers Differ in Terminal β-Galactose Content, and this Correlates with Platelet Ingestion by HepG2 Cells in Vitro Platelet surface sialidase catalyzes the release of sialic acids from the platelet surface and exposes β-galactose residues. The presence of β-galactosidase on the platelet surface suggests that the platelet surface β-galactose exposure may vary among individuals and over the course of platelet storage. To test this hypothesis, we obtained platelets from healthy volunteers from platelet concentrates and measured for β-galactose exposure by RCA lectin binding.

We have shown that the hepatoma cell line HepG2 ingests sialyltransferase-deficient mouse platelets (ST3Gal-IV$^{-/-}$ platelets) and sialic acid-deficient, refrigerated human platelets in vitro. This cell line expresses the Asgr (Ashwell Morell Receptor), which specifically recognizes platelets in vitro and in vivo. See FIG. 37. Whether platelets with high or low terminal β-galactose initiate endocytosis by hepatocytes will be determined in HepG2 cultures.
Methods:

Platelets are isolated by centrifugation, washed with PBS, and resuspended in PBS, ⅕ of original plasma volume. Platelets are counted by flow cytometry and then diluted appropriately. Lectins are diluted appropriately in PBS. Five μl of diluted platelets is added to the 100 μL of lectin and incubated for 15 min. After incubation, 300 μl PBS is added to lectin-platelet solution and analyzed by a flow cytometer.

Figure 38:
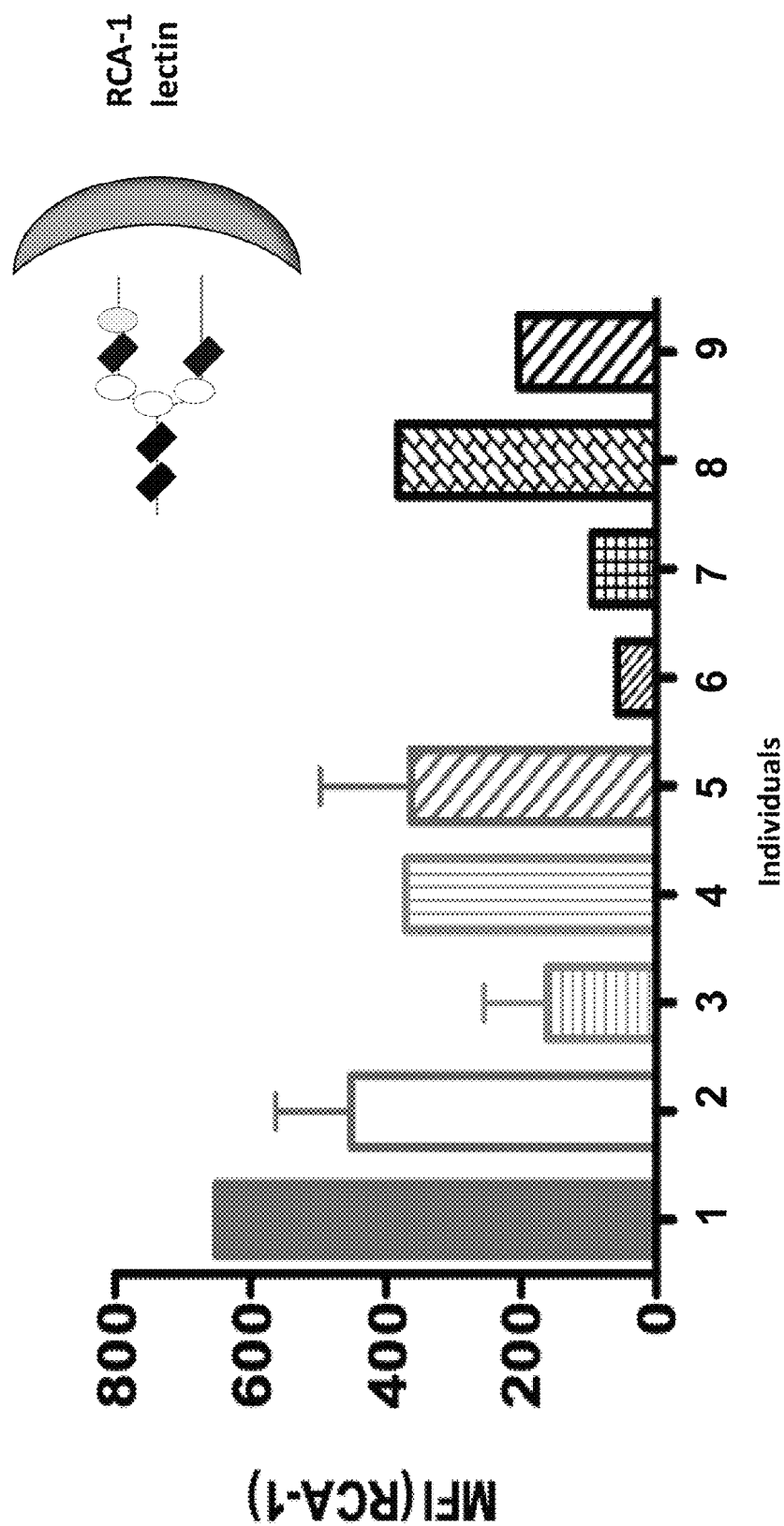
FIG. 38 is a schematic showing Platelet surface β-galactose exposure determined by lectin binding. Platelets were isolated from healthy volunteers and terminal β-galactose exposure was determined by flow cytometry using 1 µg/mL FITC-conjugated RCA-1 lectin. The scheme indicates RCA-1 lectin binding to terminal galactose. Isolated platelets from healthy volunteers differ in terminal β-galactose content and this correlates with platelet ingestion by HepG2 cells in vitro.

For the HepG2 assay, isolated human platelets were labeled with CM-Orange, added to HepG2 cells and incubated for 30 min at 37° C. The number of platelets in the media was counted by flow cytometry. The number of platelets added to HepG2 cells was set to 100% for each individual. Ingestion of fluorescently (CM-orange) labeled fresh platelets was detected using flow cytometry as an increase in hepatocyte associated orange fluorescence.
Results:

The presence of a terminal β-galactose on surface glycoproteins (e.g., glycans lacking sialic acid) on freshly-isolated platelets varies considerably among healthy subjects as measured by RCA-I lectin binding assay (FIG. 38). Platelets from subject 1 have the highest surface β-galactose exposure, while those from subject 6 have the lowest surface β-galactose exposure. These findings were confirmed by HepG2 assay. See FIGS. 39A and 39B.

Conclusion:

Our results show that fresh platelets have variable surface β-galactose exposure/sialic acid loss among healthy individuals.

Example 18

Terminal β-Galactose Content Decreases on Platelet Surfaces Over the Course of Platelet Storage and Correlates with Ingestion by HepG2 Cells In this Example, we extended our studies as described in Example 17 to platelets isolated from platelet concentrates stored under standard blood banking conditions.

Figure 37:
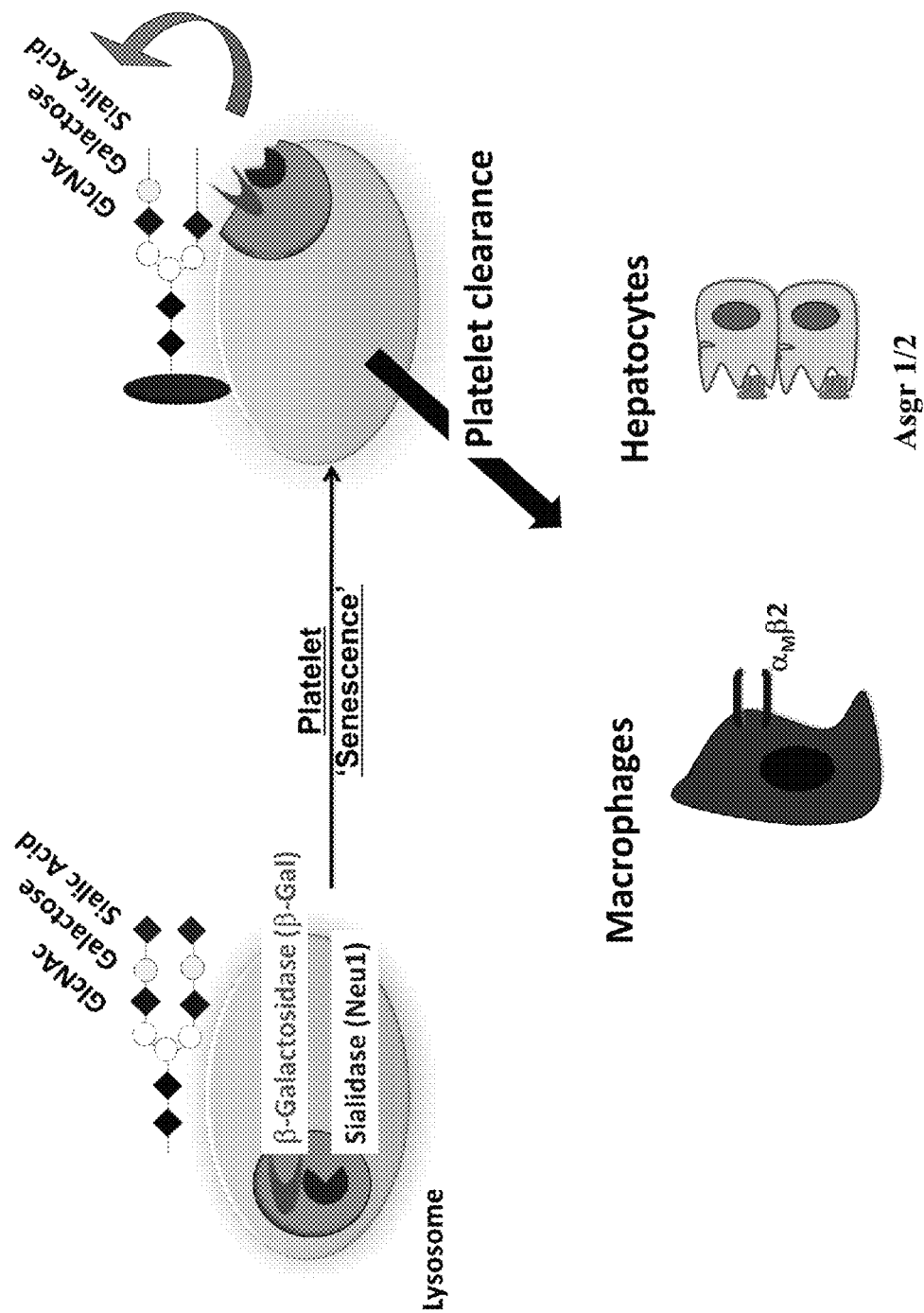
FIG. 37 is a schematic showing sialidase and β-galactosidase activity and a platelet clearance mechanism.
Figure 40:
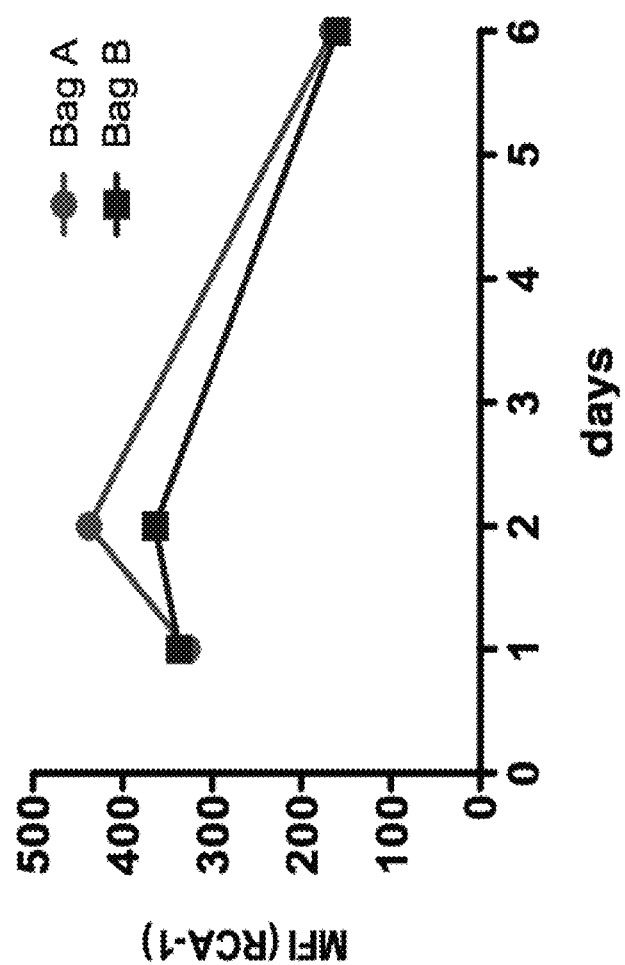
FIG. 40 is a line graph showing platelet surface terminal β-galactose changes during platelet storage. Platelets were isolated from platelet concentrates (Blood Transfusion Service, Massachusetts General Hospital) at the indicated time points and terminal β-galactose exposure was determined by flow cytometry using 1 µg/mL FITC-conjugated RCA-1 lectin. Platelet concentrates were obtained from the Blood Transfusion Service, Massachusetts General Hospital, Boston, Mass., and stored at room temperature under standard blood banking conditions. Platelets were obtained and analyzed at the indicated time points. Terminal β-galactose content decreases on isolated platelet surfaces during platelet storage and correlates with ingestion by HepG2 cells.
Figure 41B:
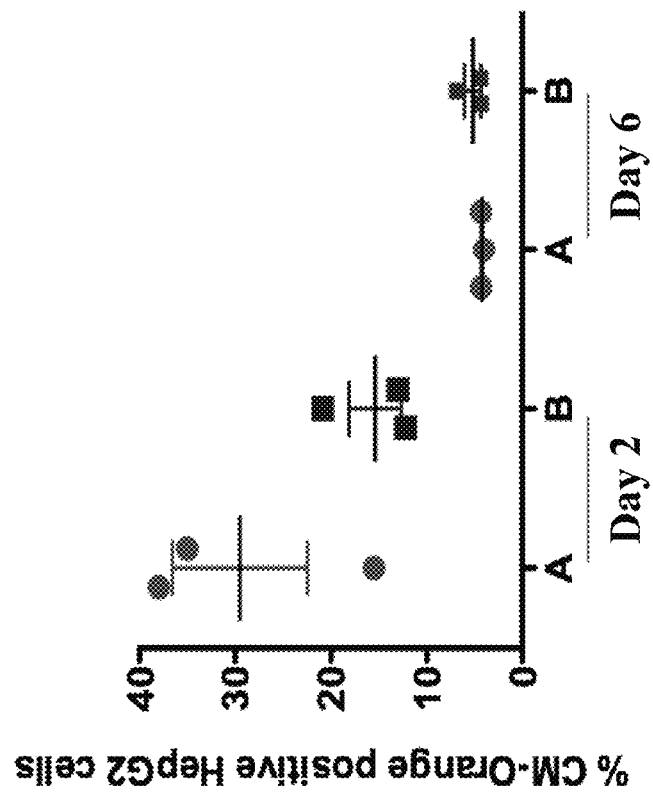
FIG. 41B is a line graph showing the ingestion of fluorescently labeled stored platelets, as detected using flow cytometry, as an increase in hepatocyte associated orange fluorescence.
Figure 41A:
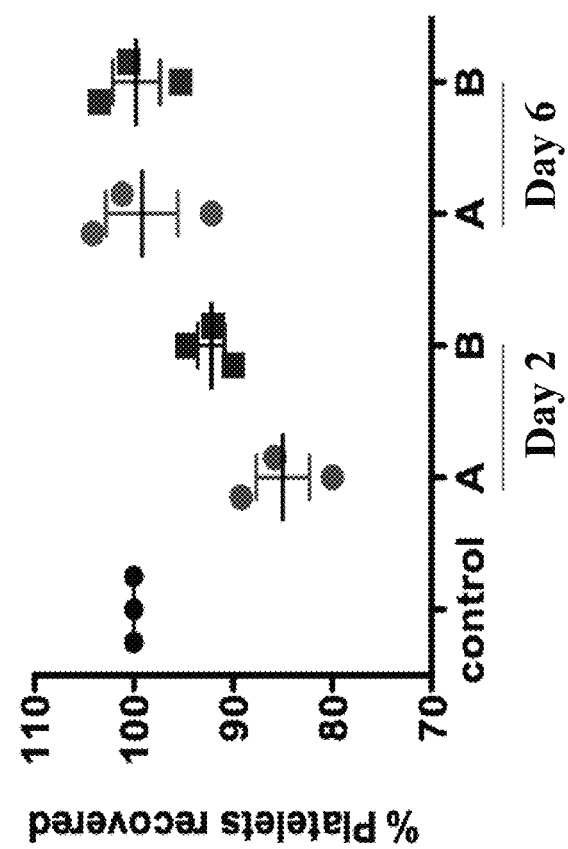
FIG. 41A is a line graph showing that the HepG2 cells ingestion of human platelets correlates with the decrease in sialic acid and β-galactose exposure. Quantification of platelets recovered from HepG2 cell incubation media is shown. Isolated human platelets were labeled with CM-Orange, added to HepG2 cells and incubated for 30 min at 37° C. The number of platelets counted before addition to HepG2 cells was set to 100% for each individual.

Results:

During storage at RT, platelet surface β-galactose exposure appears to peak at day 2, then decrease during further storage (See FIG. 40), which was confirmed by HepG2 assay. See FIGS. 41A and 41B Summary:

Human platelets have variable (among donors) surface sialidase and β-galactosidase activities, both of which are up-regulated during platelet storage at RT. In addition, human platelets have variable surface β-galactose exposure/sialic acid loss among individual donors. During storage at RT, platelet surface β-galactose exposure appears to peak at day 2, then decrease during further storage. Since the association with β-galactosidase goes along with Neu1 sialidase activity, the concerted up-regulation of sialidase and β-galactosidase activities on platelet surface indicates that the multi-enzyme complex is relocated from lysosome to platelet surface during platelet storage/aging, possibly through the fusion between platelet membrane and lysosomal membrane (FIG. 37). The relocation of both Neu1 and β-galactosidase onto platelet surface catalyzes the sequential degradation of platelet surface glycans, loss of sialic acid, followed by β-galactose, exposing terminal N-acetylglucosamine (GlcNAc). GlcNAc can potentially be further removed, exposing the mannose residues. Additionally, the mannose residues can be readily recognized by macrophage mannose receptors, triggering immediate platelet clearance.

Example 19

Fresh Platelets Bear Terminal β-Galactose, which is Readily Cleaved by β-Galactosidase Exposing β-GlcNAc Thereby Leading to Ingestion by THP-1 Cells We treated fresh isolated platelets from healthy volunteers with β-galactosidase, which cleaves terminal β-galactose from platelet surfaces.

Figure 44:
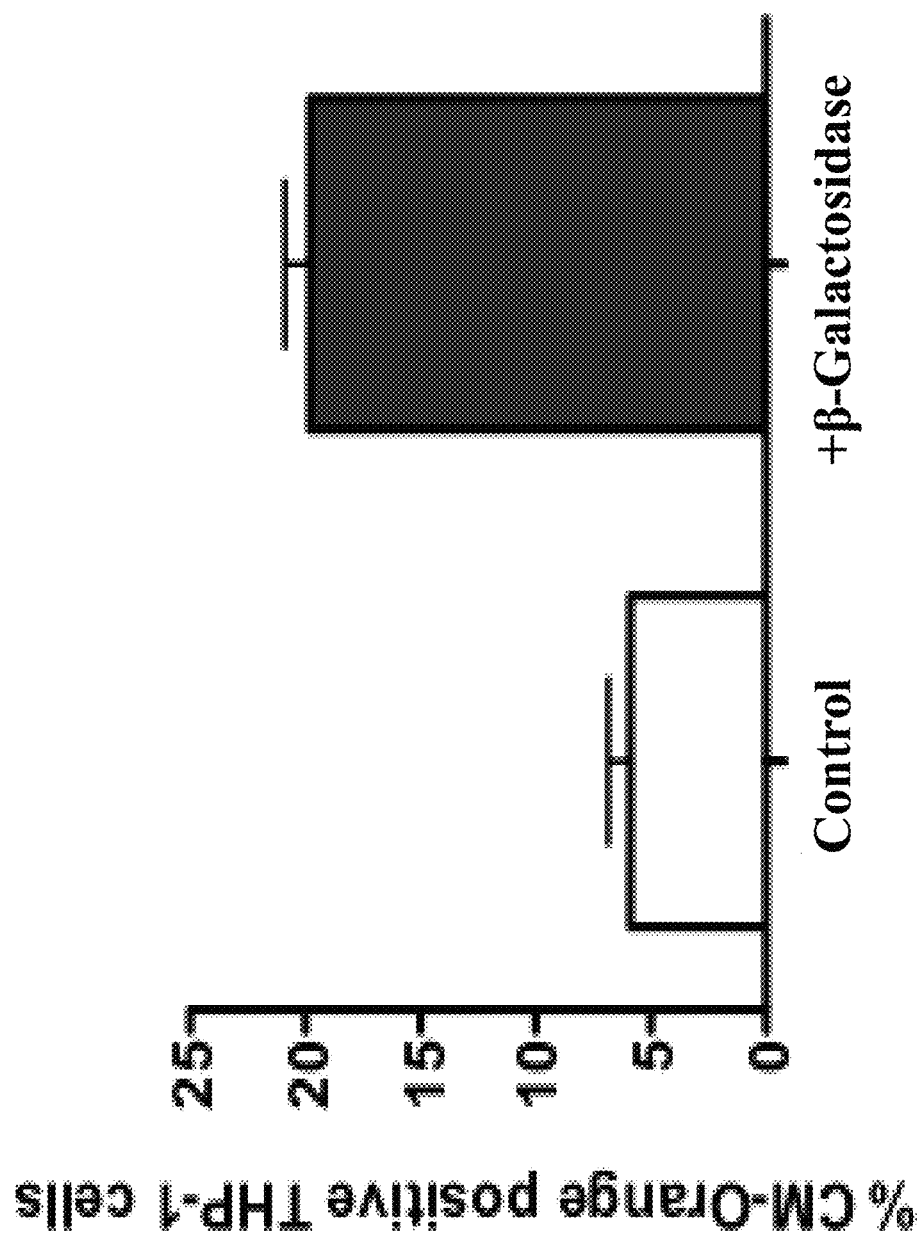
FIG. 44 is a bar graph showing that THP-2 cells ingestion of human platelets correlates with decrease in β-galactose exposure. Isolated human platelets were labeled with CM-Orange, added to THP-1 cells and incubated for 30 min at 37° C. Ingestion of fluorescently labeled control fresh room temperature platelets and platelets treated by β-galactosidase was detected using flow cytometry, as an increase in hepatocyte associated orange fluorescence.

Results:

Fresh platelets treated with β-galactosidase are readily ingested (4-fold increase) by the macrophage-like cell line THP-1 when compared to control platelets. These results show that fresh platelets have terminal β-galactose, which can be readily accessed and cleaved by β-galactosidase. This maneuver exposes underlying β-GlcNAc residues. Exposure of β-GlcNAc presumably promotes ingestion of platelets via the αMβ2 macrophage receptor. See FIG. 44.

Summary:

Fresh isolated platelets have exposed β-galactose showing that platelets contain desialylated glycans. Removal of β-galactose using β-galactosidase exposes terminal N-acetylglucosamine (GlcNAc), and exposure of GlcNAc leads to ingestion of platelets by THP-1 cells, and by macrophages. GlcNAc can potentially be further removed, exposing the mannose residues. Furthermore, the mannose residues can be readily recognized by macrophage mannose receptors, triggering immediate platelet clearance.

Example 20

Improved In Vitro Quality of Human Platelets Stored in V-PAS™ Solution Containing β-Galactosidase Inhibitor DGJ Data described in Example 19 demonstrated that loss of β-galactose from platelet surface leads to increased ingestion of platelets by $α_Mβ_2$-expressing THP-1 cells. Whether inhibition of β-galactose loss from platelet surface during platelet storage may improve the quality of stored platelets was tested. Platelets were stored in plasma/V-PAS™ solution in a ratio of 30:70, in the absence or presence of β-galactosidase inhibitor DGJ (1-deoxygalactonojirimycin), and analyzed the stored platelets over the course of storage. V-PAS™ solution is used herein to refer to a platelet additive solution having a silaidase inhibitor, and one or more storage medium components (e.g., not having a β-galactosidase inhibitor). V-PAS+™ solution or V-PAS+2 are used herein to refer to a platelet additive solution having a silaidase inhibitor, a β-galactosidase inhibitor, and one or more storage medium components. In some of the figures and examples, the term V-PAS, V-PAS+ or V-PAS+2 can be show with or without the "-" as VPAS, VPAS+, VPAS+2, respectively.

Materials and Methods:

ABO-matched random donor platelet concentrates (Blood Transfusion Service, Massachusetts General Hospital) were pooled, aliquoted into 50-mL conical tubes and centrifuged (1000×g, 20 min). After removal of 70% plasma, the pelleted platelets were allowed to rest for 1 hour, re-suspended in the remaining plasma, and pooled to homogenize the platelet suspension. The resultant platelet suspension was divided into PermaLife bags (PL 30, OriGen Biomedical) (7.2 mL/bag), to which 16.8 mL of plasma or V-PAS™ or V-PAS+(a combination of V-PAS with 2 mM DGJ) was added per bag. The platelet bags were placed on a platelet rotator and stored at room temperature. The platelet aliquots were sampled on Day 1, Day 5, Day 7, or Day 9 and diluted with PBS. The diluted platelets were stained with FITC-labeled Annexin V for PS exposure, or FITC-labeled CD62P antibodies for P-selectin exposure, and analyzed by flow cytometry.

Results:

Phosphatidylserine (abbreviated PS) is a phospholipid component, usually kept on the inner-leaflet (the cytosolic side) of cell membranes by an enzyme called flippase. When a cell undergoes apoptosis phosphatidylserine is no longer restricted to the cytosolic part of the membrane, but becomes exposed on the surface of the cell. Fresh isolated platelets have little, but readily detectable, surface exposure of PS, which can be measured by Annexin V binding. Upon storage, PS exposure on platelet surface is increased. Increased surface exposure of PS on stored platelets has been correlated with reduced platelet recovery after transfusion. The platelet PS surface exposure during platelet storage were monitored under different conditions at the indicated time points in FIG. 45 and FIG. 46.

Figure 46A:
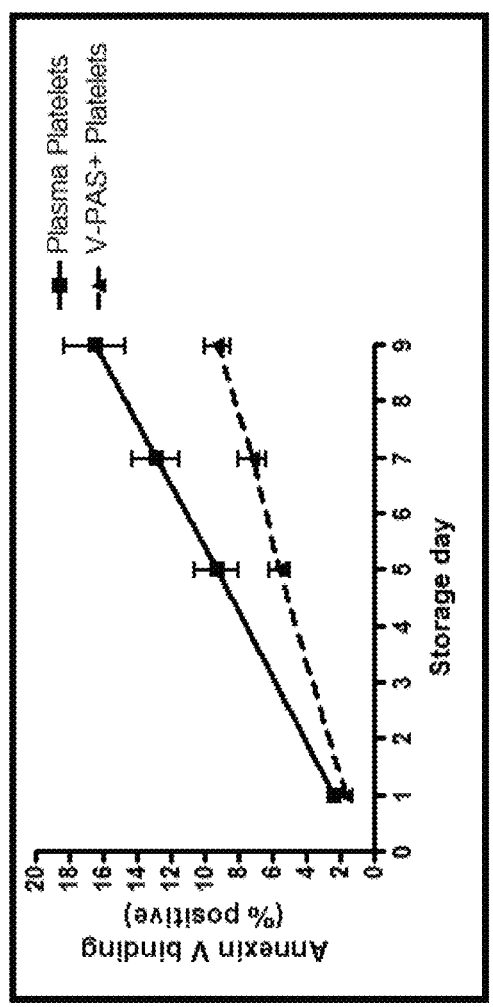
FIG. 46A is a line graph of platelet surface exposure of PS as measured by FITC labeled Annexin V binding over the time of platelet storage (n=4).

As shown in FIG. 45A, platelets stored in 100% plasma (Plasma Platelet) demonstrated a continuous increase in PS exposure, as measured by Annexin V binding, which is (roughly) linearly proportional to the storage time. As expected, platelets stored in both plasma and V-PAS (V-PAS Platelet) also demonstrated gradual increase of PS exposure over the course of the 7-day storage, but at much slower pace as compared to plasma alone. However, PS exposure on V-PAS Platelets increased after Day 5 although it is still much lower than that found on Plasma Platelets at Day 7. Introduction of DGJ to V-PAS solution (i.e., V-PAS+ solution) shows a similar impact on platelet surface exposure of PS up to Day 5 as compared to V-PAS platelets (i.e., without DGJ). However, after Day 5, V-PAS+ inhibits accelerated PS exposure, as compared to that seen in platelets stored in the presence of V-PAS (See V-PAS+ Platelet in FIG. 45B). Consistently, the difference of PS exposure between V-PAS Platelets and V-PAS+ Platelets at Day 7 is significant (FIG. 45B). Both V-PAS platelets and V-PAS+ platelets are significantly better than plasma platelets. These data strongly suggest that DGJ improves the quality of platelets subjected to prolonged storage. To confirm this preliminary but important observation, paired studies were performed between Plasma Platelets and V-PAS+ Platelets, which were stored beyond 7 days. Data from Plasma Platelets confirmed the linear relationship between platelet surface PS exposure and storage time as observed previously for platelets stored for 7 days, and such relationship can be extended to 9 days (FIG. 46A). A similar observation was made for V-PAS+ Platelets. However, the increase in PS exposure on V-PAS+ Platelets (slope=0.9402±0.1062) is much slower than plasma platelets (slope=1.765±0.2111), suggesting that V-PAS+ is a better storage medium than plasma.

Figure 46B:
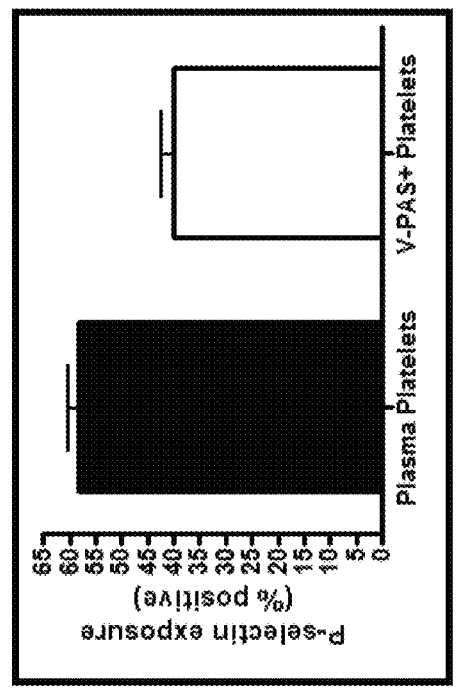
FIG. 46B is a bar graph of platelet surface exposure of P-selectin as measured by FITC labeled CD62P antibodies binding after storage for 9 days (n=4) (p<0.01).

P-selectin expression (i.e., platelet granule secretion) on platelet surface is used to evaluate the quality of stored platelets. Its expression on platelet surface is independent of PS exposure. The dramatic down-regulation of PS exposure on V-PAS+Platelets compared to Plasma Platelets led us to examine how V-PAS+ impacts the platelet activation after storage for 9 days. As shown in FIG. 46B, V-PAS+ has significant negative effect on the P-selectin exposure on platelets stored for 9 days compared with plasma, indicating that platelets stored in V-PAS+ have less platelet activation than those stored in 100% plasma.

Conclusion:

DGJ can effectively preserve the quality of human platelets, i.e., reduce platelet apoptosis, and platelet activation, when stored in 30% plasma and in the presence of a platelet additive solution. Collectively, our data show that a β-galactosidase inhibitor such as DGJ can be used as an effective component in PAS formulations for platelet storage.

Example 21

Survival of Platelets after Transfusion

Platelet Counts and Preparation:

Blood was obtained from anesthetized 8 weeks old C57/Bl6 mice by retroorbital bleeding. Platelets and platelet poor plasma (PPP) were prepared by differential centrifugation as described (Hoffmeister, K. M., et. al., "The clearance mechanism of chilled blood platelets", Cell 112:87 (2003)). Platelets were stored in 100% plasma, or in a mixture of 30% plasma and 70% VPAS, and 30% plasma and 70% VPAS+2. VPAS+2 is sometimes also referred to as V-PAS+ herein, and includes a β-galactosidase inhibitor as well as a sialidase inhibitor. In this embodiment, V-PAS+ includes DGJ as the β-galactosidase inhibitor and DANA as the sialidase inhibitor. Platelet numbers were adjusted prior to transfusion to ensure equal numbers of transfused platelets per condition. Fresh platelets were kept in 100% plasma and transfused immediately after isolation.

Figure 47:
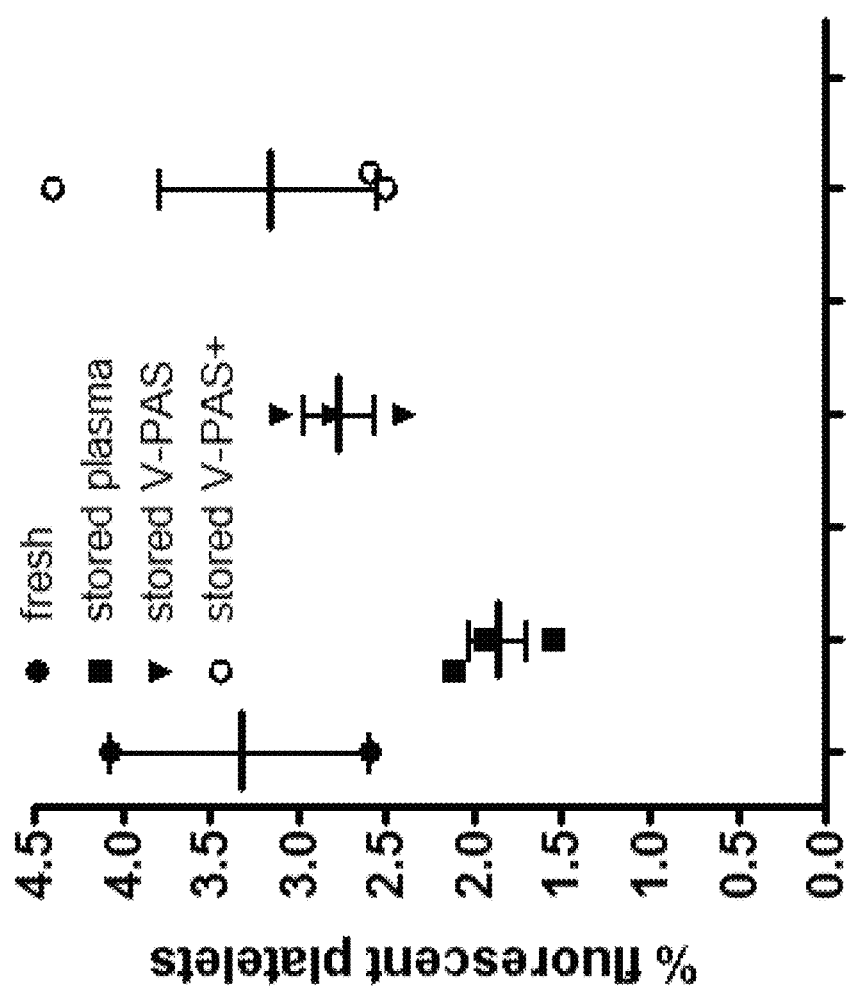
FIG. 47 is a scatter plot showing the percentage of fresh and stored platelets recovered at 5 min following tansfusion. Platelets were stored for 20 hours at room temperature in plasma, VPAS, or VPAS+2. Fresh non-stored platelets are used as control (n=3 for each group).
Figure 48:
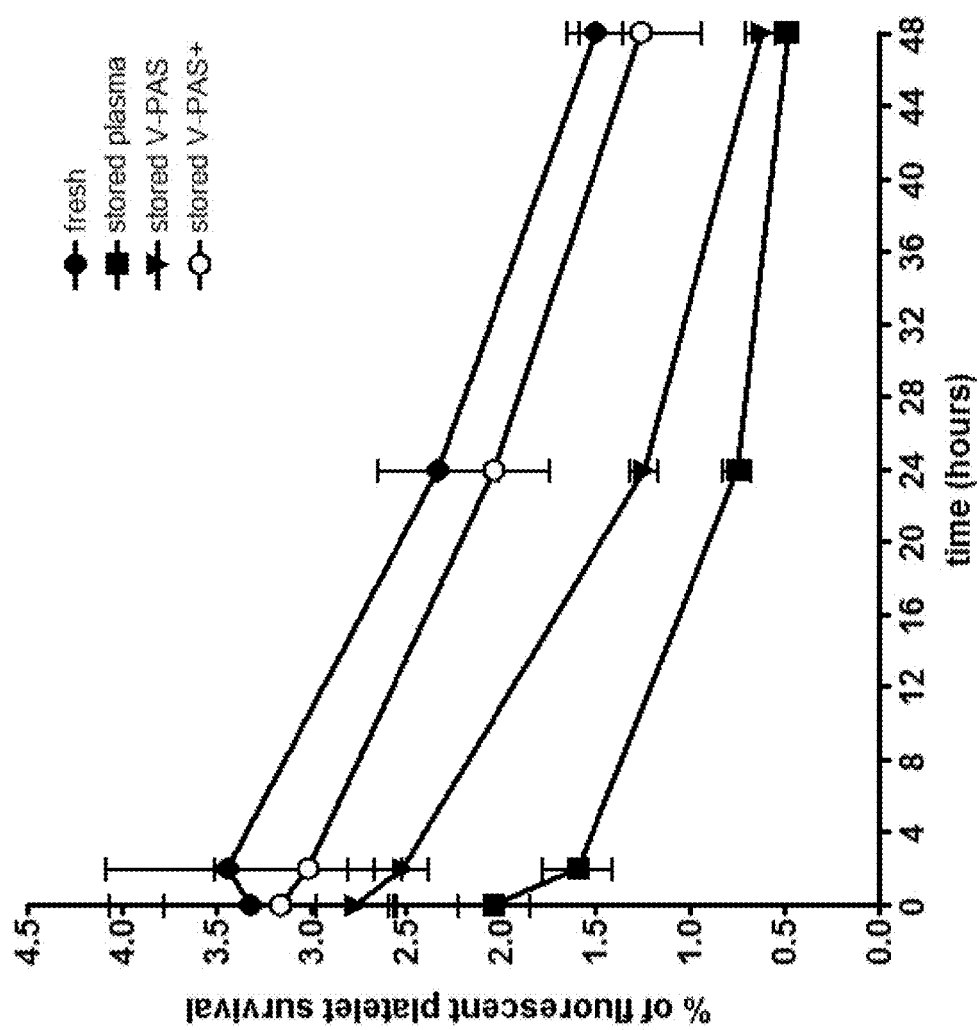
FIG. 48 is a line plot showing short-term survival of fresh and stored platelets following transfusion. Platelets were stored for 20 hours at room temperature in plasma, VPAS/

Platelet Transfusions:

Isolated platelets were labeled with 2.5 µM of CMFDA for 15 min. Following staining, platelets were pelleted and resuspended in 500 µl of plasma, V-PAS/Plasma (70:30) or V-PAS+/Plasma (70:30). Platelets were stored for 20 hours at room temperature and transfused into 8 weeks old syngeneic mice. Non-stored fresh platelets in plasma were used as control. Platelet survivals were determined by intravenous injections CMFDA-labeled mouse platelets, as described in Rumjantseva V., et al., "Dual roles for hepatic lectin receptors in the clearance of chilled platelets", Nature Medicine 15(11): 1273-80 (2009) and Sorensen A. L., et al., "Role of sialic acid for platelet life span: exposure of beta-galactose results in the rapid clearance of platelets from the circulation by asialoglycoprotein receptor-expressing liver macrophages and hepatocytes", Blood 114(8):1645-54 (2009). Blood was collected by retroorbital bleeding at 5 min, 2 hours, and 48 hours. The percentages of CMFDA-positive platelets were determined by flow cytometry. The amount of fluorescent platelets at 5 minutes is shown in FIG. 47. Short-term (2 hours) and long-term (48 hours) survivals of the transfused platelet populations are shown in FIG. 48.

This application relates to U.S. application Ser. No. 13/474,473, entitled "Increased In Vivo Circulation Time Of Platelets After Storage With a Sialidase Inhibitor" filed May 17, 2012, by Karin Hoffmeister, Qiyong Peter Liu, and Robert Sackstein; U.S. application Ser. No. 13/474,627, entitled "Improved Platelet Storage and Reduced Bacterial Proliferation in Platelet Products Using a Sialidase Inhibitor" by Qiyong Peter Liu and Karin Hoffmeister; U.S. application Ser. No. 13/474,679, entitled "Platelet Additive Solution Having a Sialidase Inhibitor" filed May 17, 2012, by Qiyong Peter Liu and Karin Hoffmeister; and PCT Application No. PCT/US2012/038462 entitled "Improved Platelet Storage Using a Sialidase Inhibitor" by Qiyong Peter Liu, Karin Hoffmeister and Robert Sackstein. This application also relates to U.S. Provisional Application No. 61/613,876, filed Mar. 21, 2012; U.S. Provisional Application No. 61/613,837, filed Mar. 21, 2012; U.S. Provisional Application No. 61/503,984, filed Jul. 1, 2011; U.S. Provisional Application No. 61/487,077, filed May 17, 2011; U.S. Provisional Application No. 61/710,273, filed Oct. 5, 2012; U.S. Provisional Application No. 61/814,325, filed Apr. 21, 2013; and U.S. Provisional Application No. 61/813,885, filed Apr. 19, 2013. The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of storing platelets having a platelet surface, wherein sialic acid loss and galactose loss are reduced on the platelet surface of isolated platelets during storage, wherein the isolated platelets are obtained from one or more donors, the method comprises:

a. contacting the isolated platelets with a Platelet Additive Solution (PAS) that comprises:
   i. from about 0.1 mM to about 100 mM of one or more β-galactosidase inhibitors and from about 0.1 mM to about 100 mM of one or more sialidase inhibitors, and optionally an amount of one or more glycan-modifying agents, or a combination thereof, wherein when platelets are stored, the sialic acid loss and galactose loss are caused by the presence of active endogenous sialidase and β-galactosidase, respectively, that have migrated to the platelet surface; and
   ii. one or more of PAS components that includes a salt, a citrate source, a carbon source, an acetate source, or any combination thereof;
   to thereby obtain a platelet composition, wherein cleavage by the endogenous sialidase and β-galactosidase of sialic acid or galactose, respectively, is reduced, as compared to isolated platelets not subjected to Step a); and wherein once the platelet composition is transfused into a recipient, circulation time of platelets is increased by at least 10% and platelet clearance of the platelets is reduced, as compared to circulation time and platelet clearance of platelets that have not been subjected to Step a).

2. The method of claim 1, wherein the one or more sialidase inhibitors is selected from the group consisting of: fetuin; 2,3-dehydro-2-deoxy-N-acetylneuraminic acid (DANA); ethyl (3R,4R,5S)-5-amino-4-acetamido-3-(pentan-3-yloxy)-cyclohex-1-ene-1-carboxylate); (2R,3R,4S)-4-guanidino-3-(prop-1-en-2-ylamino)-2-((1R,2R)-1,2,3-trihydroxypropyl)-3,4-dihydro-2H-pyran-6-carboxylic acid; (4S,5R,6R)-5-acetamido-4-carbamimidamido-6-[(1R,2R)-3-hydroxy-2-methoxypropyl]-5,6-dihydro-4H-pyran-2-carboxylic acid; (1S,2S,3S,4R)-3-[(1S)-1-acetamido-2-ethyl-butyl]-4-(diaminomethylideneamino)-2-hydroxy-cyclopentane-1-carboxylic acid; a combination thereof and a pharmaceutically acceptable salt thereof.

3. The method of claim 2, wherein the sialidase inhibitor is the sodium salt of 2,3-dehydro-2-deoxy-N-acetylneuraminic acid.

4. The method of claim 1, wherein the one or more β-galactosidase inhibitors is selected from the group consisting of: 1-deoxygalactonojirimycin (DGJ); N-(n-butyl)deoxygalactonojirimycin; N-(n-nonyl)deoxygalactonojirimycin; 5-deoxy-L-arabinose; galactostatin bisulfate; 3',4',7-trihydroxyisoflavone; D-ribonolactone; N-octyl-4-epi-β-valienamine; phenylethyl β-D-thiogalactopyranoside; difluorotetrahydropyridothiazinone; 4-aminobenzyl 1-thio-β-D-galactopryranoside; a combination thereof; and a pharmaceutically acceptable salt thereof.

5. The method of claim 1, wherein the platelet composition is stored for a period of about 1 to about 21 days.

6. The method of claim 1, wherein the platelet composition is stored at a temperature of between about 2° C. and about 25° C.

7. The method of claim 1, further comprising cooling the platelet composition to a temperature below room temperature; storing the platelet composition for a period of time; and then rewarming the platelet composition back to room temperature.

8. The method of claim 1, further comprising contacting the isolated platelets with the one or more β-galactosidase inhibitors and the one or more sialidase inhibitors, within a time period, wherein the time period is in a range between about 1 minute and about 8 hours.

9. The method of claim 1, wherein the one or more PAS components include a citrate source present in an amount ranging from 2 mM to 20 mM, and wherein the citrate source is selected from the group consisting of monosodium citrate, disodium citrate, trisodium citrate, citric acid, and a combination thereof.

10. The method of claim 1, wherein the one or more PAS components include a carbon source present in an amount ranging from 0.5 mM to 50 mM, and wherein the carbon source is selected from the group consisting of acetate, glucose, and sucrose.

11. The method of claim 1, wherein the one or more PAS components include an acetate source present in an amount ranging from 10 mM to 50 mM, and wherein the acetate source is selected from the group consisting of sodium acetate, potassium acetate, magnesium acetate, and a combination thereof.

12. The method of claim 1, wherein the one or more PAS components include a salt, and wherein the salt is selected from the group consisting of a sodium source, a chloride source, a potassium source, a magnesium source, a calcium source, and a combination thereof.

13. The method of claim 12, wherein the salt includes a sodium source, and wherein the sodium source is selected from the group consisting of sodium chloride, sodium citrate, sodium acetate, sodium phosphate, and a combination thereof.

14. The method of claim 12, wherein the salt includes a chloride source, and wherein the chloride source is selected from the group consisting of sodium chloride, magnesium chloride, potassium chloride, and a combination thereof.

15. The method of claim 12, wherein the salt includes a potassium source, and wherein the potassium source is selected from the group consisting of potassium chloride, potassium citrate, potassium acetate, potassium phosphate, potassium sulfate, and a combination thereof.

16. The method of claim 12, wherein the salt includes a magnesium source, and wherein the magnesium source is selected from the group consisting of magnesium chloride, magnesium citrate, magnesium sulfate, and a combination thereof.

17. The method of claim 12, wherein the salt includes a calcium source, and wherein the calcium source is selected from the group consisting of calcium chloride, calcium acetate, calcium citrate, and a combination thereof.

18. The method of claim 1, wherein the isolated platelets are mammalian platelets.

* * * * *